US007125901B2

United States Patent
Inoue et al.

(10) Patent No.: US 7,125,901 B2
(45) Date of Patent: Oct. 24, 2006

(54) THIAZOLE DERIVATIVES

(75) Inventors: Takayuki Inoue, Osaka (JP); Takashi Tojo, Osaka (JP); Masataka Morita, Osaka (JP); Mitsuru Ohkubo, Osaka (JP); Kousei Yoshihara, Osaka (JP); Akira Nagashima, Osaka (JP)

(73) Assignee: Astellas Pharma Inc., Tokyo (JP)

( * ) Notice: Subject to any disclaimer, the term of this patent is extended or adjusted under 35 U.S.C. 154(b) by 117 days.

(21) Appl. No.: 10/764,529

(22) Filed: Jan. 27, 2004

(65) Prior Publication Data

US 2004/0259923 A1 Dec. 23, 2004

Related U.S. Application Data

(60) Provisional application No. 60/517,377, filed on Nov. 6, 2003, provisional application No. 60/458,369, filed on Mar. 31, 2003, provisional application No. 60/442,509, filed on Jan. 27, 2003.

(51) Int. Cl.
*A61K 31/427* (2006.01)
*C07D 277/44* (2006.01)

(52) U.S. Cl. ...................... 514/371; 548/195
(58) Field of Classification Search ................ 514/371; 548/195
See application file for complete search history.

(56) References Cited

U.S. PATENT DOCUMENTS 4,888,283 A 12/1989 Bertini et al.

2002/0173521 A1 11/2002 Smith et al.

FOREIGN PATENT DOCUMENTS

| WO | WO 93/23023 | 11/1993 |
| WO | 9630350 | * 10/1996 |
| WO | WO 02/02090 | 1/2002 |
| WO | WO 02/02541 | 1/2002 |
| WO | WO 02/38152 | 5/2002 |
| WO | WO 02/38153 | 5/2002 |

OTHER PUBLICATIONS

F. Boomsma, et al., Diabetologia, vol. 42, pp. 233-237, "Circulating Semicarbazide-Sensitive Amine Oxidase is Raised Both in Type 1 (Insulin-Dependent), in Type II (Non-Insulin-Dependent) Diabetes Mellitus and even in Childhood Type 1 Diabetes at First Clinical Diagnosis", 1999.

H. Garpenstrand, et al., Diabetic Medicine, vol. 16, pp. 514-521, "Elevated Plasma Semicarbazide-Sensitive Amine Oxidase (SSAO) Activity in Type 2 Diabetes Mellitus Complicated by Retinopathy", 1999.

* cited by examiner

*Primary Examiner*—Taofiq Solola
(74) *Attorney, Agent, or Firm*—Oblon, Spivak, McClelland, Maier & Neustadt, P.C.

(57) ABSTRACT

A compound of the formula (I): $R^1$—NH—X—Y-Z (I) wherein each symbol is as defined in the specification, or a pharmaceutically acceptable salt thereof useful as a vascular adhesion protein-1 (VAP-1) inhibitor, a pharmaceutical composition, a method for preventing or treating a VAP-1 associated disease, especially macular edema, which method includes administering an effective amount of the compound or a pharmaceutically acceptable salt thereof to a mammal, and the like.

10 Claims, No Drawings

THIAZOLE DERIVATIVES

TECHNICAL FIELD

The present invention relates to a compound or a pharmaceutically acceptable salt thereof useful as a vascular adhesion protein-1 inhibitor, a pharmaceutical composition comprising the compound or salt thereof as an active ingredient, a method for preventing or treating a vascular adhesion protein-1 associated disease, especially macular edema, use of the compound, salt thereof or composition, and the like.

BACKGROUND ART

Vascular adhesion protein-1 (hereinafter to be abbreviated as VAP-1) is an amine oxidase (semicarbazide sensitive amine oxidase, SSAO) which is abundant in human plasma, and shows remarkably increased expression in vascular endothelium and vascular smooth muscle of the inflammatory region. While the physiological role of VAP-1 has not been clarified until recently, VAP-1 gene was cloned in 1998, and VAP-1 has been reported to be a membrane protein that regulates rolling and migration of lymphocyte and NK cell as an adhesion molecule under regulation of expression by inflammatory cytokine. Although the amine to be a substrate is unknown, it is considered to be methylamine generated in any part of living organisms. It is also known that hydrogen peroxide and aldehydes produced due to the amine oxidase activity in the molecule are important factors of adhesion activity.

A recent report has documented that VAP-1 enzyme activity in plasma increases in diabetic patients, whether type I or type II, and the increase is particularly remarkable in diabetic patients suffering from retinopathy complications (Diabetologia, 42 (1999) 233–237, Diabetic Medicine, 16 (1999) 514–521).

In addition, it has been reported that VAP-1 is associated with the following diseases:

(1) cirrhosis, essential stabilized hypertension, diabetes, arthrosis (see JP-A-61-239891 and U.S. Pat. No. 4,888,283);

(2) endothelium damage (in diabetes, atherosclerosis and hypertension), a cardiovascular disorder associated with diabetes and uraemia, pain associated with gout and arthritis, retinopathy (in diabetes patients) (see WO 93/23023);

(3) an (connective tissue) inflammatory disease or condition (rheumatoid arthritis, ankylosing spondylitis, psoriatic arthritis and osteoarthritis or degenerative joint disease, Reiter's syndrome, Sjögren's syndrome, Behçet's syndrome, relapsing polychondritis, systemic lupus erythematosus, discoid lupus erythematosus, systemic sclerosis, eosinophilic fasciitis, polymyositis, dermatomyositis, polymyalgia rheumatica, vasculitis, temporal arteritis, polyarteritis nodosa, Wegener's granulomatosis, mixed connective tissue disease, and juvenile rheumatoid arthritis); a gastrointestinal inflammatory disease or condition [Crohn's disease, ulcerative colitis, irritable bowel syndrome (spastic colon), fibrotic conditions of the liver, inflammation of the oral mucosa (stomatitis), and recurrent aphtous stomatitis]; a central nervous system inflammatory disease or condition (multiple sclerosis, Alzheimer's disease, and ischaemia-reperfusion injury associated with ischemic stroke); a pulmonary inflammatory disease or condition (asthma, adult respiratory distress syndrome, chronic obstructive pulmonary disease); a (chronic) skin inflammatory disease or condition (psoriasis, allegic lesions, lichen planus, pityriasis rosea, contact dermatitis, atopic dermatitis, pityriasis rubra pilaris); a disease related to carbohydrate metabolism (diabetes and complications from diabetes) including microvascular and macrovascular disease (atherosclerosis, vascular retinopathies, retinopathy, nephropathy, nephrotic syndrome and neuropathy (polyneuropathy, mononeuropathies and autonomic neuropathy), foot ulcers, joint problems, and increased risk of infection); a disease related to aberrations in adipocyte differentiation or function or smooth muscle cell function (atherosclerosis and obesity); a vascular disease [atheromatous ateriosclerosis, nonatheromatous ateriosclerosis, ischemic heart disease including myocardial infarction and peripheral arterial occlusion, Raynaud's disease and phenomenon, thromboangiitis obliterans (Buerger's disease)]; chronic arthritis; inflammatory bowel diseases; skin dermatoses (see WO 02/02090, WO 02/02541 and U.S. patent application publication No. 2002/0173521 A1);

(4) diabetes mellitus (see WO 02/38152); and (5) SSAO-mediated complication [diabetes (insulin dependent diabetes mellitus (IDDM) and non-insulin dependent diabetes mellitus (NIDDM)) and vascular complication (heart attack, angina, strokes, amputations, blindness and renal failure)] (see WO 02/38153), and the like.

Under the present circumstances, a drug treatment or prophylaxis of the above diseases has been demanded.

Macular edema is a common ocular abnormality resulting from a vast etiology and characterized by perturbation of the integrity of the blood-retinal barrier of the perifoveal capillaries and the optic nerve head. Macular edema is known to include diabetic and non-diabetic ones. Macular edema as a diabetic complication is a disease state that can occur in any stage of diabetic retinopathy, emerges before the onset of neovascularization and causes a serious visual disorder. Macular area is a highly evolved part in retina and plays a key role in controlling the eyesight. Once the macular area suffers from edema, how mild the change may be, it causes a significant failure of eyesight, and when left unattended, the edema causes irreversible changes of macular tissue, and it is considered to encourage progress of retinopathy.

At present, for macular edema, laser beam photocoagulation and vitreous surgery have been tried as a symptomatic therapy. However, irradiation of laser on the macular area is not easy and unnecessary laser treatments may produce side effects (e.g., possible encouragement of edema by causing inflammation). The vitreous surgery is considered to provide effect in 70 percent of macular edema, but physical and economical burden on patients is high, and the incidence of recurrence is also high. These treatment methods are not usually employed in the initial stage of macular edema, particularly so in the stages when the decrease of vision is comparatively small. Accordingly, a drug treatment comparatively easily applicable from the early stages of the disease has been also demanded under the present circumstances.

DISCLOSURE OF INVENTION

The present inventors have intensively worked on the problem of drug treatment of a VAP-1 associated disease and found that a VAP-1 inhibitor is useful for the prophylaxis or treatment of the disease, particularly macular edema, and completed the present invention. Thus, the present invention provides the following.

[1] A compound of the formula (I) [hereinafter sometimes referred to as Compound (I)]:

R¹—NH—X—Y-Z (I)

wherein
R¹ is acyl;
X is a bivalent residue derived from optionally substituted thiazole;
Y is a bond, lower alkylene, lower alkenylene or —CONH—; and
Z is a group of the formula:

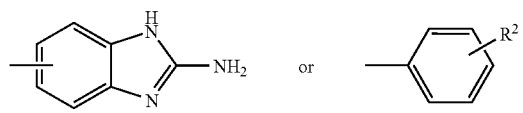

wherein R² is a group of the formula: -A-B-D-E
wherein A is a bond, lower alkylene, —NH— or —SO₂—;
B is a bond, lower alkylene, —CO— or —O—;
D is a bond, lower alkylene, —NH— or —CH₂NH—; and
E is optionally protected amino, —N=CH₂,

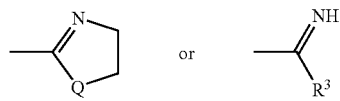

wherein
Q is —S— or —NH—; and
R³ is hydrogen, lower alkyl, lower alkylthio or —NH—R⁴ wherein R⁴ is hydrogen, —NH₂ or lower alkyl;

or a pharmaceutically acceptable salt thereof.

[2] The compound of [1], wherein Z is a group of the formula:

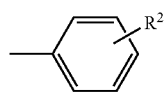

wherein R² is a group of the formula:

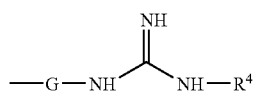

(wherein G is a bond, —NHCOCH₂— or lower alkylene and R⁴ is hydrogen, —NH₂ or lower alkyl); —NH₂; —CH₂NH₂; —CH₂ONH₂; —CH₂ON=CH₂;

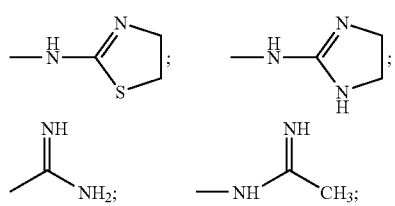

or a pharmaceutically acceptable salt thereof.

[3] The compound of [2], wherein R² is a group of the formula:

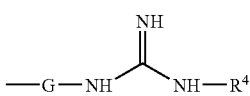

(wherein G is a bond, —NHCOCH₂— or lower alkylene and R⁴ is hydrogen or lower alkyl); —CH₂NH₂; —CH₂ONH₂; —CH₂ON=CH₂;

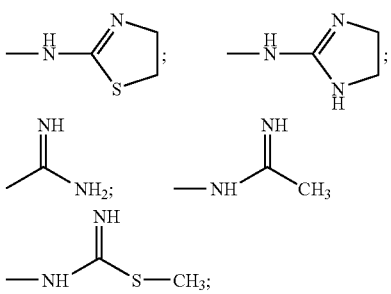

or a pharmaceutically acceptable salt thereof.

[4] The compound of any of [1] to [3], wherein R¹ is alkylcarbonyl and X is a bivalent residue derived from thiazole optionally substituted by methylsulfonylbenzyl, or a pharmaceutically acceptable salt thereof.

[5] The compound of [1], wherein the compound is
N-{4-[2-(4-{[amino(imino)methyl]amino}phenyl)ethyl]-1,3-thiazol-2-yl}acetamide,
N-{4-[2-(4-{[amino(imino)methyl]amino}phenyl)ethyl]-5-[4-(methylsulfonyl)benzyl]-1,3-thiazol-2-yl}acetamide,
N-{4-[2-(4-{[hydrazino(imino)methyl]amino}phenyl)ethyl]-5-[4-(methylsulfonyl)benzyl]-1,3-thiazol-2-yl}acetamide,
N-{4-[2-(4-{[hydrazino(imino)methyl]amino}phenyl)ethyl]-1,3-thiazol-2-yl}acetamide, or
N-(4-{2-[4-(2-{[amino(imino)methyl]amino}ethyl)phenyl]ethyl}-1,3-thiazol-2-yl)acetamide, or a pharmaceutically acceptable salt thereof.

[6] The compound of [1] or a pharmaceutically acceptable salt thereof for use as a medicament.

[7] A pharmaceutical composition, which comprises, as an active ingredient, the compound of [1] or a pharmaceutically acceptable salt thereof.

[8] A method for producing a compound of the formula (I):

R¹—NH—X—Y-Z (I)

wherein
R¹ is acyl;
X is a bivalent residue derived from optionally substituted thiazole;

Y is a bond, lower alkylene, lower alkenylene or —CONH—; and
Z is a group of the formula:

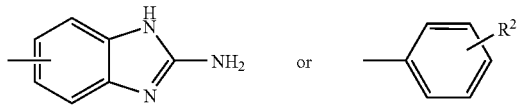

wherein R² is a group of the formula: -A-B-D-E
wherein A is a bond, lower alkylene, —NH— or —SO₂—;
B is a bond, lower alkylene, —CO— or —O—;
D is a bond, lower alkylene, —NH— or —CH₂NH—; and
E is optionally protected amino, —N=CH₂,

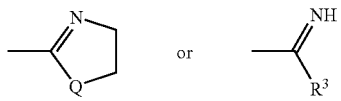

wherein
Q is —S— or —NH—; and
R³ is hydrogen, lower alkyl, lower alkylthio or —NH—R⁴ wherein R⁴ is hydrogen, —NH₂ or lower alkyl;
or a pharmaceutically acceptable salt thereof, which method comprises at least one step selected from the group consisting of (i) to (v):
(i) reacting Compound (1):

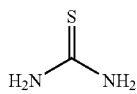

with Compound (2):

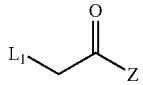

wherein L₁ is a leaving group and Z is as defined above, or a salt thereof;
(ii) reacting Compound (3): H₂N—X-Z
wherein X and Z are as defined above, or a salt thereof with Compound (4): R¹-L₂
wherein R¹ is as defined above and L₂ is a leaving group;
(iii) reacting Compound (6): R¹—NH—X—CHO
wherein R¹ and X are as defined above, or a salt thereof with Compound (7): L₃-CH₂-Z
wherein L₃ is a leaving group and Z is as defined above, or a salt thereof;
(iv) reduction of Compound (10): R¹—NH—X— (lower alkenylene)-Z
wherein R¹, X and Z are as defined above, or a salt thereof to Compound (11): R¹—NH—X-(lower alkylene)-Z
wherein R¹, X and Z are as defined above, or a salt thereof; and
(v) reacting Compound (12): R¹—NH—X—COOH or a reactive derivative thereof, wherein R¹ and X are as defined above, or a salt thereof with Compound (13): L₄-NH-Z wherein L⁴ is a hydrogen atom or a protecting group and Z is as defined above, or a salt thereof.
[9] A use of the compound of [1] or a pharmaceutically acceptable salt thereof for preparing a medicament as a VAP-1 inhibitor.
[10] The use of [9], wherein the compound is
N-{4-[2-(4-{[amino(imino)methyl]amino}phenyl)ethyl]-1,3-thiazol-2-yl}acetamide,
N-{4-[2-(4-{[amino(imino)methyl]amino}phenyl)ethyl]-5-[4-(methylsulfonyl)benzyl]-1,3-thiazol-2-yl}acetamide,
N-{4-[2-(4-{[hydrazino(imino)methyl]amino}phenyl)ethyl]-5-[4-(methylsulfonyl)benzyl]-1,3-thiazol-2-yl}acetamide,
N-{4-[2-(4-{[hydrazino(imino)methyl]amino}phenyl)ethyl]-1,3-thiazol-2-yl}acetamide, or
N-(4-{2-[4-(2-{[amino(imino)methyl]amino}ethyl)phenyl]ethyl}-1,3-thiazol-2-yl)acetamide.
[11] A use of the compound of [1] or a pharmaceutically acceptable salt thereof for preparing a medicament for the prophylaxis or treatment of a VAP-1 associated disease.
[12] The use of [11], wherein said VAP-1 associated disease is selected from the group consisting of cirrhosis, essential stabilized hypertension, diabetes, arthrosis, endothelium damage (in diabetes, atherosclerosis and hypertension), a cardiovascular disorder associated with diabetes and uraemia, pain associated with gout and arthritis, retinopathy (in diabetes patients), an (connective tissue) inflammatory disease or condition (rheumatoid arthritis, ankylosing spondylitis, psoriatic arthritis and osteoarthritis or degenerative joint disease, Reiter's syndrome, Sjögren's syndrome, Behçet's syndrome, relapsing polychondritis, systemic lupus erythematosus, discoid lupus erythematosus, systemic sclerosis, eosinophilic fasciitis, polymyositis, dermatomyositis, polymyalgia rheumatica, vasculitis, temporal arteritis, polyarteritis nodosa, Wegener's granulomatosis, mixed connective tissue disease, and juvenile rheumatoid arthritis), a gastrointestinal inflammatory disease or condition [Crohn's disease, ulcerative colitis, irritable bowel syndrome (spastic colon), fibrotic conditions of the liver, inflammation of the oral mucosa (stomatitis), and recurrent aphtous stomatitis], a central nervous system inflammatory disease or condition (multiple sclerosis, Alzheimer's disease, and ischaemia-reperfusion injury associated with ischemic stroke), a pulmonary inflammatory disease or condition (asthma, adult respiratory distress syndrome, chronic obstructive pulmonary disease), a (chronic) skin inflammatory disease or condition (psoriasis, allegic lesions, lichen planus, pityriasis rosea, contact dermatitis, atopic dermatitis, pityriasis rubra pilaris), a disease related to carbohydrate metabolism (diabetes and complications from diabetes) including microvascular and macrovascular disease (atherosclerosis, vascular retinopathies, retinopathy, nephropathy, nephrotic syndrome and neuropathy (polyneuropathy, mononeuropathies and autonomic neuropathy), foot ulcers, joint problems, and increased risk of infection), a disease related to aberrations in adipocyte differentiation or function or smooth muscle cell function (atherosclerosis and obesity), a vascular disease [atheromatous ateriosclerosis, nonatheromatous ateriosclerosis, ischemic heart disease including myocardial infarction and peripheral arterial occlusion, Raynaud's disease and phenomenon, thromboangiitis obliterans (Buerger's disease)], chronic arthritis, inflammatory bowel diseases, skin dermatoses, diabetes mellitus, SSAO-mediated complication [diabetes (insulin dependent diabetes mellitus (IDDM) and non-insulin dependent diabetes mellitus (NIDDM)) and vascular complication (heart attack, angina, strokes, amputations, blindness and renal failure)] and macular edema (diabetic and non-diabetic macular edema).

[13] The use of [12], wherein said VAP-1 associated disease is macular edema.

[14] The use of [13], wherein said macular edema is diabetic macular edema.

[15] The use of [13], wherein said macular edema is non-diabetic macular edema.

[16] A VAP-1 inhibitor, which comprises the compound of [1] or a pharmaceutically acceptable salt thereof.

[17] A method for preventing or treating macular edema, which method comprises administering to a subject in need thereof a VAP-1 inhibitor in an amount sufficient to treat said subject for macular edema.

[18] The method of [17], wherein the VAP-1 inhibitor is
N-{4-[2-(4-{[amino(imino)methyl]amino}phenyl)ethyl]-1,3-thiazol-2-yl}acetamide,
N-{4-[2-(4-{[amino(imino)methyl]amino}phenyl)ethyl]-5-[4-(methylsulfonyl)benzyl]-1,3-thiazol-2-yl}acetamide,
N-{4-[2-(4-{[hydrazino(imino)methyl]amino}phenyl)ethyl]-5-[4-(methylsulfonyl)benzyl]-1,3-thiazol-2-yl}acetamide,
N-{4-[2-(4-{[hydrazino(imino)methyl]amino}phenyl)ethyl]-1,3-thiazol-2-yl}acetamide, or
N-(4-{2-[4-(2-{[amino(imino)methyl]amino}ethyl)phenyl]ethyl}-1,3-thiazol-2-yl)acetamide,
or a pharmaceutically acceptable salt thereof.

[19] A method for preventing or treating a VAP-1 associated disease, which method comprises administering an effective amount of the compound of [1] or a pharmaceutically acceptable salt thereof to a mammal.

[20] The method of [19], wherein said VAP-1 associated disease is selected from the group consisting of cirrhosis, essential stabilized hypertension, diabetes, arthrosis, endothelium damage (in diabetes, atherosclerosis and hypertension), a cardiovascular disorder associated with diabetes and uraemia, pain associated with gout and arthritis, retinopathy (in diabetes patients), an (connective tissue) inflammatory disease or condition (rheumatoid arthritis, ankylosing spondylitis, psoriatic arthritis and osteoarthritis or degenerative joint disease, Reiter's syndrome, Sjögren's syndrome, Behçet's syndrome, relapsing polychondritis, systemic lupus erythematosus, discoid lupus erythematosus, systemic sclerosis, eosinophilic fasciitis, polymyositis, dermatomyositis, polymyalgia rheumatica, vasculitis, temporal arteritis, polyarteritis nodosa, Wegener's granulomatosis, mixed connective tissue disease, and juvenile rheumatoid arthritis), a gastrointestinal inflammatory disease or condition [Crohn's disease, ulcerative colitis, irritable bowel syndrome (spastic colon), fibrotic conditions of the liver, inflammation of the oral mucosa (stomatitis), and recurrent aphtous stomatitis], a central nervous system inflammatory disease or condition (multiple sclerosis, Alzheimer's disease, and ischaemia-reperfusion injury associated with ischemic stroke), a pulmonary inflammatory disease or condition (asthma, adult respiratory distress syndrome, chronic obstructive pulmonary disease), a (chronic) skin inflammatory disease or condition (psoriasis, allegic lesions, lichen planus, pityriasis rosea, contact dermatitis, atopic dermatitis, pityriasis rubra pilaris), a disease related to carbohydrate metabolism (diabetes and complications from diabetes) including microvascular and macrovascular disease (atherosclerosis, vascular retinopathies, retinopathy, nephropathy, nephrotic syndrome and neuropathy (polyneuropathy, mononeuropathies and autonomic neuropathy), foot ulcers, joint problems, and increased risk of infection), a disease related to aberrations in adipocyte differentiation or function or smooth muscle cell function (atherosclerosis and obesity), a vascular disease [atheromatous ateriosclerosis, nonatheromatous ateriosclerosis, ischemic heart disease including myocardial infarction and peripheral arterial occlusion, Raynaud's disease and phenomenon, thromboangiitis obliterans (Buerger's disease)], chronic arthritis, inflammatory bowel diseases, skin dermatoses, diabetes mellitus, SSAO-mediated complication [diabetes (insulin dependent diabetes mellitus (IDDM) and non-insulin dependent diabetes mellitus (NIDDM)) and vascular complication (heart attack, angina, strokes, amputations, blindness and renal failure)] and macular edema (diabetic and non-diabetic macular edema).

[21] The method of [20], wherein said VAP-1 associated disease is macular edema.

[22] The method of [21], wherein said macular edema is diabetic macular edema.

[23] The method of [21], wherein said macular edema is non-diabetic macular edema.

DETAILED DESCRIPTION OF THE INVENTION

The present invention is predicated on the discovery that an inhibitor of vascular adhesion protein-1 (VAP-1; also referred to as semicarbazide sensitive amine oxidase (SSAO) or copper-containing amine oxidase) is effective in treating or ameliorating a VAP-1 associated disease, especially macular edema, and the like. Accordingly, the present invention provides Compound (I) or a pharmaceutically acceptable salt thereof useful as a VAP-1 inhibitor, a pharmaceutical composition, a method for preventing or treating a VAP-1 associated disease, and the like.

In the above and subsequent descriptions of the present specification, suitable examples and illustration of the various definitions to be included within the scope of the invention are explained in detail as follows.

Suitable "halogen" includes fluorine, chlorine, bromine and iodine.

The term "lower" is used to intend a group having 1 to 6, preferably 1 to 4, carbon atom(s), unless otherwise provided.

Suitable "lower alkyl" includes straight or branched alkyl having 1 to 6 carbon atom(s), such as methyl, ethyl, propyl, isopropyl, butyl, isobutyl, sec-butyl, tert-butyl, pentyl, tert-pentyl and hexyl, in which more preferred one is $C_1$–$C_4$ alkyl.

Suitable "lower alkylthio" includes lower alkylthio containing the above lower alkyl, such as methylthio, ethylthio, propylthio, isopropylthio, butylthio, isobutylthio, sec-butylthio, tert-butylthio, pentylthio, tert-pentylthio and hexylthio.

Suitable "lower alkylene" includes straight or branched alkylene having 1 to 6 carbon atom(s), such as methylene, ethylene, trimethylene, tetramethylene, propylene, ethylidene and propylidene, in which more preferred one is $C_1$–$C_4$ alkylene.

Suitable "lower alkenylene" includes straight or branched alkenylene having 2 to 6 carbon atom(s), such as —CH=CH—, —CH$_2$—CH=CH—, —CH$_2$—CH=CH—CH$_2$—, —CH$_2$—CH$_2$—CH=CH—, —CH=CH—CH=CH—, —CH=CH—CH$_2$—CH$_2$—CH$_2$—, —CH=CH—CH=CH—CH₂—CH₂— and —CH=CH—CH=CH—CH=CH—, in which more preferred one is $C_2$–$C_4$ alkenylene.

The above lower alkenylene may be in E or Z form, respectively. Thus, those skilled in the art will recognize that the lower alkenylene includes all E, Z-structures when it has 2 or more double bonds.

Suitable "aryl" includes $C_6$–$C_{10}$ aryl such as phenyl and naphthyl, in which more preferred one is phenyl. The "aryl" may be substituted by 1 to 3 substituent(s) and the substitution sites are not particularly limited.

Suitable "aralkyl" includes aralkyl wherein the aryl moiety has 6 to 10 carbon atoms [i.e. the aryl moiety is $C_6$–$C_{10}$ aryl of the above "aryl"] and the alkyl moiety has 1 to 6 carbon atom(s) [i.e. the alkyl moiety is $C_1$–$C_6$ alkyl of the above "lower alkyl"], such as benzyl, phenethyl, 1-naphthylmethyl, 2-naphthylmethyl, 3-phenylpropyl, 4-phenylbutyl and 5-phenylpentyl.

The "optionally protected amino" means that an amino group may be protected with a suitable protecting group according to a method known per se, such as the methods described in Protective Groups in Organic Synthesis, published by John Wiley and Sons (1980), and the like. The suitable "protecting group" includes tert-butoxycarbonyl (i.e., Boc), an acyl group as mentioned below, substituted or unsubstituted aryl(lower)alkylidene [e.g., benzylidene, hydroxybenzylidene, etc.], aryl(lower)alkyl such as mono-, di- or triphenyl-(lower)alkyl [e.g., benzyl, phenethyl, benzhydryl, trityl, etc.] and the like.

Suitable "optionally protected amino" includes amino and tert-butoxycarbonylamino (i.e. —NHBoc).

Suitable "heterocycle" includes "aromatic heterocycle" and "non-aromatic heterocycle".

Suitable "aromatic heterocycle" includes 5 to 10-membered aromatic heterocycle containing 1 to 3 heteroatom(s) selected from nitrogen, oxygen and sulfur atoms besides carbon atom(s), and includes, for example, thiophene, furan, pyrrole, imidazole, pyrazole, thiazole, isothiazole, oxazole, isoxazole, pyridine, pyridazine, pyrimidine, pyrazine and the like.

Suitable "non-aromatic heterocycle" includes 5 to 10-membered non-aromatic heterocycle containing 1 to 3 heteroatom(s) selected from nitrogen, oxygen and sulfur atoms besides carbon atom(s), and includes, for example, pyrrolidine, imidazoline, pyrazolidine, pyrazoline, piperidine, piperazine, morpholine, thiomorpholine, dioxolan, oxazolidine, thiazolidine, triazolidine and the like.

Suitable "acyl" includes acyl having 1 to 20 carbon atom(s), such as formyl, alkylcarbonyl, arylcarbonyl, alkoxycarbonyl and aralkyloxycarbonyl.

Suitable "alkylcarbonyl" includes alkylcarbonyl wherein the alkyl moiety has 1 to 6 carbon atom(s) [i.e. the alkyl moiety is $C_1$–$C_6$ alkyl of the above "lower alkyl"], such as acetyl, propionyl, butyryl, isobutyryl, valeryl, isovaleryl, pivaloyl, hexanoyl and heptanoyl, in which more preferred one is $C_1$–$C_4$ alkyl-carbonyl.

Suitable "arylcarbonyl" includes arylcarbonyl wherein the aryl moiety has 6 to 10 carbon atom(s) [i.e. the aryl moiety is $C_6$–$C_{10}$ aryl of the above "aryl"], such as benzoyl and naphthoyl.

Suitable "alkoxycarbonyl" includes alkoxycarbonyl wherein the alkoxy moiety has 1 to 6 carbon atom(s), such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, tert-pentyloxycarbonyl and hexyloxycarbonyl, in which more preferred one is alkoxycarbonyl wherein the alkoxy moiety has 1 to 4 carbon atom(s).

Suitable "aralkyloxycarbonyl" includes aralkyloxycarbonyl wherein the aryl moiety has 6 to 10 carbon atom(s) [i.e. the aryl moiety is $C_6$–$C_{10}$ aryl of the above "aryl"] and the alkyl moiety has 1 to 6 carbon atom(s) [i.e. the alkyl moiety is $C_1$–$C_6$ alkyl of the above "lower alkyl"], such as benzyloxycarbonyl, phenethyloxycarbonyl, 1-naphthylmethyloxycarbonyl, 2-naphthylmethyloxycarbonyl, 3-phenylpropyloxycarbonyl, 4-phenylbutyloxycarbonyl and 5-phenylpentyloxycarbonyl.

Suitable "bivalent residue derived from thiazole" of the "bivalent residue derived from optionally substituted thiazole" includes

The "thiazole" may have 1 to 3 substituent(s) and the substitution sites are not particularly limited.

Suitable "substituent" of the above "optionally substituted thiazole" includes, for example, (1) halogen which is as defined above;

(2) alkoxycarbonyl which is as defined above, such as ethoxycarbonyl;

(3) optionally substituted aryl, which aryl is as defined above and the substitution sites are not particularly limited, such as phenyl and 4-(methylsulfonyl)phenyl;

(4) a group of the formula: —CONR$^a$R$^b$ wherein R$^a$ is hydrogen, lower alkyl, aryl or aralkyl and R$^b$ is hydrogen, lower alkyl, aryl or aralkyl, wherein the lower alkyl, aryl and aralkyl are as defined above, such as N-methylaminocarbonyl, N-phenylaminocarbonyl, N,N-dimethylaminocarbonyl and N-benzylaminocarbonyl;

(5) a group of the formula: —CONH—(CH$_2$)$_k$-aryl wherein k is an integer of 0 to 6; the aryl is as defined above, which may have 1 to 5 substituent(s) selected from the group consisting of —NO$_2$, —SO$_2$-(lower alkyl) wherein the lower alkyl is as defined above, —CF$_3$ and —O-aryl wherein the aryl is as defined above, and the substitution sites are not particularly limited;

(6) a group of the formula: —CONH—(CH$_2$)$_m$-heterocycle wherein m is an integer of 0 to 6; the heterocycle is as defined above, such as pyridine;

(7) a group of the formula: —CO-heterocycle wherein the heterocycle is as defined above, such as pyrrolidine, piperidine, piperazine, thiomorpholine, which may have 1 to 5 substituent(s) selected from the group consisting of —CO-(lower alkyl) wherein the lower alkyl is as defined above, —CO—O-(lower alkyl) wherein the lower alkyl is as defined above, —SO$_2$-(lower alkyl) wherein the lower alkyl is as defined above, oxo (i.e. =O) and a group of the formula: —CONR$^c$R$^d$ wherein R$^c$ is hydrogen, lower alkyl, aryl or aralkyl and R$^d$ is hydrogen, lower alkyl, aryl or aralkyl wherein the lower alkyl, aryl and aralkyl are as defined above, and the substitution sites are not particularly limited;

(8) a group of the formula: —(CH$_2$)$_n$-aryl wherein n is an integer of 1 to 6; the aryl is as defined above, which may have 1 to 5 substituent(s) selected from the group consisting of —S-(lower alkyl) wherein the lower alkyl is as defined above, —SO₂-(lower alkyl) wherein the lower alkyl is as defined above, —CO₂-(lower alkyl) wherein the lower alkyl is as defined above, —NHCO—O-(lower alkyl) wherein the lower alkyl is as defined above and a group of the formula: —CONR$^e$R$^f$ wherein R$^e$ is hydrogen, lower alkyl, aryl or aralkyl and R$^f$ is hydrogen, lower alkyl, aryl or aralkyl wherein the lower alkyl, aryl and aralkyl are as defined above, and the substitution sites are not particularly limited;

(9) a group of the formula: —(CH₂)$_o$-heterocycle wherein o is an integer of 0 to 6; the heterocycle is as defined above, such as pyrrolidine, piperidine, piperazine, morpholine, thiomorpholine, which may have 1 to 5 substituent(s) selected from the group consisting of oxo (i.e. =O); —CO-(lower alkyl) wherein the lower alkyl is as defined above; —CO—O-(lower alkyl) wherein the lower alkyl is as defined above; —SO₂-(lower alkyl) wherein the lower alkyl is as defined above; —CO-(heterocycle) wherein the heterocycle is as defined above such as pyrrolidine, piperazine and morpholine, which may have 1 to 5 substituent(s) selected from the group consisting of lower alkyl and halogen, wherein the lower alkyl and halogen are as defined above, and the substitution sites are not particularly limited; and a group of the formula: —CONR$^g$R$^h$ wherein R$^g$ is hydrogen, lower alkyl, aryl or aralkyl and R$^h$ is hydrogen, lower alkyl, aryl or aralkyl wherein the lower alkyl, aryl and aralkyl are as defined above, and the substitution sites are not particularly limited;

(10) a group of the formula: —(CH₂)$_p$—NR$^i$R$^j$ wherein p is an integer of 0 to 6; R$^i$ is hydrogen, acyl, lower alkyl, aryl or aralkyl and R$^j$ is hydrogen, acyl, lower alkyl, aryl or aralkyl wherein the acyl, lower alkyl, aryl and aralkyl are as-defined above, and the lower alkyl may have 1 to 5 substituent(s) selected from the group consisting of a group of the formula: —CONR$^k$R$^l$ wherein R$^k$ is hydrogen, lower alkyl, aryl or aralkyl and R$^l$ is hydrogen, lower alkyl, aryl or aralkyl wherein the lower alkyl, aryl and aralkyl are as defined above, and the substitution sites are not particularly limited;

(11) a group of the formula: —CON(H or lower alkyl)-(CHR$^m$)$_q$-T wherein q is an integer of 0 to 6; the lower alkyl is as defined above; R$^m$ is hydrogen, aralkyl which is as defined above, or alkyl which is as defined above, which may be substituted by 1 to 3 substituent(s) selected from the group consisting of —OH and —CONH₂ and the substitution sites are not particularly limited; and T is hydrogen; a group of the formula: —CONR″R° wherein R″ is hydrogen, lower alkyl, aryl or aralkyl and R° is hydrogen, lower alkyl, aryl or aralkyl wherein the lower alkyl, aryl and aralkyl are as defined above; —NH—CO—R$^p$ wherein R$^p$ is lower alkyl which is as defined above or aralkyl which is as defined above; —NH—SO₂-(lower alkyl) wherein the lower alkyl is as defined above; —SO₂-(lower alkyl) wherein the lower alkyl is as defined above; -heterocycle wherein the heterocycle is as defined above, such as pyridine, pyrrolidine and morpholine, which may have 1 to 3 substituent(s) such as oxo (i.e. =O), and the substitution sites are not particularly limited; or —CO-(heterocycle) wherein the heterocycle is as defined above, such as piperidine and morpholine; and

(12) a group of the formula: —(CH₂)$_r$—CO—NR$^t$R$^u$ wherein r is an integer of 1 to 6; R$^t$ is hydrogen, lower alkyl, aryl or aralkyl and R$^u$ is hydrogen, lower alkyl, aryl or aralkyl wherein the lower alkyl, aryl and aralkyl are as defined above.

The substitution site on the aryl or heterocycle is any suitable position thereof, but not particularly limited.

Preferable "substituent" of the above "optionally substituted thiazole" is methylsulfonylbenzyl.

The substitution sites of R² on the phenyl in Compound (I) is not particularly limited.

When Z is a group of the formula:

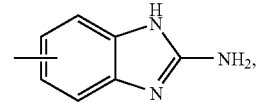

the substitution sites on the group are not particularly limited.

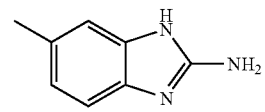

is particularly preferable.

Any nitrogen atom in the amino (i.e. —NH₂), imino (i.e. =NH or —NH—) or the like contained in Compound (I) may be protected according to the methods, which are known to those skilled in the art, such as the methods described in Protective Groups in Organic Synthesis, published by John Wiley and Sons (1980), and the like.

When Compound (I) has an asymmetric carbon atom in the structure, those skilled in the art will recognize that Compound (I) includes all stereoisomers.

The "vascular adhesion protein-1 (VAP-1) associated disease" comprise a disease selected from the group consisting of cirrhosis, essential stabilized hypertension, diabetes, arthrosis; endothelium damage (in diabetes, atherosclerosis and hypertension), a cardiovascular disorder associated with diabetes and uraemia, pain associated with gout and arthritis, retinopathy (in diabetes patients); an (connective tissue) inflammatory disease or condition (rheumatoid arthritis, ankylosing spondylitis, psoriatic arthritis and osteoarthritis or degenerative joint disease, Reiter's syndrome, Sjögren's syndrome, Behçet's syndrome, relapsing polychondritis, systemic lupus erythematosus, discoid lupus erythematosus, systemic sclerosis, eosinophilic fasciitis, polymyositis, dermatomyositis, polymyalgia rheumatica, vasculitis, temporal arteritis, polyarteritis nodosa, Wegener's granulomatosis, mixed connective tissue disease, and juvenile rheumatoid arthritis); a gastrointestinal inflammatory disease or condition [Crohn's disease, ulcerative colitis, irritable bowel syndrome (spastic colon), fibrotic conditions of the liver, inflammation of the oral mucosa (stomatitis), and recurrent aphtous stomatitis]; a central nervous system inflammatory disease or condition (multiple sclerosis, Alzheimer's disease, and ischaemia-reperfusion injury associated with ischemic stroke); a pulmonary inflammatory disease or condition (asthma, adult respiratory distress syndrome, chronic obstructive pulmonary disease); a (chronic) skin inflammatory disease or condition (psoriasis, allegic lesions, lichen planus, pityriasis rosea, contact dermatitis, atopic dermatitis, pityriasis rubra pilaris); a disease related to carbohydrate metabolism (diabetes and complications from diabetes) including microvascular and macrovascular disease (atherosclerosis, vascular retinopathies, retinopathy, nephropathy, nephrotic syndrome and neuropathy (polyneuropathy, mononeuropathies and autonomic neuropathy), foot ulcers, joint problems, and increased risk of infection); a disease related to aberrations in adipocyte differentiation or function or smooth muscle cell function (atherosclerosis and obesity); a vascular disease [atheromatous ateriosclerosis, nonatheromatous ateriosclerosis, ischemic heart disease including myocardial infarction and peripheral arterial occlusion, Raynaud's disease and phenomenon, thromboangiitis obliterans (Buerger's disease)]; chronic arthritis; inflammatory bowel diseases; skin dermatoses; diabetes mellitus; SSAO-mediated complication [diabetes (insulin dependent diabetes-mellitus (IDDM) and non-insulin dependent diabetes mellitus (NIDDM)) and vascular complication (heart attack, angina, strokes, amputations, blindness and renal failure)]; macular edema (e.g., diabetic and non-diabetic macular edema), and the like.

The "preventing or treating a vascular adhesion protein-1 (VAP-1) associated disease" and "prophylaxis or treatment of a vascular adhesion protein-1 (VAP-1) associated disease", particularly "preventing or treating macular edema" and "prophylaxis or treatment of macular edema" are intended to include administration of a compound having VAP-1 inhibitory activity (i.e. VAP-1 inhibitor) to a subject for therapeutic purposes, which may include prophylaxis, amelioration, prevention and cure of the above described VAP-1 associated disease, particularly macular edema. As used herein, by the "subject" is meant a target of the administration of VAP-1 inhibitor in the present invention, which is specifically various animals such as mammal, e.g., human, mouse, rat, swine, dog, cat, horse, bovine and the like, especially human.

The method comprises administration of VAP-1 inhibitor in an amount sufficient to treat the VAP-1 associated disease, especially macular edema. Any VAP-1 inhibitor can be used in the method of the present invention as long as it is safe and efficacious. Herein, "VAP-1 inhibitor" will be used to refer to such compounds, which include Compound (I), and is intended to encompass all compounds that inhibit enzyme activity of VAP-1 at any and all points in the action mechanism thereof.

For example, the compounds of the present invention and derivatives thereof, or compounds reported to have inhibited VAP-1 enzyme (SSAO) may include fluoroallylamine derivatives, semicarbazide derivatives, hydrazide derivatives, hydrazino derivatives, 1,3,4-oxadiazine derivatives, 2,6-diethoxybenzylamine, 2,6-di(n-propoxy)benzylamine, 2,6-diisopropoxybenzylamine, 2,6-di(n-butoxy)benzylamine, 2,6-bis(methoxymethoxy)benzylamine, 2,6-bis(methoxymethyl)benzylamine, 2,6-diethylbenzylamine, 2,6-di-n-propylbenzylamine, 2,6-bis(2-hydroxyethoxy)benzylamine, and the like.

The above compounds can be exemplified as follows.
1) fluoroallylamine derivatives, semicarbazide derivatives and hydrazide derivatives described in WO 93/23023,
2) hydrazino derivatives described in WO 02/02090,
3) 1,3,4-oxadiazine derivatives described in WO 02/02541,
4) 4-alkyl-5-alkoxycarbonyl-4,5,6,7-tetrahydroimidazo[4,5-c]pyridine derivatives described in WO 02/38153,
5) 2,6-diethoxybenzylamine, 2,6-di(n-propoxy)benzylamine, 2,6-diisopropoxybenzylamine, 2,6-di(n-butoxy)benzylamine, 2,6-bis(methoxymethoxy)benzylamine, 2,6-bis(methoxymethyl)benzylamine, 2,6-diethylbenzylamine, 2,6-di-n-propylbenzylamine and 2,6-bis(2-hydroxyethoxy)benzylamine described in U.S. Pat. No. 4,888,283.

The compounds exemplified in the present invention as a VAP-1 inhibitor and in WO 93/23023 as an SSAO inhibitor, such as those described in Lyles et al. (Biochem. Pharmacol. 36:2847, 1987) and in U.S. Pat. No. 4,650,907, U.S. Pat. No. 4,916,151, U.S. Pat. No. 4,943,593, U.S. Pat. No. 4,965,288, U.S. Pat. No. 5,021,456, U.S. Pat. No. 5,059,714, U.S. Pat. No. 4,699,928, European patent application 295604, European patent application 224924 and European patent application 168013, are also encompassed in the VAP-1 inhibitor.

Of the above-mentioned compounds, preferred are Compound (I), more preferably,

N-{4-[2-(4-{[amino(imino)methyl]amino}phenyl)ethyl]-1,3-thiazol-2-yl}acetamide (hereinafter Compound A; see Production Example 1), N-{4-[2-(4-{[amino(imino)methyl]amino}phenyl)ethyl]-5-[4-(methylsulfonyl)benzyl]-1,3-thiazol-2-yl}acetamide (see Production Example 48), N-{4-[2-(4-{[hydrazino(imino)methyl]amino}phenyl)ethyl]-5-[4-(methylsulfonyl)benzyl]-1,3-thiazol-2-yl}acetamide (see Production Example 50), N-{4-[2-(4-{[hydrazino(imino)methyl]amino}phenyl)ethyl]-1,3-thiazol-2-yl}acetamide (see Production Example 58), and N-(4-{2-[4-(2-{[amino(imino)methyl]amino}ethyl)phenyl]ethyl}-1,3-thiazol-2-yl)acetamide (see Production Example 110), particularly N-{4-[2-(4-{[amino(imino)methyl]amino}phenyl)ethyl]-1,3-thiazol-2-yl}acetamide and derivatives thereof.

The term "derivative" is intended to include all compounds derived from the original compound.

In the present invention, the VAP-1 inhibitor can be administered as a prodrug to a subject. The term "prodrug" is intended to include all compounds that convert to the VAP-1 inhibitor in the body of administration subject. The prodrug can be any pharmaceutically acceptable prodrug of VAP-1 inhibitor. Moreover, the VAP-1 inhibitor can be administered to an administration subject as a pharmaceutically acceptable salt.

The pharmaceutically acceptable salt of VAP-1 inhibitor of the present invention is nontoxic and a pharmaceutically acceptable conventional salt, which is exemplified by salts with inorganic or organic base such as alkali metal salt (e.g., sodium salt, potassium salt and the like), alkaline earth metal salt (e.g., calcium salt, magnesium salt and the like), ammonium salt, and amine salt (e.g., triethylamine salt, N-benzyl-N-methylamine salt and the like).

The VAP-1 inhibitor can be also formulated as a pharmaceutically acceptable acid addition salt. Examples of the pharmaceutically acceptable acid addition salts for use in the pharmaceutical composition include those derived from mineral acids, such as hydrochloric, hydrobromic, hydriodic, phosphoric, metaphosphoric, nitric and sulfuric acids, and organic acids, such as tartaric, acetic, citric, malic, lactic, fumaric, benzoic, glycolic, gluconic, succinic and arylsulfonic acids, for example, p-toluenesulfonic acid.

As a pharmaceutically acceptable salt of VAP-1 inhibitor represented by the formula (I), a pharmaceutically acceptable acid addition salt such as (mono-, di- or tri-) hydrochloride and hydriodide, particuraly hydrochloride, is preferable.

The above-mentioned VAP-1 inhibitor may be commercially available or can be produced based on a known reference.

Also, Compound (I), particularly Compound A: N-{4-[2-(4-{[amino(imino)methyl]amino}phenyl)ethyl]-1,3-thiazol-2-yl}acetamide, can be synthesized according to the Production Method given below.

Those compounds or derivatives thereof that are not commercially available can be prepared using organic synthetic methods known in the art.

The VAP-1 inhibitor or a pharmaceutically acceptable salt thereof can be administered in accordance with the present inventive method by any suitable route. Suitable routes of administration include systemic, such as orally or by injection, topical, periocular (e.g., subTenon's), subconjunctival, intraocular, subretinal, suprachoroidal and retrobulbar administrations. The manner in which the VAP-1 inhibitor is administered is dependent, in part, upon whether the treatment of a VAP-1 associated disease is prophylactic or therapeutic.

The VAP-1 inhibitor is preferably administered as soon as possible after it has been determined that a subject such as mammal, specifically a human, is at risk for a VAP-1 associated disease (prophylactic treatments) or has begun to develop a VAP-1 associated disease (therapeutic treatments). Treatment will depend, in part, upon the particular VAP-1 inhibitor to be used, the amount of the VAP-1 inhibitor to be administered, the route of administration, and the cause and extent, if any, of a VAP-1 associated disease realized.

One skilled in the art will appreciate that suitable methods of administering a VAP-1 inhibitor, which is useful in the present inventive method, are available. Although more than one route can be used to administer a particular VAP-1 inhibitor, a particular route can provide a more immediate and more effective reaction than another route. Accordingly, the described routes of administration are merely exemplary and are in no way limiting.

The dose of the VAP-1 inhibitor administered to the administration subject such as animal including human, particularly a human, in accordance with the present invention should be sufficient to effect the desired response in the subject over a reasonable time frame. One skilled in the art will recognize that dosage will depend upon a variety of factors, including the strength of the particular VAP-1 inhibitor to be employed, the age, species, conditions or disease states, and body weight of the subject, as well as the degree of a VAP-1 associated disease. The size of the dose also will be determined by the route, timing and frequency of administration as well as the existence, nature, and extent of any adverse side effects that might accompany the administration of a particular VAP-1 inhibitor and the desired physiological effect. It will be appreciated by one of ordinary skill in the art that various conditions or disease states may require prolonged treatment involving multiple administrations.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached.

Generally, the VAP-1 inhibitor can be administered in the dose of from about 1 µg/kg/day to about 300 mg/kg/day, preferably from about 0.1 mg/kg/day to about 10 mg/kg/day, which is given in a single dose or 2 to 4 doses a day or in a sustained manner.

Pharmaceutical compositions for use in the present inventive method preferably comprise a "pharmaceutically acceptable carrier" and an amount of a VAP-1 inhibitor sufficient to treat a VAP-1 associated disease, especially macular edema, prophylactically or therapeutically as an active ingredient. The carrier can be any of those conventionally used and is limited only by chemico-physical considerations, such as solubility and lack of reactivity with the compound, and by the route of administration.

The VAP-1 inhibitor can be administered in various manners to achieve the desired VAP-1 inhibitory effect. The VAP-1 inhibitors can be administered alone or in combination with pharmaceutically acceptable carriers or diluents, the properties and nature of which are determined by the solubility and chemical properties of the inhibitor selected, the chosen administration route, and standard pharmaceutical practice. The VAP-1 inhibitor may be administered orally in solid dosage forms, e.g., capsules, tablets, powders, or in liquid forms, e.g., solutions or suspensions. The inhibitor may also be injected parenterally in the form of sterile solutions or suspensions. Solid oral forms may contain conventional excipients, for instance, lactose, sucrose, magnesium stearate, resins, and like materials. Liquid oral forms may contain various flavoring, coloring, preserving, stabilizing, solubilizing, or suspending agents. Parenteral preparations are sterile aqueous or non-aqueous solutions or suspensions which may contain certain various preserving, stabilizing, buffering, solubilizing, or suspending agents. If desired, additives, such as saline or glucose, may be added to make the solutions isotonic.

The present inventive method also can involve the co-administration of other pharmaceutically active compounds. By "co-administration" is meant administration before, concurrently with, e.g., in combination with the VAP-1 inhibitor in the same formulation or in separate formulations, or after administration of a VAP-1 inhibitor as described above. For example, corticosteroids, prednisone, methylprednisolone, dexamethasone, or triamcinolone acetinide, or noncorticosteroid anti-inflammatory compounds, such as ibuprofen or flubiprofen, can be co-administered. Similarly, vitamins and minerals, e.g., zinc, anti-oxidants, e.g., carotenoids (such as a xanthophyll carotenoid like zeaxanthin or lutein), and micronutrients can be co-administered.

In addition, the VAP-1 inhibitor according to the present invention is useful for preparing a medicament such as a therapeutic or prophylactic agent for the VAP-1 associated diseases.

Production Method of Compound (I)

Compound (I) is prepared in accordance with, but is not limited to, the following procedures. Those skilled in the art will recognize that the procedures can be modified according to the conventional methods known per se.

Procedure A: Synthesis of Compound (I) wherein Y is a bond

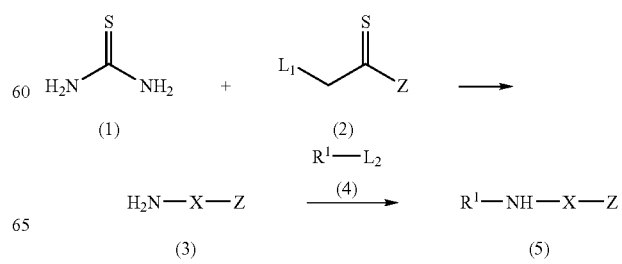

wherein
L₁ is a leaving group such as halogen (e.g., chlorine, bromine, iodine);
Z is as defined above;
X is as defined above, in this case,

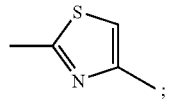

R¹ is acyl; and
L₂ is a leaving group such as —OH, halogen (e.g., chlorine, bromine, iodine), —O-acyl wherein the acyl is as defined above (e.g., —O-acetyl and the like).

Formation of Thiazole Moiety X

Compound (1) is reacted with Compound (2) or its salt to give Compound (3).

Suitable salt of Compound (2) may be the same as those exemplified for Compound (I).

Compounds (1) and (2) or its salt may be commercially available or can be prepared in accordance with the methods known per se (see Production Example 11).

The reaction is usually carried out in a conventional solvent such as ethanol, acetone, dichloromethane, acetic acid, and other organic solvent which does not adversely affect the reaction, or a mixture thereof.

The reaction temperature is not critical, and the reaction can be carried out under cooling to heating.

Compound (3) thus obtained can be isolated or purified by known separation or purification means, such as concentration, concentration in vacuo, solvent extraction, crystallization, recrystallization, phase transfer, chromatography and the like, and can be converted to a salt same as those exemplified for Compound (I).

Acylation

Compound (3) or its salt is reacted with Compound (4) to give Compound (5). Since R¹ is an acyl group, this reaction is an acylation.

The conventional acylation method may be employed in the present invention.

Compound (4) may be commercially available or can be prepared in accordance with the methods known per se.

The reaction is usually carried out in a conventional solvent such as dichloromethane, chloroform, methanol, and other organic solvent which does not adversely affect the reaction, or a mixture thereof.

The reaction is also preferably carried out in the presence of a conventional base such as 4-dimethylaminopyridine, pyridine etc. A liquid base can be also used as the solvent.

The reaction temperature is not critical, and the reaction can be carried out under cooling to heating.

Compound (5) thus obtained can be isolated or purified by known separation or purification means, such as concentration, concentration in vacuo, solvent extraction, crystallization, recrystallization, phase transfer, chromatography and the like, and can be converted to a salt same as those exemplified for Compound (I).

The acylation may be applied to Compound (1) in advance.

The nitrogen atom in Compound (1), (2), (3) or (5) may be protected or deprotected, as necessary, in accordance with methods known-per se such as the methods described in Protective Groups in Organic Synthesis, published by John Wiley and Sons (1980), and the like.

Procedure B: Synthesis of Compound (I) wherein Y is lower alkylene such as ethylene (i.e. —CH₂—CH₂—) or lower alkenylene such as vinylene (i.e. —CH═CH—), for example,

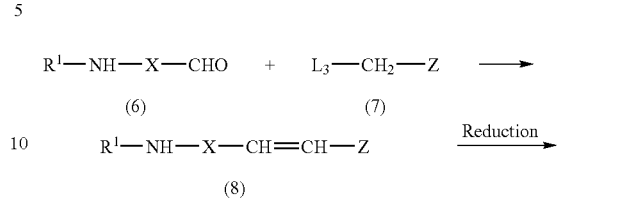

wherein
L₃ is a leaving group such as halogen (e.g., chlorine, bromine, iodine); and
R¹, X and Z are as defined above.

Formation of Olefin Compound

Compound (6) or its salt is reacted with Compound (7) or its salt to give an olefin compound (8).

Suitable salts of Compounds (6) and (7) may be the same as those exemplified for Compound (I).

Compounds (6) and (7) or salts thereof may be commercially available or can be prepared in accordance with the methods known per se (see Production Example 1 and 3).

The reaction is usually carried out in a conventional solvent such as N,N-dimethylformamide, dimethylsulfoxide, tetrahydrofuran, dichloromethane, and other organic solvent which does not adversely affect the reaction, or a mixture thereof.

The reaction is also usually carried out in the presence of triphenylphosphine and a conventional base such as potassium tert-butoxide, sodium hydride, sodium hydroxide and the like.

The reaction temperature is not critical, and the reaction can be carried out under cooling to heating.

Compound (8) thus obtained can be isolated or purified by known separation or purification means, such as concentration, concentration in vacuo, solvent extraction, crystallization, recrystallization, phase transfer, chromatography and the like, and can be converted to a salt same as those exemplified for Compound (I).

Reduction

Compound (8) or its salt is reduced in accordance with a conventional method to give Compound (9).

The conventional reduction includes hydrogenation, catalytic hydrogenation, etc.

Among others, catalytic hydrogenation is preferable.

The catalytic hydrogenation is carried out in the presence of a catalyst such as palladium carbon, preferably 10% palladium carbon.

The catalytic hydrogenation is usually carried out in a conventional solvent such as tetrahydrofuran, ethanol, ethyl acetate, and other solvent which does not adversely affect the reaction, or a mixture thereof.

The catalytic hydrogenation is also preferably carried out in the presence of a conventional acid such as acetic acid, hydrochloric acid and the like. A liquid acid can be also used as the solvent.

The reaction temperature is not critical, and the reaction can be carried out under cooling to heating.

Compound (9) thus obtained can be isolated or purified by known separation or purification means, such as concentration, concentration in vacuo, solvent extraction, crystallization, recrystallization, phase transfer, chromatography and the like, and can be converted to a salt same as those exemplified for Compound (I).

Therefore, Compound (11) or a salt thereof can be prepared from Compound (10) or a salt thereof in a similar manner as described above. Suitable salts of Compounds (10) and (11) may be the same as those exemplified for Compound (I).

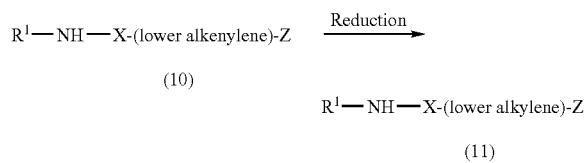

The nitrogen atom in Compound (6), (7), (8), (9), (10) or (11) may be protected or deprotected, as necessary, in accordance with methods known per se such as the methods described in Protective Groups in Organic Synthesis, published by John Wiley and Sons (1980), and the like.

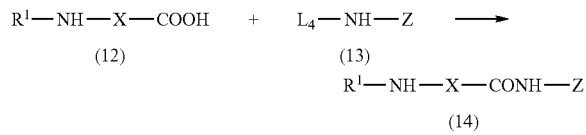

wherein
$L_4$ is a hydrogen atom or a protecting group, which is known per se, such as tert-butoxycarbonyl as described in the above "optionally protected amino" (see Protective Groups in Organic Synthesis, published by John Wiley and Sons (1980), etc.); and
$R^1$, X and Z are as defined above.

Amidation

Compound (12) or a reactive derivative thereof, or its salt is reacted with Compound (13) or its salt to give an amidated compound (14).

Suitable reactive derivative of Compound (12) includes an acid halide, an acid anhydride and an activated ester.

The suitable example may be an acid chloride; an acid azide; a mixed acid anhydride with an acid such as substituted phosphoric acid (e.g., dialkylphosphoric acid, phenylphosphoric acid, diphenylphosphoric acid, dibenzylphosphoric acid, hologenated phosphoric acid, etc.), dialkylphosphorous acid, sulfurous acid, thiosulfuric acid, alkanesulfonic acid (e.g., methanesulfonic acid, ethanesulfonic acid, etc.), sulfuric acid, alkylcarbonic acid, aliphatic carboxylic acid (e.g., pivalic acid, pentanoic acid, isopentanoic acid, 2-ethylbutyric acid, trichloroacetic acid, etc.); aromatic carboxylic acid (e.g., benzoic acid, etc.); a symmetrical acid anhydride; an activated amide with imidazole, 4-substituted imidazole, dimethylpyrazole, triazole or tetrazole; an activated ester (e.g., cyanomethyl ester, methoxymethyl ester, dimethyliminomethyl [$(CH_3)_2N^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.); or an ester with an N-hydroxy compound (e.g., N,N-dimethlhydroxylamine, 1-hydroxy-2-(1H)-pyridone, N-hydroxysuccinimide, N-hydroxybenzotriazole, N-hydroxyphthalimide, 1-hydroxy-6-chloro-1H-benzotriazole, etc.). These reactive derivatives can be optionally selected from them according to the kind of Compound (12) to be used.

Suitable salts of Compound (12) and a reactive derivative thereof as well as Compound (13) may be the same as those exemplified for Compound (I).

Compound (12) and a reactive derivative thereof as well as Compound (13) or salts thereof may be commercially available or can be prepared in accordance with the methods known per se (see Production Example 7).

The conventional amidation method may be employed in the present invention.

The reaction is usually carried out in a conventional solvent such as dichloromethane, methanol, ethanol, acetone, tetrahydrofuran, N,N-dimethylformamide, and any other organic solvent which does not adversely influence the reaction, or a mixture thereof.

The reaction is also preferably carried out in the presence of a conventional condensing agent such as 1-ethyl-3-(3-dimethylaminopropyl)carbodiimide hydrochloride, N,N'-dicyclohexylcarbodiimide, N,N'-carbonylbis(2-methylimidazole)triphenylphosphine, and an additive such as 1-hydroxybenzotriazole, 1-hydroxysuccinimide, 3,4-dihydro-3-hydroxy-4-oxo-1,2,3-benzotriazine.

The reaction temperature is not critical, and the reaction can be carried out under cooling to heating.

Compound (14) thus obtained can be isolated or purified by known separation or purification means, such as concentration, concentration in vacuo, solvent extraction, crystallization, recrystallization, phase transfer, chromatography and the like, and can be converted to a salt same as those exemplified for Compound (I).

The nitrogen atom in Compound (12), (13) or (14) may be protected or deprotected, as necessary, in accordance with methods known per se such as the methods described in Protective Groups in Organic Synthesis, published by John Wiley and Sons (1980), and the like.

The present invention is explained in more detail in the following by way of Production Examples and Examples, which are not to be construed as limitative.

The test compound used in the Example was N-{4-[2-(4-{[amino(imino)methyl]amino}phenyl)ethyl]-1,3-thiazol-2-yl}acetamide (hereinafter Compound A) synthesized in Production Example 1.

PRODUCTION EXAMPLE 1

Step 1

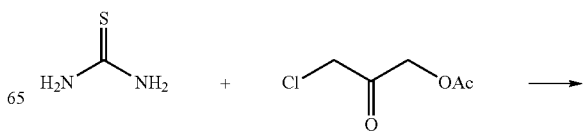

-continued

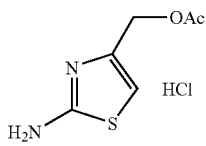

A mixture of 3-chloro-2-oxopropyl acetate (5 g) and thiourea (2.5 g) in ethanol (25 ml) was refluxed for 4 hours. The reaction mixture was cooled to ambient temperature and the resulting crystalline precipitate was collected by filtration and washed with ethanol (20 ml) to give (2-amino-1,3-thiazol-4-yl)methyl acetate hydrochloride (3.5 g) as white crystals.

$^1$H-NMR (DMSO-$d_6$), δ (ppm): 2.07(3H, s), 4.92(2H, s), 6.87(1H, s).

MS: 173(M+H)$^+$

Step 2

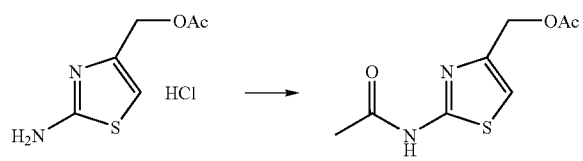

To a mixture of (2-amino-1,3-thiazol-4-yl)methyl acetate hydrochloride (56 g) and pyridine (45 g) in dichloromethane (560 ml) was added acetyl chloride (23 g) over a period of 30 minutes at 5° C., and the reaction mixture was stirred for 10 minutes at the same temperature. The reaction mixture was poured into water (500 ml) and extracted with chloroform (1 L). The organic layer was dried over sodium sulfate and concentrated in vacuo. The residual solid was collected by filtration with isopropyl ether to give (2-(acetylamino)-1,3-thiazol-4-yl)methyl acetate (47 g) as white crystals.

$^1$H-NMR (CDCl$_3$), δ (ppm): 2.12(3H, s), 2.29(3H, s), 5.08(2H, s), 6.93(1H, s).

MS: 215(M+H)$^+$

Step 3

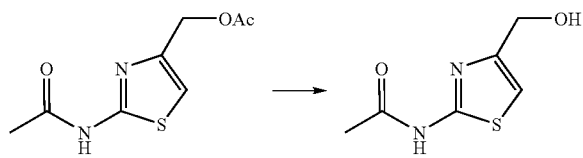

A mixture of (2-(acetylamino)-1,3-thiazol-4-yl)methyl acetate (46 g) and potassium carbonate (30 g) in methanol (640 ml) was stirred for 3 hours at ambient temperature. The reaction mixture was concentrated in vacuo. The residue was diluted with chloroform, and the insoluble material was filtered off. The resulting solution was purified by flash column chromatography on silica-gel with methanol/chloroform (1/99). The resulted solid was collected by filtration with isopropyl ether to give N-(4-(hydroxymethyl)-1,3-thiazol-2-yl)acetamide (35 g) as white crystals.

$^1$H-NMR (DMSO-$d_6$), δ (ppm): 2.12(3H, s), 4.44(2H, d, J=5.0 Hz), 5.20(1H, t, J=5.0 Hz), 6.88(1H, s), 12.02(1H, brs).

MS: 173(M+H)$^+$

Step 4

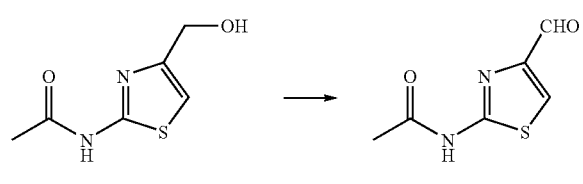

N-(4-(Hydroxymethyl)-1,3-thiazol-2-yl)acetamide (2.8 g) was dissolved in methanol (10 ml) and chloroform (200 ml). Then manganese (IV) oxide (28.3 g) was added to the solution under nitrogen atmosphere. The reaction mixture was stirred at room temperature for 7 hours, and filtered through a celite pad. The filtrate was concentrated in vacuo. The resulting solid was washed with ethyl ether to give N-(4-formyl-1,3-thiazol-2-yl)acetamide (2.01 g) as an off-white solid.

mp. 195.5–199° C.

$^1$H-NMR (DMSO-$d_6$), δ (ppm): 2.17(3H, s), 8.28(1H, s), 9.79(1H, s), 12.47(1H, brs).

Step 5

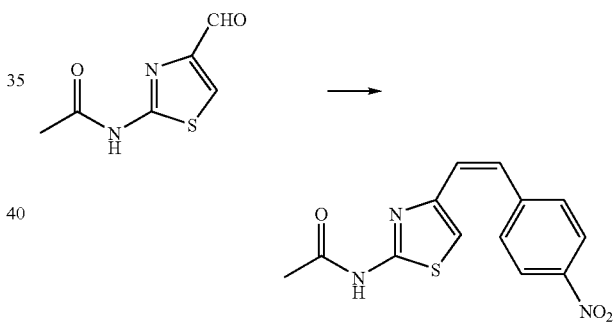

1-(Bromomethyl)-4-nitrobenzene (1.9 g), triphenylphosphine (2.31 g) and N,N-dimethylformamide (20 ml) were combined under nitrogen atmosphere. The reaction mixture was stirred at room temperature for 2.5 hours. Then potassium tert-butoxide (1.19 g) and N-(4-formyl-1,3-thiazol-2-yl)acetamide (1.5 g) were added and the mixture was stirred at room temperature for 14 hours. The reaction mixture was poured into ice-water and extracted with ethyl acetate. The organic layer was washed with 1N-hydrochloric acid, water and saturated sodium chloride solution, dried over anhydrous magnesium sulfate, and concentrated in vacuo. The residue was purified by flash column chromatography over silica gel with n-hexane/ethyl acetate (1:1)→(1:2) as an eluent, and triturated with ethyl ether to give N-{4-[(Z)-2-(4-nitrophenyl)ethenyl]-1,3-thiazol-2-yl}acetamide (1.59 g) as a yellow solid.

mp. 155–157° C.

$^1$H-NMR (DMSO-$d_6$), δ (ppm): 2.13(3H, s), 6.64(1H, d, J=12.5 Hz), 6.71(1H, d, J=12.5 Hz), 7.18(1H, s), 7.79(2H, d, J=9.0 Hz), 8.17(2H, d, J=9.0 Hz), 12.02(1H, brs).

MS: 290(M+H)$^+$

Step 6

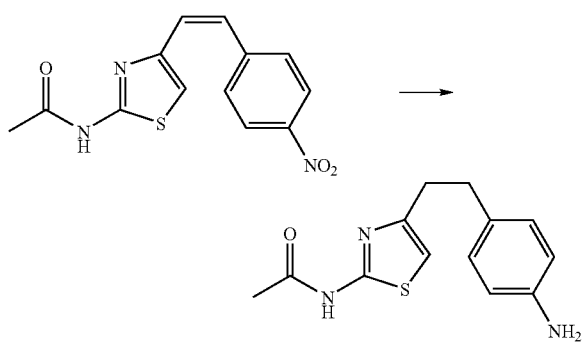

A mixture of N-{4-[(Z)-2-(4-nitrophenyl)ethenyl]-1,3-thiazol-2-yl}acetamide (2 g) and 10% palladium carbon (400 mg) in methanol (25 ml), tetrahydrofuran (25 ml) and acetic acid (18 ml) was stirred under 4 atm hydrogen at ambient temperature for 5 hours. The reaction mixture was filtered through a celite pad, and the filtrate was concentrated in vacuo. The residue was dissolved in ethyl acetate. The organic solution was washed with saturated sodium hydrogen carbonate solution and saturated sodium chloride solution, dried over anhydrous magnesium sulfate, and concentrated in vacuo. The residue was purified by flash column chromatography over silica gel with n-hexane/ethyl acetate (1:2)→ethyl acetate as an eluent, and triturated with ethyl alcohol/ethyl ether to give N-(4-(2-(4-aminophenyl)ethyl)-1,3-thiazol-2-yl)acetamide (539.6 mg) as an off-white solid.

mp. 102.5–104° C.

$^1$H-NMR (DMSO-d$_6$), δ (ppm): 2.11(3H, s), 2.75(4H, brs), 4.82(2H, s), 6.46(2H, d, J=8.5 Hz), 6.69(1H, s), 6.83 (2H, d, J=8.5 Hz), 12.07(1H, brs).

MS: 262(M+H)$^+$

Step 7

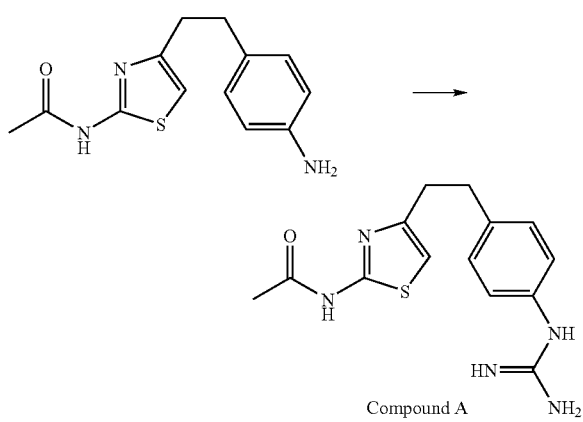

Compound A

To a suspension of N-(4-(2-(4-aminophenyl)ethyl)-1,3-thiazol-2-yl)acetamide (26 g) in ethanol (500 ml) was added 4N hydrogen chloride in ethyl acetate (25 ml) and cyanamide (6.3 g). The mixture was refluxed for 26 hours. The reaction mixture was cooled to ambient temperature and poured into a mixture of ethyl acetate (500 ml) and saturated sodium hydrogen carbonate solution (500 ml). The resulted precipitate was collected by filtration and washed with water (300 ml) and ethanol (300 ml) to give N-{4-[2-(4-{[amino (imino)methyl]amino}phenyl)ethyl]-1,3-thiazol-2-yl}acetamide (18 g) as white crystals.

$^1$H-NMR (DMSO-d$_6$), δ (ppm): 2.10(3H, s), 2.85(4H, s), 6.79(1H, s), 6.83(2H, d, J=7 Hz), 7.10(2H, d, J=7 Hz).

MS: 304(M+H)$^+$

PRODUCTION EXAMPLE 2

Synthesis of N-(4-(2-(4-(4,5-dihydro-1,3-thiazol-2-ylamino)phenyl)ethyl)-1,3-thiazol-2-yl)acetamide N-(4-(2-(4-Aminophenyl)ethyl)-1,3-thiazol-2-yl)acetamide (1.8 g) prepared in a similar manner according to Step 6 of Production Example 1, 2-(methylsulfanyl)-4,5-dihydro-1,3-thiazole (918 mg), hydrochloric acid concentrate (0.57 ml) and 2-methoxyethanol (28 ml) were combined under nitrogen atmosphere, and stirred at 120° C. for 10 hours. After cooled to room temperature, the reaction mixture was concentrated in vacuo. The residue was dissolved in tetrahydrofuran/water, and made basic with aqueous potassium carbonate. The mixture was extracted with ethyl acetate. The organic layer was dried over magnesium sulfate, and evaporated in vacuo. The residue was purified by flash column chromatography over silica gel with chloroform/methanol (30:1→20:1) as an eluent, and triturated with ethyl acetate to give N-(4-(2-(4-(4,5-dihydro-1,3-thiazol-2-ylamino)phenyl)ethyl)-1,3-thiazol-2-yl)acetamide (484.7 mg) as an off-white solid.

mp. 218–219.5° C.

$^1$H-NMR (DMSO-d$_6$), δ (ppm): 2.11(3H, s), 2.84(4H, s), 3.26(2H, t, J=7.5 Hz), 3.35(2H, t, J=7.5 Hz), 4.02(1H, brs), 6.71(1H, brs), 7.05(2H, d, J=8.5 Hz), 7.51(1H, brs), 9.25 (1H, brs), 12.10(1H, brs).

MS: 347(M+H)$^+$

PRODUCTION EXAMPLE 3

Synthesis of N-(4-{(E)-2-[4-(4,5-dihydro-1,3-thiazol-2-ylamino)phenyl]ethenyl}-1,3-thiazol-2-yl) acetamide Step 1

A mixture of 4-nitrobenzyl bromide (6.35 g), triphenylphosphine (7.71 g) and N,N-dimethylformamide (50 ml) was stirred for 5 hours at room temperature. To the mixture were added potassium butoxide (3.96 g), and then N-(4-formyl-1,3-thiazol-2-yl)acetamide (5.0 g) prepared in a similar manner according to Step 4 of Production Example 1, and the mixture was stirred for 13 hours at the same temperature. The reaction mixture was poured into ethyl acetate (200 ml) and water (200 ml). The organic layer was washed with water (20 ml), dried over sodium sulfate and concentrated in vacuo. The crystalline residue was collected and washed with 30% ethyl acetate/diisopropyl ether to give N-{4-[(E)-2-(4-nitrophenyl)ethenyl]-1,3-thiazol-2-yl}acetamide (7.8 g).

$^1$H-NMR (DMSO-d$_6$), δ (ppm): 2.16(3H, s), 7.29(1H, d, J=16 Hz), 7.48(1H, d, J=16 Hz), 7.88(2H, d, J=7 Hz), 8.22(2H, d, J=7 Hz).

MS (M+H)=290

Step 2

A mixture of N-{4-[(E)-2-(4-nitrophenyl)ethenyl]-1,3-thiazol-2-yl}acetamide (250 mg), palladium on carbon (25 mg) and methanol (2.5 ml) was stirred under hydrogen atmosphere for 2 hours at ambient temperature. The catalyst was filtered off and the filtrate was concentrated in vacuo.

The crystalline residue was collected and washed with isopropyl ether to give N-{4-[(E)-2-(4-aminophenyl)ethenyl]-1,3-thiazol-2-yl}acetamide (160 mg).

$^1$H-NMR (DMSO-$d_6$), δ (ppm): 2.14(3H, s), 5.33(2H, s), 6.55(2H, d, J=7 Hz), 6.82(1H, d, J=10 Hz), 6.44(1H, s), 7.09(1H, d, J=10 Hz), 7.20(2H, d, J=7 Hz).

MS: 260(M+H)$^+$

Step 3

A mixture of N-{4-[(E)-2-(4-aminophenyl)ethenyl]-1,3-thiazol-2-yl}acetamide (200 mg), 2-(methylsulfanyl)-4,5-dihydro-1,3-thiazole (103 mg), hydrochrolic acid (0.064 ml) and 2-methoxyethanol (2 ml) was stirred at 120° C. for 8 hours. The reaction mixture was concentrated in vacuo. The residue was purified by silica-gel flash column chromatography with hexane:ethyl acetate (3:1) as an eluent. The crystalline residue was collected and washed with ethyl acetate to give N-(4-{(E)-2-[4-(4,5-dihydro-1,3-thiazol-2-ylamino)phenyl]ethenyl}-1,3-thiazol-2-yl)acetamide (150 mg).

$^1$H-NMR (CDCl$_3$), δ (ppm): 2.27(3H, s), 3.33–3.40(2H, m), 3.57–3.65(2H, m), 6.94(1H, s), 7.05(1H, d, J=12 Hz), 7.29(1H, d, J=12 Hz), 7.30(2H, d, J=7 Hz), 7.57(2H, d, J=7 Hz).

MS: 345(M+H)$^+$

PRODUCTION EXAMPLE 4

Synthesis of methyl N-(4-{2-[2-(acetylamino)-1,3-thiazol-4-yl]ethyl}phenyl)imidothiocarbamate hydriodide Step 1

To an ice-cold solution of N-(4-(2-(4-aminophenyl)ethyl)-1,3-thiazol-2-yl)acetamide (300 mg) prepared in a similar manner according to Step 6 of Production Example 1 in acetone (5 ml) was added benzoyl isothiocyanate (187 mg) and the mixture was refluxed for 2 hours. The reaction mixture was cooled to 0° C. The precipitated crystals were filtered and washed with ice-cold acetone to give N-{4-[2-(4-{[(benzoylamino)carbonothioyl]amino}phenyl)ethyl]-1,3-thiazol-2-yl}acetamide (359 mg).

$^1$H-NMR (CDCl$_3$), δ (ppm): 2.25(3H, s), 2.90–3.05(4H, m), 6.51(1H, s), 7.21(2H, d, J=7 Hz), 7.50–7.70(5H, m), 7.89(2H, d, J=7 Hz), 9.03(1H, s), 9.12(1H, s).

MS (M+H)=425

Step 2

A mixture of N-{4-[2-(4-{[(benzoylamino)carbonothioyl]amino}phenyl)ethyl]-1,3-thiazol-2-yl}acetamide (200 mg), 6N aqueous sodium hydroxide (0.19 ml) and ethanol (2 ml) was stirred at 60° C. for 2 hours. The reaction mixture was cooled to ambient temperature and neutralized with 1N hydrochloric acid (1.2 ml). The precipitated crystals were filtered and washed with water to give N-[4-(2-{4-[(aminocarbonothioyl)amino]phenyl}ethyl)-1,3-thiazol-2-yl]acetamide (120 mg).

$^1$H-NMR (DMSO-$d_6$), δ (ppm): 2.11(3H, s), 2.88(4H, s), 6.75(1H, s), 7.15(2H, d, J=7 Hz), 7.27(2H, d, J=7 Hz), 9.60(1H, s).

MS (M+H)=321

Step 3

A mixture of N-[4-(2-{4-[(aminocarbonothioyl)amino]phenyl}ethyl)-1,3-thiazol-2-yl]acetamide (100 mg), methyl iodide (0.023 ml) and methanol (2 ml) was refluxed for 3 hours. The reaction mixture was concentrated in vacuo. The residue was diluted with ethyl acetate and stirred for 30 minutes. The precipitated crystals were filtered and washed with ethyl acetate to give methyl N-(4-{2-[2-(acetylamino)-1,3-thiazol-4-yl]ethyl}phenyl)imidothiocarbamate hydriodide (130 mg).

$^1$H-NMR (DMSO-$d_6$), δ (ppm): 2.13(3H, s), 2.68(3H, s), 2.87–3.05(4H, m), 6.75(1H, s), 7.24(2H, d, J=7 Hz), 7.35 (2H, d, J=7 Hz).

MS (M+H)=463

PRODUCTION EXAMPLE 5

Synthesis of N-(4-{2-[4-(4,5-dihydro-1H-imidazol-2-ylamino)phenyl]ethyl}-1,3-thiazol-2-yl)acetamide A mixture of N-(4-(2-(4-aminophenyl)ethyl)-1,3-thiazol-2-yl)acetamide (65 mg) prepared in a similar manner according to Step 6 of Production Example 1, ethyl 2-(methylsulfanyl)-4,5-dihydro-1H-imidazole-1-carboxylate (56 mg), acetic acid (0.1 ml), ethanol (0.9 ml) was stirred at 65° C. for 6 hours, and then refluxed for 5 hours. The reaction mixture was poured into ethyl acetate (5 ml) and saturated aqueous sodium bicarbonate. The precipitated solid was filtered, and the solid was dissolved in 50% methanol/chloroform. The insoluble materials were filtered off and the filtrate was concentrated in vacuo. The solid residue was collected and washed with ethyl acetate to give N-(4-{2-[4-(4,5-dihydro-1H-imidazol-2-ylamino)phenyl]-ethyl}-1,3-thiazol-2-yl)acetamide (40 mg).

$^1$H-NMR (DMSO-$d_6$), δ (ppm): 2.11(3H, s), 2.72(4H, s), 3.33(4H, s), 6.73(1H, s), 6.85–7.08(4H, m).

MS (M+H)=330

PRODUCTION EXAMPLE 6

Synthesis of N-{4-[2-(4-{[amino(imino)methyl]amino}phenyl)ethyl]-1,3-thiazol-2-yl}-2-methylpropanamide Step 1

To an ice-cold mixture of ethyl 2-amino-1,3-thiazole-4-carboxylate (2 g) prepared in a similar manner according to Step 1 of the following Production Example 7, pyridine (1.3 ml) and dichloromethane (20 ml) was added isobutyryl chloride (0.91 ml) and stirred for 30 minutes. To the mixture was added saturated aqueous hydrogen bicarbonate (30 ml), and the organic layer was separated, dried over sodium sulfate and concentrated in vacuo. The crystalline residue was collected and washed with ethyl acetate to give ethyl 2-(isobutyrylamino)-1,3-thiazole-4-carboxylate (1.34 g).

$^1$H-NMR (CDCl$_3$), δ (ppm): 1.30(6H, d, J=7 Hz), 1.40 (3H, t, J=7 Hz), 2.57–2.73(1H, m), 4.41(2H, q, J=7 Hz), 7.83(1H, s), 8.98(1H, s).

MS: 243(M+H)$^+$

Step 2

To a mixture of ethyl 2-(isobutyrylamino)-1,3-thiazole-4-carboxylate (1.4 g) and tetrahydrofuran (28 ml) was added lithium borohydride (252 mg) portionwise, and the mixture was refluxed for 6 hours. The reaction mixture was cooled to 0° C., quenched with methanol (5 ml) and concentrated in vacuo. The residue was suspended with 10% methanol/chloroform (100 ml), and the insoluble materials were filtered off. The filtrate was purified by flash column chromatography on silica-gel with 5% methanol/chloroform as an eluent. The crystalline residue was collected and washed with diisopropyl ether to give N-[4-(hydroxymethyl)-1,3-thiazol-2-yl]-2-methylpropanamide (1.0 g).

$^1$H-NMR (CDCl$_3$), δ (ppm): 1.32(6H, d, J=5 Hz), 2.58–2.73(1H, m), 4.68(2H, s), 6.82(1H, s).

MS (M+H)=200

Step 3

A mixture of N-[4-(hydroxymethyl)-1,3-thiazol-2-yl]-2-methylpropanamide (520 mg), manganese (IV) oxide (2.26 g), methanol (0.5 ml) and chloroform (5 ml) was stirred at ambient temperature for 18 hours. The reaction mixture was filtered through a celite pad, and the filtrate was concentrated in vacuo. The crystalline residue was collected and washed with diisopropyl ether to give N-(4-formyl-1,3-thiazol-2-yl)-2-methylpropanamide (365 mg).

$^1$H-NMR (CDCl$_3$), δ (ppm): 1.13(6H, d, J=5 Hz), 2.60–2.77(1H, m), 7.86(1H, s).

MS (M+H)=199

Step 4

A mixture of 4-nitrobenzyl bromide (381 mg), triphenylphosphine (463 mg) and N,N-dimethylformamide (3 ml) was stirred for 5 hours at room temperature. To the mixture were added potassium butoxide (238 mg) and then N-(4-formyl-1,3-thiazol-2-yl)-2-methylpropanamide (350 mg), and the mixture was stirred for 13 hours at the same temperature. The reaction mixture was poured into ethyl acetate (20 ml) and water (20 ml). The organic layer was washed with water (20 ml), dried over sodium sulfate and concentrated in vacuo. The crystalline residue was collected and washed to give 2-methyl-N-{4-[(E)-2-(4-nitrophenyl)ethenyl]-1,3-thiazol-2-yl}propanamide (360 mg).

$^1$H-NMR (CDCl$_3$), δ (ppm): 1.25(6×⅔H, d, J=5 Hz), 1.30(6×⅓H, d, J=5 Hz), 2.50–5.70(1H, m), 6.63(1H, s), 6.79(1×⅔H, s), 6.97(1×⅔H, s), 7.14(1×⅓H, d, J=12 Hz), 7.33(1×⅓H, d, J=12 Hz), 7.53(2×⅔H, d, J=7 Hz), 7.62(2×⅓H, d, J=7 Hz), 8.13(2×⅔H, d, J=7 Hz), 8.22(2×⅓H, d, J=7 Hz).

MS (M+H)=318

Step 5

A mixture of 2-methyl-N-{4-[(E)-2-(4-nitrophenyl)ethenyl]-1,3-thiazol-2-yl}propanamide (333 mg), palladium on carbon (33 mg), acetic acid (1 ml), methanol (2 ml) and tetrahydrofuran (2 ml) was stirred under hydrogen atmosphere (4 atm) at ambient temperature for 5 hours. The catalyst was filtered off, and the filtrate was concentrated in vacuo. The residue was purified by flash column chromatography on silica gel with 5% methanol/ethyl acetate as an eluent. The solid residue was collected and washed with diisopropyl ether to give N-{4-[2-(4-aminophenyl)ethyl]-1,3-thiazol-2-yl}-2-methylpropanamide (260 mg).

$^1$H-NMR (CDCl$_3$), δ (ppm): 1.38(6H, d, J=5 Hz), 2.57–2.73(1H, m), 2.39–2.43(4H, m), 6.45(1H, s), 6.62(2H, d, J=7 Hz), 6.97(2H, d, J=7 Hz).

MS (M+H)=290

Step 6

The title compound was prepared in a similar manner according to Step 7 of Production Example 1.

$^1$H-NMR (DMSO-d$_6$), δ (ppm): 1.01(6H, d, J=5 Hz), 2.62–2.78(1H, m), 2.83(4H, m), 6.72(2H, d, J=7 Hz), 6.75(1H, s), 7.04(2H, d, J=7 Hz).

MS (M+H)=332

PRODUCTION EXAMPLE 7

Synthesis of 2-(acetylamino)-N-(4-{[amino(imino)methyl]amino}phenyl)-1,3-thiazole-4-carboxamide Step 1

A mixture of ethyl 3-bromo-2-oxopropanoate (100 g), thiourea (39 g) and ethanol (500 ml) was refluxed for 2 hours. The reaction mixture was concentrated in vacuo. The crystalline residue was collected and washed with ethyl acetate to give ethyl 2-amino-1,3-thiazole-4-carboxylate hydrobromide (116 g).

$^1$H-NMR (DMSO-d$_6$), δ (ppm): 1.28(3H, t, J=7 Hz), 4.26(2H, q, J=7 Hz), 7.60(1H, s).

Step 2

To an ice-cold mixture of ethyl 2-amino-1,3-thiazole-4-carboxylate hydrobromide (80 g), pyridine (52.5 g) and dichloromethane (800 ml) was added acetyl chloride (27.3 g) dropwise at 0° C., and the mixture was stirred for 30 minutes at the same temperature. The reaction mixture was washed with water (500 ml), dried over sodium sulfate and concentrated in vacuo. The crystalline residue was collected and washed with ethyl acetate to give ethyl 2-(acetylamino)-1,3-thiazole-4-carboxylate (60 g).

$^1$H-NMR (DMSO-d$_6$), δ (ppm): 1.29(3H, t, J=7 Hz), 2.15(3H, s), 4.27(2H, q, J=7 Hz), 8.03(1H, s).

MS (M+H)=215

Step 3

A mixture of ethyl 2-(acetylamino)-1,3-thiazole-4-carboxylate (2 g), 2N sodium hydroxide (7 ml) and methanol (13 ml) was stirred at ambient temperature for 5 hours. The reaction mixture was neutralized by 1N hydrochloric acid (14 ml). The precipitated crystals were filtered and washed with water to give 2-(acetylamino)-1,3-thiazole-4-carboxylic acid (1.3 g).

$^1$H-NMR (DMSO-d$_6$), δ (ppm): 2.14(3H, s), 7.94(1H, s).

Step 4

A mixture of 2-(acetylamino)-1,3-thiazole-4-carboxylic acid (500 mg), tert-butyl 4-aminophenylcarbamate (615 mg), 1-ethyl-3-(3-dimethylaminopropyl)carbodiimide hydrochloride (566 mg), 1-hydroxybenzotriazole (399 mg) and dichloromethane (5 ml) was stirred at ambient temperature for 3 hours. The reaction mixture was washed with saturated aqueous sodium hydrogen bicarbonate, and the organic layer was concentrated in vacuo. The residue was purified by flash column chromatography on silica gel with 3% methanol/chloroform as an eluent. The crystalline residue was collected and washed with ethyl acetate to give tert-butyl 4-({[2-(acetylamino)-1,3-thiazol-4-yl]carbonyl}amino)phenylcarbamate (580 mg).

$^1$H-NMR (DMSO-d$_6$), δ (ppm): 1.48(9H, s), 2.18(3H, s), 7.42(2H, d, J=7 Hz), 7.61(2H, d, J=7 Hz), 7.91(1H, s), 9.32(1H, s), 9.63(1H, s).

MS (M+H)=377

Step 5

To a solution of tert-butyl 4-({[2-(acetylamino)-1,3-thiazol-4-yl]carbonyl}amino)phenylcarbamate (85 mg) in methanol (1 ml) was added 4N hydrogen chloride in ethyl acetate (1 ml), and the mixture was stirred at ambient temperature for 1 hour. The reaction mixture was concentrated in vacuo. The solid residue was collected and washed with ethyl acetate to give 2-(acetylamino)-N-(4-aminophenyl)-1,3-thiazole-4-carboxamide hydrochloride (70 mg).

¹H-NMR (DMSO-d₆), δ (ppm): 2.15(3H, s), 7.42(2H, d, J=7 Hz), 7.37(2H, d, J=7 Hz), 7.41(1H, s).

MS (M+H)=313

Step 6

A mixture of 2-(acetylamino)-N-(4-aminophenyl)-1,3-thiazole-4-carboxamide hydrochloride (70 mg), cyanamide (11 mg) and 2-methoxyethanol (2 ml) was stirred at 100° C. for 72 hours. The reaction mixture was concentrated in vacuo. To the residue was added ethyl acetate (5 ml) and saturated aqueous sodium hydrogen bicarbonate (5 ml). The precipitated solid was filtered and washed with ethyl acetate and water to give 2-(acetylamino)-N-(4-{[amino(imino)methyl]amino}phenyl)-1,3-thiazole-4-carboxamide (45 mg).

¹H-NMR (DMSO-d₆), δ (ppm): 2.18(3H, s), 7.60–7.88 (4H, br), 7.95(1H, s).

MS (M+H)=319

PRODUCTION EXAMPLE 8

Synthesis of N-(4-{2-[4-(ethanimidoylamino)phenyl]ethyl}-1,3-thiazol-2-yl)acetamide N-(4-(2-(4-Aminophenyl)ethyl)-1,3-thiazol-2-yl)acetamide (100 mg) prepared in a similar manner according to Step 6 of Production Example 1, methyl ethanimidothioate hydriodide (166 mg) and methanol (3 ml) were combined, and refluxed for 1.5 hours. After cooled to room temperature, the mixture was concentrated in vacuo. The residue was purified by flash column chromatography over NH silica gel with chloroform/methanol (20:1→10:1) as an eluent to give N-(4-{2-[4-(ethanimidoylamino)phenyl]ethyl}-1,3-thiazol-2-yl)acetamide (165 mg) as a pale yellow amorphous substance.

¹H-NMR (CDCl₃), δ (ppm): 2.03(3H, brs), 2.19(3H, s), 2.92(4H, s), 6.47(1H, s), 6.78(2H, d, J=8.0 Hz), 7.08(2H, d, J=8.0 Hz).

MS: 303(M+H)⁺

PRODUCTION EXAMPLE 9

Synthesis of N-[4-(2-{4-[amino(imino)methyl]phenyl}ethyl)-1,3-thiazol-2-yl]acetamide hydrochloride Step 1

4-(Bromomethyl)benzonitrile (1.73 g), triphenylphosphine (2.31 g) and N,N-dimethylformamide (20 ml) were combined under nitrogen atmosphere. The reaction mixture was stirred at room temperature for 1.5 hours. Then potassium tert-butoxide (1.19 g) and N-(4-formyl-1,3-thiazol-2-yl)acetamide (1.5 g) prepared in a similar manner according to Step 4 of Production Example 1 were added to the mixture, and stirred at room temperature for 3 hours. The reaction mixture was poured into ice-water, and extracted with ethyl acetate. The organic layer was washed with 1N-hydrochloric acid, water and saturated sodium chloride solution, dried over anhydrous magnesium sulfate, and concentrated in vacuo. The residue was purified by flash column chromatography over silica gel with n-hexane/ethyl acetate (1:1) as an eluent, and triturated with ethyl ether to give a mixture of N-{4-[(Z)-2-(4-cyanophenyl)ethenyl]-1,3-thiazol-2-yl}acetamide and N-{4-[(E)-2-(4-cyanophenyl)ethenyl]-1,3-thiazol-2-yl}acetamide (Z:E=3:1) (1.63 g) as a pale yellow solid.

mp. 175–176° C.

¹H-NMR (DMSO-d₆), δ (ppm): 2.13(3H×¾, s), 2.16(3H×¼, s), 6.59(1H×¾, d, J=13.0 Hz), 6.65(1H×¾, d, J=13.0 Hz), 7.11(1H×¾, s), 7.24(1H×¼, d, J=16.0 Hz), 7.28(1H×¼, s), 7.40(1H×¼, d, J=16.0 Hz), 7.65(2H×¾, d, J=8.5 Hz), 7.74(2H×¼, d, J=8.5 Hz), 7.75(2H×¾, d, J=8.5 Hz), 7.83(2H×¼, d, J=8.5 Hz), 12.00(1H, brs).

MS: 270(M+H)⁺

Step 2

A mixture of N-{4-[(Z)-2-(4-cyanophenyl)ethenyl]-1,3-thiazol-2-yl}acetamide and N-{4-[(E)-2-(4-cyanophenyl)ethenyl]-1,3-thiazol-2-yl}acetamide (Z:E=3:1) (1.5 g), 10% palladium on carbon (323 mg), methanol (20 ml), tetrahydrofuran (10 ml) and acetic acid (5 ml) were combined. The reaction mixture was stirred under 4 atm hydrogen at ambient temperature for 9 hours, and filtered through a celite pad. The filtrate was concentrated in vacuo. The residue was purified by flash column chromatography over silica gel with n-hexane/ethyl acetate (1:1)→chloroform/methanol (30:1) as an eluent, and triturated with ethyl ether to give N-{4-[2-(4-cyanophenyl)ethyl]-1,3-thiazol-2-yl}acetamide (1.18 g) as a colorless solid.

mp. 205–206.5° C.

¹H-NMR (DMSO-d₆), δ (ppm): 2.11(3H, s), 2.90(2H, t, J=8.0 Hz), 3.01(2H, t, J=8.0 Hz), 6.73(1H, s), 7.40(2H, d, J=8.0 Hz), 7.74(2H, d, J=8.0 Hz), 12.09(1H, brs).

MS: 272(M+H)⁺

Step 3

N-{4-[2-(4-Cyanophenyl)ethyl]-1,3-thiazol-2-yl}acetamide (600 mg) was dissolved in ethanol (5 ml) and chloroform (5 ml), and then hydrochloric acid gas was bubbled at 0° C. for 5 minutes with stirring. The reaction mixture was stood for 15 hours, and concentrated in vacuo. The residual solid was washed with diethyl ether to give ethyl 4-{2-[2-(acetylamino)-1,3-thiazol-4-yl]ethyl}benzenecarboximidoate hydrochloride (924.7 mg) as a pale green solid.

mp. 129–130° C.

¹H-NMR (DMSO-d₆), δ (ppm): 1.48(3H, t, J=7.0 Hz), 2.12(3H, s), 2.95(2H, t, J=8.0 Hz), 3.07(2H, t, J=8.0 Hz), 4.61(2H, q, J=7.0 Hz), 6.72(1H, s), 7.46(2H, d, J=8.5 Hz), 8.02(2H, d, J=8.5 Hz), 11.25(1H, brs), 11.98(1H, brs), 12.11(1H, brs).

MS: 318(M+H)⁺ free

Step 4

Ethyl 4-{2-[2-(acetylamino)-1,3-thiazol-4-yl]ethyl}benzenecarboximidoate hydrochloride (300 mg) was dissolved in ethanol (6 ml). Then ammonium chloride (68 mg) and ammonia in methanol (1 ml) were added to the solution. The reaction mixture was refluxed for 5 hours under nitrogen atmosphere. After cooled to room temperature, the suspension was filtered in vacuo. The filtrate was concentrated in vacuo, and the residue was solidified with ethanol/diethyl ether to give N-[4-(2-{4-[amino(imino)methyl]phenyl}ethyl)-1,3-thiazol-2-yl]acetamide hydrochloride (234 mg) as a colorless solid.

mp. 229.5–231° C.

¹H-NMR (DMSO-d₆), δ (ppm): 2.12(3H, s), 2.94(2H, t, J=8.0 Hz), 3.06(2H, t, J=8.0 Hz), 6.75(1H, s), 7.44(2H, d, J=8.5 Hz), 7.76(2H, d, J=8.5 Hz), 12.10(1H, brs).

MS: 289(M+H)⁺ free

PRODUCTION EXAMPLE 10

Synthesis of N-(4-{2-[2-(acetylamino)-1,3-thiazol-4-yl]ethyl}phenyl)-2-{[amino(imino)methyl]amino}acetamide hydrochloride Step 1

A mixture of N-(4-(2-(4-aminophenyl)ethyl)-1,3-thiazol-2-yl)acetamide (100 mg) prepared in a similar manner according to Step 6 of Production Example 1, ((tert-butoxycarbonyl)amino)acetic acid (74 mg), 1-ethyl-3-(3-dimethylaminopropyl)carbodiimide hydrochloride (81 mg), 1-hydroxybenzotriazole (57 mg) and dichloromethane (5 ml) was stirred at ambient temperature for 3 hours. The reaction mixture was washed with saturated aqueous sodium hydrogen bicarbonate, and the organic layer was concentrated in vacuo. The residue was purified by flash column chromatography on silica-gel with 3% methanol/chloroform as an eluent. The crystalline residue was collected and washed with ethyl acetate to give tert-butyl 2-[(4-{2-[2-(acetylamino)-1,3-thiazol-4-yl]ethyl}phenyl)amino]-2-oxoethylcarbamate (580 mg).

$^1$H-NMR (CDCl$_3$), δ (ppm): 1.47(9H, s), 2.25(3H, s), 2.92(4H, s), 3.92(2H, d, J=5 Hz), 6.46(1H, s), 7.10(2H, d, J=7 Hz), 7.38(2H, d, J=7 Hz).

MS (M+H)=419

Step 2

To a solution of tert-butyl 2-[(4-{2-[2-(acetylamino)-1,3-thiazol-4-yl]ethyl}phenyl)amino]-2-oxoethylcarbamate (100 mg) in ethyl acetate (1 ml) was added 4N hydrogen chloride in ethyl acetate (1 ml), and the mixture was stirred at ambient temperature for 103 hours. The precipitated solid was filtered and washed with ethyl acetate to give N-(4-{2-[2-(acetylamino)-1,3-thiazol-4-yl]ethyl}phenyl)-2-aminoacetamide hydrochloride (80 mg).

$^1$H-NMR (DMSO-d$_6$), δ (ppm): 2.11(3H, s), 2.87(4H, s), 6.70(1H, s), 7.17(2H, d, J=7 Hz), 7.49(2H, d, J=7 Hz).

MS (M+H)=319

Step 3

The title compound was prepared in a similar manner according to Step 7 of Production Example 1.

$^1$H-NMR (DMSO-d$_6$), δ (ppm): 2.11(3H, s), 2.80–2.95 (4H, m), 3.76(2H, s), 6.70(1H, s), 7.26(2H, d, J=7 Hz), 7.49(2H, d, J=7 Hz), 8.16(2H, s).

MS (M+H)=361

PRODUCTION EXAMPLE 11

Synthesis of N-{4-[4-(2-{[amino(imino)methyl]amino}ethyl)phenyl]-1,3-thiazol-2-yl}acetamide hydrochloride Step 1

Aluminium chloride (1.63 g) was dissolved in 1,2-dichloroethane (15 mL). Chloroacetylchloride (0.732 mL) was added to the mixture at 0° C., and stirred additionally for 20 minutes, then N-(2-phenylethyl)acetamide (1 g) in 1,2-dichloroethane (5 mL) was added dropwise. The mixture was stirred for 1 hour at room temperature, and then poured into ice water. The mixture was extracted with chloroform, washed with water and saturated sodium chloride solution, dried over sodium sulfate and concentrated in vacuo. The solid was washed with ethyl acetate and ethyl ether, and dried in vacuo to give N-{2-[4-(2-chloroacetyl)phenyl]ethyl}acetamide as a white powder (1.18 g, 80.4%).

$^1$H-NMR (300 MHz, DMSO-d$_6$), δ (ppm): 7.92(2H, d, J=6 Hz), 7.34(2H, d, J=6 Hz), 5.66(1H, br), 4.70(2H, s), 3.55–3.60(2H, m), 2.90–2.94(2H, m), 1.98(3H, s).

Step 2

N-{2-[4-(2-Chloroacetyl)phenyl]ethyl}acetamide (1.06 g) and thiourea (505 mg) were dissolved in ethanol (20 mL). The mixture was refluxed for 1 hour and allowed to cool to room temperature. The white solid was collected with filtration and washed with ethanol to give N-{2-[4-(2-amino-1,3-thiazol-4-yl)phenyl]ethyl}acetamide hydrochloride (1.19 g, 90.4%).

MS m/z 262 (M++1).

$^1$H-NMR (300 MHz, DMSO-d$_6$), δ (ppm): 7.93–7.96(2H, m), 7.69(2H, d, J=6 Hz), 7.30(2H, d, J=6 Hz), 7.16(1H, s), 3.23–3.30(2H, m), 2.70–2.76(2H, m), 1.78 (3H, s).

Step 3

N-{2-[4-(2-Amino-1,3-thiazol-4-yl)phenyl]ethyl}acetamide (0.6 g) was dissolved in ethanol (10 mL) and hydrochloric acid concentrate (10 mL). The mixture was refluxed for 5 hours. The solvent was evaporated in vacuo. The residue was washed with ethyl ether to give 4-[4-(2-aminoethyl)phenyl]-1,3-thiazol-2-amine dihydrochrolide (0.5 g, 84.6%).

MS m/z 220 (M++1).

$^1$H-NMR (300 MHz, DMSO-d$_6$), δ (ppm): 8.15(3H, br), 7.78(2H, d, J=6 Hz), 7.39(2H, d, J=6 Hz), 7.24(1H, s), 3.03–3.10(2H, m), 2.90–2.98(2H, m).

Step 4

4-[4-(2-Aminoethyl)phenyl]-1,3-thiazol-2-amine dihydrochrolide (0.45 g) was dissolved in 1,4-dioxane (10 mL), water (3 mL) and 1N sodium hydroxide solution (3.1 mL). Di-tert-butyl dicarbonate (336 mg) was added at 0° C. The mixture was stirred at room temperature overnight, then extracted with ethyl acetate, washed with water and saturated sodium chloride solution, dried over sodium sulfate and concentrated in vacuo. The solid was washed with ethyl ether, and dried in vacuo to give tert-butyl {2-[4-(2-amino-1,3-thiazol-4-yl)phenyl]ethyl}carbamate as a white solid (311 mg, 63.2%).

MS m/z 320 (M++1).

$^1$H-NMR (300 MHz, DMSO-d$_6$), δ (ppm): 7.69(2H, d, J=6 Hz), 7.18(2H, d, J=6 Hz), 7.02(2H, br), 7.69(1H, s), 3.10–3.27(2H, m), 2.65–2.72(2H, m), 1.37(9H, s).

Step 5 tert-Butyl {2-[4-(2-amino-1,3-thiazol-4-yl)phenyl]ethyl}carbamate (290 mg) was dissolved in dichloromethane (5 mL), then acetic anhydride (0.103 mL), 4-dimethylaminopyridine (10 mg) and pyridine (0.147 mL) were added. The mixture was stirred overnight. The mixture was extracted with chloroform, washed with water and saturated sodium chloride solution, dried over sodium sulfate and concentrated in vacuo. The solid was washed with ethyl ether, and dried in vacuo to give tert-butyl (2-{4-[2-(acetylamino)-1,3-thiazol-4-yl]phenyl}ethyl)carbamate as a white solid (280 mg, 85.3%).

MS m/z 362 (M++1).

$^1$H-NMR (300 MHz, DMSO-d$_6$), δ (ppm): 7.80(2H, d, J=6 Hz), 7.53(1H, s), 7.24(2H, d, J=6 Hz), 6.90(1H, m), 3.12–3.18(2H, m), 2.16–2.63(2H, m), 2.16(3H, s), 1.37(9H, s).

Step 6 tert-Butyl (2-{4-[2-(acetylamino)-1,3-thiazol-4-yl]phenyl}ethyl)carbamate (250 mg) was dissolved in ethyl acetate (4 mL) and 4 N hydrogen chloride in ethyl acetate (2 mL). The solvent was evaporated in vacuo. The solid was washed with ethyl acetate and ethyl ether to give N-{4-[4-(2-aminoethyl)phenyl]-1,3-thiazol-2-yl}acetamide hydrochloride (220 mg, 106%).

MS m/z 262 (M++1).

$^1$H-NMR (300 MHz, DMSO-$d_6$), δ (ppm): 8.05(3H, br), 7.85(2H, d, J=6 Hz), 7.58(1H, s), 7.32(2H, d, J=6 Hz), 3.12–3.18(2H, m), 2.88–2.94(2H, m), 2.16(3H, s).

Step 7

N-{4-[4-(2-Aminoethyl)phenyl]-1,3-thiazol-2-yl}acetamide hydrochloride (200 mg) and diisopropylethylamine (0.175 mL) were dissolved in tetrahydrofuran (5 mL). The mixture was stirred at room temperature overnight, then evaporated in vacuo. The residue was purified with silica gel chromatography (5% methanol/chloroform) to give di-tert-butyl {[(2-{4-[2-(acetylamino)-1,3-thiazol-4-yl]phenyl}ethyl)amino]methylidene}-biscarbamate (268 mg, 79.2%).

MS m/z 504 (M++1).

Step 8

Di-tert-butyl {[(2-{4-[2-(acetylamino)-1,3-thiazol-4-yl]phenyl}ethyl)amino]methylidene}biscarbamate (268 mg, 79.2%) (170 mg) was dissolved in 4 N hydrogen chloride in 1,4-dioxane (5 mL). The mixture was stirred at room temperature for 2 days, and then evaporated in vacuo. The residue was washed with ethyl ether, dried in vacuo to give N-{4-[4-(2-{[amino(imino)methyl]amino}ethyl)phenyl]-1,3-thiazol-2-yl}acetamide hydrochloride (50 mg, 43.6%).

MS m/z 304 (M++1).

$^1$H-NMR (300 MHz, DMSO-$d_6$), δ (ppm): 7.83(2H, d, J=8 Hz), 7.62–7.66(1H, m), 7.56(1H, s), 7.34(2H, d, J=8 Hz), 3.37–3.45(2H, m), 2.78–2.85(2H, m), 2.16(3H, s).

PRODUCTION EXAMPLE 12

Synthesis of N-(4-{2-[4-(aminomethyl)phenyl]ethyl}-1,3-thiazol-2-yl)acetamide

Step 1

To a mixture of N-(4-{2-[4-(hydroxymethyl)phenyl]ethyl}-1,3-thiazol-2-yl)acetamide (50 mg) prepared in a similar manner according to Step 3 of the following Production Example 16, carbon tetrabromide (72 mg) and dichloromethane (1 ml) was added triphenylphosphine (71 mg), and the mixture was stirred at ambient temperature for 1 hour. The reaction mixture was purified by flash column chromatography on silica gel with 1% methanol/chloroform as an eluent. The crystalline residue was collected and washed with diisopropyl ether to give N-(4-{2-[4-(bromomethyl)phenyl]ethyl}-1,3-thiazol-2-yl)acetamide (48 mg).

$^1$H-NMR (CDCl$_3$), δ (ppm): 2.25(3H, s), 2.85–3.03(4H, m), 4.49(2H, s), 6.48(1H, s), 7.13(2H, d, J=7 Hz), 7.30(2H, d, J=7 Hz).

MS (M+H)=339

Step 2

To a mixture of N-(4-{2-[4-(bromomethyl)phenyl]ethyl}-1,3-thiazol-2-yl)acetamide (100 mg), tetrahydrofuran (2 ml) and N,N-dimethylformamide (2 ml) was added sodium diformylimide (42 mg), and the mixture was stirred at ambient temperature for 1 hour. The reaction mixture was diluted with water (3 ml), and the precipitated solid was filtered and washed with water to give N-[4-(2-{4-[(diformylamino)methyl]phenyl}ethyl)-1,3-thiazol-2-yl]acetamide (80 mg).

$^1$H-NMR (CDCl$_3$), δ (ppm): 2.23(3H, s), 2.83–3.00(4H, m), 4.72(2H, s), 6.48(1H, s), 7.10(2H, d, J=7 Hz), 7.38(2H, d, J=7 Hz).

MS (M+H)=318

Step 3

To a solution of N-[4-(2-{4-[(diformylamino)methyl]phenyl}ethyl)-1,3-thiazol-2-yl]acetamide (56 mg) in methanol (0.5 ml) was added 4N hydrogen chloride in ethyl acetate (0.5 ml), and the mixture was stirred at ambient temperature for 1 hour. The reaction mixture was concentrated in vacuo. The residue was separated between chloroform (5 ml) and saturated aqueous sodium hydrogen bicarbonate (5 ml), and the aqueous layer was extracted with chloroform (5 ml). The organic layer was dried over sodium sulfate and concentrated in vacuo to give N-(4-{2-[4-(aminomethyl)phenyl]ethyl}-1,3-thiazol-2-yl)acetamide (50 mg).

$^1$H-NMR (DMSO-$d_6$), δ (ppm): 2.12(3H, s), 2.80–3.00 (4H, m), 3.92–4.05(2H, m), 6.72(1H, s), 7.24(2H, d, J=7 Hz), 7.37(2H, d, J=7 Hz).

MS (M+H)=276

PRODUCTION EXAMPLE 13

Synthesis of ethyl 4-[2-(4-{[amino(imino)methyl]amino}phenyl)ethyl]-1,3-thiazol-2-ylcarbamate hydrochloride Step 1: ethyl 4-(hydroxymethyl)-1,3-thiazol-2-ylcarbamate A mixed solution of ethyl 4-(chloromethyl)-1,3-thiazol-2-ylcarbamate (500 mg) in 1,4-dioxane (5 ml) and water (10 ml) was refluxed with stirring for 3.5 hours. After cooling, it was concentrated under reduced pressure. The mixture was partitioned between ethyl acetate and water. The organic phase was separated, washed with brine, dried over magnesium sulfate, and concentrated under reduced pressure. The residue was purified by column chromatography on silica gel (10 g) using a mixed solvent of hexane and ethyl acetate (2:1). The fractions containing the objective compound were collected and evaporated under reduced pressure to give colorless syrup (450 mg, 98.2%).

MS (ES+); 203 (M+H)$^+$ $^1$H-NMR (CDCl$_3$), δ (ppm): 1.39(3H, t, J=7.0 Hz), 4.39 (2H, q, J=7.0 Hz), 4.61(2H, s), 6.80(1H, s).

Step 2: ethyl 4-formyl-1,3-thiazol-2-ylcarbamate

To a mixed solution of ethyl 4-(hydroxymethyl)-1,3-thiazol-2-ylcarbamate (446 mg) in chloroform (30 ml) and methanol (3 ml) was added portionwise manganese (IV) oxide chemicals treated (1.92 g) at room temperature. After the mixture was stirred at the same temperature for 2 hours, then treated manganese (IV) oxide chemicals (250 mg) was added again to the solution, and it was stirred at 50° C. for 3 hours. Manganese (IV) oxide was removed by filtration and the filtrate was concentrated under reduced pressure. The residue was purified by column chromatography on silica gel (10 g) using a mixed solvent of hexane and ethyl acetate (4:1). The fractions containing the objective compound were collected and evaporated under reduced pressure to give colorless powder (470 mg, 106.4%).

$^1$H-NMR (CDCl$_3$), δ (ppm): 1.36(3H, t, J=7.0 Hz), 4.34 (2H, q, J=7.0 Hz), 7.83(1H, s), 9.54(1H, br), 9.88(1H, s).

Step 3

Ethyl 4-[2-(4-nitrophenyl)ethenyl]-1,3-thiazol-2-ylcarbamate (E-Z mixture) was obtained in a similar manner according to Step 5 of Production Example 1.

¹H-NMR (CDCl₃) (cis-trans product mixture), δ (ppm): 1.20–1.40(3H, m), 4.20–4.40(2H, m), 6.60, 6.66(1.2H, ABq, J=13 Hz), 6.74(0.6H, s), 6.94(0.4H, s), 7.12, 7.30(0.8H, ABq, J=16 Hz), 7.53(1.2H, d, J=8.9 Hz), 7.61(0.8H, d, J=8.9 Hz), 8.11(1.2H, d, J=8.9 Hz), 8.22(0.8H, d, J=8.9 Hz).

Step 4

Ethyl 4-[2-(4-aminophenyl)ethyl]-1,3-thiazol-2-ylcarbamate was obtained in a similar manner according to Step 6 of Production Example 1.

MS (ES+); 292(M+H)⁺

¹H-NMR (DMSO-d₆), δ (ppm): 1.24(3H, t, J=7.1 Hz), 2.65–2.80(4H, m), 4.18(2H, q, J=7.1 Hz), 4.82(2H, br), 6.46(2H, d, J=8.5 Hz), 6.69(1H, s), 6.84(2H, d, J=8.5 Hz).

Step 5

Ethyl 4-[2-(4-{N',N''-bis(tert-butoxycarbonyl)-[amino(imino)methyl]amino}phenyl)ethyl]-1,3-thiazol-2-ylcarbamate was obtained in a similar manner according to Step 3 of the following Production Example 14.

¹H-NMR (CDCl₃), δ (ppm): 1.29(3H, t, J=7.0 Hz), 1.40–1.70(18H, m), 2.94(4H, s), 4.27(2H, q, J=7.0 Hz), 6.45(1H, s), 7.12(2H, d, J=8.4 Hz), 7.48(2H, d, J=8.4 Hz), 10.25(1H, s).

Step 6

The title compound was prepared in a similar manner according to Step 5 of the following Production Example 14.

MS (ES+); 334 (M+H)⁺ free

¹H-NMR (DMSO-d₆), δ (ppm): 1.24(3H, t, J=7.0 Hz), 2.80–3.00(4H, m), 4.19(2H, q, J=7.0 Hz), 6.76(1H, s), 7.14(2H, d, J=8.4 Hz), 7.28(2H, d, J=8.4 Hz), 7.46(3H, br), 9.91(1H, s).

PRODUCTION EXAMPLE 14

Synthesis of N-{4-[2-(3-{[amino(imino)methyl]amino}phenyl)ethyl]-5-bromo-1,3-thiazol-2-yl}acetamide hydrochloride Step 1: N-{4-[2-(3-nitrophenyl)ethenyl]-1,3-thiazol-2-yl}acetamide (E-Z mixture)

To a solution of 1-(bromomethyl)-3-nitrobenzene (276 mg) in N,N-dimethylformamide (7 mL) was added triphenylphosphine (335 mg) at room temperature. After the mixed solution was stirred for 4 hours, potassium tert-butoxide (172 mg) and N-(4-formyl-1,3-thiazol-2-yl)acetamide (217 mg) were successively added to the solution at the same temperature. After the whole solution was stirred at room temperature for 5 hours, the mixture was poured into water, the pH of the aqueous layer was adjusted to 7 with 1N-hydrochloric acid. The resulting mixture was extracted with ethyl acetate. The extract was washed with brine, dried over sodium sulfate and evaporated under reduced pressure. The resulting residue was purified by column chromatography on silica gel (10 g) using a mixed solvent of n-hexane and ethyl acetate (4:1). The fractions containing the objective compound were collected and evaporated under reduced pressure to give brown powder of the title compound (E-Z mixture) (323 mg, 87.4%).

¹H-NMR (DMSO-d₆) (cis-trans product mixture), δ (ppm): 2.11(2.49H, s), 2.16(0.51H, s), 6.66(1.66H, s), 7.13 (0.83H, s), 7.28(0.17H, s), 7.29, 7.46(0.34H, ABq, J=16 Hz), 7.60(1H, t, J=7.9 Hz), 7.91(0.83H, d, J=7.9 Hz), 8.01(0.17H, d, J=7.9 Hz), 8.09–8.13(1H, m), 8.28(0.83H, m), 8.38(0.17H, m).

Step 2: N-{4-[2-(3-aminophenyl)ethyl]-1,3-thiazol-2-yl}acetamide

N-{4-[2-(3-Nitrophenyl)ethenyl]-1,3-thiazol-2-yl}acetamide (E,Z mixture) (315 mg) in a mixed solvent of methyl alcohol (3 ml), tetrahydrofuran (6 ml), and acetic acid (1 ml) was hydrogenated over 10% Palladium on carbon (50% wet, 200 mg) under 4.3 atmospheric pressure at room temperature for 3 hours. The catalyst was removed off by filtration, and the filtrate was evaporated in vacuo. The residue was poured into water, the pH of the aqueous layer was adjusted to 9 with aqueous sodium hydrogen carbonate. The resulting mixture was extracted with ethyl acetate. The extract was washed with brine, dried over magnesium sulfate and evaporated under reduced pressure. The resulting residue was purified by column chromatography on silica gel (9 g) using a mixed solvent of n-hexane and ethyl acetate (2:1 to 1:1). The fractions containing the objective compound were collected and evaporated under reduced pressure to give syrup. The syrup of the objective compound was changed to solid in freezer (275 mg, 96.6%).

MS (ES+); 262 (M+H)⁺

¹H-NMR (CDCl₃), δ (ppm): 2.23(3H, s), 2.80–3.00(4H, m), 3.60(2H, br), 6.51(1H, s), 6.45–6.65(3H, m), 7.06(1H, t, J=7.9 Hz), 9.45(1H, br).

Step 3: N-{4-[2-(3-{[N',N''-bis(tert-butoxycarbonyl)amino(imino)methyl]amino}phenyl)ethyl]-1,3-thiazol-2-yl}acetamide To a solution of N-{4-[2-(3-aminophenyl)ethyl]-1,3-thiazol-2-yl}acetamide (267 mg) in tetrahydrofuran (3 ml) was added N,N'-bis(tert-butoxycarbonyl)-1H-pyrazole-1-carboxamidine (317 mg) at room temperature. After the mixed solution was stirred for 3 days at the same temperature, and then evaporated under reduced pressure, the resulting residue was purified by column chromatography on silica gel (10 g) using a mixed solvent of n-hexane and ethyl acetate (4:1 to 3:2). The fractions containing the objective compound were collected and evaporated under reduced pressure to give colorless foam of the title compound (316 mg, 61.4%).

MS (ES+); 504 (M+H)⁺

¹H-NMR (CDCl₃), δ (ppm): 1.40–1.80(18H, m), 2.25(3H, s), 2.97(4H, m), 6.37(1H, m), 6.53(1H, s), 6.91(1H, d, J=7.9 Hz), 7.23(1H, t, J=7.9 Hz), 7.34(1H, s), 7.52(1H, d, J=7.9 Hz), 7.63–7.64(1H, m), 10.28(1H, s).

Step 4: N-{4-[2-(3-{[N',N''-bis(tert-butoxycarbonyl)amino(imino)methyl]amino}phenyl)ethyl]-5-bromo-1,3-thiazol-2-yl}acetamide To a suspension of N-{4-[2-(3-{[N',N''-bis(tert-butoxycarbonyl)amino(imino)methyl]amino}phenyl)ethyl]-1,3-thiazol-2-yl}acetamide (115 mg) in methanol (3 ml) was added N-bromosuccinimide (44.7 mg) at room temperature. After the mixed solution was stirred at the same temperature for 1 hour, the resulting precipitate was collected by filtration, washed with a mixed solvent of diisopropyl ether and n-hexane (1:1). The title compound was obtained as white powder (70 mg, 52.6%).

MS (ES+); 582 (M+H)⁺

¹H-NMR (CDCl₃), δ (ppm): 1.40–1.75(18H, m), 2.21(3H, s), 2.85–3.00(4H, m), 6.93(1H, d, J=7.9 Hz), 7.23(1H, t, J=7.9 Hz), 7.30(1H, s), 7.51(1H, d, J=7.9 Hz), 9.26(1H, br), 10.26(1H, br), 11.63(1H, br).

Step 5

To a solution of N-{4-[2-(3-{[N',N''-bis(tert-butoxycarbonyl)amino(imino)methyl]amino}phenyl)ethyl]-5-bromo-1,3-thiazol-2-yl}acetamide (64 mg) in dichloromethane (0.5 ml) was added dropwise 4N-hydrogen chloride in 1,4-dioxane (2 ml) at room temperature. After being stirred at the same temperature for 20 hours, the reaction mixture was concentrated under reduced pressure. The resulting residue was dissolved in a minimum methanol, and the solution was gradually diluted with ethyl acetate. The resulting precipitate was collected by filtration, washed with diisopropyl ether. The title compound was obtained as colorless powder (37 mg, 80.4%).

MS (ES+); 382 (M+H)$^+$ free $^1$H-NMR (DMSO-d$_6$), δ (ppm): 2.14(3H, s), 2.80–3.00 (4H, m), 7.00–7.15(3H, m), 7.35(1H, t, J=7.9 Hz), 7.51(4H, br), 10.01(1H, br), 12.42(1H, br).

PRODUCTION EXAMPLE 15

Synthesis of N-{4-[2-(4-{[amino(imino)methyl]amino}phenyl)ethyl]-5-bromo-1,3-thiazol-2-yl}acetamide hydrochloride Step 1-a Di-tert-butyl {[(4-{2-[2-(acetylamino)-1,3-thiazol-4-yl]ethyl}phenyl)amino]methylidene}biscarbamate was prepared from the compound of Step 6 of Production Example 1 in a similar manner according to the following Step 5 of Production Example 18.

mp. 275.5–276° C.

$^1$H-NMR (DMSO-d$_6$), δ (ppm): 1.39(9H, s), 1.51(9H, s), 2.11(3H, s), 2.82–2.96(4H, m), 6.74(1H, s), 7.18(2H, d, J=8.5 Hz), 7.42(2H, d, J=8.5 Hz), 9.94(1H, brs), 11.44(1H, brs), 12.09(1H, brs).

MS: 504(M+H)$^+$

Step 1-b

Di-tert-butyl {[(4-{2-[2-(acetylamino)-1,3-thiazol-4-yl]ethyl}phenyl)amino]methylidene}biscarbamate (310 mg) prepared in a similar manner according to Step 5 of the following Production Example 18 was dissolved in methanol (6 ml) and tetrahydrofuran (3 ml) under nitrogen atmosphere. Then N-bromosuccinimide (164 mg) was added to the solution at 0° C. The reaction mixture was stirred at room temperature for 4 hours, and concentrated in vacuo. Chloroform and saturated sodium hydrogen carbonate solution were added to the residue. The organic layer was washed with water and saturated sodium chloride solution, dried over anhydrous magnesium sulfate, and concentrated in vacuo. The residue was purified by flash column chromatography over silica gel with n-hexane/ethyl acetate (2:1) as an eluent to give di-tert-butyl {[(4-{2-[2-(acetylamino)-5-bromo-1,3-thiazol-4-yl]ethyl}phenyl)amino]methylidene}biscarbamate (271.4 mg) as a colorless amorphous substance.

$^1$H-NMR (CDCl$_3$), δ (ppm): 1.49(9H, s), 1.53(9H, s), 2.22(3H, s), 2.90(4H, s), 7.13(2H, d, J=8.0 Hz), 7.45(2H, d, J=8.0 Hz).

MS: 582(M+H)$^+$

Step 2

Di-tert-butyl {[(4-{2-[2-(acetylamino)-5-bromo-1,3-thiazol-4-yl]ethyl}phenyl)amino]methylidene}biscarbamate (113 mg) and 4N hydrochloric acid in 1,4-dioxane solution (2 ml) were combined under nitrogen atmosphere. The reaction mixture was stirred at room temperature for 24 hours. The solvent was removed in vacuo. The residue was washed with ethyl acetate to give N-{4-[2-(4-{[amino(imino)methyl]amino}phenyl)ethyl]-5-bromo-1,3-thiazol-2-yl}acetamide hydrochloride (16.8 mg) as a pale yellow amorphous solid.

$^1$H-NMR (DMSO-d$_6$), δ (ppm): 2.14(3H, s), 2.82–2.97 (4H, m), 7.14(2H, d, J=8.5 Hz), 7.25(2H, d, J=8.5 Hz), 7.40(3H, brs), 9.81(1H, brs), 12.41(1H, brs).

MS: 382(M+H)$^+$ free

PRODUCTION EXAMPLE 16

Synthesis of N-[4-(2-{4-[(aminooxy)methyl]phenyl}ethyl)-1,3-thiazol-2-yl]acetamide Step 1

[4-(Methoxycarbonyl)benzyl](triphenyl)phosphonium bromide (6.06 g) and N,N-dimethylformamide (50 ml) were combined under nitrogen atmosphere. Then potassium tert-butoxide (1.66 g) and N-(4-formyl-1,3-thiazol-2-yl)acetamide (2.1 g) prepared in a similar manner according to Step 4 of Production Example 1 were added to the suspension at 0° C. The reaction mixture was stirred at room temperature for 6 hours, poured into ice-water, and extracted with ethyl acetate. The organic layer was washed with 1N-hydrochloric acid, water and saturated sodium chloride solution, dried over anhydrous magnesium sulfate, and concentrated in vacuo. The residue was purified by flash column chromatography over silica gel with chloroform/methanol (20:1→10:1) as an eluent, and triturated with ethyl ether to give a mixture of methyl 4-{(Z)-2-[2-(acetylamino)-1,3-thiazol-4-yl]ethenyl}benzoate and methyl 4-{(E)-2-[2-(acetylamino)-1,3-thiazol-4-yl]ethenyl}benzoate (Z:E=3:1) (4.05 g) as a colorless solid.

mp. 164–165.5° C.

$^1$H-NMR (DMSO-d$_6$), δ (ppm): 2.13(3H×¾, s), 2.16(3H×¼, s), 3.85(3H, s), 6.61(2H×¾, s), 7.05(1H×¾, s), 7.26(1H×¼, d, J=15.5 Hz), 7.27(1H×¼, s), 7.37(1H×¼, d, J=15.5 Hz), 7.64(2H×¾, d, J=8.5 Hz), 7.69(2H×¼, d, J=8.5 Hz), 7.90(2H×¾, d, J=8.5 Hz), 7.94(2H×¼, d, J=8.5 Hz), 12.05 (1H, brs).

MS: 303(M+H)$^+$

Step 2

Methyl 4-{2-[2-(acetylamino)-1,3-thiazol-4-yl]ethyl}benzoate was prepared in a similar manner according to Step 2 of Production Example 9.

mp. 170–171° C.

$^1$H-NMR (DMSO-d$_6$), δ (ppm): 2.11(3H, s), 2.86–2.95 (2H, m), 2.97–3.05(2H, m), 3.83(3H, s), 6.72(1H, s), 7.35 (2H, d, J=8.5 Hz), 7.87(2H, d, J=8.5 Hz), 12.08(1H, brs).

MS: 305 (M+H)$^+$

Step 3

To a stirred solution of methyl 4-{2-[2-(acetylamino)-1,3-thiazol-4-yl]ethyl}benzoate (1.8 g) in dry tetrahydrofuran (36 ml) was added dropwise 1.0 M diisobutylaluminium hydride solution in toluene (20.7 ml) at −78° C. over 15 minutes under nitrogen atmosphere. The reaction mixture was stirred at room temperature for 1.5 hours, and then the reaction was quenched with water (1 ml). The mixture was stirred at room temperature for 30 minutes, dried over anhydrous magnesium sulfate, and filtered through a pad of Celite. The solvent was evaporated in vacuo. The residual solid was washed with ethyl ether to give N-(4-{2-[4-(hydroxymethyl)phenyl]ethyl}-1,3-thiazol-2-yl)acetamide (1.03 g) as a colorless solid.

mp. 162–165° C.

$^1$H-NMR (DMSO-d$_6$), δ (ppm): 2.11(3H, s), 2.80–2.95 (4H, m), 4.44(2H, d, J=5.5 Hz), 5.09(1H, t, J=5.5 Hz), 6.72(1H, s), 7.14(2H, d, J=8.0 Hz), 7.21(2H, d, J=8.0 Hz), 12.08(1H, brs).

MS: 277(M+H)$^+$

Step 4

N-(4-{2-[4-(Hydroxymethyl)phenyl]ethyl}-1,3-thiazol-2-yl)acetamide (250 mg), 2-hydroxy-1H-isoindole-1,3(2H)-dione (155 mg), triphenylphosphine (249 mg) and tetrahydrofuran (5 ml) were combined under nitrogen atmosphere, and then diethyl azodicarboxylate (0.15 ml) was added to the solution at 0° C. The reaction mixture was stirred at room temperature for 6 hours, poured into saturated sodium hydrogen carbonate solution, and extracted with ethyl acetate. The organic layer was washed with saturated sodium chloride solution, dried over anhydrous magnesium sulfate, and concentrated in vacuo. The residue was purified by flash column chromatography over silica gel with chloroform/methanol (20:1) as an eluent, and triturated with ethyl acetate to give N-{4-[2-(4-{[(1,3-dioxo-1,3-dihydro-2H-isoindol-2-yl)oxy]methyl}phenyl)ethyl]-1,3-thiazol-2-yl}acetamide (218.2 mg) as a colorless solid.

mp. 225–226° C.

$^1$H-NMR (DMSO-$d_6$), δ (ppm): 2.11(3H, s), 2.82–3.00 (4H, m), 5.12(2H, s), 6.69(1H, s), 7.23(2H, d, J=8.0 Hz), 7.41(2H, d, J=8.0 Hz), 7.86(4H, s), 12.08(1H, brs).

MS: 422(M+H)$^+$

Step 5

N-{4-[2-(4-{[(1,3-Dioxo-1,3-dihydro-2H-isoindol-2-yl)oxy]methyl}phenyl)ethyl]-1,3-thiazol-2-yl}acetamide (200 mg), methylhydrazine (0.038 ml) and dichloromethane (4 ml) were combined under nitrogen atmosphere. The reaction mixture was stirred at room temperature for 1.5 hours, and filtered in vacuo. The filtrate was washed with saturated sodium hydrogen carbonate solution, water and saturated sodium chloride solution, dried over anhydrous magnesium sulfate, and concentrated in vacuo. The residual solid was washed with acetonitrile to give N-[4-(2-{4-[(aminooxy)methyl]phenyl}ethyl)-1,3-thiazol-2-yl]acetamide (81.8 mg) as a colorless solid.

mp. 130–130.5° C.

$^1$H-NMR (DMSO-$d_6$), δ (ppm): 2.11(3H, s), 2.82–2.97 (4H, m), 4.51(2H, s), 6.01(2H, s), 6.73(1H, s), 7.17(2H, d, J=8.0 Hz), 7.22(2H, d, J=8.0 Hz), 12.09(1H, brs).

MS: 292(M+H)$^+$

PRODUCTION EXAMPLE 17

Synthesis of N-{4-[2-(4-{[(methyleneamino)oxy]methyl}phenyl)ethyl]-1,3-thiazol-2-yl}acetamide N-[4-(2-{4-[(Aminooxy)methyl]phenyl}ethyl)-1,3-thiazol-2-yl]acetamide (30 mg) prepared in a similar manner according to Production Example 16, 37% formaldehyde (8 μl) and dry methanol (1 ml) were combined under nitrogen atmosphere. The reaction mixture was stirred at room temperature for 6 hours and concentrated in vacuo. The residue was purified by preparative silica gel column chromatography with chloroform/methanol (20:1) as an eluent, and triturated with ethyl ether to give N-{4-[2-(4-{[(methyleneamino)oxy]methyl}-phenyl)ethyl]-1,3-thiazol-2-yl}acetamide (20.9 mg) as a colorless solid.

mp. 136.5–137° C.

$^1$H-NMR (DMSO-$d_6$), δ (ppm): 2.11(3H, s), 2.83–2.97 (4H, m), 5.01(2H, s), 6.61(1H, d, J=7.5 Hz), 6.73(1H, s), 7.09(1H, d, J=7.5 Hz), 7.18(2H, d, J=8.0 Hz), 7.24(2H, d, J=8.0 Hz), 12.08(1H, brs).

MS: 304(M+H)$^+$

PRODUCTION EXAMPLE 18

Synthesis of N-{5-[2-(4-{[amino(imino)methyl]amino}phenyl)ethyl]-1,3-thiazol-2-yl}acetamide hydrochloride Step 1

A solution of 1,1,3,3-tetramethoxypropane (10 g) and hydrochloric acid concentrate (0.43 ml) in water (11 ml) was stirred at room temperature for 10 minutes. Bromine (3.14 ml) was added dropwise to the solution at room temperature over 50 minutes. The reaction mixture was stirred at room temperature for 20 minutes, and concentrated in vacuo. The residual solid was washed with water to give 2-bromomalonaldehyde (3.6 g) as a yellow solid.

mp. 147–148° C.

$^1$H-NMR (CDCl$_3$), δ (ppm): 4.73–4.80(1H, m), 8.47(2H, brs).

MS: 149(M−H)$^+$

Step 2

N'-((E)-Ethanoyl)carbamimidothioic acid (2.74 g) and acetone (20 ml) were combined under nitrogen atmosphere. Then 2-bromomalonaldehyde (3.5 g) was added to the solution under reflux. The reaction mixture was refluxed for an hour, and cooled to room temperature. The precipitate was filtered in vacuo. The solid was washed with water and acetone, and purified by flash column chromatography over silica gel with chloroform/methanol (20:1) as an eluent to give N-(5-formyl-1,3-thiazol-2-yl)acetamide (1.21 g) as an off-white solid.

mp. 235–235.5° C.

$^1$H-NMR (DMSO-$d_6$), δ (ppm): 2.21(3H, s), 8.41(1H, s), 9.95(1H, s), 12.71(1H, brs).

MS: 169(M−H)$^+$

Step 3

N-{5-[(Z)-2-(4-Nitrophenyl)ethenyl]-1,3-thiazol-2-yl}acetamide was prepared in a similar manner according to Step 5 of Production Example 1.

mp. 221–223° C.

$^1$H-NMR (DMSO-$d_6$), δ (ppm): 2.07(3H, s), 6.63(1H, d, J=12.0 Hz), 6.92(1H, d, J=12.0 Hz), 7.55(1H, s), 7.62(2H, d, J=9.0 Hz), 8.24(2H, d, J=9.0 Hz), 12.16(1H, brs).

MS: 290(M+H)$^+$

Step 4

A mixture of N-{5-[(Z)-2-(4-nitrophenyl)ethenyl]-1,3-thiazol-2-yl}acetamide (1 g) and 10% palladium carbon (1.04 g) in ethyl acetate (100 ml) and N,N-dimethylformamide (20 ml) was stirred under 4 atm hydrogen at ambient temperature for 4 hours. The reaction mixture was filtered through a celite pad, and the filtrate was concentrated in vacuo. The residue was purified by flash column chromatography over silica gel with chloroform/methanol (30:1→20:1) as an eluent, and triturated with ethyl ether to give N-{5-[2-(4-aminophenyl)ethyl]-1,3-thiazol-2-yl}acetamide (240.9 mg) as an off-white solid.

mp. 218–219.5° C.

$^1$H-NMR (DMSO-$d_6$), δ (ppm): 2.09(3H, s), 2.70(2H, t, J=7.5 Hz), 2.92(2H, t, J=7.5 Hz), 4.85(2H, s), 6.47(2H, d, J=8.5 Hz), 6.86(2H, d, J=8.5 Hz), 7.08(1H, s), 11.86(1H, brs).

MS: 262(M+H)$^+$

Step 5

N-{5-[2-(4-Aminophenyl)ethyl]-1,3-thiazol-2-yl}acetamide (100 mg), N,N'-bis(tert-butoxycarbonyl)-1H- pyrazole-1-carboxamidine (119 mg), N,N-dimethylformamide (1 ml) and tetrahydrofuran (2 ml) were combined under nitrogen atmosphere. The reaction mixture was stirred at 50° C. for 5.5 hours. After cooled to room temperature, the reaction mixture was concentrated in vacuo. The residue was purified by preparative silica gel column chromatography with n-hexane/ethyl acetate (1:2) as an eluent to give di-tert-butyl {[(4-{2-[2-(acetylamino)-1,3-thiazol-5-yl]ethyl}phenyl)amino]methylidene}biscarbamate (93.9 mg) as a colorless solid.

mp. 203–205° C.

$^1$H-NMR (DMSO-d$_6$), δ (ppm): 1.40(9H, s), 1.51(9H, s), 2.10(3H, s), 2.87(2H, t, J=7.5 Hz), 3.02(2H, t, J=7.5 Hz), 7.11(1H, s), 7.21(2H, d, J=8.5 Hz), 7.45(2H, d, J=8.5 Hz), 9.96(1H, brs), 11.43(1H, brs), 11.88(1H, brs).

MS: 504(M+H)$^+$

Step 6

The title compound was prepared in a similar manner according to Step 2 of Production Example 15.

mp. 105–107° C.

$^1$H-NMR (DMSO-d$_6$), δ (ppm): 2.11(3H, s), 2.91(2H, t, J=7.5 Hz), 3.04(2H, t, J=7.5 Hz), 7.14(1H, s), 7.14(2H, d, J=8.5 Hz), 7.32(2H, d, J=8.5 Hz), 7.46(3H, brs), 9.89(1H, s), 11.95(1H, brs).

MS: 304(M+H)$^+$ free

PRODUCTION EXAMPLE 19

Synthesis of N-{4-[2-(4-{[imino(methylamino)methyl]amino}phenyl)ethyl]-1,3-thiazol-2-yl}acetamide A mixture of methyl N-(4-{2-[2-(acetylamino)-1,3-thiazol-4-yl]ethyl}phenyl)imidothiocarbamate hydriodide (50 mg) prepared in a similar manner according to Production Example 4, 40% methylamine in methanol (0.056 ml) and ethanol (1 ml) was stirred at ambient temperature for 20 hours. The precipitated crystals were filtered and washed with ethanol to give N-{4-[2-(4-{[imino(methylamino)methyl]amino}phenyl)ethyl]-1,3-thiazol-2-yl}acetamide (18 mg).

$^1$H-NMR (DMSO-d$_6$), δ (ppm): 2.11(3H, s), 2.64(3H, s), 2.83(4H, s), 6.67(2H, d, J=7 Hz), 6.73(1H, s), 7.01(2H, d, J=7 Hz).

MS (M+H)=318

PRODUCTION EXAMPLE 20

Synthesis of N-{4-[2-(4-{[amino(imino)methyl]amino}phenyl)ethyl]-5-chloro-1,3-thiazol-2-yl}acetamide hydrochloride Step 1

Di-tert-butyl {[(4-{2-[2-(acetylamino)-1,3-thiazol-4-yl]ethyl}phenyl)amino]methylidene}biscarbamate (150 mg) prepared in a similar manner according to Step 5 of Production Example 18 was dissolved in methanol (1.5 ml) and tetrahydrofuran (3 ml) under nitrogen atmosphere. Then N-chlorosuccinimide (59.7 mg) was added to the solution at 0° C. The reaction mixture was stirred at room temperature for 29 hours, and diluted in ethyl acetate. The organic solution was washed with saturated sodium hydrogen carbonate solution, water and saturated sodium chloride solution, dried over anhydrous magnesium sulfate, and concentrated in vacuo. The residual solid was washed with ethyl ether to give di-tert-butyl {[(4-{2-[2-(acetylamino)-5-chloro-1,3-thiazol-4-yl]ethyl}phenyl)amino]methylidene}biscarbamate (111 mg) as an off-white solid.

mp. 220–221° C.

$^1$H-NMR (DMSO-d$_6$), δ (ppm): 1.39(9H, s), 1.51(9H, s), 2.13(3H, s), 2.81–2.94(4H, m), 7.15(2H, d, J=8.5 Hz), 7.43(2H, d, J=8.5 Hz), 9.95(1H, brs), 11.43(1H, brs), 12.38(1H, brs).

MS: 538(M+H)$^+$

Step 2

The title compound was prepared in a similar manner according to Step 2 of Production Example 15.

mp. 82–84° C.

$^1$H-NMR (DMSO-d$_6$), δ (ppm): 2.14(3H, s), 2.82–2.97 (4H, m), 7.14(2H, d, J=8.5 Hz), 7.25(2H, d, J=8.5 Hz), 7.42(3H, brs), 9.85(1H, brs), 12.38(1H, brs).

MS: 338(M+H)$^+$ free

PRODUCTION EXAMPLE 21

Synthesis of N-(4-{2-[4-({[amino(imino)methyl]amino}methyl)phenyl]ethyl}-1,3-thiazol-2-yl)acetamide hydrochloride Step 1

A mixture of N-(4-{2-[4-(aminomethyl)phenyl]ethyl}-1,3-thiazol-2-yl)acetamide (20 mg) prepared in a similar manner according to Production Example 12, N,N'-bis(tert-butoxycarbonyl)-1H-pyrazole-1-carboxamidine (23 mg) and tetrahydrofuran (0.5 ml) was stirred at ambient temperature for 1 hour. The reaction mixture was concentrated in vacuo, and the residue was purified by flash column chromatography on silica-gel with chloroform as an eluent. The crystalline residue was collected and washed with diisopropyl ether to give di-tert-butyl{[(4-{2-[2-(acetylamino)-1,3-thiazol-4-yl]ethyl}benzyl)amino]methylidene}biscarbamate (22 mg).

$^1$H-NMR (CDCl$_3$), δ (ppm): 1.47(9H, s), 1.50(9H, s), 2.24(3H, s), 2.87–3.03(4H, m), 6.50(1H, s), 7.13(2H, d, J=7 Hz), 7.22(2H, d, J=7 Hz).

MS (M+H)=518

Step 2

A mixture of di-tert-butyl{[(4-{2-[2-(acetylamino)-1,3-thiazol-4-yl]ethyl}benzyl)amino]methylidene}biscarbamate (20 mg), dichloromethane (2 drops) and 4N hydrogen chloride in 1,4-dioxane (0.5 ml) was stirred for 15 hours. The precipitated crystals were filtered and washed with 1,4-dioxane to give N-(4-{2-[4-({[amino(imino)methyl]amino}methyl)phenyl]ethyl}-1,3-thiazol-2-yl)acetamide hydrochloride (13 mg).

$^1$H-NMR (DMSO-d$_6$), δ (ppm): 2.12(3H, s), 2.80–3.00 (4H, m), 4.32(2H, d, J=7 Hz), 6.73(1H, s), 7.20(4H, s), 8.04(1H, t, J=7 Hz).

MS (M+H)=318

PRODUCTION EXAMPLE 22

Synthesis of ethyl 2-(acetylamino)-4-[2-(4-{[amino(imino)methyl]amino}phenyl)ethyl]-1,3-thiazole-5-carboxylate hydrochloride Step 1

Ethyl 4-chloro-3-oxobutanoate (35 g) was dissolved in dichloromethane (70 ml), and then sulfuryl chloride (17.1 ml) in dichloromethane (20 ml) was added dropwise to the solution at 0° C. over 15 minutes under nitrogen atmosphere. The reaction mixture was stirred at room temperature for 3 hours, and concentrated in vacuo. The residual oil, N'-((E)-ethanoyl)carbamimidothioic acid (25.1 g) and acetone (600 ml) were combined. The reaction mixture was refluxed for 2.5 hours. After cooled to room temperature, the mixture was concentrated in vacuo. The residual solid was washed with water and isopropyl ether to give ethyl 2-(acetylamino)-4-(chloromethyl)-1,3-thiazole-5-carboxylate (21.2 g) as a pale yellow solid.

mp. 164–165° C.

$^1$H-NMR (DMSO-d$_6$), δ (ppm): 1.30(3H, t, J=7.0 Hz), 2.19(3H, s), 4.29(2H, q, J=7.0 Hz), 5.00(2H, s), 12.72(1H, s).

MS: 263(M+H)$^+$

Step 2: ethyl 2-(acetylamino)-4-[(E)-2-(4-nitrophenyl)ethenyl]-1,3-thiazole-5-carboxylate To a stirring solution of ethyl 2-(acetylamino)-4-(chloromethyl)-1,3-thiazole-5-carboxylate (1.0 g, 3.81 mmol) in N,N-dimethylformamide (20 mL) was added triphenylphosphine (1.2 g, 4.57 mmol) at room temperature. The resultant mixture was stirred at 65° C. for 5 hours. To the mixture was added potassium tert-butoxide (555 mg, 4.95 mmol) at 5° C., and the resultant mixture was stirred at 5° C. for 30 minutes. p-Nitrobenzaldehyde (805 mg, 5.33 mmol) was added at 5° C.

After stirring for 1 hour at room temperature, the reaction was quenched with water, and the mixture was filtered to give the title compound (1.0 g, 72.7%) as a yellow solid.

$^1$H-NMR (CDCl$_3$), δ (ppm): 1.40(3H, t, J=7.2 Hz), 2.33 (3H, s), 4.38(2H, q, J=7.2 Hz), 7.59(1H, d, J=16.0 Hz), 7.70(2H, d, J=8.8 Hz), 8.18(1H, d, J=16.0 Hz), 8.22(2H, d, J=8.8 Hz), 8.90(1H, m).

Step 3

Ethyl 2-(acetylamino)-4-[2-(4-aminophenyl)ethyl]-1,3-thiazole-5-carboxylate was prepared in a similar manner according to Step 6 of Production Example 1.

$^1$H-NMR (CDCl$_3$), δ (ppm): 1.35(3H, t, J=7.0 Hz), 2.27 (3H, s), 2.84(2H, m), 3.28(2H, m), 3.56(2H, m), 4.31(2H, q, J=7.0 Hz), 6.61(2H, d, J=8.3 Hz), 7.01(2H, d, J=8.3 Hz), 9.12(1H, m).

Step 4

Ethyl 2-(acetylamino)-4-{2-[4-({(Z)-[(tert-butoxycarbonyl)amino][(tert-butoxycarbonyl)imino]methyl}amino)phenyl]ethyl}-1,3-thiazole-5-carboxylate was prepared in a similar manner according to Step 5 of Production Example 18.

$^1$H-NMR (CDCl$_3$), δ (ppm): 1.36(3H, t, J=7.4 Hz), 1.49 (9H, s), 1.53(9H, s), 2.25(3H, s), 2.94(2H, m), 3.34(2H, m), 4.31(2H, q, J=7.4 Hz), 7.15(2H, d, J=8.4 Hz), 7.41(2H, d, J=8.4 Hz), 9.69(1H, m), 10.20(1H, s), 11.63(1H, s).

Step 5

The title compound was prepared in a similar manner according to Step 2 of Production Example 15.

$^1$H-NMR (DMSO-d$_6$), δ (ppm): 1.28(3H, t, J=7.0 Hz), 2.18(3H, s), 2.94(2H, m), 3.28(2H, m), 4.23(2H, q, J=7.0 Hz), 7.16(2H, d, J=8.4 Hz), 7.29(2H, d, J=8.4 Hz), 7.37(3H, s), 9.71(1H, s), 12.55(1H, s).

PRODUCTION EXAMPLE 23

Synthesis of N-{4-[2-(4-{[(ethylamino)(imino)methyl]amino}phenyl)ethyl]-1,3-thiazol-2-yl}acetamide The title compound was prepared in a similar manner according to Production Example 19.

$^1$H-NMR (DMSO-d$_6$), δ (ppm): 1.13(3H, t, J=6 Hz), 2.11(3H, s), 2.70–3.00(6H, m), 6.70(1H, s), 6.77(2H, d, J=7 Hz), 7.17(2H, d, J=7 Hz).

MS (M+H)=332

PRODUCTION EXAMPLE 24

Synthesis of benzyl 4-[2-(4-{[amino(imino)methyl]amino}phenyl)ethyl]-1,3-thiazol-2-carbamate Step 1

To an ice-cold mixture of ethyl 2-amino-1,3-thiazole-4-carboxylate (5 g), pyridine (3.36 ml) and dichloromethane (50 ml) was added benzyloxycarbonyl chloride (3.1 ml), and the mixture was stirred at ambient temperature for 1 hour. The reaction mixture was washed with saturated aqueous sodium hydrogen bicarbonate (30 ml), dried over sodium sulfate and concentrated in vacuo. The crystalline residue was collected and washed with diisopropyl ether to give ethyl 2-{[(benzyloxy)carbonyl]amino}-1,3-thiazole-4-carboxylate (5.1 g).

$^1$H-NMR (CDCl$_3$), δ (ppm): 1.48(3H, t, J=7 Hz), 4.38 (2H, q, J=7 Hz), 5.27(2H, s), 7.36–7.44(5H, m), 7.82(1H, s).

MS (M+H)=307

Step 2

Benzyl 4-(hydroxymethyl)-1,3-thiazol-2-ylcarbamate was prepared in a similar manner according to Step 2 of Production Example 6.

$^1$H-NMR (CDCl$_3$), δ (ppm): 4.56(2H, s), 5.27(2H, s), 6.80(1H, s), 7.30–7.46(5H, m).

MS (M+H)=265

Step 3

Benzyl 4-formyl-1,3-thiazol-2-ylcarbamate was prepared in a similar manner according to Step 3 of Production Example 6.

$^1$H-NMR (CDCl$_3$), δ (ppm): 5.29(2H, s), 7.35–7.45(5H, m), 7.81(1H, s), 9.80(1H, s).

MS (M+H)=263

Step 4

Benzyl 4-[(E)-2-(4-nitrophenyl)ethenyl]-1,3-thiazol-2-ylcarbamate was prepared in a similar manner according to Step 4 of Production Example 6.

$^1$H-NMR (DMSO-d$_6$), δ (ppm): 5.23(2×⅗H, s), 5.25(2× ⅖H, s), 6.56–6.70(1H, m), 7.23(1H, s), 7.30–7.50(5H, m), 7.82(2×⅖H, d, J=7 Hz), 7.92(2×⅗H, d, J=7 Hz), 8.14(2× ⅗H, d, J=7 Hz), 8.21(2×⅖H, d, J=7 Hz).

MS (M+H)=382

Step 5

A mixture of benzyl 4-[(E)-2-(4-nitrophenyl)ethenyl]-1,3-thiazol-2-ylcarbamate (1.4 g), palladium on carbon (140 mg) and methanol (2 ml) was stirred under hydrogen atmosphere (4 atm) at ambient temperature for 8 hours. The catalyst was filtered off, and the filtrate was concentrated in vacuo to give benzyl 4-[2-(4-aminophenyl)ethyl]-1,3-thiazol-2-ylcarbamate (1.2 g).

¹H-NMR (CDCl₃), δ (ppm): 2.77–2.90(4H, m), 5.22(2H, s), 6.43(1H, s), 6.60(2H, d, J=7 Hz), 6.92(2H, d, J=7 Hz), 7.32–7.40(5H, m).

MS (M+H)=354

Step 6

A mixture of benzyl 4-[2-(4-aminophenyl)ethyl]-1,3-thiazol-2-ylcarbamate (25 mg), cyanamide (6.0 mg), 4N hydrogen chloride in ethyl acetate (0.018 ml) and ethanol (1 ml) was stirred at 100° C. for 72 hours. The reaction mixture was concentrated in vacuo. To the residue was added ethyl acetate (5 ml) and saturated aqueous sodium hydrogen bicarbonate (5 ml). The precipitated solid was filtered and washed with ethylacetate and water to give benzyl 4-[2-(4-{[amino(imino)methyl]amino}phenyl)ethyl]-1,3-thiazol-2-carbamate (15 mg).

¹H-NMR (DMSO-d₆), δ (ppm): 2.63–2.75(4H, m), 5.07 (2H, s), 6.40(1H, s), 6.94(2H, d, J=7 Hz), 7.25–7.40(7H, m).

MS (M+H)=396

PRODUCTION EXAMPLE 25

Synthesis of N-{4-[2-(4-{[amino(imino)methyl]amino}phenyl)ethyl]-1,3-thiazol-2-yl}benzamide hydrochloride Step 1

Benzyl 4-[(E)-2-(4-nitrophenyl)ethenyl]-1,3-thiazol-2-ylcarbamate (2.7 g) prepared in a similar manner according to Step 4 of Production Example 24 and 6N hydrochloric acid (50 ml) were combined. The reaction mixture was refluxed for 3 hours. After cooled to room temperature, the precipitate was filtered in vacuo. The solid was washed with water and acetonitrile to give 4-[(E)-2-(4-nitrophenyl)ethenyl]-1,3-thiazol-2-amine (1.34 g) as a yellow solid.

mp. 278–278.5° C.

¹H-NMR (DMSO-d₆), δ (ppm): 7.02(1H, s), 7.33(2H, s), 7.77(2H, d, J=8.5 Hz), 8.25(2H, d, J=8.5 Hz).

MS: 248(M+H)⁺

Step 2

4-[(E)-2-(4-Nitrophenyl)ethenyl]-1,3-thiazol-2-amine (300 mg) and N,N-dimethylaniline (4 ml) were combined under nitrogen atmosphere, and then benzoyl chloride (0.31 ml) was added dropwise to the suspension. The reaction mixture was stirred at 110° C. for 2 hours. After cooled to room temperature, the mixture was diluted with ethyl acetate. The organic solution was washed with 1N hydrochloric acid, water, saturated sodium hydrogen carbonate solution and saturated sodium chloride solution, dried over anhydrous magnesium sulfate, and concentrated in vacuo. The residual solid was washed with ethyl ether to give N-{4-[(E)-2-(4-nitrophenyl)ethenyl]-1,3-thiazol-2-yl}benzamide (298.6 mg) as a yellow solid.

mp. 224.5–225° C.

¹H-NMR (DMSO-d₆), δ (ppm): 7.40(1H, d, J=16.0 Hz), 7.45(1H, s), 7.53(1H, d, J=16.0 Hz), 7.56(2H, t, J=7.0 Hz), 7.66(1H, t, J=7.0 Hz), 7.84(2H, d, J=8.5 Hz), 8.13(2H, d, J=7.0 Hz), 8.23(2H, d, J=8.5 Hz), 12.80(1H, brs).

MS: 352(M+H)⁺

Step 3

N-{4-[2-(4-Aminophenyl)ethyl]-1,3-thiazol-2-yl}benzamide was prepared in a similar manner according to Step 2 of Production Example 9.

¹H-NMR (CDCl₃), δ (ppm): 2.82(4H, s), 3.57(2H, brs), 6.53(1H, s), 6.61(2H, d, J=8.0 Hz), 6.92(2H, d, J=8.0 Hz), 7.50(2H, t, J=7.0 Hz), 7.60(1H, t, J=7.0 Hz), 7.93(2H, d, J=7.0 Hz), 10.15(1H, brs).

MS: 324(M+H)⁺

Step 4

Di-tert-butyl {[(4-{2-[2-(benzoylamino)-1,3-thiazol-4-yl]ethyl}phenyl)amino]methylidene}biscarbamate was prepared in a similar manner according to Step 5 of Production Example 18.

mp. 143–144° C.

¹H-NMR (DMSO-d₆), δ (ppm): 1.39(9H, s), 1.51(9H, s), 2.95(4H, s), 6.86(1H, s), 7.22(2H, d, J=8.5 Hz), 7.44(2H, d, J=8.5 Hz), 7.54(2H, t, J=7.5 Hz), 7.63(1H, t, J=7.5 Hz), 8.10(2H, d, J=7.5 Hz), 9.94(1H, s), 11.44(1H, brs), 12.66 (1H, brs).

MS: 566(M+H)⁺

Step 5

The title compound was prepared in a similar manner according to Step 2 of Production Example 15.

mp. 229–232° C.

¹H-NMR (DMSO-d₆), δ (ppm): 2.91–3.05(4H, m), 6.88 (1H, s), 7.15(2H, d, J=8.5 Hz), 7.32(2H, d, J=8.5 Hz), 7.44(3H, brs), 7.54(2H, t, J=7.5 Hz), 7.64(1H, t, J=7.5 Hz), 8.10(2H, d, J=7.5 Hz), 9.88(1H, s).

MS: 366(M+H)⁺ free

PRODUCTION EXAMPLE 26

Synthesis of N-{4-[2-(4-{[amino(imino)methyl]amino}phenyl)ethyl]-5-[4-(methylsulfonyl)phenyl]-1,3-thiazol-2-yl}acetamide hydrochloride Step 1

4-(Methylsulfanyl)benzaldehyde (31.8 g), (acetylamino)acetic acid (24.5 g) and acetic anhydride (35 ml) were combined, and then sodium acetate (8.57 g) was added to the suspension at room temperature under nitrogen atmosphere. The reaction mixture was refluxed for 3.5 hours. After cooled to room temperature, the mixture was poured into ice-water and ethyl acetate with stirring, and filtered in vacuo. The filtrate was separated. The organic layer was washed with saturated sodium chloride solution, dried over anhydrous magnesium sulfate, and concentrated in vacuo. The residue and the previously obtained solid were combined, and the mixture was purified by flash column chromatography over silica gel with chloroform/ethyl acetate (30:1) as an eluent, and triturated with isopropyl ether to give (4Z)-2-methyl-4-(4-(methylsulfanyl)benzylidene)-1,3-oxazol-5(4H)-one (17.8 g) as a brown solid.

mp. 154–155° C.

¹H-NMR (DMSO-d₆), δ (ppm): 2.38(3H, s), 2.53(3H, s), 7.19(1H, s), 7.36(2H, d, J=8.5 Hz), 8.12(2H, d, J=8.5 Hz).

Step 2

(4Z)-2-Methyl-4-(4-(methylsulfanyl)benzylidene)-1,3-oxazol-5(4H)-one (17.5 g), 1,4-dioxane (100 ml) and 4N-hydrochloric acid (27 ml) were combined. The reaction mixture was refluxed for 3 hours. After cooled to room temperature, the mixture was concentrated in vacuo. Ethyl acetate and water were added to the residue, and the precipitate was filtered in vacuo to give 3-(4-(methylsulfanyl)phenyl)-2-oxopropanoic acid (6.7 g) as a pale brown solid.

mp. 165–167° C.

¹H-NMR (DMSO-d₆), δ (ppm): 2.48(3H, s), 6.37(1H, s), 7.23(2H, d, J=8.5 Hz), 7.70(2H, d, J=8.5 Hz), 9.44(1H, s).

MS: 209(M−H)⁺

Step 3

3-(4-(Methylsulfanyl)phenyl)-2-oxopropanoic acid (16.2 g), N,N-dimethylformamide (81 ml) and 1,8-diazabicyclo[5.4.0]undec-7-ene (11.5 ml) were combined at 0° C. under nitrogen atmosphere. The mixture was stirred at the same temperature for an hour, and then iodomethane (9.59 ml) was added to the solution at the same temperature. The reaction mixture was stirred at room temperature for 4 hours, poured into 1N-hydrochloric acid, and extracted with ethyl acetate (twice). The combined organic layer was washed with saturated sodium chloride solution, dried over anhydrous magnesium sulfate, and concentrated in vacuo. The residue was purified by flash column chromatography over silica gel with chloroform/ethyl acetate (30:1) as an eluent, and triturated with isopropyl ether/n-hexane to give methyl 3-(4-(methylsulfanyl)phenyl)-2-oxopropanoate (8.6 g) as a dark yellow solid.

mp. 112–113° C.

$^1$H-NMR (DMSO-$d_6$), δ (ppm): 2.48(3H, s), 3.79(3H, s), 6.41(1H, s), 7.24(2H, d, J=8.5 Hz), 7.72(2H, d, J=8.5 Hz), 9.52(1H, brs).

MS: 223(M−H)$^+$

Step 4

Methyl 3-(4-(methylsulfanyl)phenyl)-2-oxopropanoate (2.84 g), pyridinium tribromide (4.95 g), dichloromethane (140 ml) and acetic acid (0.5 ml) were combined at 0° C. under nitrogen atmosphere. The reaction mixture was stirred at 0° C. for 2 hours, and poured into water. The mixture was extracted with ethyl acetate (twice). The combined organic layer was dried over anhydrous magnesium sulfate, and concentrated in vacuo. The residual oil was dissolved in ethanol (55 ml), and then thiourea (1.25 g) was added to the solution. The reaction mixture was refluxed for 1 hour under nitrogen atmosphere. After cooled to 0° C., water was added to the solution. The precipitate was filtered in vacuo to give methyl 2-amino-5-[4-(methylthio)phenyl]-1,3-thiazole-4-carboxylate (2.67 g) as a brown solid.

mp. 184–185° C.

$^1$H-NMR (DMSO-$d_6$), δ (ppm): 2.50(3H, s), 3.64(3H, s), 7.25(2H, d, J=8.5 Hz), 7.34(2H, d, J=8.5 Hz).

MS: 281(M+H)$^+$

Step 5

Methyl 2-amino-5-[4-(methylthio)phenyl]-1,3-thiazole-4-carboxylate (8.8 g) was dissolved in pyridine (88 ml), and then acetyl chloride (6.7 ml) was added dropwise to the solution at 0° C. under nitrogen atmosphere. The reaction mixture was stirred at room temperature for 30 minutes and at 50° C. for 2 hours. After cooled to 0° C., water was added to the solution. The precipitate was filtered in vacuo, and the solid was washed with ethyl ether to give methyl 2-(acetylamino)-5-[4-(methylthio)phenyl]-1,3-thiazole-4-carboxylate (9.3 g) as an off-white solid.

mp. 253–254.5° C.

$^1$H-NMR (DMSO-$d_6$), δ (ppm): 2.16(3H, s), 2.52(3H, s), 3.70(3H, s), 7.30(2H, d, J=8.5 Hz), 7.44(2H, d, J=8.5 Hz).

MS: 323(M+H)$^+$

Step 6

Methyl 2-(acetylamino)-5-[4-(methylthio)phenyl]-1,3-thiazole-4-carboxylate (200 mg) was dissolved in tetrahydrofuran (2 ml), and then lithium aluminium hydride (35.3 mg) was added portionwise to the solution at 0° C. The reaction mixture was stirred at 0° C. for 30 minutes and at room temperature for 30 minutes, and quenched with methanol. Ethyl acetate and 1N hydrochloric acid were added to the mixture, and extracted. The aqueous layer was extracted with ethyl acetate (twice). The combined organic layer was washed with saturated sodium chloride solution, dried over anhydrous magnesium sulfate, and concentrated in vacuo. The residual solid was dissolved in methanol (0.4 ml) and chloroform (7 ml). Then manganase (IV) oxide (1.08 g) was added to the solution under nitrogen atmosphere. The reaction mixture was stirred at room temperature for 13 hours, and filtered through a celite pad. The filtrate was concentrated in vacuo. The residue was purified by flash column chromatography over silica gel with chloroform/methanol (20:1) as an eluent to give N-{4-formyl-5-[4-(methylthio)phenyl]-1,3-thiazol-2-yl}acetamide (153.6 mg) as a pale brown amorphous substance.

$^1$H-NMR (DMSO-$d_6$), δ (ppm): 2.18(3H, s), 2.54(3H, s), 7.38(2H, d, J=8.5 Hz), 7.58(2H, d, J=8.5 Hz), 9.77(1H, s), 12.59(1H, 20 brs).

MS: 293(M+H)$^+$

Step 7

N-{5-[4-(Methylthio)phenyl]-4-[(E)-2-(4-nitrophenyl)ethenyl]-1,3-thiazol-2-yl}acetamide was prepared in a similar manner according to Step 1 of Production Example 9.

mp. 228–230° C.

$^1$H-NMR (DMSO-$d_6$), δ (ppm): 2.19(3H, s), 2.54(3H, s), 7.32(1H, d, J=16.0 Hz), 7.40(2H, d, J=8.5 Hz), 7.46(1H, d, J=16.0 Hz), 7.47(2H, d, J=8.5 Hz), 7.79(2H, d, J=9.0 Hz), 8.19(2H, d, J=9.0 Hz), 12.38(1H, brs).

MS: 412(M+H)$^+$

Step 8

Potassium peroxymonosulfate (408 mg) was suspended in water (1 ml) and tetrahydrofuran (1 ml), and then N-{5-[4-(methylthio)phenyl]-4-[(E)-2-(4-nitrophenyl)ethenyl]-1,3-thiazol-2-yl}acetamide (182 mg) in tetrahydrofuran (3 ml) was added dropwise to the suspension at 0° C. The reaction mixture was stirred at room temperature for 2 hours, and then water was added to the suspension. The precipitate was filtered in vacuo. The solid was washed with water and ethyl acetate to give N-{5-[4-(methylsulfonyl)phenyl]-4-[(E)-2-(4-nitrophenyl)ethenyl]-1,3-thiazol-2-yl}acetamide (83 mg) as a yellow solid.

mp. 294–295° C.

$^1$H-NMR (DMSO-$d_6$), δ (ppm): 2.21(3H, s), 3.30(3H, s), 7.40(1H, d, J=16.0 Hz), 7.54(1H, d, J=16.0 Hz), 7.82(2H, d, J=8.5 Hz), 7.84(2H, d, J=8.5 Hz), 8.05(2H, d, J=8.5 Hz), 8.20(2H, d, J=8.5 Hz), 12.51(1H, brs).

MS: 442(M−H)$^+$

Step 9

N-{4-[2-(4-Aminophenyl)ethyl]-5-[4-(methylsulfonyl)phenyl]-1,3-thiazol-2-yl}acetamide was prepared in a similar manner according to Step 2 of Production Example 9.

mp. 202–204° C.

$^1$H-NMR (DMSO-$d_6$), δ (ppm): 2.17(3H, s), 2.77–2.88 (4H, m), 3.24(3H, s), 6.84(2H, brs), 6.45(2H, d, J=8.5 Hz), 6.77(2H, d, J=8.5 Hz), 7.49(2H, d, J=8.5 Hz), 7.91(2H, d, J=8.5 Hz), 12.34(1H, brs).

MS: 416(M+H)$^+$

Step 10

Di-tert-butyl {[(4-{2-[2-(acetylamino)-5-(4-(methylsulfonyl)phenyl)-1,3-thiazol-4-yl]ethyl}phenyl)amino]methylidene}biscarbamate was prepared in similar manner according to Step 5 of Production Example 18.

$^1$H-NMR (DMSO-$d_6$), δ (ppm): 1.39(9H, s), 1.51(9H, s), 2.17(3H, s), 2.97(4H, s), 3.24(3H, s), 7.11(2H, d, J=8.5 Hz), 7.38(2H, d, J=8.5 Hz), 7.56(2H, d, J=8.5 Hz), 7.92(2H, d, J=8.5 Hz), 9.92(1H, s), 11.43(1H, brs), 12.34(1H, brs).

MS: 658(M+H)$^+$

Step 11

The title compound was prepared in a similar manner according to Step 2 of Production Example 15.

mp. 145–146.5° C.

$^1$H-NMR (DMSO-d$_6$), δ (ppm): 2.18(3H, s), 2.99(4H, brs), 3.25(3H, s), 7.11(2H, d, J=8.0 Hz), 7.22(2H, d, J=8.0 Hz), 7.38(3H, brs), 7.57(2H, d, J=8.0 Hz), 7.94(2H, d, J=8.0 Hz), 9.79(1H, s), 12.36(1H, brs).

MS: 458(M+H)$^+$ free

PRODUCTION EXAMPLE 27

Synthesis of 2-(acetylamino)-4-[2-(4-{[amino(imino)methyl]amino}phenyl)ethyl]-N-methyl-1,3-thiazole-5-carboxamide hydrochloride Step 1

Ethyl 2-(acetylamino)-4-[2-(4-aminophenyl)ethyl]-1,3-thiazole-5-carboxylate (310 mg) prepared in a similar manner according to Step 3 of Production Example 22 was dissolved in tetrahydrofuran (6 ml) under nitrogen atmosphere. Then di(tert-butyl)dicarbonate (223 mg) in tetrahydrofuran (1 ml) was added to the solution at room temperature. The reaction mixture was refluxed for 2 hours. After cooled to room temperature, the mixture was concentrated in vacuo. The residual solid was washed with ethyl ether to give ethyl 2-(acetylamino)-4-(2-{4-[(tert-butoxycarbonyl)amino]phenyl}ethyl)-1,3-thiazole-5-carboxylate (370.7 mg) as an off-white 30 solid.

mp. 213–214° C.

$^1$H-NMR (DMSO-d$_6$), δ (ppm): 1.26(3H, t, J=7.0 Hz), 1.46(9H, s), 2.17(3H, s), 2.85(2H, t, J=7.5 Hz), 3.23(2H, t, J=7.5 Hz), 4.22(2H, q, J=7.0 Hz), 7.04(2H, d, J=8.5 Hz), 7.33(2H, d, J=8.5 Hz), 9.23(1H, brs), 12.55(1H, brs).

MS: 434(M+H)$^+$

Step 2

Ethyl 2-(acetylamino)-4-(2-{4-[(tert-butoxycarbonyl)amino]phenyl}ethyl)-1,3-thiazole-5-carboxylate (3 g), 1N-aqueous sodium hydroxide solution (17.3 ml) and ethanol (30 ml) were combined, and the mixture was refluxed for 5 hours. After cooled to room temperature, the organic solvent was removed in vacuo. The aqueous solution was acidified (pH=4) with 1N-hydrochloric acid, and extracted with ethyl acetate (twice). The combined organic layer was dried over anhydrous magnesium sulfate, and concentrated in vacuo. The residual solid was dissolved in pyridine (45 ml), and then acetyl chloride (1.48 ml) was added dropwise to the solution at 0° C. under nitrogen atmosphere. The reaction mixture was stirred at room temperature for 13 hours, and pyridine was removed in vacuo. Water was added to the residue, and acidified with 1N-hydrochloric acid. The precipitate was collected in vacuo. The solid was washed with water and ethyl ether to give 2-(acetylamino)-4-(2-{4-[(tert-butoxycarbonyl)amino]phenyl}ethyl)-1,3-thiazole-5-carboxylic acid (2.23 g) as an off-white solid.

mp. 237–238° C.

$^1$H-NMR (DMSO-d$_6$), δ (ppm): 1.46(9H, s), 2.16(3H, s), 2.85(2H, m), 3.23(2H, m), 7.04(2H, d, J=8.5 Hz), 7.33(2H, d, J=8.5 Hz), 9.24(1H, brs), 12.46(1H, s).

MS: 404(M−H)$^+$

Step 3

A mixture of 2-(acetylamino)-4-(2-{4-[(tert-butoxycarbonyl)amino]phenyl}ethyl)-1,3-thiazole-5-carboxylic acid (80 mg), 30% methylamine in ethanol solution (0.02 ml), 1-hydroxybenzotriazole (29.3 mg) and 1-ethyl-3-(3-dimethylaminopropyl)carbodiimide hydrochloride (39.7 mg) in dichloromethane (1 ml) and N,N-dimethylformamide (0.5 ml) was stirred at ambient temperature for 20 hours. The reaction mixture was poured into saturated sodium hydrogen carbonate solution, and extracted with chloroform. The organic layer was washed with water and saturated sodium chloride solution, dried over anhydrous magnesium sulfate, and concentrated in vacuo to give tert-butyl 4-(2-{2-(acetylamino)-5-[(methylamino)carbonyl]-1,3-thiazol-4-yl}ethyl)phenylcarbamate (92.8 mg) as an off-white amorphous substance.

$^1$H-NMR (DMSO-d$_6$), δ (ppm): 1.46(9H, s), 2.15(3H, s), 2.69(3H, d, J=4.5 Hz), 2.78–2.86(2H, m), 3.12–3.20(2H, m), 7.06(2H, d, J=8.5 Hz), 7.33(2H, d, J=8.5 Hz), 7.91(1H, q, J=4.5 Hz), 9.22(1H, brs), 12.34(1H, brs).

MS: 419(M+H)$^+$

Step 4 tert-Butyl 4-(2-{2-(acetylamino)-5-[(methylamino)carbonyl]-1,3-thiazol-4-yl}ethyl)phenylcarbamate (95 mg) and trifluoroacetic acid (2 ml) were combined at 0° C. The reaction mixture was stirred at room temperature for an hour, and concentrated in vacuo. The residue was dissolved in chloroform. The organic solution was washed with 1N sodium hydroxide solution, water and saturated sodium chloride solution, dried over anhydrous magnesium sulfate, and concentrated in vacuo. The residue was purified by preparative silica gel column chromatography with chloroform/methanol (10:1) as an eluent to give 2-(acetylamino)-4-[2-(4-aminophenyl)ethyl]-N-methyl-1,3-thiazole-5-carboxamide (49 mg) as an off-white amorphous substance.

$^1$H-NMR (DMSO-d$_6$), δ (ppm): 2.15(3H, s), 2.68(3H, d, J=4.5 Hz), 2.67–2.75(2H, m), 3.05–3.15(2H, m), 4.83(2H, brs), 6.47(2H, d, J=8.5 Hz), 6.84(2H, d, J=8.5 Hz), 7.85(1H, q, J=4.5 Hz), 12.33(1H, brs).

MS: 319(M+H)$^+$

Step 5

Di-tert-butyl {[(4-{2-[2-(acetylamino)-5-(methylaminocarbonyl)-1,3-thiazol-4-yl]ethyl}phenyl)amino]methylidene}biscarbamate was prepared in a similar manner according to Step 5 of Production Example 18.

mp. 245–246° C.

$^1$H-NMR (DMSO-d$_6$), δ (ppm): 1.40(9H, s), 1.51(9H, s), 2.14(3H, s), 2.68(3H, d, J=4.5 Hz), 2.85–2.94(2H, m), 3.14–3.25(2H, m), 7.17(2H, d, J=8.5 Hz), 7.41(2H, d, J=8.5 Hz), 7.88(1H, q, J=4.5 Hz), 9.94(1H, s), 11.44(1H, brs), 12.38(1H, brs).

MS: 561(M+H)$^+$

Step 6

The title compound was prepared in a similar manner according to Step 2 of Production Example 15.

mp. 101–104° C.

$^1$H-NMR (DMSO-d$_6$), δ (ppm): 2.16(3H, s), 2.67(3H, d, J=4.5 Hz), 2.86–2.96(2H, m), 3.16–3.26(2H, m), 7.14(2H, d, J=8.5 Hz), 7.26(2H, d, J=8.5 Hz), 7.41(3H, brs), 7.99(1H, q, J=4.5 Hz), 9.81(1H, s), 12.36(1H, brs).

MS: 361(M+H)$^+$ free

PRODUCTION EXAMPLE 28

Synthesis of 2-(acetylamino)-4-[2-(4-{[amino(imino)methyl]amino}phenyl)ethyl]-N-phenyl-1,3-thiazole-5-carboxamide hydrochloride Step 1

A mixture of 2-(acetylamino)-4-(2-{4-[(tert-butoxycarbonyl)amino]phenyl}ethyl)-1,3-thiazole-5-carboxylic acid (80.mg), aniline (0.019 ml), benzotriazole-1-yl-oxy-tris-pyrrolidino-phosphonium hexafluorophosphate (113 mg) and N,N-diisopropylethylamine (0.076 ml) in N,N-dimethylformamide (2 ml) was stirred at ambient temperature for 21 hours and at 55° C. for 3 hours. The reaction mixture was poured into 1N hydrochloric acid, and extracted with chloroform. The organic layer was washed with water, saturated sodium hydrogen carbonate solution and saturated sodium chloride solution, dried over anhydrous magnesium sulfate, and concentrated in vacuo. The residual solid was washed with ethyl ether to give tert-butyl 4-{2-[2-(acetylamino)-5-(anilinocarbonyl)-1,3-thiazol-4-yl]ethyl}phenylcarbamate (57.2 mg) as a colorless solid.

mp. 199–200° C.

$^1$H-NMR (DMSO-$d_6$), δ (ppm): 1.46(9H, s), 2.18(3H, s), 2.81–2.91(2H, m), 3.14–3.24(2H, m), 7.05(2H, d, J=8.5 Hz), 7.08(1H, t, J=8.5 Hz), 7.26–7.36(4H, m), 7.64(2H, d, J=8.5 Hz), 9.22(1H, brs), 9.95(1H, brs), 12.44(1H, brs).

MS: 481(M+H)$^+$

Step 2

2-(Acetylamino)-4-[2-(4-aminophenyl)ethyl]-N-phenyl-1,3-thiazole-5-carboxamide was prepared from tert-butyl 4-{2-[2-(acetylamino)-5-(anilinocarbonyl)-1,3-thiazol-4-yl]ethyl}phenylcarbamate in a similar manner according to Step 4 of Production Example 27.

mp. 104–105° C.

$^1$H-NMR (DMSO-$d_6$), δ (ppm): 2.18(3H, s), 2.71–2.81(2H, m), 3.09–3.18(2H, m), 5.07(2H, brs), 6.48(2H, d, J=8.0 Hz), 6.85(2H, d, J=8.0 Hz), 7.08(1H, t, J=8.0 Hz), 7.33(2H, t, J=8.0 Hz), 7.65(2H, d, J=8.0 Hz), 9.93(1H, brs), 12.44(1H, brs).

MS: 381(M+H)$^+$

Step 3

Di-tert-butyl {(Z)-[(4-{2-[2-(acetylamino)-5-(anilinocarbonyl)-1,3-thiazol-4-yl]ethyl}phenyl)amino]methylidene}biscarbamate was prepared from 2-(acetylamino)-4-[2-(4-aminophenyl)ethyl]-N-phenyl-1,3-thiazole-5-carboxamide in a similar manner according to Step 5 of Production Example 18.

$^1$H-NMR (DMSO-$d_6$), δ (ppm): 1.39(9H, s), 1.51(9H, s), 2.18(3H, s), 2.87–2.98(2H, m), 3.17–3.29(2H, m), 7.08(1H, t, J=8.0 Hz), 7.16(2H, d, J=8.5 Hz), 7.31(2H, t, J=8.0 Hz), 7.41(2H, d, J=8.5 Hz), 7.64(2H, d, J=8.0 Hz), 9.93(2H, s), 11.43(1H, brs), 12.46(1H, brs).

MS: 623(M+H)$^+$

Step 4

The title compound was prepared from di-tert-butyl {(Z)-[(4-{2-[2-(acetylamino)-5-(anilinocarbonyl)-1,3-thiazol-4-yl]ethyl}phenyl)amino]methylidene}biscarbamate in a similar manner according to Step 6 of Production Example 27.

mp. 152–155° C.

$^1$H-NMR (DMSO-$d_6$), δ (ppm): 2.19(3H, s), 2.90–3.01(2H, m), 3.17–3.29(2H, m), 7.09(1H, t, J=8.0 Hz), 7.13(2H, d, J=8.0 Hz), 7.26(2H, d, J=8.0 Hz), 7.33(2H, t, J=8.0 Hz), 7.40(3H, brs), 7.64(2H, d, J=8.0 Hz), 9.79(1H, s), 10.02(1H, s), 12.46(1H, s).

MS: 423(M+H)$^+$ free

PRODUCTION EXAMPLE 29

Synthesis of 2-(acetylamino)-4-[2-(4-{[amino(imino)methyl]amino}phenyl)ethyl]-N,N-dimethyl-1,3-thiazole-5-carboxamide hydrochloride Step 1 tert-Butyl [4-(2-{2-(acetylamino)-5-[(dimethylamino)carbonyl]-1,3-thiazol-4-yl}ethyl)phenyl]carbamate was prepared from the compound of Step 2 of Production Example 27 in a similar manner according to Step 3 of Production Example 27.

$^1$H-NMR (DMSO-$d_6$), δ (ppm): 1.46(9H, s), 2.14(3H, s), 2.84(4H, s), 2.85(6H, s), 7.01(2H, d, J=8.5 Hz), 7.31(2H, d, J=8.5 Hz), 9.21(1H, brs), 12.33(1H, brs).

MS: 433(M+H)$^+$

Step 2

2-(Acetylamino)-4-[2-(4-aminophenyl)ethyl]-N,N-dimethyl-1,3-thiazole-5-carboxamide was prepared from tert-butyl [4-(2-{2-(acetylamino)-5-[(dimethylamino)carbonyl]-1,3-thiazol-4-yl}ethyl)phenyl]carbamate in a similar manner according to Step 4 of Production Example 27.

$^1$H-NMR (DMSO-$d_6$), δ (ppm): 2.14(3H, s), 2.70–2.77(4H, m), 2.86(6H, s), 4.83(2H, s), 6.45(2H, d, J=8.5 Hz), 6.78(2H, d, J=8.5 Hz), 12.32(1H, brs).

MS: 333(M+H)$^+$

Step 3

Di-tert-butyl ((Z)-{[4-(2-{2-(acetylamino)-5-[(dimethylamino)carbonyl]-1,3-thiazol-4-yl}ethyl)phenyl]amino}methylidene)biscarbamate was prepared from 2-(acetylamino)-4-[2-(4-aminophenyl)ethyl]-N,N-dimethyl-1,3-thiazole-5-carboxamide in a similar manner according to Step 5 of Production Example 18.

$^1$H-NMR (DMSO-$d_6$), δ (ppm): 1.39(9H, s), 1.51(9H, s), 2.14(3H, s), 2.85(6H, s), 2.89(4H, s), 7.12(2H, d, J=8.5 Hz), 7.40(2H, d, J=8.5 Hz), 9.92(1H, s), 11.43(1H, brs), 12.36(1H, brs).

MS: 575(M+H)$^+$

Step 4

The title compound was prepared from di-tert-butyl ((Z)-{[4-(2-{2-(acetylamino)-5-[(dimethylamino)carbonyl]-1,3-thiazol-4-yl}ethyl)phenyl]amino}methylidene)biscarbamate in a similar manner according to Step 6 of Production Example 27.

mp. 78–80° C.

$^1$H-NMR (DMSO-$d_6$), δ (ppm): 2.15(3H, s), 2.81–2.96(4H, m), 2.88(6H, s), 7.11(2H, d, J=8.5 Hz), 7.18(2H, d, J=8.5 Hz), 7.38(3H, brs), 9.77(1H, s), 12.34(1H, s).

MS: 375(M+H)$^+$ free

PRODUCTION EXAMPLE 30

Synthesis of 2-(acetylamino)-4-[2-(4-{[amino(imino)methyl]amino}phenyl)ethyl]-N-benzyl-1,3-thiazole-5-carboxamide hydrochloride Step 1 tert-Butyl [4-(2-{2-(acetylamino)-5-[(benzylamino)carbonyl]-1,3-thiazol-4-yl}ethyl)phenyl]carbamate was prepared from the compound of Step 2 of Production Example 27 in a similar manner according to Step 3 of Production Example 27.

mp. 184–185° C.

$^1$H-NMR (DMSO-$d_6$), δ (ppm): 1.46(9H, s), 2.15(3H, s), 2.79–2.87(2H, m), 3.12–3.22(2H, m), 4.37(2H, d, J=6.5 Hz), 7.02(2H, d, J=8.5 Hz), 7.18–7.36(7H, m), 8.56(1H, t, J=6.5 Hz), 9.22(1H, brs), 12.37(1H, brs).

MS: 495(M+H)$^+$

Step 2

2-(Acetylamino)-4-[2-(4-aminophenyl)ethyl]-N-benzyl-1,3-thiazole-5-carboxamide was prepared from tert-butyl [4-(2-{2-(acetylamino)-5-[(benzylamino)carbonyl]-1,3-thiazol-4-yl}ethyl)phenyl]carbamate in a similar manner according to Step 4 of Production Example 27.

mp. 200–201° C.

$^1$H-NMR (DMSO-$d_6$), δ (ppm): 2.15(3H, s), 2.66–2.76 (2H, m), 3.07–3.15(2H, m), 4.38(2H, d, J=6.0 Hz), 4.83(2H, s), 6.46(2H, d, J=8.5 Hz), 6.81(2H, d, J=8.5 Hz), 7.20–7.36 (5H, m), 8.52(1H, t, J=6.0 Hz), 12.32(1H, brs).

MS: 395(M+H)$^+$

Step 3

Di-tert-butyl ((Z)-{[4-(2-{2-(acetylamino)-5-[(benzylamino)carbonyl]-1,3-thiazol-4-yl}ethyl)phenyl]amino}methylidene)biscarbamate was prepared from 2-(acetylamino)-4-[2-(4-aminophenyl)ethyl]-N-benzyl-1,3-thiazole-5-carboxamide in a similar manner according to Step 5 of Production Example 18.

$^1$H-NMR (DMSO-$d_6$), δ (ppm): 1.39(9H, s), 1.51(9H, s), 2.15(3H, s), 2.85–2.94(2H, m), 3.16–3.25(2H, m), 4.37(2H, d, J=6.0 Hz), 7.12(2H, d, J=8.5 Hz), 7.22–7.36(5H, m), 7.40(2H, d, J=8.5 Hz), 8.32(1H, s), 8.54(1H, t, J=6.0 Hz), 9.94(1H, brs), 11.44(1H, brs).

MS: 637(M+H)$^+$

Step 4

The title compound was prepared from di-tert-butyl ((Z)-{[4-(2-{2-(acetylamino)-5-[(benzylamino)carbonyl]-1,3-thiazol-4-yl}ethyl)phenyl]amino}methylidene)biscarbamate in a similar manner according to Step 6 of Production Example 27.

mp. 128–130° C.

$^1$H-NMR (DMSO-$d_6$), δ (ppm): 2.17(3H, s), 2.85–2.96 (2H, m), 3.16–3.27(2H, m), 4.36(2H, d, J=6.0 Hz), 7.12(2H, d, J=8.5 Hz), 7.17–7.35(7H, m), 7.40(3H, brs), 8.66(1H, t, J=6.0 Hz), 9.78(1H, s), 12.38(1H, s).

MS: 437(M+H)$^+$ free

PRODUCTION EXAMPLE 31

Synthesis of 2-(acetylamino)-4-[2-(4-{[amino (imino)methyl]amino}phenyl)ethyl]-N-(4-nitrobenzyl)-1,3-thiazole-5-carboxamide hydrochloride Step 1

A mixture of 2-(acetylamino)-4-(2-{4-[(tert-butoxycarbonyl)amino]phenyl}ethyl)-1,3-thiazole-5-carboxylic acid (100 mg), (4-nitrobenzyl)amine hydrochloride (46.5 mg), 1-hydroxybenzotriazole (36.7 mg) and 1-ethyl-3-(3-dimethylaminopropyl)carbodiimide (40.2 mg) in DMF (2 ml) was stirred at ambient temperature for 73 hours. The reaction mixture was poured into saturated NaHCO$_3$, and extracted with CHCl$_3$. The organic layer was washed with water and brine, dried over anhydrous MgSO$_4$, and concentrated in vacuo to give tert-butyl{4-[2-(2-(acetylamino)-5-{[(4-nitrobenzyl)amino]carbonyl}-1,3-thiazol-4-yl)ethyl]phenyl}carbamate (123.7 mg) as a pale yellow solid.

mp. 204–205° C.

$^1$H-NMR (DMSO-$d_6$), δ (ppm): 1.46(9H, s), 2.16(3H, s), 2.77–2.91(2H, m), 3.12–3.27(2H, m), 4.49(2H, d, J=5.5 Hz), 7.01(2H, d, J=8.5 Hz), 7.32(2H, d, J=8.5 Hz), 7.52(2H, d, J=8.5 Hz), 8.21(2H, d, J=8.5 Hz), 8.68(1H, t, J=5.5 Hz), 9.21(1H, s), 12.40(1H, s).

MS: 540(M+H)$^+$

Step 2 tert-Butyl {4-[2-(2-(acetylamino)-5-{[(4-nitrobenzyl)amino]carbonyl}-1,3-thiazol-4-yl)ethyl]phenyl}carbamate (135 mg) and TFA (2 ml) were combined at 0° C. The reaction mixture was stirred at room temperature for an hour, and concentrated in vacuo. The residue was dissolved in MeOH and CHCl$_3$, and made basic (pH=8) by 1N—NaOH. The mixture was concentrated in vacuo. The residual solid was washed with water to give 2-(acetylamino)-4-[2-(4-aminophenyl)ethyl]-N-(4-nitrobenzyl)-1,3-thiazole-5-carboxamide (92.5 mg) as a pale yellow solid.

mp. 120–121° C.

$^1$H-NMR (DMSO-$d_6$), δ (ppm): 2.16(3H, s), 2.65–2.81 (2H, m), 3.04–3.21(2H, m), 4.49(2H, d, J=5.5 Hz), 5.65(2H, brs), 6.54(2H, d, J=8.0 Hz), 6.86(2H, d, J=8.0 Hz), 7.54(2H, d, J=8.5 Hz), 8.21(2H, d, J=8.5 Hz), 8.67(1H, t, J=5.5 Hz), 12.39(1H, s).

MS: 440(M+H)$^+$

Step 3

2-(Acetylamino)-4-[2-(4-aminophenyl)ethyl]-N-(4-nitrobenzyl)-1,3-thiazole-5-carboxamide (83 mg), N,N'-bis(tert-butoxycarbonyl)-1H-pyrazole-1-carboxamidine (58.6 mg) and THF (1 ml) were combined under N$_2$ atmosphere. The reaction mixture was stirred at r.t. for 2 hours, and concentrated in vacuo. The residual solid was washed with AcOEt to give di-tert-butyl [(Z)-({4-[2-(2-(acetylamino)-5-{[(4-nitrobenzyl)amino]carbonyl}-1,3-thiazol-4-yl)ethyl]phenyl}amino)methylidene]biscarbamate (95.4 mg) as an off-white solid.

mp. 251–253° C.

$^1$H-NMR (DMSO-$d_6$), δ (ppm): 1.38(9H, s), 1.51(9H, s), 2.16(3H, s), 2.81–2.98(2H, m), 3.16–3.29(2H, m), 4.49(2H, d, J=5.5 Hz), 7.12(2H, d, J=8.0 Hz), 7.40(2H, d, J=8.0 Hz), 7.53(2H, d, J=8.5 Hz), 8.20(2H, d, J=8.5 Hz), 8.67(1H, t, J=5.5 Hz), 9.93(1H, s), 11.44(1H, s), 12.42(1H, s).

MS: 682(M+H)$^+$

Step 4

Di-tert-butyl [(Z)-({4-[2-(2-(acetylamino)-5-{[(4-nitrobenzyl)amino]carbonyl}-1,3-thiazol-4-yl)ethyl]phenyl}amino)methylidene]biscarbamate (70 mg) and 4N HCl in 1,4-dioxane solution (1.5 ml) were combined under N$_2$ atmosphere. The reaction mixture was stirred at r.t. for 14 hours. The solvent was removed in vacuo. The residue was washed with AcOEt to give 2-(acetylamino)-4-[2-(4-{[amino(imino)methyl]amino}phenyl)ethyl]-N-(4-nitrobenzyl)-1,3-thiazole-5-carboxamide hydrochloride (63.7 mg) as a pale green solid.

mp. 138–140° C.

$^1$H-NMR (DMSO-$d_6$), δ (ppm): 2.17(3H, s), 2.81–3.00 (2H, m), 3.17–3.30(2H, m), 4.48(2H, d, J=5.5 Hz), 7.12(2H, d, J=8.0 Hz), 7.25(2H, d, J=8.0 Hz), 7.40(3H, s), 7.55(2H, d, J=8.0 Hz), 8.21(2H, d, J=8.5 Hz), 8.80(1H, t, J=5.5 Hz), 9.81(1H, s), 12.42(1H, s).

MS: 482(M+H)$^+$ free

PRODUCTION EXAMPLE 32

Synthesis of 2-(acetylamino)-4-[2-(4-{[amino(imino)methyl]amino}phenyl)ethyl]-N-[4-(methylsulfonyl)benzyl]-1,3-thiazole-5-carboxamide hydrochloride Step 1

A mixture of 2-(acetylamino)-4-(2-{4-[(tert-butoxycarbonyl)amino]phenyl}ethyl)-1,3-thiazole-5-carboxylic acid (120 mg), [4-(methylthio)benzyl]amine (45.4 mg), 1-hydroxybenzotriazole (44 mg) and 1-ethyl-3-(3-dimethylaminopropyl)carbodiimide hydrochloride (59.6 mg) in DMF (2 ml) was stirred at r.t. for 17 hours. The reaction mixture was poured into saturated NaHCO₃, and extracted with CHCl₃. The organic layer was washed with water and brine, dried over anhydrous MgSO₄, and concentrated in vacuo. The residue was purified by preparative silica gel chromatography with CHCl₃/AcOEt (1:1) as an eluent to give tert-butyl (4-{2-[2-(acetylamino)-5-({[4-(methylthio)benzyl]amino}carbonyl)-1,3-thiazol-4-yl]ethyl}phenyl)carbamate (163.5 mg) as an off-white solid.

mp. 182–183° C.

$^1$H-NMR (DMSO-$d_6$), δ (ppm): 1.46(9H, s), 2.15(3H, s), 2.45(3H, s), 2.77–2.91(2H, m), 3.09–3.24(2H, m), 4.32(2H, d, J=5.5 Hz), 7.02(2H, d, J=8.5 Hz), 7.22(4H, s), 7.33(2H, d, J=8.5 Hz), 8.54(1H, t, J=5.5 Hz), 9.22(1H, s), 12.36(1H, s).

MS: 541(M+H)⁺

Step 2

Potassium peroxymonosulfate (264 mg) was suspended in water (1 ml) and THF (1 ml), and then tert-butyl (4-{2-[2-(acetylamino)-5-({[4-(methylthio)benzyl]amino}carbonyl)-1,3-thiazol-4-yl]ethyl}phenyl)carbamate (155 mg) in THF (2 ml) was added dropwise to the suspension at 0° C. The reaction mixture was stirred at r.t. for an hour, and then water was added to the suspension. The solution was extracted with AcOEt (twice). The combined organic layer was washed with brine, dried over anhydrous MgSO₄, and concentrated in vacuo to give tert-butyl (4-{2-[2-(acetylamino)-5-({[4-(methylsulfonyl)benzyl]amino}carbonyl)-1,3-thiazol-4-yl]ethyl}phenyl)carbamate (140.6 mg) as an off-white solid.

mp. 192.5–193° C.

$^1$H-NMR (DMSO-$d_6$), δ (ppm): 1.46(9H, s), 2.16(3H, s), 2.73–2.90(2H, m), 3.11–3.27(2H, m), 3.18(3H, s), 4.47(2H, d, J=5.5 Hz), 7.03(2H, d, J=8.5 Hz), 7.33(2H, d, J=8.5 Hz), 7.53(2H, d, J=8.5 Hz), 7.89.(2H, d, J=8.5 Hz), 8.68(1H, t, J=5.5 Hz), 9.22(1H, s), 12.39(1H, s).

MS: 573(M+H)⁺

Step 3

2-(Acetylamino)-4-[2-(4-aminophenyl)ethyl]-N-[4-(methylsulfonyl)benzyl]-1,3-thiazole-5-carboxamide was prepared in a similar manner according to Step 2 of Production Example 31.

mp. 78–80° C.

$^1$H-NMR (DMSO-$d_6$), δ (ppm): 2.16(3H, s), 2.65–2.80 (2H, m), 3.04–3.22(2H, m), 3.19(3H, s), 4.46(2H, d, J=5.5 Hz), 4.82(2H, s), 6.46(2H, d, J=8.0 Hz), 6.81(2H, d, J=8.0 Hz), 7.53(2H, d, J=8.0 Hz), 7.89(2H, d, J=8.0 Hz), 8.63(1H, t, J=5.5 Hz), 12.39(1H, s).

MS: 473(M+H)⁺

Step 4

Di-tert-butyl {(Z)-[(4-{2-[2-(acetylamino)-5-({[4-(methylsulfonyl)benzyl]amino}carbonyl)-1,3-thiazol-4-yl]ethyl}phenyl)amino]methylidene}biscarbamate was prepared in a similar manner according to Step 3 of Production Example 31.

$^1$H-NMR (DMSO-$d_6$), δ (ppm): 1.39(9H, s), 1.51(9H, s), 2.16(3H, s), 2.81–2.98(2H, m), 3.18(3H, s), 3.18–3.29(2H, m), 4.46(2H, d, J=5.5 Hz), 7.14(2H, d, J=8.5 Hz), 7.41(2H, d, J=8.5 Hz), 7.54(2H, d, J=8.5 Hz), 7.88(2H, d, J=8.5 Hz), 8.67(1H, t, J=5.5 Hz), 9.94(1H, s), 11.44(1H, s), 12.41(1H, s).

MS: 715(M+H)⁺

Step 5

The title compound was prepared in a similar manner according to Step 4 of Production Example 31.

mp. 94–96° C.

$^1$H-NMR (DMSO-$d_6$), δ (ppm): 2.17(3H, s), 2.85–2.99 (2H, m), 3.19(3H, s), 3.19–3.30(2H, m), 4.46(2H, d, J=5.5 Hz), 7.13(2H, d, J=8.5 Hz), 7.25(2H, d, J=8.5 Hz), 7.40(3H, s), 7.54(2H, d, J=8.5 Hz), 7.89(2H, d, J=8.5 Hz), 8.78(1H, t, J=5.5 Hz), 9.80(1H, s), 12.41(1H, s).

MS: 515(M+H)⁺ free

PRODUCTION EXAMPLE 33

Synthesis of 2-(acetylamino)-4-[2-(4-{[amino(imino)methyl]amino}phenyl)ethyl]-N-[4-(trifluoromethyl)benzyl]-1,3-thiazole-5-carboxamide hydrochloride Step 1 tert-Butyl (4-{2-[2-(acetylamino)-5-({[4-(trifluoromethyl)benzyl]amino}carbonyl)-1,3-thiazol-4-yl]ethyl}phenyl)carbamate was prepared from 2-(acetylamino)-4-(2-{4-[(tert-butoxycarbonyl)amino]phenyl}ethyl)-1,3-thiazole-5-carboxylic acid in a similar manner according to Step 1 of Production Example 32.

$^1$H-NMR (DMSO-$d_6$), δ (ppm): 1.46(9H, s), 2.16(3H, s), 2.73–2.92(2H, m), 3.12–3.25(2H, m), 4.45(2H, d, J=5.5 Hz), 7.01(2H, d, J=8.5 Hz), 7.33(2H, d, J=8.5 Hz), 7.47(2H, d, J=8.5 Hz), 7.69(2H, d, J=8.5 Hz), 8.64(1H, t, J=5.5 Hz), 9.22(1H, s), 12.39(1H, s).

MS: 563(M+H)⁺

Step 2

2-(Acetylamino)-4-[2-(4-aminophenyl)ethyl]-N-[4-(trifluoromethyl)benzyl]-1,3-thiazole-5-carboxamide was prepared in a similar manner according to Step 2 of Production Example 31.

mp. 199–201° C.

$^1$H-NMR (DMSO-$d_6$), δ (ppm): 2.10(3H, s), 2.63–2.78 (2H, m), 3.02–3.18(2H, m), 4.44(2H, d, J=5.5 Hz), 4.81(2H, s), 6.46(2H, d, J=8.0 Hz), 6.81(2H, d, J=8.0 Hz), 7.49(2H, d, J=8.0 Hz), 7.69(2H, d, J=8.0 Hz), 8.44(1H, t, J=5.5 Hz), 12.39(1H, s).

MS: 463(M+H)⁺

Step 3

Di-tert-butyl {(Z)-[(4-{2-[2-(acetylamino)-5-({[4-(trifluoromethyl)benzyl]amino}carbonyl)-1,3-thiazol-4-yl]ethyl}phenyl)amino]methylidene}biscarbamate was prepared in a similar manner according to Step 3 of Production Example 31.

mp. 188–190° C.

$^1$H-NMR (DMSO-$d_6$), δ (ppm): 1.39(9H, s), 1.51(9H, s), 2.16(3H, s), 2.83–2.97(2H, m), 3.17–3.29(2H, m), 4.44(2H, d, J=5.5 Hz), 7.12(2H, d, J=8.5 Hz), 7.40(2H, d, J=8.5 Hz), 7.48(2H, d, J=8.0 Hz), 7.69(2H, d, J=8.0 Hz), 8.63(1H, t, J=5.5 Hz), 9.94(1H, s), 11.44(1H, s), 12.40(1H, s).

MS: 705(M+H)⁺

Step 4

The title compound was prepared in a similar manner according to Step 4 of Production Example 31.

mp. 156–158° C.

¹H-NMR (DMSO-d₆), δ (ppm): 2.17(3H, s), 2.82–2.99 (2H, m), 3.18–3.31(2H, m), 4.44(2H, d, J=5.5 Hz), 7.12(2H, d, J=8.0 Hz), 7.25(2H, d, J=8.0 Hz), 7.40(3H, s), 7.51(2H, d, J=8.0 Hz), 7.71(2H, d, J=8.0 Hz), 8.76(1H, t, J=5.5 Hz), 9.81(1H, s), 12.41(1H, s).

MS: 505(M+H)⁺ free

PRODUCTION EXAMPLE 34

Synthesis of 2-(acetylamino)-4-[2-(4-{[amino (imino)methyl]amino}phenyl)ethyl]-N-(3-pyridinyl)-1,3-thiazole-5-carboxamide dihydrochloride Step 1

2-(Acetylamino)-4-[2-(4-aminophenyl)ethyl]-1,3-thiazole-5-carboxylic acid was prepared from 2-(acetylamino)-4-(2-{4-[(tert-butoxycarbonyl)amino]phenyl}ethyl)-1,3-thiazole-5-carboxylic acid in a similar manner according to Step 2 of Production Example 31.

mp. 211.5–212° C.

¹H-NMR (DMSO-d₆), δ (ppm): 2.15(3H, s), 2.67–2.80 (2H, m), 3.09–3.23(2H, m), 6.51(2H, d, J=8.0 Hz), 6.85(2H, d, J=8.0 Hz), 12.44(1H, brs).

MS: 306(M+H)⁺

Step 2

2-(Acetylamino)-4-[2-(4-aminophenyl)ethyl]-1,3-thiazole-5-carboxylic acid (106 mg) was suspended in THF (2 ml) under N₂ atmosphere. Bis(trimethylsilyl)acetamide (0.253 ml) was added to the suspension at r.t., and the mixture was stirred at r.t. for 15 minutes. Then, N,N'-bis (tert-butoxycarbonyl)-1H-pyrazole-1-carboxamidine (119 mg) was added to the solution at r.t. The reaction mixture was stirred at r.t. for 20 hours, and concentrated in vacuo. The residue was dissolved in CHCl₃. The organic solution was washed with 1N-HCl, water and brine, dried over anhydrous MgSO₄, and concentrated in vacuo. The residual solid was washed with ethyl ether to give 2-(acetylamino)-4-{2-[4-({(Z)-[(tert-butoxycarbonyl)amino](tert-butoxycarbonyl)iminomethyl}amino)phenyl]ethyl}-1,3-thiazole-5-carboxylic acid (115.8 mg) as a pale brown solid.

15 mp. 221.5–223° C.

¹H-NMR (DMSO-d₆), δ (ppm): 1.44(18H, brs), 2.16(3H, s), 2.91(2H, t, J=7.0 Hz), 3.26(2H, t, J=7.0 Hz), 7.17(2H, d, J=8.5 Hz), 7.43(2H, d, J=8.5 Hz), 9.95(1H, brs), 11.43(1H, brs), 12.48(1H, s).

MS: 548(M+H)⁺

Step 3

Di-tert-butyl ((Z)-{[4-(2-{2-(acetylamino)-5-[(3-pyridinylamino)carbonyl]-1,3-thiazol-4-yl}ethyl)phenyl] amino}methylidene)biscarbamate was prepared in a similar manner according to Step 1 of Production Example 32.

¹H-NMR (DMSO-d₆), δ (ppm): 1.39(9H, s), 1.51(9H, s), 2.19(3H, s), 2.87–3.00(2H, m), 3.19–3.32(2H, m), 7.16(2H, d, J=8.5 Hz), 7.35(1H, dd, J=8.5, 4.5 Hz), 7.41(2H, d, J=8.5 Hz), 8.07(1H, m), 8.28(1H, dd, J=4.5, 1.5 Hz), 8.81(1H, d, J=1.5 Hz), 9.93(1H, s), 10.11(1H, s), 11.43(1H, s), 12.51 (1H, s).

MS: 624(M+H)⁺

Step 4

The title compound was prepared in a similar manner according to Step 4 of Production Example 31.

¹H-NMR (DMSO-d₆), δ (ppm): 2.21(3H, s), 2.84–3.07 (2H, m), 3.19–3.39(2H, m), 7.13(2H, d, J=7.5 Hz), 7.28(2H, d, J=7.5 Hz), 7.45(3H, brs), 7.37–8.81(4H, m), 9.93(1H, s), 10.75(1H, s), 12.61(1H, s).

MS: 424(M+H)⁺ free

PRODUCTION EXAMPLE 35

Synthesis of 2-(acetylamino)-4-[2-(4-{[amino (imino)methyl]amino}phenyl)ethyl]-N-(4-phenoxybenzyl)-1,3-thiazole-5-carboxamide hydrochloride Step 1

Di-tert-butyl [(Z)-({4-[2-(2-(acetylamino)-5-{[(4-phenoxybenzyl)amino]carbonyl}-1,3-thiazol-4-yl)ethyl] phenyl}amino)methylidene]biscarbamate was prepared from the compound obtained in Step 2 of Production Example 34 in a similar manner according to Step 1 of Production Example 32.

¹H-NMR (DMSO-d₆), δ (ppm): 1.38(9H, s), 1.51(9H, s), 2.15(3H, s), 2.81–2.97(2H, m), 3.13–3.28(2H, m), 4.35(2H, d, J=5.5 Hz), 6.97(4H, d, J=8.5 Hz), 7.11(1H, t, J=8.5 Hz), 7.13(2H, d, J=8.5 Hz), 7.29–7.41(6H, m), 8.54(1H, t, J=5.5 Hz), 9.93(1H, s), 11.44(1H, brs), 12.37(1H, brs).

MS: 729(M+H)⁺

Step 2

The title compound was prepared in a similar manner according to Step 4 of Production Example 31.

¹H-NMR (DMSO-d₆), δ (ppm): 2.17(3H, s), 2.81–3.00 (2H, m), 3.13–3.30(2H, m), 4.35(2H, d, J=5.5 Hz), 6.98(4H, d, J=8.5 Hz), 7.12(2H, d, J=8.5 Hz), 7.13(1H, t, J=8.5 Hz), 7.25(2H, d, J=8.5 Hz), 7.32(2H, d, J=8.5 Hz), 7.40(2H, t, J=8.5 Hz), 7.46(3H, brs), 8.67(1H, t, J=5.5 Hz), 9.92(1H, s), 12.39(1H, brs).

MS: 529(M+H)⁺ free

PRODUCTION EXAMPLE 36

Synthesis of ethyl 4-({2-(acetylamino)-4-[2-(4-{[amino(imino)methyl]amino}phenyl)ethyl]-1,3-thiazol-5-yl}carbonyl)-1-piperazinecarboxylate Step 1

Ethyl 4-[(2-(acetylamino)-4-{2-[4-({(Z)-[(tert-butoxycarbonyl)amino][(tert-butoxycarbonyl)imino]methyl}amino) phenyl]ethyl}-1,3-thiazol-5-yl)carbonyl]-1-piperazinecarboxylate was prepared from the compound obtained in Step 2 of Production Example 34 in a similar manner according to Step 1 of Production Example 32.

¹H-NMR (DMSO-d₆), δ (ppm): 1.17(3H, t, J=7.0 Hz), 1.39(9H, brs), 1.50(9H, brs), 2.15(3H, s), 2.90(4H, m), 3.38(8H, brs), 4.03(2H, q, J=7.0 Hz), 7.12(2H, d, J=8.5 Hz), 7.41(2H, d, J=8.5 Hz), 9.94(1H, s), 11.46(1H, brs), 12.40 (1H, brs).

MS: 688(M+H)⁺

Step 2

The title compound was prepared in a similar manner according to Step 2 of the following Production Example 48.

mp. 180–182.5° C.

¹H-NMR (DMSO-d₆), δ (ppm): 1.18(3H, t, J=7.0 Hz), 2.07(3H, s), 2.77(4H, s), 3.43(8H, brs), 4.05(2H, q, J=7.0 Hz), 6.89(2H, d, J=7.5 Hz), 7.02(2H, d, J=7.5 Hz).

MS: 488(M+H)⁺

PRODUCTION EXAMPLE 37

Synthesis of N-{5-[(4-acetyl-1-piperazinyl)carbonyl]-4-[2-(4-{[amino(imino)methyl]amino}phenyl)ethyl]-1,3-thiazol-2-yl}acetamide Step 1

Di-tert-butyl ((Z)-{[4-(2-{2-(acetylamino)-5-[(4-acetyl-1-piperazinyl)carbonyl]-1,3-thiazol-4-yl}ethyl)phenyl]amino}methylidene)biscarbamate was prepared from the compound obtained in Step 2 of Production Example 34 in a similar manner according to Step 1 of Production Example 32.

$^1$H-NMR (DMSO-d$_6$), δ (ppm): 1.39(9H, brs), 1.50(9H, brs), 1.98(3H, s), 2.15(3H, s), 2.90(4H, m), 3.40(8H, brs), 7.13(2H, d, J=8.5 Hz), 7.41(2H, d, J=8.5 Hz), 9.93(1H, s), 11.43(1H, brs), 12.40(1H, brs).

MS: 658(M+H)$^+$

Step 2

The title compound was prepared in a similar manner according to Step 2 of the following Production Example 48.

mp. 206–207.5° C.

$^1$H-NMR (DMSO-d$_6$), δ (ppm): 2.01(3H, s), 2.05(3H, s), 2.73(4H, s), 3.42(8H, brs), 6.77–7.08(4H, m).

MS: 458(M+H)$^+$

PRODUCTION EXAMPLE 38

Synthesis of N-(4-[2-(4-{[amino(imino)methyl]amino}phenyl)ethyl]-5-{[4-(methylsulfonyl)-1-piperazinyl]carbonyl}-1,3-thiazol-2-yl)acetamide hydrochloride Step 1

Di-tert-butyl [(Z)-({4-[2-(2-(acetylamino)-5-{[4-(methylsulfonyl)-1-piperazinyl]carbonyl}-1,3-thiazol-4-yl)ethyl]phenyl}amino)methylidene]biscarbamate was prepared from the compound obtained in Step 2 of Production Example 34 in a similar manner according to Step 1 of Production Example 31.

$^1$H-NMR (DMSO-d$_6$), δ (ppm): 1.39(9H, s), 1.51(9H, s), 2.15(3H, s), 2.89(3H, s), 2.82–2.96(4H, m), 3.01–3.13(4H, m), 3.44–3.59(4H, m), 7.14(2H, d, J=8.5 Hz), 7.42(2H, d, J=8.5 Hz), 9.94(1H, s), 11.44(1H, brs), 12.40(1H, brs).

MS: 694(M+H)$^+$

Step 2

The title compound was prepared in a similar manner according to Step 4 of Production Example 31.

mp. 118–119° C.

$^1$H-NMR (DMSO-d$_6$), δ (ppm): 2.16(3H, s), 2.90(3H, s), 2.83–2.98(4H, m), 3.06–3.18(4H, m), 3.50–3.61(4H, m), 7.12(2H, d, J=8.5 Hz), 7.21(2H, d, J=8.5 Hz), 7.43(3H, s), 9.90(1H, s), 12.41(1H, s).

MS: 494(M+H)$^+$ free

PRODUCTION EXAMPLE 39

Synthesis of N-[4-[2-(4-{[amino(imino)methyl]amino}phenyl)ethyl]-5-(4-thiomorpholinylcarbonyl)-1,3-thiazol-2-yl]acetamide hydrochloride Step 1

Di-tert-butyl {(Z)-[(4-{2-[2-(acetylamino)-5-(4-thiomorpholinylcarbonyl)-1,3-thiazol-4-yl]ethyl}phenyl)amino]methylidene}biscarbamate was prepared from the compound obtained in Step 2 of Production Example 34 in a similar manner according to Step 1 of Production Example 32.

$^1$H-NMR (DMSO-d$_6$), δ (ppm): 1.39(9H, s), 1.51(9H, s), 2.15(3H, s), 2.45–2.61(4H, m), 2.79–2.99(4H, m), 3.55–3.70(4H, m), 7.13(2H, d, J=8.5 Hz), 7.41(2H, d, J=8.5 Hz), 9.92(1H, s), 11.44(1H, brs), 12.38(1H, brs).

Step 2

The title compound was prepared in a similar manner according to Step 4 of Production Example 31.

mp. 134–135.5° C.

$^1$H-NMR (DMSO-d$_6$), δ (ppm): 2.16(3H, s), 2.47–2.62(4H, m), 2.80–3.00(4H, m), 3.59–3.73(4H, m), 7.12(2H, d, J=8.5 Hz), 7.20(2H, d, J=8.5 Hz), 7.39(3H, s), 9.80(1H, s), 12.38(1H, s).

MS: 433(M+H)$^+$ free

PRODUCTION EXAMPLE 40

Synthesis of N-{4-[2-(4-{[amino(imino)methyl]amino}phenyl)ethyl]-5-[(1,1-dioxido-4-thiomorpholinyl)carbonyl]-1,3-thiazol-2-yl}acetamide hydrochloride Step 1

Di-tert-butyl ((Z)-{[4-(2-{2-(acetylamino)-5-[(1,1-dioxido-4-thiomorpholinyl)carbonyl]-1,3-thiazol-4-yl}ethyl)phenyl]amino}methylidene)biscarbamate was prepared from the compound obtained in Step 1 of Production Example 39 in a similar manner according to Step 2 of Production Example 32.

mp. 270–271.5° C.

$^1$H-NMR (DMSO-d$_6$), δ (ppm): 1.39(9H, s), 1.51(9H, s), 2.15(3H, s), 2.85–2.96(4H, m), 3.09–3.21(4H, m), 3.69–3.83(4H, m), 7.13(2H, d, J=8.5 Hz), 7.40(2H, d, J=8.5 Hz), 9.93(1H, s), 11.47(1H, brs), 12.42(1H, brs).

MS: 665(M+H)$^+$

Step 2

The title compound was prepared in a similar manner according to Step 4 of Production Example 31.

mp. 185–186° C.

$^1$H-NMR (DMSO-d$_6$), δ (ppm): 2.16(3H, s), 2.92(4H, s), 3.11–3.28(4H, m), 3.76–3.91(4H, m), 7.12(2H, d, J=8.5 Hz), 7.22(2H, d, J=8.5 Hz), 7.40(3H, s), 9.84(1H, s), 12.40(1H, s).

MS: 465(M+H)$^+$ free

PRODUCTION EXAMPLE 41

Synthesis of ethyl 1-({2-(acetylamino)-4-[2-(4-{[amino(imino)methyl]amino}phenyl)ethyl]-1,3-thiazol-5-yl}carbonyl)-4-piperidinecarboxylate hydrochloride Step 1

Ethyl 1-{[2-(acetylamino)-4-{2-[4-({(Z)-[(tert-butoxycarbonyl)amino][(tert-butoxycarbonyl)imino]methyl}amino)phenyl]ethyl}-1,3-thiazol-5-yl]carbonyl}-4-piperidinecarboxylate was prepared from the compound obtained in Step 2 of Production Example 34 in a similar manner according to Step 1 of Production Example 32.

$^1$H-NMR (DMSO-d$_6$), δ (ppm): 1.17(3H, t, J=7.01 Hz), 1.32–1.56(2H, m), 1.39(9H, s), 1.50(9H, s), 1.73–1.89(2H, m), 2.15(3H, s), 2.44–2.64(1H, m), 2.80–3.01(6H, m), 3.74–3.93(2H, m), 4.06(2H, q, J=7.0 Hz), 7.11(2H, d, J=8.5 Hz), 7.41(2H, d, J=8.5 Hz), 9.93(1H, s), 11.45(1H, brs), 12.36(1H, brs).

MS: 687(M+H)⁺

Step 2

The title compound was prepared in a similar manner according to Step 4 of Production Example 31.

¹H-NMR (DMSO-d₆), δ (ppm): 1.18(3H, t, J=7.0 Hz), 1.29–1.54(2H, m), 1.73–1.93(2H, m), 2.15(3H, s), 2.44–2.71(1H, m), 2.79–3.09(6H, m), 3.79–3.96(2H, m), 4.09(2H, q, J=7.0 Hz), 7.11(2H, d, J=8.5 Hz), 7.19(2H, d, J=8.5 Hz), 7.40(3H, s), 9.83(1H, s), 12.37(1H, s).

MS: 487(M+H)⁺ free

PRODUCTION EXAMPLE 42

Synthesis of 1-({2-(acetylamino)-4-[2-(4-{[amino (imino)methyl]amino}phenyl)ethyl]-1,3-thiazol-5-yl}carbonyl)-4-piperidinecarboxamide hydrochloride Step 1

Ethyl 1-[(2-(acetylamino)-4-{2-[4-({(Z)-[(tert-butoxycarbonyl)amino][(tert-butoxycarbonyl)imino]methyl}amino)phenyl]ethyl}-1,3-thiazol-5-yl)carbonyl]-4-piperidinecarboxylate (277.9 mg), 1N-NaOH (1.01 ml) and 1,4-dioxane (3 ml) were combined at 0° C., and the reaction mixture was stirred at r.t. for 3 hours. The mixture was neutralized with 1N-HCl, and the organic solvent was evaporated in vacuo. The residual aqueous solution was extracted with AcOEt. The organic layer was washed with water and brine, dried over anhydrous MgSO₄, and concentrated in vacuo to give 1-[(2-(acetylamino)-4-{2-[4-({(Z)-[(tert-butoxycarbonyl)amino][(tert-butoxycarbonyl)imino]methyl}amino)phenyl]ethyl}-1,3-thiazol-5-yl)carbonyl]-4-piperidinecarboxylic acid (262.4 mg) as a pale yellow amorphous substance.

¹H-NMR (DMSO-d₆), δ (ppm): 1.28–1.59(2H, m), 1.45 (18H, s), 1.72–1.90(2H, m), 2.15(3H, s), 2.40–2.59(1H, m), 2.78–3.03(6H, m), 3.77–3.94(2H, m), 7.12(2H, d, J=8.5 Hz), 7.40(2H, d, J=8.5 Hz), 9.94(1H, brs), 11.44(1H, brs), 12.36 (1H, s).

MS: 659(M+H)⁺

Step 2

Di-tert-butyl [(Z)-({4-[2-(2-(acetylamino)-5-{[4-(aminocarbonyl)-1-piperidinyl]carbonyl}-1,3-thiazol-4-yl)ethyl]phenyl}amino)methylidene]biscarbamate was prepared in a similar manner according to Step 1 of Production Example 32.

¹H-NMR (DMSO-d₆), δ (ppm): 1.29–1.55(2H, m), 1.39 (9H, s), 1.50(9H, s), 1.62–1.79(2H, m), 2.14(3H, s), 2.22–2.43(1H, m), 2.78–2.99(6H, m), 3.89–4.07(2H, m), 6.80(1H, s), 7.14(2H, d, J=8.5 Hz), 7.27(1H, s), 7.41(2H, d, J=8.5 Hz), 9.93(1H, s), 11.44(1H, brs), 12.36(1H, s).

MS: 658(M+H)⁺

Step 3

The title compound was prepared in a similar manner according to Step 4 of Production Example 31.

¹H-NMR (200 MHz, DMSO-d₆), δ (ppm): 1.27–1.52(2H, m), 1.64–1.79(2H, m), 2.15(3H, s), 2.25–2.44(2H, m), 2.76–3.02(6H, m), 6.82(1H, br), 7.11(2H, d, J=8.5 Hz), 7.19(2H, d, J=8.5 Hz), 7.34(1H, br), 7.41(4H, s), 9.83(1H, s), 12.36(1H, s).

MS: 458(M+H)⁺ free

PRODUCTION EXAMPLE 43

Synthesis of 1-({2-(acetylamino)-4-[2-(4-{[amino (imino)methyl]amino}phenyl)ethyl]-1,3-thiazol-5-yl}carbonyl)-N-methyl-4-piperidinecarboxamide hydrochloride Step 1

Di-tert-butyl {(Z)-[(4-{2-[2-(acetylamino)-5-({4-[(methylamino)carbonyl]-1-piperidinyl}carbonyl)-1,3-thiazol-4-yl]ethyl}phenyl)amino]methylidene}biscarbamate was prepared from the compound obtained in Step 1 of Production Example 42 in a similar manner according to Step 1 of Production Example 32.

¹H-NMR (DMSO-d₆), δ (ppm): 1.30–1.75(4H, m), 1.39 (9H, s), 1.50(9H, s), 2.14(3H, s), 2.22–2.42(1H, m), 2.55 (2H, d, J=4.5 Hz), 2.78–2.99(6H, m), 3.90–4.03(2H, m), 7.14(2H, d, J=8.5 Hz), 7.41(2H, d, J=8.5 Hz), 7.73(1H, q, J=4.5 Hz), 9.93(1H, s), 11.43(1H, brs), 12.36(1H, brs).

MS: 672(M+H)⁺

Step 2

The title compound was prepared in a similar manner according to Step 4 of Production Example 31.

¹H-NMR (200 MHz, DMSO-d₆), δ (ppm): 1.29–1.52(2H, m), 1.60–1.77(2H, m), 2.15(3H, s), 2.55(3H, d, J=4.5 Hz), 2.78–2.98(6H, m), 3.88–4.06(3H, m), 7.11(2H, d, J=8.5 Hz), 7.19(2H, d, J=8.5 Hz), 7.37(4H, br), 7.81(1H, m), 9.75(1H, s), 12.36(1H, s).

MS: 472(M+H)⁺ free

PRODUCTION EXAMPLE 44

Synthesis of 1-({2-(acetylamino)-4-[2-(4-{[amino (imino)methyl]amino}phenyl)ethyl]-1,3-thiazol-5-yl}carbonyl)-N,N-dimethyl-4-piperidinecarboxamide hydrochloride Step 1

Di-tert-butyl {(Z)-[(4-{2-[2-(acetylamino)-5-({4-[(dimethylamino)carbonyl]-1-piperidinyl}carbonyl)-1,3-thiazol-4-yl]ethyl}phenyl)amino]methylidene}biscarbamate was prepared from the compound obtained in Step 1 of Production Example 42 in a similar manner according to Step 1 of Production Example 32.

¹H-NMR (DMSO-d₆), δ (ppm): 1.30–1.70(4H, m), 1.39 (9H, s), 1.50(9H, s), 2.15(3H, s), 2.80(3H, s), 2.79–3.01(7H, m), 3.00(3H, s), 3.88–4.06(2H, m), 7.13(2H, d, J=8.5 Hz), 7.41(2H, d, J=8.5 Hz), 9.92(1H, s), 11.42(1H, brs), 12.36 (1H, brs).

MS: 686(M+H)⁺

Step 2

The title compound was prepared in a similar manner according to Step 4 of Production Example 31.

¹H-NMR (200 MHz, DMSO-d₆), δ (ppm): 1.27–1.51(2H, m), 1.55–1.72(2H, m), 2.15(3H, s), 2.80(3H, s), 2.81–3.00 (6H, m), 3.03(3H, s), 3.89–3.96(3H, m), 7.11(2H, d, J=8.5 Hz), 7.20(2H, d, J=8.5 Hz), 7.37(4H, br), 9.79(1H, s), 12.36(1H, s).

MS: 486(M+H)⁺

PRODUCTION EXAMPLE 45

Synthesis of N-{4-[2-(4-{[amino(imino)methyl]amino}phenyl)ethyl]-5-phenyl-1,3-thiazol-2-yl}acetamide hydrochloride Step 1

2-Oxo-3-phenylpropanoic acid (20 g), DMF (100 ml) and DBU (18.2 ml) were combined at 0° C. under $N_2$ atmosphere, and the mixture was stirred at 0° C. for an hour. Then iodomethane (15.2 ml) was added to the solution at 0° C. The reaction mixture was stirred at r.t. for 3 hours, and poured into 1N-HCl. The mixture was extracted with AcOEt (twice). The combined organic layer was washed with brine, dried over anhydrous $MgSO_4$, and concentrated in vacuo. The residue was purified by flash column chromatography over silica gel with $CHCl_3$/AcOEt (30:1) as an eluent, and triturated with IPE/n-Hexane to give methyl 2-oxo-3-phenylpropanoate (11.2 g) as a pale yellow wax.

$^1$H-NMR ($CDCl_3$), δ (ppm): 3.92(3H, s), 6.42(1H, s), 6.53(1H, s), 7.28–7.42(3H, m), 7.77(2H, dd, J=8.5, 1.5 Hz).

MS: 179(M+H)$^+$

Step 2

Methyl 2-oxo-3-phenylpropanoate (11 g), pyridinium tribromide (24.1 g), $CH_2Cl_2$ (490 ml) and AcOH (1.5 ml) were combined at 0° C. under $N_2$ atmosphere. The reaction mixture was stirred at 0° C. for 1.5 hours, poured into water and participated. The organic layer was dried over anhydrous $MgSO_4$, and concentrated in vacuo. The residual oil was dissolved in EtOH (190 ml), and then thiourea (6.11 g) was added to the solution. The reaction mixture was refluxed for an hour under $N_2$ atmosphere. After cooled to 0° C., water was added to the solution. The precipitate was filtered in vacuo to give methyl 2-amino-5-phenyl-1,3-thiazole-4-carboxylate (6.63 g) as an off-white solid.

mp. 208–208.5° C.

$^1$H-NMR (DMSO-$d_6$), δ (ppm): 3.67(3H, s), 7.38–7.53 (5H, m).

MS: 235(M+H)$^+$

Step 3

Methyl 2-amino-5-phenyl-1,3-thiazole-4-carboxylate (3 g) was dissolved in pyridine (30 ml), and then acetyl chloride (2.73 ml) was added dropwise to the solution at 0° C. under $N_2$ atmosphere. The reaction mixture was stirred at r.t. for 1.5 hours. Water was added to the solution at 0° C. The precipitate was filtered in vacuo, and the solid was washed with ethyl ether to give methyl 2-(acetylamino)-5-phenyl-1,3-thiazole-4-carboxylate (2.37 g) as a pale brown solid.

mp. 224.5–225.5° C.

$^1$H-NMR (DMSO-$d_6$), δ (ppm): 2.16(3H, s), 3.68(3H, s), 7.39–7.57(5H, m), 12.56(1H, s).

MS: 277(M+H)$^+$

Step 4

Methyl 2-(acetylamino)-5-phenyl-1,3-thiazole-4-carboxylate (2.34 g) was suspended in THF (23 ml), and then lithium aluminium hydride (482 mg) was added portionwise to the solution at 0° C. The reaction mixture was stirred at 0° C. for 1.5 hours and quenched with MeOH. AcOEt and 1N HCl were added to the mixture, and the mixture was extracted. The aqueous layer was extracted with AcOEt (twice). The combined organic layer was washed with brine, dried over anhydrous $MgSO_4$, and concentrated in vacuo. The residual solid was dissolved in MeOH (5 ml) and $CHCl_3$ (90 ml). Then manganase(IV) oxide (11 g) was added to the solution under $N_2$ atmosphere. The reaction mixture was stirred at r.t. for 13 hours, and filtered through a celite pad. The filtrate was concentrated in vacuo. The residue was purified by flash column chromatography over silica gel with $CHCl_3$/MeOH (20:1) as an eluent to give N-(4-formyl-5-phenyl-1,3-thiazol-2-yl)acetamide (705.2 mg) as a brown amorphous substance.

$^1$H-NMR (DMSO-$d_6$), δ (ppm): 2.19(3H, s), 7.49–7.58 (3H, m), 7.60–7.69(2H, m), 9.78(1H, s), 12.60(1H, s).

MS: 247(M+H)$^+$

Step 5

1-(Bromomethyl)-4-nitrobenzene (1.03 g), triphenylphosphine (1.25 g) and DMF (14 ml) were combined under $N_2$ atmosphere. The reaction mixture was stirred at r.t. for 6 hours. Then potassium tert-butoxide (629 mg) and N-(4-formyl-5-phenyl-1,3-thiazol-2-yl)acetamide (690 mg) were added to the mixture, and the mixture was stirred at r.t. for 13 hours. The reaction mixture was poured into ice-water, and extracted with AcOEt. The organic layer was washed with 1N-HCl, water and brine, dried over anhydrous $MgSO_4$, and concentrated in vacuo. The residue was purified by flash column chromatography over silica gel with $CHCl_3$/AcOEt (1:1) as an eluent to give a mixture of N-{4-[(E)-2-(4-nitrophenyl)vinyl]-5-phenyl-1,3-thiazol-2-yl}acetamide and N-{4-[(Z)-2-(4-nitrophenyl)vinyl]-5-phenyl-1,3-thiazol-2-yl}acetamide (E:Z=2:1) (1.02 g) as an orange wax.

$^1$H-NMR (DMSO-$d_6$), δ (ppm): 2.13(3H×⅓, s), 2.19(3H× ⅔, s), 6.65(1H×⅓, d, J=12.5 Hz), 6.78(1H×⅓, d, J=12.5 Hz), 7.32(1H×⅔, d, J=15.5 Hz), 7.39–7.59(5H+1H×⅔, m), 7.61(2H×⅓, d, J=9.0 Hz), 7.77(2H×⅔, d, J=9.0 Hz), 8.13 (2H×⅓, d, J=9.0 Hz), 8.19(2H×⅔, d, J=9.0 Hz), 12.33(1H, brs).

MS: 366(M+H)$^+$

Step 6

A mixture of N-{4-[(E)-2-(4-nitrophenyl)vinyl]-5-phenyl-1,3-thiazol-2-yl}acetamide and N-{4-[(Z)-2-(4-nitrophenyl)vinyl]-5-phenyl-1,3-thiazol-2-yl}acetamide (E:Z=2:1) (600 mg), 10% palladium carbon (657 mg), MeOH (6 ml), THF (6 ml) and AcOH (1 ml) were combined. The reaction mixture was stirred under 3 atm $H_2$ at r.t. for 3.5 hours, and filtered through a celite pad. The filtrate was concentrated in vacuo. 1N-NaOH was added to the residue, and the mixture was extracted with AcOEt. The organic layer was washed with water and brine, dried over $MgSO_4$, and concentrated in vacuo to give N-{4-[2-(4-aminophenyl)ethyl]-5-phenyl-1,3-thiazol-2-yl}acetamide (528.6 mg) as a pale brown amorphous substance.

$^1$H-NMR (DMSO-$d_6$), δ (ppm): 2.15(3H, s), 2.80(4H, s), 4.82(2H, s), 6.45(2H, d, J=8.5 Hz), 6.78(2H, d, J=8.5 Hz), 7.21–7.44(5H, m), 12.18(1H, brs).

MS: 338(M+H)$^+$

Step 7

Di-tert-butyl {(Z)-[(4-{2-[2-(acetylamino)-5-phenyl-1,3-thiazol-4-yl]ethyl}phenyl)amino]methylidene}biscarbamate was prepared in a similar manner according to Step 3 of Production Example 31.

$^1$H-NMR (DMSO-$d_6$), δ (ppm): 1.21(9H, s), 1.44(9H, s), 2.15(3H, s), 2.83–2.98(4H, m), 7.10(2H, d, J=8.5 Hz), 7.22–7.47(7H, m), 9.92(1H, s), 11.43(1H, s), 12.22(1H, s).

MS: 580(M+H)$^+$

Step 8
The title compound was prepared in a similar manner according to Step 4 of Production Example 31.
mp. 80–82° C.
$^1$H-NMR (DMSO-d$_6$), δ (ppm): 2.16(3H, s), 2.83–3.08 (4H, m), 7.11(2H, d, J=8.0 Hz), 7.21(2H, d, J=8.0 Hz), 7.29–7.54(8H, m), 9.94(1H, s), 12.22(1H, brs).
MS: 380(M+H)$^+$ free

PRODUCTION EXAMPLE 46

Synthesis of N-{4-[2-(4-{[amino(imino)methyl]amino}phenyl)ethyl]-5-benzyl-1,3-thiazol-2-yl}acetamide hydrochloride Step 1
To a suspension of copper(II) bromide (9.75 g) in AcOEt (150 ml) was added a solution of ethyl 2-oxo-4-phenylbutanoate (3 g) in 75 ml of CHCl$_3$. The reaction mixture was refluxed for 23 hours, cooled to r.t., and filtered through a short pad of silica gel eluting with AcOEt/n-hexane (1:1). The solvent was removed in vacuo to give ethyl 3-bromo-2-oxo-4-phenylbutanoate (4.2 g) as a yellow liquid.
$^1$H-NMR (CDCl$_3$), δ (ppm): 1.37(3H, t, J=7.0 Hz), 3.25 (1H, dd, J=14.5, 7.5 Hz), 3.54(1H, dd, J=14.5, 7.5 Hz), 4.35(2H, q, J=7.0 Hz), 5.27(1H, d, J=7.5 Hz), 7.18–7.41(5H, m).

Step 2
Ethyl 3-bromo-2-oxo-4-phenylbutanoate (5.8 g) was dissolved in EtOH (110 ml), and then thiourea (3.1 g) was added to the solution. The reaction mixture was refluxed for 2 hours under N$_2$ atmosphere. The cooled reaction mixture was evaporated in vacuo. The residual solid was suspended (pH=8) in saturated NaHCO$_3$ and water. The solid was collected by filtration, and purified by flash column chromatography over silica gel with CHCl$_3$/MeOH (10:1) as an eluent to give ethyl 2-amino-5-benzyl-1,3-thiazole-4-carboxylate (808.2 mg) as a yellow wax.
$^1$H-NMR (DMSO-d$_6$), δ (ppm): 1.25(3H, t, J=7.0 Hz), 4.21(2H, q, J=7.0 Hz), 4.33(2H, s), 7.02(2H, s), 7.11–7.39 (5H, m).
MS: 263(M+H)$^+$ Step 3
Ethyl 2-(acetylamino)-5-benzyl-1,3-thiazole-4-carboxylate was prepared in a similar manner according to Step 3 of Production Example 45.
mp. 178–180° C.
$^1$H-NMR (DMSO-d$_6$), δ (ppm): 1.28(3H, t, J=7.0 Hz), 2.09(3H, s), 4.28(2H, q, J=7.0 Hz), 4.48(2H, s), 7.19–7.39 (5H, m), 12.41(1H, s).
MS: 305(M+H)$^+$ Step 4
Ethyl 2-(acetylamino)-5-benzyl-1,3-thiazole-4-carboxylate (1.0 g) was dissolved in THF(20 ml), and then lithium borohydride (124 mg) was added portionwise to the solution at 0° C. The reaction mixture was refluxed for 4.5 hours and quenched with MeOH. The mixture was concentrated in vacuo, and purified by flash column chromatography over silica gel with CHCl$_3$/MeOH (20:1) as an eluent. The residual amorphous substance was dissolved in MeOH (1 ml) and CHCl$_3$ (8 ml). Then manganase(IV) oxide (1.26 g) was added to the solution under N$_2$ atmosphere. The reaction mixture was stirred at r.t. for 12 hours, and filtered through a celite pad. The filtrate was concentrated in vacuo. The residue was purified by flash column chromatography over silica gel with CHCl$_3$/MeOH (20:1) as an eluent to give N-(5-benzyl-4-formyl-1,3-thiazol-2-yl)acetamide (251 mg) as a pale yellow solid.
mp. 191–192.5° C.
$^1$H-NMR (DMSO-d$_6$), δ (ppm): 2.12(3H, s), 4.53(2H, s), 7.19–7.40(5H, m), 10.04(1H, s), 12.34(1H, s).
MS: 261(M+H)$^+$ Step 5
N-{5-Benzyl-4-[(Z)-2-(4-nitrophenyl)vinyl]-1,3-thiazol-2-yl}acetamide was prepared in a similar-manner according to Step 5 of Production Example 45.
Z:E=2:1
$^1$H-NMR (DMSO-d$_6$), δ (ppm): 2.08(3H×⅔, s), 2.12(3H× ⅓, s), 4.08(2H×⅔, s), 4.34(2H×⅓, s), 6.72(1H×⅔, d, J=12.5 Hz), 6.86(1H×⅔, d, J=12.5 Hz), 7.17–7.39(5H+2H×⅓, m), 7.66(2H×⅔, d, J=9.0 Hz), 7.92(2H×⅓, d, J=9.0 Hz), 8.14 (2H×⅔, d, J=9.0 Hz), 8.22(2H×⅓, d, J=9.0 Hz), 11.85(1H× ⅔, s), 12.16(1H×⅓, s).
MS: 380(M+H)$^+$ Step 6
N-{4-[2-(4-Aminophenyl)ethyl]-5-benzyl-1,3-thiazol-2-yl}acetamide was prepared in a similar manner according to Step 6 of Production Example 45.
$^1$H-NMR (DMSO-d$_6$), δ (ppm): 2.07(3H, s), 2.59–2.85 (4H, m), 3.85(2H, s), 4.84(2H, s), 6.46(2H, d, J=8.5 Hz), 6.78(2H, d, J=8.5 Hz), 7.07(2H, d, J=8.0 Hz), 7.16–7.31(3H, m), 11.96(1H, s).
MS: 352(M+H)$^+$ Step 7
Di-tert-butyl {(Z)-[(4-{2-[2-(acetylamino)-5-benzyl-1,3-thiazol-4-yl]ethyl}phenyl)amino]methylidene}biscarbamate was prepared in a similar manner according to Step 3 of Production Example 31.
$^1$H-NMR (DMSO-d$_6$), δ (ppm): 1.39(9H, s), 1.51(9H, s), 2.07(3H, s), 2.85(4H, s), 3.89(2H, s), 7.05–7.33(7H, m), 7.42(2H, d, J=8.5 Hz), 9.95(1H, s), 11.44(1H, s), 11.99(1H, s).
MS: 594(M+H)$^+$ Step 8
The title compound was prepared in a similar manner according to Step 4 of Production Example 31.
mp. 97–99° C.
$^1$H-NMR (DMSO-d$_6$), δ (ppm): 2.09(3H, s), 2.86(4H, s), 3.93(2H, s), 7.05–7.37(9H, m), 7.47(3H, s), 9.98(1H, s), 12.01(1H, brs).
MS: 394(M+H)$^+$ free

PRODUCTION EXAMPLE 47

Synthesis of N-{4-[2-(4-aminophenyl)ethyl]-5-[4-(methylsulfonyl)benzyl]-1,3-thiazol-2-yl}acetamide Step 1
3-(4-Mercaptophenyl)propanoic acid (5 g), K$_2$CO$_3$ (11.4 g) and DMF (30 ml) were combined, and iodomethane (5.12 ml) was added dropwise to the mixture at 0° C. under N$_2$ atmosphere. The reaction mixture was stirred at r.t. for 13 hours, and poured into ice-water. The mixture was extracted with AcOEt. The organic layer was washed with water (twice) and brine, dried over anhydrous MgSO$_4$, and concentrated in vacuo to give methyl 3-[4-(methylthio)phenyl]propanoate (4.19 g) as pale yellow oil.

¹H-NMR (CDCl₃), δ (ppm): 2.47(3H, s), 2.61(2H, t, J=8.0 Hz), 2.91(2H, t, J=8.0 Hz), 3.67(3H, s), 7.12(2H, d, J=8.5 Hz), 7.20(2H, d, J=8.5 Hz).

Step 2

Sodium methoxide, 28% solution in MeOH (3.67 ml), was added dropwise to the mixture of methyl 3-[4-(methylthio)phenyl]propanoate (4 g) and diethyl oxalate (5.17 ml) at 0° C. with stirring. The reaction mixture was stirred at 65° C. for 30 minutes under reduced pressure. 15% Aqueous H₂SO₄ (35 ml) was added to the mixture, and the mixture was refluxed for 15 hours. After cooled to r.t., the mixture was extracted with AcOEt. The organic layer was washed with water and brine, dried over anhydrous MgSO₄, and concentrated in vacuo. The residual oil was dissolved in EtOH (20 ml), and concentrated H₂SO₄ (0.4 ml) was added dropwise to the solution. The reaction mixture was refluxed for 2 hours. After cooled to r.t., EtOH was removed in vacuo. AcOEt and water were added to the residue, and extracted. The organic layer was washed with water and brine, dried over anhydrous MgSO₄, and concentrated in vacuo. The residue was purified by flash column chromatography over silica gel with n-hexane/AcOEt (6:1) as an eluent to give ethyl 4-[4-(methylthio)phenyl]-2-oxobutanoate (2.43 g) as a yellow liquid.

¹H-NMR (CDCl₃), δ (ppm): 1.35(3H, t, J=7.0 Hz), 2.46 (3H, s), 2.92(2H, t, J=7.0 Hz), 3.16(2H, t, J=7.0 Hz), 4.31(2H, q, J=7.0 Hz), 7.13(2H, d, J=8.5 Hz), 7.20(2H, d, J=8.5 Hz).

Step 3

Ethyl 3-bromo-4-[4-(methylthio)phenyl]-2-oxobutanoate was prepared in a similar manner according to Step 1 of Production Example 46.

¹H-NMR (CDCl₃), δ (ppm): 1.37(3H, t, J=7.0 Hz), 2.47 (3H, s), 3.20(1H, dd, J=14.5, 7.5 Hz), 3.49(1H, dd, J=14.5, 7.5 Hz), 4.35(2H, q, J=7.0 Hz), 5.22(1H, d, J=7.5 Hz), 7.17(2H, d, J=8.5 Hz), 7.20(2H, d, J=8.5 Hz).

Step 4

Ethyl 2-amino-5-[4-(methylthio)benzyl]-1,3-thiazole-4-carboxylate was prepared in a similar manner according to Step 2 of Production Example 46.

¹H-NMR (DMSO-d₆), δ (ppm): 1.25(3H, t, J=7.0 Hz), 2.44(3H, s), 4.20(2H, q, J=7.0 Hz), 4.28(2H, s), 7.02(2H, s), 7.19(4H, s).

MS: 309(M+H)⁺

Step 5

Ethyl 2-(acetylamino)-5-[4-(methylthio)benzyl]-1,3-thiazole-4-carboxylate was prepared in a similar manner according to Step 3 of Production Example 45.

mp. 205–206° C.

¹H-NMR (DMSO-d₆), δ (ppm): 1.28(3H, t, J=7.0 Hz), 2.09(3H, s), 2.45(3H, s), 4.27(2H, q, J=7.0 Hz), 4.43(2H, s), 7.22(4H, s), 12.41(1H, s).

MS: 351(M+H)⁺

Step 6

N-{4-Formyl-5-[4-(methylthio)benzyl]-1,3-thiazol-2-yl}acetamide was prepared in a similar manner according to Step 4 of Production Example 46.

¹H-NMR (DMSO-d₆), δ (ppm): 2.12(3H, s), 2.45(3H, s), 4.48(2H, s), 7.23(4H, s), 10.03(1H, s), 12.33(1H, s).

MS: 307(M+H)⁺

Step 7

N-{5-[4-(Methylthio)benzyl]-4-[(Z)-2-(4-nitrophenyl)vinyl]-1,3-thiazol-2-yl}acetamide was prepared in a similar manner according to Step 5 of Production Example 45.

Z:E=2:1

¹H-NMR (DMSO-d₆), δ (ppm): 2.08(3H×⅔, s), 2.12(3H×⅓, s), 2.44(3H, s), 4.04(2H×⅔, s), 4.30(2H×⅓, s), 6.71(1H×⅔, d, J=12.5 Hz), 6.84(1H×⅔, d, J=12.5 Hz), 7.18(4H×⅔, s), 7.23(4H×⅓, s), 7.24(1H×⅓, d, J=15.5 Hz), 7.40(1H×⅓, d, J=15.5 Hz), 7.65(2H×⅔, d, J=9.0 Hz), 7.92(2H×⅓, d, J=9.0 Hz), 8.12(2H×⅔, d, J=9.0 Hz), 8.22(2H×⅓, d, J=9.0 Hz), 11.85(1H×⅔, brs), 12.16(1H×⅓, brs).

MS: 426(M+H)⁺

Step 8

N-{5-[4-(Methylsulfonyl)benzyl]-4-[(Z)-2-(4-nitrophenyl)vinyl]-1,3-thiazol-2-yl}acetamide was prepared in a similar manner according to Step 2 of Production Example 32.

Z:E=2:1

¹H-NMR (DMSO-d₆), δ (ppm): 2.09(3H×⅔, s), 2.13(3H×⅓, s), 3.18(3H, s), 4.24(2H×⅔, s), 4.49(2H×⅓, s), 6.73(1H×⅔, d, J=12.5 Hz), 6.86(1H×⅔, d, J=12.5 Hz), 7.33(1H×⅓, d, J=15.5 Hz), 7.41–7.97(5/3H, m), 7.48(2H×⅔, d, J=9.0 Hz), 7.55(2H×⅓, d, J=9.0 Hz), 7.65(2H×⅔, d, J=9.0 Hz), 7.85(2H×⅔, d, J=9.0 Hz), 8.14(2H×⅔, d, J=9.0 Hz), 8.22 (2H×⅓, d, J=9.0 Hz), 11.90(1H×⅔, s), 12.22(1H×⅓, s).

MS: 458(M+H)⁺

Step 9

The title compound was prepared in a similar manner according to Step 6 of Production Example 45.

¹H-NMR (DMSO-d₆), δ (ppm): 2.08(3H, s), 2.58–2.87 (4H, m), 3.18(3H, s), 3.98(2H, s), 4.85(2H, s), 6.46(2H, d, J=8.5 Hz), 6.77(2H, d, J=8.5 Hz), 7.27(2H, d, J=8.5 Hz), 7.82(2H, d, J=8.5 Hz), 12.02(1H, s).

MS: 430(M+H)⁺

PRODUCTION EXAMPLE 48

Synthesis of N-{4-[2-(4-{[amino(imino)methyl]amino}phenyl)ethyl]-5-[4-(methylsulfonyl)benzyl]-1,3-thiazol-2-yl}acetamide Step 1

Di-tert-butyl ((Z)-{[4-(2-{2-(acetylamino)-5-[4-(methylsulfonyl)benzyl]-1,3-thiazol-4-yl}ethyl)phenyl]amino}methylidene)biscarbamate was prepared from the compound obtained in Example 47 in a similar manner according to Step 3 of Production Example 31.

¹H-NMR (DMSO-d₆), δ (ppm): 1.39(9H, s), 1.51(9H, s), 2.08(3H, s), 2.86(4H, s), 3.16(3H, s), 4.03(2H, s), 7.13(2H, d, J=8.5 Hz), 7.33(2H, d, J=8.5 Hz), 7.43(2H, d, J=8.5 Hz), 7.81(2H, d, J=8.5 Hz), 9.97(1H, s), 11.45(1H, s), 12.05(1H, s).

MS: 672(M+H)⁺

Step 2

Di-tert-butyl ((Z)-{[4-(2-{2-(acetylamino)-5-[4-(methylsulfonyl)benzyl]-1,3-thiazol-4-yl}ethyl)phenyl]amino}methylidene)biscarbamate (953 mg) and 4N HCl in 1,4-dioxane solution (10 ml) were combined under N₂ atmosphere. The reaction mixture was stirred at r.t. for 7 hours. The solvent was removed in vacuo. The residue was dissolved in water and AcOEt. The solution was made basic (pH=8) by saturated NaHCO₃. The precipitate was filtered in vacuo to give N-{4-[2-(4-{[amino(imino)methyl]

amino}phenyl)ethyl]-5-[4-(methylsulfonyl)benzyl]-1,3-thiazol-2-yl}acetamide (667.7 mg) as a pale yellow solid.

mp. 228–229.5° C.

$^1$H-NMR (DMSO-d$_6$), δ (ppm): 2.08(3H, s), 2.79(4H, m), 3.18(3H, s), 4.05(2H, s), 6.72(2H, d, J=8.0 Hz), 6.99(2H, d, J=8.0 Hz), 7.37(2H, d, J=8.5 Hz), 7.84(2H, d, J=8.5 Hz).

MS: 472(M+H)$^+$

PRODUCTION EXAMPLE 49

Synthesis of N-{4-[2-(4-{[amino(imino)methyl]amino}phenyl)ethyl]-5-[4-(methylsulfonyl)benzyl]-1,3-thiazol-2-yl}acetamide hydrochloride The title compound was prepared from the compound obtained in Step 1 of Production Example 48 in a similar manner according to Step 4 of Production Example 31.

mp. 107–110° C.

$^1$H-NMR (DMSO-d$_6$), δ (ppm): 2.09(3H, s), 2.87(4H, s), 3.19(3H, s), 4.08(2H, s), 7.13(2H, d, J=8.5 Hz), 7.25(2H, d, J=8.5 Hz), 7.40(2H, d, J=8.5 Hz), 7.44(3H, s), 7.85(2H, d, J=8.5 Hz), 9.94(1H, s), 12.05(1H, brs).

MS: 472(M+H)$^+$ free

PRODUCTION EXAMPLE 50

Synthesis of N-{4-[2-(4-{[hydrazino(imino)methyl]amino}phenyl)ethyl]-5-[4-(methylsulfonyl)benzyl]-1,3-thiazol-2-yl}acetamide Step 1

To a ice-cold solution of N-{4-[2-(4-aminophenyl)ethyl]-5-[4-(methylsulfonyl)benzyl]-1,3-thiazol-2-yl}acetamide (247.6 mg) in acetone (4.8 ml) was added benzoyl isothiocyanate (94.1 mg), and the mixture was stirred at r.t. for 1 hour. Water was added to the mixture, and the mixture was extracted with AcOEt. The organic layer was washed with water and brine, dried over anhydrous MgSO$_4$, and concentrated in vacuo. The residual amorphous substance was dissolved in EtOH (5 ml), and 6N-NaOH (0.288 ml) was added to the solution at 0° C. The reaction mixture was stirred at r.t. for 2 hours, and neutralized with 1N-HCl at 0° C. The mixture was extracted with AcOEt. The organic layer was washed with water and brine, dried over anhydrous MgSO$_4$, and concentrated in vacuo. The residue was solidified with ethyl ether to give N-{4-(2-{4-[(aminocarbonothioyl)amino]phenyl}ethyl)-5-[4-(methylsulfonyl)benzyl]-1,3-thiazol-2-yl}acetamide (290.7 mg) as an off-white solid.

mp. 102–103° C.

$^1$H-NMR (DMSO-d$_6$), δ (ppm): 2.09(3H, s), 2.85(4H, s), 3.18(3H, s), 4.03(2H, s), 7.11(2H, d, J=8.5 Hz), 7.30(2H, d, J=8.5 Hz), 7.36(2H, d, J=8.5 Hz), 7.84(2H, d, J=8.5 Hz), 9.64(1H, s), 12.04(1H, s).

MS: 489(M+H)$^+$

Step 2

A mixture of N-(4-(2-{4-[(aminocarbonothioyl)amino]phenyl}ethyl)-5-[4-(methylsulfonyl)benzyl]-1,3-thiazol-2-yl)acetamide (281.8 mg), methyl iodide (0.0431 ml) and MeOH (3 ml) was refluxed for 3.5 hours. The reaction mixture was concentrated in vacuo. The residue was diluted with AcOEt and stirred for 30 minutes. The precipitated crystals were filtered and washed with AcOEt to give methyl N-[4-(2-{2-(acetylamino)-5-[4-(methylsulfonyl)benzyl]-1,3-thiazol-4-yl}ethyl)phenyl]imidothiocarbamate hydroiodide (291.5 mg) as an off-white amorphous solid.

$^1$H-NMR (DMSO-d$_6$), δ (ppm): 2.09(3H, s), 2.68(3H, s), 2.90(4H, s), 3.18(3H, s), 4.07(2H, s), 7.22(2H, d, J=8.5 Hz), 7.32(2H, d, J=8.5 Hz), 7.39(2H, d, J=8.5 Hz), 7.86(2H, d, J=8.5 Hz), 9.22(1H, brs), 11.11(1H, brs), 12.03(1H, s).

MS: 503(M+H)$^+$ free

Step 3

The title compound was prepared in a similar manner according to the following Production Example 58.

$^1$H-NMR (DMSO-d$_6$), δ (ppm): 2.09(3H, s), 2.87(4H, s), 3.19(3H, s), 4.08(2H, s), 7.12(2H, d, J=8.5 Hz), 7.23(2H, d, J=8.5 Hz), 7.41(2H, d, J=8.5 Hz), 7.85(2H, d, J=8.5 Hz), 8.92(2H, brs), 12.03(1H, brs).

MS: 487(M+H)$^+$

PRODUCTION EXAMPLE 51

Synthesis of N-{4-[2-(4-{[amino(imino)methyl]amino}phenyl)ethyl]-5-[4-(ethylsulfonyl)benzyl]-1,3-thiazol-2-yl}acetamide hydrochloride Step 1

Ethyl 3-[4-(ethylthio)phenyl]propanoate was prepared from 4-(2-carboxyethyl)thiophenol in a similar manner according to Step 1 of Production Example 47.

$^1$H-NMR (CDCl$_3$), δ (ppm): 1.23(3H, t, J=7.0 Hz), 1.29 (3H, t, J=7.0 Hz), 2.60(2H, t, J=8.5 Hz), 2.82–2.99(4H, m), 4.12(2H, q, J=7.0 Hz), 7.12(2H, d, J=8.5 Hz), 7.26(2H, d, J=8.5 Hz).

Step 2

Ethyl 4-[4-(ethylthio)phenyl]-2-oxobutanoate was prepared in a similar manner according to Step 2 of Production Example 47.

$^1$H-NMR (CDCl$_3$), δ (ppm): 1.31(3H, t, J=7.0 Hz), 1.36 (3H, t, J=7.0 Hz), 2.92(2H, q, J=7.0 Hz), 2.93(2H, t, J=7.0 Hz), 3.16(2H, t, J=7.0 Hz), 4.27(2H, q, J=7.0 Hz), 7.08(2H, d, J=9.0 Hz), 7.26(2H, d, J=9.0 Hz).

Step 3

Ethyl 3-bromo-4-[4-(ethylthio)phenyl]-2-oxobutanoate was prepared in a similar manner according to Step 1 of Production Example 46.

$^1$H-NMR (CDCl$_3$), δ (ppm): 1.31(3H, t, J=7.5 Hz), 1.38(3H, t, J=7.5 Hz), 2.93(2H, q, J=7.5 Hz), 3.21(1H, dd, J=14.5, 7.5 Hz), 3.49(1H, dd, J=14.5, 7.5 Hz), 4.35(2H, q, J=7.5 Hz), 5.23(1H, t, J=7.5 Hz), 7.16(2H, d, J=8.5 Hz), 7.27(2H, d, J=8.5 Hz).

Step 4

Ethyl 2-amino-5-[4-(ethylthio)benzyl]-1,3-thiazole-4-carboxylate was prepared in a similar manner according to Step 2 of Production Example 46.

$^1$H-NMR (DMSO-d$_6$), δ (ppm): 1.22(6H, t, J=7.0 Hz), 2.94(2H, q, J=7.0 Hz), 4.20(2H, q, J=7.0 Hz), 4.29(2H, s), 7.03(2H, s), 7.18(2H, d, J=8.5 Hz), 7.26(2H, d, J=8.5 Hz).

MS: 323(M+H)$^+$

Step 5

Ethyl 2-(acetylamino)-5-[4-(ethylthio)benzyl]-1,3-thiazole-4-carboxylate was prepared in a similar manner according to Step 3 of Production Example 45.

mp. 189.5–190° C.

$^1$H-NMR (DMSO-d$_6$), δ (ppm): 1.21(3H, t, J=7.5 Hz), 1.28(3H, t, J=7.0 Hz), 2.09(3H, s), 2.95(2H, q, J=7.5 Hz), 4.27(2H, q, J=7.0 Hz), 4.44(2H, s), 7.22(2H, d, J=8.5 Hz), 7.26(2H, d, J=8.5 Hz), 12.42(1H, s).

MS: 365(M+H)$^+$

Step 6

N-{5-[4-(Ethylthio)benzyl]-4-formyl-1,3-thiazol-2-yl}acetamide was prepared in a similar manner according to Step 4 of Production Example 46.

$^1$H-NMR (DMSO-d$_6$), δ (ppm): 1.21(3H, t, J=7.5 Hz), 2.17(3H, s), 2.95(2H, q, J=7.5 Hz), 4.49(2H, s), 7.26(4H, s), 10.03(1H, s), 12.34(1H, s).

Step 7

N-{5-[4-(Ethylthio)benzyl]-4-[(Z)-2-(4-nitrophenyl)vinyl]-1,3-thiazol-2-yl}acetamide was prepared in a similar manner according to Step 5 of Production Example 45.

Z:E=3:2

$^1$H-NMR (DMSO-d$_6$), δ (ppm): 1.20(3H, t, J=7.5 Hz), 2.08(3H×⅗, s), 2.12(3H×⅖, s), 2.93(2H, q, J=7.5 Hz), 4.05(2H×⅗, s), 4.31(2H×⅖, s), 6.71(1H×⅗, d, J=12.5 Hz), 6.84(1H×⅖, d, J=12.5 Hz), 7.13–8.16(6H+⅘H, m), 8.12 (2H×⅗, d, J=9.0 Hz), 8.22(2H×⅖, d, J=9.0 Hz), 11.86(1H×⅗, brs), 12.18(1H×⅖, brs).

MS: 440(M+H)$^+$

Step 8

N-{5-[4-(Ethylsulfonyl)benzyl]-4-[(Z)-2-(4-nitrophenyl)vinyl]-1,3-thiazol-2-yl}acetamide was prepared in a similar manner according to Step 2 of Production Example 32.

Z:E=3:2

$^1$H-NMR (DMSO-d$_6$), δ (ppm): 1.06(3H, t, J=7.5 Hz), 2.09(3H×⅗, s), 2.13(3H×⅖, s), 3.25(2H, q, J=7.5 Hz), 4.24(2H×⅗, s), 4.50(2H×⅖, s), 6.73(1H×⅗, d, J=12.5 Hz), 6.87(1H×⅖, d, J=12.5 Hz), 7.43–8.31(8H+⅘H, m), 11.91 (1H×⅗, brs), 12.22(1H×⅖, brs).

MS: 472(M+H)$^+$

Step 9

Di-tert-butyl ((Z)-{[4-(2-{2-(acetylamino)-5-[4-(ethylsulfonyl)benzyl]-1,3-thiazol-4-yl}ethyl)phenyl] amino}methylidene)biscarbamate was prepared in a similar manner according to Step 3 of Production Example 31.

$^1$H-NMR (DMSO-d$_6$), δ (ppm): 1.05(3H, t, J=7.5 Hz), 1.39(9H, s), 1.51(9H, s), 2.09(3H, s), 2.85(4H, s), 3.22(2H, q, J=7.5 Hz), 4.04(2H, s), 7.11(2H, d, J=8.5 Hz), 7.32(2H, d, J=8.5 Hz), 7.43(2H, d, J=8.5 Hz), 7.77(2H, d, J=8.5 Hz), 9.97(1H, s), 11.44(1H, s), 12.05(1H, s).

MS: 686(M+H)$^+$

Step 10

The title compound was prepared in a similar manner according to Step 4 of Production Example 31.

$^1$H-NMR (DMSO-d$_6$), δ (ppm): 1.07(3H, t, J=7.5 Hz), 2.09(3H, s), 2.86(4H, s), 3.26(2H, q, J=7.5 Hz), 4.09(2H, s), 7.13(2H, d, J=8.0 Hz), 7.24(2H, d, J=8.0 Hz), 7.44(3H, brs), 7.60(2H, d, J=8.0 Hz), 7.81(2H, d, J=8.0 Hz), 9.89(1H, s), 12.05(1H, brs).

MS: 486(M+H)$^+$ free

PRODUCTION EXAMPLE 52

Synthesis of ethyl {4-[2-(4-{[amino(imino)methyl] amino}phenyl)ethyl]-5-[4-(methylsulfonyl)benzyl]-1,3-thiazol-2-yl}carbamate Step 1

N-{4-[2-(4-Aminophenyl)ethyl]-5-[4-(methylsulfonyl)benzyl]-1,3-thiazol-2-yl}acetamide (300 mg) was dissolved in THF (3 ml) under N$_2$ atmosphere. Then di(tert-butyl) dicarbonate (168 mg) in THF (3 ml) was added to the solution at r.t. The reaction mixture was stirred at r.t. for 14 hours, and concentrated in vacuo. The residue was purified by flash column chromatography over silica gel with CHCl$_3$/AcOEt (1:1) as an eluent to give tert-butyl [4-(2-{2-(acetylamino)-5-[4-(methylsulfonyl)benzyl]-1,3-thiazol-4-yl}ethyl)phenyl]carbamate (248.5 mg) as an off-white amorphous substance.

$^1$H-NMR (DMSO-d$_6$), δ (ppm): 1.47(9H, s), 2.08(3H, s), 2.82(4H, s), 3.16(3H, s), 3.99(2H, s), 7.00(2H, d, J=8.5 Hz), 7.25(2H, d, J=8.5 Hz), 7.33(2H, d, J=8.5 Hz), 7.79(2H, d, J=8.5 Hz), 9.24(1H, s), 12.03(1H, s).

MS: 530(M+H)$^+$

Step 2 tert-Butyl [4-(2-{2-(acetylamino)-5-[4-(methylsulfonyl)benzyl]-1,3-thiazol-4-yl}ethyl)phenyl]carbamate (230 mg), 1N-NaOH (1.09 ml) and EtOH (5 ml) were combined, and the mixture was refluxed for 16 hours. After cooled to r.t., the organic solvent was removed in vacuo. The aqueous solution was neutrallized with 1N-HCl, and extracted with AcOEt. The organic layer was washed with water and brine, dried over anhydrous MgSO$_4$, and concentrated in vacuo. The residue was purified by preparative silica gel chromatography with CHCl$_3$/MeOH (30:1) as an eluent to give tert-butyl [4-(2-{2-amino-5-[4-(methylsulfonyl)benzyl]-1,3-thiazol-4-yl}ethyl)phenyl]carbamate (151.2 mg) as an off-white amorphous substance.

$^1$H-NMR (DMSO-d$_6$), δ (ppm): 1.47(9H, s), 2.58–2.82 (4H, m), 3.16(3H, s), 3.84(2H, s), 6.73(2H, s), 7.02(2H, d, J=8.5 Hz), 7.21(2H, d, J=8.5 Hz), 7.33(2H, d, J=8.5 Hz), 7.77(2H, d, J=8.5 Hz), 9.24(1H, s).

MS: 488(M+H)$^+$

Step 3 tert-Butyl [4-(2-{2-amino-5-[4-(methylsulfonyl)benzyl]-1,3-thiazol-4-yl}ethyl)phenyl]carbamate (140 mg) was dissolved in pyridine (2 ml) under N$_2$ atmosphere. Then, ethyl chloroformate (30.2 ml) was added to the solution at 0° C. The reaction mixture was stirred at r.t. for 2 hours, and concentrated in vacuo. The residue was dissolved in AcOEt, and washed with 1N-HCl, water and brine. The organic layer was dried over anhydrous MgSO$_4$, and concentrated in vacuo to give ethyl {4-(2-{4-[(tert-butoxycarbonyl)amino] phenyl}ethyl)-5-[4-(methylsulfonyl)benzyl]-1,3-thiazol-2-yl}carbamate (155.8 mg) as an off-white amorphous substance.

$^1$H-NMR (DMSO-d$_6$), δ (ppm): 1.21(3H, t, J=7.0 Hz), 1.47(9H, s), 2.79(4H, s), 3.16(3H, s), 3.97(2H, s), 4.14(2H, q, J=7.0 Hz), 7.00(2H, d, J=8.5 Hz), 7.24(2H, d, J=8.5 Hz), 7.33(2H, d, J=8.5 Hz), 7.79(2H, d, J=8.5 Hz), 9.54(1H, s), 11.64(1H, brs).

MS: 560(M+H)$^+$

Step 4

Ethyl {4-(2-{4-[(tert-butoxycarbonyl)amino] phenyl}ethyl)-5-[4-(methylsulfonyl)benzyl]-1,3-thiazol-2-yl}carbamate (140 mg) and 4N HCl in 1,4-dioxane solution (3 ml) were combined under N$_2$ atmosphere. The reaction mixture was stirred at r.t. for 2 hours. The solvent was removed in vacuo. The residue was dissolved in water and AcOEt. The mixture was made basic (pH=8) by 1N-NaOH. The organic layer was washed with water and brine, dried over anhydrous MgSO$_4$, and concentrated in vacuo to give ethyl {4-[2-(4-aminophenyl)ethyl]-5-[4-(methylsulfonyl) benzyl]-1,3-thiazol-2-yl}carbamate (125.6 mg) as an off-white amorphous substance.

$^1$H-NMR (DMSO-d$_6$), δ (ppm): 1.21(3H, t, J=7.0 Hz), 2.60–2.80(4H, m), 3.18(3H, s), 3.97(2H, s), 4.14(2H, q, J=7.0 Hz), 4.85(2H, brs), 6.46(2H, d, J=8.5 Hz), 6.77(2H, d, J=8.5 Hz), 7.29(2H, d, J=8.5 Hz), 7.82(2H, d, J=8.5 Hz), 11.62(1H, brs).

MS: 460(M+H)$^+$

Step 5

Di-tert-butyl ((Z)-{[4-(2-{2-[(ethoxycarbonyl)amino]-5-[4-(methylsulfonyl)benzyl]-1,3-thiazol-4-yl}ethyl)phenyl]amino}methylidene)biscarbamate was prepared in a similar manner according to Step 3 of Production Example 31.

$^1$H-NMR (DMSO-d$_6$), δ (ppm): 1.21(3H, t, J=7.0 Hz), 1.39(9H, s), 1.51(9H, s), 2.84(4H, s), 3.16(3H, s), 4.01(2H, s), 4.14(2H, q, J=7.0 Hz), 7.13(2H, d, J=8.5 Hz), 7.33(2H, d, J=8.5 Hz), 7.43(2H, d, J=8.5 Hz), 7.81(2H, d, J=8.5 Hz), 9.97(1H, s), 11.45(1H, s), 11.61(1H, brs).

MS: 702(M+H)$^+$

Step 6

The title compound was prepared in a similar manner according to Step 2 of Production Example 48.

$^1$H-NMR (DMSO-d$_6$), δ (ppm): 1.17(3H, t, J=7.0 Hz), 2.57(4H, s), 3.17(3H, s), 4.01(2H, q, J=7.0 Hz), 4.03(2H, s), 7.00(4H, s), 7.42(2H, d, J=8.5 Hz), 7.83(2H, d, J=8.5 Hz).

MS: 502(M+H)$^+$

PRODUCTION EXAMPLE 53

Synthesis of N-{4-{2-[4-(aminomethyl)phenyl]ethyl}-5-[4-(methylsulfonyl)benzyl]-1,3-thiazol-2-yl}acetamide Step 1

[4-(Methoxycarbonyl)benzyl](triphenyl)phosphonium bromide (4.81 g) and DMF (60 ml) were combined under N$_2$ atmosphere. Then potassium tert-butoxide (1.32 g) and N-{4-formyl-5-[4-(methylthio)benzyl]-1,3-thiazol-2-yl}acetamide (3 g) were added to the suspension at 0° C. The reaction mixture was stirred at r.t. for 18 hours, poured into ice-water, and extracted with AcOEt. The organic layer was washed with water and brine, dried over anhydrous MgSO$_4$, and concentrated in vacuo. The residue was purified by flash column chromatography over silica gel with CHCl$_3$/AcOEt (2:1) as an eluent. The solid was suspended in AcOEt, and the suspension was filtered. The filtrate was concentrated in vacuo to give methyl 4-((Z)-2-{2-(acetylamino)-5-[4-(methylthio)benzyl]-1,3-thiazol-4-yl}vinyl)benzoate (4.16 g) as a yellow amorphous substance.

$^1$H-NMR (DMSO-d$_6$), δ (ppm): 2.08(3H, s), 2.43(3H, s), 3.84(3H, s), 3.96(2H, s), 6.67(1H, d, J=12.5 Hz), 6.74(1H, d, J=12.5 Hz), 7.11(2H, d, J=8.5 Hz), 7.17(2H, d, J=8.5 Hz), 7.50(2H, d, J=8.5 Hz), 7.85(2H, d, J=8.5 Hz), 11.88(1H, s).

MS: 439(M+H)$^+$

Step 2

Methyl 4-{(Z)-2-(2-(acetylamino)-5-[4-(methylsulfonyl)benzyl]-1,3-thiazol-4-yl}vinyl)benzoate was prepared in a similar manner according to Step 2 of Production Example 32.

Z:E=2:1

$^1$H-NMR (DMSO-d$_6$), δ (ppm): 2.08(3H×⅔, s), 2.12(3H×⅓, s), 3.18(3H, s), 3.84(3H×⅔, s), 3.86(3H×⅓, s), 4.15(2H×⅔, s), 4.47(2H×⅓, s), 6.68(1H×⅔, d, J=12.5 Hz), 6.77(1H×⅔, d, J=12.5 Hz), 7.30(1H×⅓, d, J=15.5 Hz), 7.43(2H, d, J=8.5 Hz), 7.50–7.97(19/3H, m), 11.93(1H×⅔, s), 12.19(1H×⅓, s).

MS: 471(M+H)$^+$

Step 3

Methyl 4-(2-{2-(acetylamino)-5-[4-(methylsulfonyl)benzyl]-1,3-thiazol-4-yl}ethyl)benzoate was prepared in a similar manner according to Step 6 of Production Example 45.

mp. 209–210° C.

$^1$H-NMR (DMSO-d$_6$), δ (ppm): 2.09(3H, s), 2.94(4H, m), 3.17(3H, s), 3.84(3H, s), 4.01(2H, s), 7.25(2H, d, J=8.5 Hz), 7.28(2H, d, J=8.5 Hz), 7.76(2H, d, J=8.5 Hz), 7.85(2H, d, J=8.5 Hz), 12.05(1H, brs).

MS: 473(M+H)$^+$

Step 4

To a stirred solution of methyl 4-(2-{2-(acetylamino)-5-[4-(methylsulfonyl)benzyl]-1,3-thiazol-4-yl}ethyl)benzoate (2 g) in dry THF (40 ml) was added dropwise 1.0M diisobutylaluminium hydride solution in toluene (14.8 ml) at −78° C. under N$_2$ atmosphere. The reaction mixture was stirred at r.t. for 4 hours, and then quenched with MeOH. AcOEt and 1N-HCl were added to the mixture, and extracted. The organic layer was washed with brine, dried over anhydrous MgSO$_4$, and concentrated in vacuo. The residue was purified by flash column chromatography over silica gel with CHCl$_3$/MeOH (20:1) as an eluent to give N-{4-{2-[4-(hydroxymethyl)phenyl]ethyl}-5-[4-(methylsulfonyl)benzyl]-1,3-thiazol-2-yl}acetamide (552.3 mg) as a colorless solid.

mp. 209.5–211° C.

$^1$H-NMR (DMSO-d$_6$), δ (ppm): 2.09(3H, s), 2.86(4H, s), 3.17(3H, s), 4.01(2H, s), 4.46(2H, d, J=5.5 Hz), 5.12(1H, t, J=5.5 Hz), 7.09(2H, d, J=8.0 Hz), 7.20(2H, d, J=8.0 Hz), 7.28(2H, d, J=8.5 Hz), 7.80(2H, d, J=8.5 Hz), 12.04(1H, brs).

MS: 445(M+H)$^+$

Step 5

N-{4-{2-[4-(Hydroxymethyl)phenyl]ethyl}-5-[4-(methylsulfonyl)benzyl]-1,3-thiazol-2-yl}acetamide (539.5 mg), CH$_2$Cl$_2$ (5 ml) and DMF (5 ml) were combined under N$_2$ atmosphere. Then, Et$_3$N (0.211 ml) and MsCl (0.108 ml) were added to the suspension at 0° C. The reaction mixture was stirred at r.t. for 3.5 hours. The reaction mixture was poured into water, and extracted with CHCl$_3$. The organic layer was washed with brine, dried over anhydrous MgSO$_4$, and concentrated in vacuo. The residual solid was washed with ethyl ether to give N-{4-{2-[4-(chloromethyl)phenyl]ethyl}-5-[4-(methylsulfonyl)benzyl]-1,3-thiazol-2-yl}acetamide (537.5 mg) as an off-white solid.

mp. 202–203° C.

$^1$H-NMR (DMSO-d$_6$), δ (ppm): 2.09(3H, s), 2.88(4H, s), 3.17(3H, s), 4.01(2H, s), 4.73(2H, s), 7.15(2H, d, J=8.0 Hz), 7.30(2H, d, J=8.5 Hz), 7.34(2H, d, J=8.0 Hz), 7.81(2H, d, J=8.5 Hz), 12.05(1H, brs).

MS: 463(M+H)$^+$

Step 6

N-{4-{2-[4-(Chloromethyl)phenyl]ethyl}-5-[4-(methylsulfonyl)benzyl]-1,3-thiazol-2-yl}acetamide (150 mg) was suspended in CH$_3$CN (6 ml), and then 28% ammonia solution (0.4 ml) was added to the suspension at 0° C. The reaction mixture was stirred at r.t. for 16 hours, and concentrated in vacuo. The residual solid was washed with water, and purified by preparative silica gel chromatography with CHCl$_3$/MeOH (10:1) as an eluent to give N-{4-{2-[4-(aminomethyl)phenyl]ethyl}-5-[4-(methylsulfonyl)benzyl]-1,3-thiazol-2-yl}acetamide (32.1 mg) as a pale yellow amorphous substance.

$^1$H-NMR (DMSO-d$_6$), δ (ppm): 2.09(3H, s), 2.85(4H, s), 3.17(3H, s), 3.69(2H, s), 4.01(2H, s), 7.07(2H, d, J=8.0 Hz), 7.21(2H, d, J=8.0 Hz), 7.29(2H, d, J=8.5 Hz), 7.80(2H, d, J=8.5 Hz).
MS: 444(M+H)$^+$

PRODUCTION EXAMPLE 54

Synthesis of N-{4-{2-[4-(4,5-dihydro-1,3-thiazol-2-ylamino)phenyl]ethyl}-5-[4-(methylsulfonyl)benzyl]-1,3-thiazol-2-yl}acetamide A mixture of N-{4-[2-(4-aminophenyl)ethyl]-5-[4-(methylsulfonyl)benzyl]-1,3-thiazol-2-yl}-acetamide (200 mg), 2-(methylsulfanyl)-4,5-dihydro-1,3-thiazole (62 mg), concentrated HCl (0.064 ml) and 2-methoxyethanol (3 ml) was stirred at 120° C. for 13 hours under N$_2$ atmosphere. After cooled to r.t., the reaction mixture was made basic with saturated NaHCO$_3$. The mixture was extracted with AcOEt. The organic layer was dried over anhydrous MgSO$_4$, and concentrated in vacuo. The residue was purified by preparative silica gel chromatography with CHCl$_3$/MeOH (10:1) as an eluent to give N-{4-{2-[4-(4,5-dihydro-1,3-thiazol-2-ylamino)phenyl]ethyl}-5-[4-(methylsulfonyl)benzyl]-1,3-thiazol-2-yl}acetamide (139.8 mg) as a pale yellow amorphous substance.
$^1$H-NMR (DMSO-d$_6$), δ (ppm): 2.08(3H, s), 2.82(4H, s), 3.16(3H, s), 3.17–3.34(4H, m), 3.98(2H, s), 6.99(2H, d, J=8.5 Hz), 7.25(2H, d, J=8.5 Hz), 7.45(2H, brd, J=8.5 Hz), 7.80(2H, d, J=8.5 Hz), 9.24(1H, brs), 12.04(1H, s).
MS: 515(M+H)$^+$

PRODUCTION EXAMPLE 55

Synthesis of N-{4-{2-[4-(4,5-dihydro-1H-imidazol-2-ylamino)phenyl]ethyl}-5-[4-(methylsulfonyl)benzyl]-1,3-thiazol-2-yl}acetamide A mixture of N-(4-[2-(4-aminophenyl)ethyl]-5-[4-(methylsulfonyl)benzyl]-1,3-thiazol-2-yl)acetamide (150 mg), ethyl 2-(methylthio)-4,5-dihydro-1H-imidazole-1-carboxylate (78.9 mg), ACOH (0.3 ml) and EtOH (3 ml) was refluxed for 7 hours under N$_2$ atmosphere. After cooled to r.t., the reaction mixture was made basic with saturated NaHCO$_3$. The mixture was extracted with AcOEt. The organic layer was washed with brine, dried over anhydrous MgSO$_4$, and concentrated in vacuo. The residue was purified by preparative silica gel chromatography with CHCl$_3$/MeOH (10:1) as an eluent. The amorphous substance was solidified with ethyl ether to give N-{4-{2-[4-(4,5-dihydro-1H-imidazol-2-ylamino)phenyl]ethyl}-5-[4-(methylsulfonyl)benzyl]-1,3-thiazol-2-yl}acetamide (17.9 mg) as an off-white amorphous solid.
mp. 139–140° C.
$^1$H-NMR (DMSO-d$_6$), δ (ppm): 2.08(3H, s), 2.71–2.87 (4H, m), 3.18(3H, s), 3.25–3.41(4H, m), 4.03(2H, s), 6.95 (4H, s), 7.32(2H, d, J=8.5 Hz), 7.82(2H, d, J=8.5 Hz).
MS: 498(M+H)$^+$

PRODUCTION EXAMPLE 56

Synthesis of N-{4-{2-[4-(ethanimidoylamino)phenyl]ethyl}-5-[4-(methylsulfonyl)benzyl]-1,3-thiazol-2-yl}acetamide N-{4-[2-(4-Aminophenyl)ethyl]-5-[4-(methylsulfonyl)benzyl]-1,3-thiazol-2-yl}acetamide (200 mg), methyl ethanimidothioate hydroiodide (202 mg) and MeOH (4 ml) were combined under N$_2$ atmosphere. The reaction mixture was refluxed for 3 hours. After cooled to room temperature, the mixture was concentrated in vacuo. The residue was purified by preparative NH silica gel chromatography with CHCl$_3$/MeOH (10:1) as an eluent. The amorphous substance was solidified with ethyl ether to give N-{4-{2-[4-(ethanimidoylamino)phenyl]ethyl}-5-[4-(methylsulfonyl)benzyl]-1,3-thiazol-2-yl}acetamide (102.4 mg) as a pale yellow amorphous solid.
mp. 81.5–83° C.
$^1$H-NMR (CDCl$_3$), δ (ppm): 1.83(3H, brs), 2.08(3H, s), 2.81(4H, m), 3.18(3H, s), 4.02(2H, s), 6.64(2H, brd, J=8.5 Hz), 6.99(2H, d, J=8.5 Hz), 7.36(2H, d, J=8.5 Hz), 7.83(2H, d, J=8.5 Hz), 12.03(1H, brs).
MS: 471(M+H)$^+$

PRODUCTION EXAMPLE 57

Synthesis of N-[4-(2-{4-[(iminomethyl)amino]phenyl}ethyl)-1,3-thiazol-2-yl]acetamide N-(4-[2-(4-Aminophenyl)ethyl]-1,3-thiazol-2-yl)acetamide (150 mg) was dissolved in THF (2 ml) and pH=7 buffer (2 ml). Then, ethyl imidoformate hydrochloride (1.26 g) was added to the solution at 0° C. The reaction mixture was stirred at 0° C. for 2 hours, and concentrated in vacuo. The residue was purified by flash column chromatography over silica gel with CH$_3$CN/water (7:3) as an eluent. The oil was purified again by preparative silica gel chromatography with CHCl$_3$/MeOH (5:1) as an eluent to give N-[4-(2-{4-[(iminomethyl)amino]phenyl}ethyl)-1,3-thiazol-2-yl]acetamide (110 mg) as pale brown oil.
$^1$H-NMR (DMSO-d$_6$), δ (ppm): 2.12(3H, s), 2.81–3.01 (4H, m), 6.71(1H, s), 7.09–8.00(7H, m), 12.07(1H, s).
MS: 289(M+H)$^+$

PRODUCTION EXAMPLE 58

Synthesis of N-{4-[2-(4-{[hydrazino(imino)methyl]amino}phenyl)ethyl]-1,3-thiazol-2-yl}acetamide A mixture of methyl N-(4-{2-[2-(acetylamino)-1,3-thiazol-4-yl]ethyl}phenyl)imidothiocarbamate hydroiodide (100 mg), hydrazine monohydrate (0.0525 ml) and THF (3 ml) was stirred at r.t. for 95 hours. The precipitate was filtered off. The filtrate was concentrated in vacuo. The residue was purified by preparative silica gel chromatography with CHCl$_3$/MeOH (10:1) as an eluent to give N-{4-[2-(4-{[hydrazino(imino)methyl]amino}phenyl)ethyl]-1,3-thiazol-2-yl}acetamide (62.7 mg) as a pale pink solid.
mp. 216.5–218° C.
$^1$H-NMR (DMSO-d$_6$), δ (ppm): 2.12(3H, s), 2.92(4H, m), 6.75(1H, s), 7.12(2H, d, J=8.5 Hz), 7.27(2H, d, J=8.5 Hz), 8.88(1H, brs), 12.07(1H, brs).
MS: 319(M+H)$^+$ PRODUCTION EXAMPLE 59: Synthesis of N-(4-{2-[4-(2-amino-2-iminoethyl)phenyl]ethyl}-1,3-thiazol-2-yl)acetamide Step 1
N-(4-{2-[4-(Chloromethyl)phenyl]ethyl}-1,3-thiazol-2-yl)acetamide was prepared from N-(4-{2-[4-(hydroxymethyl)phenyl]ethyl}-1,3-thiazol-2-yl)acetamide in a similar manner according to Step 5 of Production Example 53.

mp. 145–146° C.

¹H-NMR (DMSO-d₆), δ (ppm): 2.11(3H, s), 2.82–2.99 (4H, m), 4.72(2H, s), 6.73(1H, s), 7.20(2H, d, J=8.0 Hz), 7.33(2H, d, J=8.0 Hz), 12.08(1H, brs).

MS: 295(M+H)⁺

Step 2

NaCN (115 mg), KI (130 mg) and water (1.8 ml) were combined, and then a solution of N-(4-{2-[4-(chloromethyl)phenyl]ethyl}-1,3-thiazol-2-yl)acetamide (230 mg) in DMF (7 ml) was added dropwise to the mixture at 0° C. The reaction mixture was stirred at r.t. for 19 hours, poured into water, and extracted with CHCl₃. The organic layer was washed with brine, dried over anhydrous MgSO₄ and concentrated in vacuo. The residual solid was washed with ethyl ether to give N-(4-{2-[4-(cyanomethyl)phenyl]ethyl}-1,3-thiazol-2-yl)acetamide (149.1-mg) as a colorless solid.

mp. 160–161° C.

¹H-NMR (DMSO-d₆), δ (ppm): 2.11(3H, s), 2.82–2.97 (4H, m), 3.97(2H, s), 6.73(1H, s), 7.21(2H, d, J=8.5 Hz), 7.25(2H, d, J=8.5 Hz), 12.08(1H, brs).

MS: 286(M+H)⁺

Step 3

N-(4-{2-[4-(Cyanomethyl)phenyl]ethyl}-1,3-thiazol-2-yl)acetamide (600 mg) was dissolved in MeOH (5 ml) and CHCl₃ (5 ml), and then HCl gas was bubbled at 0° C. for 5 minutes with stirring. The reaction mixture was stood for 17 hours, and concentrated in vacuo. The residual solid was washed with ethyl ether to give methyl 2-(4-{2-[2-(acetylamino)-1,3-thiazol-4-yl]ethyl}phenyl)ethanimidoate hydrochloride (632.5 mg) as an off-white solid.

mp. 77–78° C.

¹H-NMR (DMSO-d₆), δ (ppm): 2.12(3H, s), 2.88(4H, s), 4.92(6H, brs), 6.75(1H, s), 7.10–7.20(4H, m), 12.11(1H, brs).

MS: 318(M+H)⁺ free

Step 4

Methyl 2-(4-{2-[2-(acetylamino)-1,3-thiazol-4-yl]ethyl}phenyl)ethanimidoate hydrochloride (600 mg) was dissolved in EtOH (12 ml). Then ammonium chloride (136 mg) and ammonia in methanol (2 ml) were added to the solution. The reaction mixture was refluxed for 4 hours under N₂ atmosphere. After cooled to r.t., the suspension was filtered in vacuo. The filtrate was concentrated in vacuo, and the residue was solidified with EtOH/diethyl ether to give N-(4-{2-[4-(2-amino-2-iminoethyl)phenyl]ethyl}-1,3-thiazol-2-yl)acetamide hydrochloride (338.6 mg) as an off-white solid.

mp. 190.5–192° C.

¹H-NMR (DMSO-d₆), δ (ppm): 2.12(3H, s), 2.89(4H, m), 3.68(2H, s), 6.74(1H, s), 7.20(2H, d, J=8.0 Hz), 7.39(2H, d, J=8.0 Hz).

MS: 303(M+H)⁺ free

Step 5

N-(4-{2-[4-(2-Amino-2-iminoethyl)phenyl]ethyl}-1,3-thiazol-2-yl)acetamide hydrochloride (67 mg) was dissolved in water (1 ml) and CH₃CN (1 ml). The solution was made basic (pH=8) with saturated NaHCO₃, and concentrated in vacuo. The residue was purified by preparative NH silica gel chromatography with CH₃CN/water (7:3) as an eluent to give N-(4-{2-[4-(2-amino-2-iminoethyl)phenyl]ethyl}-1,3-thiazol-2-yl)acetamide (26 mg) as an off-white amorphous substance.

¹H-NMR (DMSO-d₆), δ (ppm): 2.11(3H, s), 2.89(4H, m), 3.59(2H, s), 6.72(1H, s), 7.20(2H, d, J=8.0 Hz), 7.30(2H, d, J=8.0 Hz), 9.38(3H, brs).

MS: 303(M+H)⁺

PRODUCTION EXAMPLE 60

Synthesis of N-{4-[2-(4-{[amino(imino)methyl]amino}phenyl)ethyl]-5-[4-(methylthio)benzyl]-1,3-thiazol-2-yl}acetamide Step 1

A mixture of N-{5-[4-(methylthio)benzyl]-4-[(Z)-2-(4-nitrophenyl)vinyl]-1,3-thiazol-2-yl}acetamide and N-{5-[4-(methylthio)benzyl]-4-[(E)-2-(4-nitrophenyl)vinyl]-1,3-thiazol-2-yl}acetamide (Z:E=2:1) (570 mg) was dissolved in CH₂Cl₂ (6 ml) under N₂ atmosphere. Then m-CPBA (254 mg) was added portionwise to the solution at 0° C. The reaction mixture was stirred at r.t. for 1.5 hours, and diluted in MeOH/CHCl₃. The organic solution was washed with 1N-Na₂CO₃, water and brine, dried over MgSO₄, and concentrated in vacuo to give a mixture of N-{5-[4-(methylsulfinyl)benzyl]-4-[(Z)-2-(4-nitrophenyl)vinyl]-1,3-thiazol-2-yl}acetamide and N-{5-[4-(methylsulfinyl)benzyl]-4-[(E)-2-(4-nitrophenyl)vinyl]-1,3-thiazol-2-yl}acetamide (Z:E=2:1) (282.8 mg) as a yellow amorphous substance.

Z:E=2:1

¹H-NMR (DMSO-d₆), δ-(ppm): 2.08(3H×⅔, s), 2.13 (3H×⅓, s), 2.71(3H, s), 4.18(2H×⅔, s), 4.44(2H×⅓, s), 6.73(1H×⅔, d, J=12.5 Hz), 6.87(1H×⅔, d, J=12.5 Hz), 7.34(1H×⅓, d, J=15.5 Hz), 7.41–8.17(7/3H, m), 7.41(2H×⅔, d, J=8.0 Hz), 7.50(2H×⅓, d, J=8.0 Hz), 7.63(2H×⅔, d, J=8.0 Hz), 7.93(2H×⅓, d, J=8.0 Hz), 8.14(2H×⅔, d, J=8.0 Hz), 8.22(2H×⅓, d, J=8.0 Hz), 11.89(1H×⅔, s), 12.20(1H×⅓, s).

MS: 442(M+H)⁺

Step 2

N-{4-[2-(4-Aminophenyl)ethyl]-5-[4-(methylsulfinyl)benzyl]-1,3-thiazol-2-yl}acetamide was prepared in a similar manner according to Step 6 of Production Example 45.

¹H-NMR (DMSO-d₆), δ (ppm): 2.08(3H, s), 2.62–2.84 (4H, m), 2.70(3H, s), 3.94(2H, s), 4.85(2H, s), 6.46(2H, d, J=8.5 Hz), 6.77(2H, d, J=8.5 Hz), 7.23(2H, d, J=8.5 Hz), 7.58(2H, d, J=8.5 Hz), 12.00(1H, s).

MS: 414(M+H)⁺

Step 3

Di-tert-butyl ((Z)-{[4-(2-{2-(acetylamino)-5-[4-(methylsulfinyl)benzyl]-1,3-thiazol-4-yl}ethyl)phenyl]amino}methylidene)biscarbamate was prepared in a similar manner according to Step 3 of Production Example 31.

¹H-NMR (DMSO-d₆), δ (ppm): 1.39(9H, s), 1.51(9H, s), 2.08(3H, s), 2.69(3H, s), 2.86(4H, s), 3.98(2H, s), 7.12(2H, d, J=8.5 Hz), 7.26(2H, d, J=8.0 Hz), 7.43(2H, d, J=8.5 Hz), 7.57(2H, d, J=8.0 Hz), 9.95(1H, s), 11.43(1H, s), 12.02(1H, s).

MS: 656(M+H)⁺

Step 4

The title compound was prepared in a similar manner according to Step 2 of Production Example 48.

mp. 159.5–161° C.

¹H-NMR (DMSO-d₆), δ (ppm): 2.07(3H, s), 2.44(3H, s), 2.79(4H, s), 3.86(2H, s), 6.78(2H, d, J=8.5 Hz), 7.02(2H, d, J=8.5 Hz), 7.04(2H, d, J=8.5 Hz), 7.30(2H, d, J=8.5 Hz).

MS: 440(M+H)⁺

PRODUCTION EXAMPLE 61

Synthesis of N-{4-[4-(3-{[amino(imino)methyl]amino}propyl)phenyl]-5-[4-(methylsulfonyl)phenyl]-1,3-thiazol-2-yl}acetamide hydrochloride Step 1

To a solution of methyl 4-{[4-(methylthio)phenyl]acetyl}benzoate (5 g) in dichloromethane (250 ml) were added acetic acid (0.65 ml) and pyridinium bromide perbromide (6.51 g) at 0° C., and the mixture was stirred for 1 h at the same temperature. The reaction mixture was poured into water (250 ml) and extracted with ethyl acetate (250 ml). The organic layer was washed with water and brine, dried over magnesium sulfate and evapolated. The residue was washed with diisopropylethyl ether and collected by filtration to give methyl 4-{2-bromo[4-(methylthio)phenyl]acetyl}benzoate as an off-white solid.

$^1$H-NMR (CDCl$_3$), δ (ppm): 2.47(3H, s), 3.94(3H, s), 6.33(3H, s), 7.23(2H, d, J=8.5 Hz), 7.43(2H, d, J=8.5 Hz).

Step 2

Methyl 4-{2-amino-5-[4-(methylthio)phenyl]-1,3-thiazol-4-yl}benzoate was prepared in a similar manner according to Step 2 of Production Example 46.

$^1$H-NMR (DMSO-d$_6$), δ (ppm): 2.47(3H, s), 3.83(3H, s), 7.08–7.32(4H, m), 7.52(2H, d, J=8.5 Hz), 7.85(2H, d, J=8.5 Hz).

MS: 357.1(M+H)$^+$

Step 3

To a solution of methyl 4-{2-amino-5-[4-(methylthio)phenyl]-1,3-thiazol-4-yl}benzoate (100 mg) in tetrahydrofuran (4 ml) was added portionwise lithium aluminium hydride (21.3 mg), and the mixture was stirred for 1 h at 20° C. To the reaction mixture were added ethyl acetate (10 ml) and water (3 ml). The resulting precipitate was removed by filtration, and the filtrate was washed with brine, dried over sodium sulfate and evaporated to give (4-{2-amino-5-[4-(methylthio)phenyl]-1,3-thiazol-4-yl}phenyl)methanol as a yellow solid, that was used as crude in the next reaction.

$^1$H-NMR (DMSO-d$_6$), δ (ppm): 2.46(3H, s), 4.46(2H, d, J=6.0 Hz), 5.17(t, 1H, J=5.5 Hz), 7.13(d, 2H, J=5.5 Hz), 7.17(d, 2H, J=5.5 Hz), 7.20(d, 2H, J=8.5 Hz), 7.34(d, 2H, J=8.5 Hz).

MS: 329.2(M+H)$^+$

Step 4

To a suspension of (4-{2-amino-5-[4-(methylthio)phenyl]-1,3-thiazol-4-yl}phenyl)methanol (89.3 mg) in dichloromethane (1 ml) were added pyridine (0.11 ml) and acetylchloride (42.5 μl) at 0° C., and the mixture was stirred at the same temperature for 1 hr. To the reaction mixture was added 1N-hydrochloric acid (10 ml), and the mixture was extracted with ethyl acetate (20 ml×2). The organic layer was washed with water and brine, dried over magnesium sulfate and evaporated to give a crude green solid (77.6 mg). To a solution of the crude green solid in dichloromethane (3 ml) was added 3-chloroperbenzoic acid (80.7 mg) at 0° C., and the mixture was stirred for 2 hr at 20° C. To the reaction mixture was added saturated sodium hydrogencarbonate aqueous solution (10 ml), and the mixture was extracted with ethyl acetate (20 ml×2), washed with water and brine, dried over magnesium sulfate, and evaporated to give 4-{2-(acetylamino)-5-[4-(methylsulfonyl)phenyl]-1,3-thiazol-4-yl}benzyl acetate as a brown solid.

$^1$H-NMR (CDCl$_3$), δ (ppm): 1.77(3H, s), 2.14(3H, s), 3.10(3H, s), 5.12(2H, s), 7.32(2H, d, J=8.5 Hz), 7.45(2H, d, J=8.5 Hz), 7.52(2H, d, J=8.5 Hz), 7.88(2H, d, J=8.5 Hz), 11.1(1H, brs).

MS: 467.0(M+Na)$^+$

Step 5

To a suspension of 4-(2-(acetylamino)-5-[4-(methylsulfonyl)phenyl]-1,3-thiazol-4-yl)benzyl acetate (1.218 g) in metanol (24 ml) was added pottasium carbonate (379 mg) at 20° C., and the mixture was stirred for 1 h. To the reaction mixture was added 0.1N-hydrochloric acid (27.4 ml), and the mixture was extracted with chloroform (500 ml), dried over magnesium sulfate and evaporated to give N-{4-[4-(hydroxymethyl)phenyl]-5-[4-(methylsulfonyl)phenyl]-1,3-thiazol-2-yl}acetamide as a yellow solid.

$^1$H-NMR (CDCl$_3$), δ (ppm): 1.87(3H, s), 3.09(3H, s), 4.72(2H, s), 7.31(2H, d, J=8.5 Hz), 7.42(2H, d, J=8.5 Hz), 7.51(2H, d, J=8.5 Hz), 7.87(2H, d, J=8.5 Hz), 10.83(1H, brs).

MS: 425.0(M+Na)$^+$

Step 6

To a solution of N-{4-[4-(hydroxymethyl)phenyl]-5-[4-(methylsulfonyl)phenyl]-1,3-thiazol-2-yl}acetamide (867.4 mg) in methanol (0.6 ml) and chloroform (10 ml) was added manganese(IV) oxide (6.65 g) at 20° C. under N$_2$ atmosphere, and the mixture was stirred for 19 hrs. The reaction mixture was filtered through a celite pad. The filtrate was evaporeted to give N-{4-(4-formylphenyl)-5-[4-(methylsulfonyl)phenyl]-1,3-thiazol-2-yl}acetamide as a yellow solid, that was used as crude in the next reaction.

$^1$H-NMR (DMSO-d$_6$), δ (ppm): 2.20(3H, s), 3.26(3H, s), 7.63(2H, d, J=8.5 Hz), 7.64(2H, d, J=8.0 Hz), 7.90(2H, d, J=8.0 Hz), 7.92(2H, d, J=8.5 Hz), 10.00(1H, s), 12.5(1H, brs).

Step 7

To a suspension of N-{4-(4-formylphenyl)-5-[4-(methylsulfonyl)phenyl]-1,3-thiazol-2-yl}acetamide (360 mg) in chloroform (7 ml) was added (carbethoxymethylene)triphenylphosphorane (626 mg) at 20° C., and the mixture was stirred for 1 h. The reaction mixture was evaporated. The residue was purified by column chromatography over silica gel (150 ml) with hexane/ethyl acetate (1:1–1:2) as an eluent to give ethyl (2E)-3-(4-{2-(acetylamino)-5-[4-(methylsulfonyl)phenyl]-1,3-thiazol-4-yl}phenyl)acrylate as a pale yellow solid.

$^1$H-NMR (CDCl$_3$), δ (ppm): 1.34(3H, t, J=7.0 Hz), 1.93 (3H, s), 3.10(3H, s), 4.28(2H, q, J=7.0 Hz), 6.45(1H, d, J=16.1 Hz), 7.48(4H, s), 7.54(2H, d, J=8.5 Hz), 7.67(2H, d, J=16.1 Hz), 7.89(2H, d, J=8.5 Hz), 10.39(1H, s).

MS: 493.1(M+Na)$^+$

Step 8

To a suspension of ethyl (2E)-3-(4-{2-(acetylamino)-5-[4-(methylsulfonyl)phenyl]-1,3-thiazol-4-yl}phenyl)acrylate (306.5 mg) in tetrahydrofuran (3 ml) was added portionwise lithium borohydride (271 mg) at 0° C., and the mixture was stirred for 6.5 h at 20° C. The reaction mixture was poured into a mixture of saturated ammonium chloride aqueous solution (50 ml) and chloroform (50 ml) at 0° C. The organic layer was separeted, dried over maganesium sulfate and evaporarted to give a crude yellow solid (300 mg). The residue was purified by column chromatography over silica gel (80 ml) with hexane/ethyl acetate (1:2–1:5) as an eluent to give N-{4-[4-(3-hydroxypropyl)phenyl]-5-[4-(methylsulfonyl)phenyl]-1,3-thiazol-2-yl}acetamide as a pale yellow solid.

¹H-NMR (CDCl₃), δ (ppm): 1.71(3H, s), 1.80–1.99(2H, m), 2.61–2.82(2H, m), 3.09(3H, s), 3.69(2H, dd, J=6.0, 10.0 Hz), 7.17(2H, d, J=8.0 Hz), 7.37(2H, d, J=8.5 Hz), 7.53(2H, d, J=8.5 Hz), 7.87(2H, d, J=8.5 Hz), 11.1(1H, s).

MS: 431.20(M+1)⁺

Step 9

To a solution of N-{4-[4-(3-hydroxypropyl)phenyl]-5-[4-(methylsulfonyl)phenyl]-1,3-thiazol-2-yl}acetamide (75 mg) in tetrahydrofuran (0.7 ml) were added triphenylphosphine (68.5 mg) and carbon tetrabromide (86.7 mg) at 0° C., and the mixture was stirred for 1 h at 20° C. The reaction mixture was purified by preparative thin-layer chromatography over silica gel with hexane/ethyl acetate (1:2) as an eluent to give N-{4-[4-(3-bromopropyl)phenyl]-5-[4-(methylsulfonyl)phenyl]-1,3-thiazol-2-yl}acetamide as colorless oil.

¹H-NMR (DMSO-d₆), δ (ppm): 1.67(3H, s), 2.08–2.28 (2H, m), 2.80(2H, t, J=7.5 Hz), 3.10(3H, s), 3.41(2H, t, J=6.5 Hz), 7.18(2H, d, J=8.0 Hz), 7.39(2H, d, J=8.0 Hz), 7.53(2H, d, J=8.5 Hz), 7.87(2H, d, J=8.5 Hz), 11.1(1H, s).

MS: 515.0(M+Na)⁺

Step 10

To a solution of N-{4-[4-(3-bromopropyl)phenyl]-5-[4-(methylsulfonyl)phenyl]-1,3-thiazol-2-yl}acetamide (82 mg) in N,N-dimethylformamide (0.82 ml) was added phthalimide potassium salt (30.8 mg), and the mixture was stirred for 2 hrs. at 50° C. The reaction mixture was cooled to 20° C., then water was added to the reaction mixture, and the mixture was extracted with ethyl acetate, washed with brine, dried over magnesium sulfate and evaporated to give a crude material (92.0 mg). The crude material was purified by preparative thin-layer chromatography over silica gel to give N-{4-{4-[3-(1,3-dioxo-1,3-dihydro-2H-isoindol-2-yl)propyl]phenyl}-5-[4-(methylsulfonyl)phenyl]-1,3-thiazol-2-yl}acetamide.

¹H-NMR (CDCl₃), δ (ppm): 1.72(3H, s), 1.90–2.13(2H, m), 2.60–2.79(2H, m), 3.09(3H, s), 3.74(2H, t, J=7.3 Hz), 7.18(2H, d, J=8.0 Hz), 7.37(2H, d, J=8.0 Hz), 7.52(2H, d, J=8.5 Hz), 7.66–7.78(2H, m), 7.80–7.92(4H, m), 1.0(1H, s).

MS: 582.1(M+Na)⁺

Step 11

To a solution of N-{4-(4-[3-(1,3-dioxo-1,3-dihydro-2H-isoindol-2-yl)propyl]phenyl}-5-[4-(methylsulfonyl)phenyl]-1,3-thiazol-2-yl)acetamide (53.2 mg) in acetonitrile (0.5 ml) was added hydrazine monohydrate (46.1 μl), and the mixture was stirred at 50° C. for 30 min. The volatiles were evaporated. To the mixture was added chloroform (1 ml), and an insoluble material was removed by filtration. The filtrate was purified by preparative thin-layer chromatography over NH silica gel with chloroform/methanol (10: 1) as an eluent to give N-{4-[4-(3-aminopropyl)phenyl]-5-[4-(methylsulfonyl)phenyl]-1,3-thiazol-2-yl}acetamide as a yellow solid.

¹H-NMR (DMSO-d₆), δ (ppm): 1.69(3H, s), 1.69–1.88 (2H, m), 2.60–2.74(2H, m), 2.76(2H, t, J=7.0 Hz), 3.09(3H, s), 7.15(2H, d, J=8.5 Hz), 7.36(2H, d, J=8.5 Hz), 7.53(2H, d, J=8.5 Hz), 7.86(2H, d, J=8.5 Hz).

MS: 428.2(M–H)⁻

Step 12

Di-tert-butyl ((E)-{[3-(4-{2-(acetylamino)-5-[4-(methylsulfonyl)phenyl]-1,3-thiazol-4-yl}phenyl)propyl]amino}methylidene)biscarbamate was prepared in a similar manner according to Step 3 of Production Example 31.

¹H-NMR (CDCl₃), δ (ppm): 1.49(9H, s), 1.50(9H, s), 1.87–1.97(2H, m), 2.01(3H, s), 2.69(2H, t, J=8.1 Hz), 3.09 (3H, s), 3.41–3.54(2H, m), 7.16(2H, d, J=8.1 Hz), 7.36(2H, d, J=8.1 Hz), 7.54(2H, d, J=8.5 Hz), 7.87(2H, d, J=8.4 Hz), 8.38(1H, t, J=5.1 Hz), 9.87(1H, brs), 11.5(1H, s).

MS: 694.2(M+Na)⁺

Step 13

The title compound was prepared in a similar manner according to Step 4 of Production Example 31.

¹H-NMR (DMSO-d₆), δ (ppm): 1.72–1.85(2H, m), 2.19 (3H, s), 2.58–2.66(2H, m), 3.08–3.18(2H, m), 3.25(3H, s), 6.65–7.58(4H, brs), 7.21(2H, d, J=8.4 Hz), 7.36(2H, d, J=8.1 Hz), 7.56(2H, d, J=8.4 Hz), 7.67(1H, t, J=5.1 Hz), 7.89(2H, d, J=8.4 Hz), 12.4(1H, s).

MS: 472.1(M+H)⁺ free

PRODUCTION EXAMPLE 62

Synthesis of N-{4-(2-{4-[(aminooxy)methyl] phenyl}ethyl)-5-[4-(methylsulfonyl)phenyl]-1,3-thiazol-2-yl}acetamide Step 1

Methyl 4-((E)-2-{2-(acetylamino)-5-[4-(methylthio)phenyl]-1,3-thiazol-4-yl}vinyl)benzoate was prepared from N-{5-[4-(methylthio)phenyl]-4-formyl-1,3-thiazol-2-yl}acetamide in a similar manner according to Step 1 of Production Example 53.

¹H-NMR (DMSO-d₆), δ (ppm): 2.12(3H×⅓, s), 2.19(3H× ⅔, s), 2.54(3H, s), 3.85(3H, s), 6.55(1H×⅓, d, J=12.6 Hz), 6.73(1H×⅓, d, J=12.6 Hz), 7.17–7.72(8H+2H×⅔, m), 7.84 (2H×⅓, d, J=8.5 Hz), 7.93(2H×⅔, d, J=8.5 Hz), 12.31(1H, brs).

MS: 423.1(M–H)⁻

Step 2

Methyl 4-((E)-2-{2-(acetylamino)-5-[4-(methylsulfonyl) phenyl]-1,3-thiazol-4-yl}vinyl)benzoate was prepared in a similar manner according to Step 2 of Production Example 32.

¹H-NMR (DMSO-d₆), δ (ppm): 2.15(3H×⅕, s), 2.21(3H× ⅘, s), 3.24(3H×⅕, s), 3.30(3H×⅘, s), 3.84(3H×⅕, s), 3.85(3H×⅘, s), 6.64(1H×⅕, d, J=12.6 Hz), 6.81(1H×⅕, d, J=12.6 Hz), 7.31(1H×⅘, d, J=15.6 Hz), 7.52(1H×⅘, d, J=15.6 Hz), 7.30–8.11(8H, m), 12.24(1H×⅕, s), 12.49(1H× ⅘, s).

MS: 479.0(M+Na)⁺

Step 3

Methyl 4-(2-{2-(acetylamino)-5-[4-(methylsulfonyl)phenyl]-1,3-thiazol-4-yl}ethyl)benzoate was prepared in a similar manner according to Step 6 of Production Example 45.

¹H-NMR (DMSO-d₆), δ (ppm): 2.31(3H, s), 2.97–3.07 (4H, m), 3.08(3H, s), 3.91(3H, s), 7.09(2H, d, J=8.1 Hz), 7.32(2H, d, J=8.1 Hz), 7.87(4H, d, J=8.1 Hz), 8.75(1H, s).

MS: 481.0(M+Na)⁺

Step 4

N-{4-{2-[4-(Hydroxymethyl)phenyl]ethyl}-5-[4-(methylsulfonyl)phenyl]-1,3-thiazol-2-yl}acetamide was prepared in a similar manner according to Step 4 of Production Example 53.

¹H-NMR (DMSO-d₆), δ (ppm): 2.17(3H, s), 2.96(4H, s), 3.24(3H, s), 4.43(2H, s), 7.06(2H, d, J=8.1 Hz), 7.18(2H, d, J=8.1 Hz), 7.50(2H, d, J=8.4 Hz), 7.91(2H, d, J=8.4 Hz), 12.33(1H, s).

MS: 453.1(M+Na)⁺

Step 5

N-{4-{2-[4-(Hydroxymethyl)phenyl]ethyl}-5-[4-(methylsulfonyl)phenyl]-1,3-thiazol-2-yl}acetamide (100 mg), N-hydroxyphthalimide (39.8 mg), triphenylphosphine (64 mg) and tetrahydrofuran (2 ml) were combined under nitrogen atmosphere, then, diethyl azodicarboxylate (40 wt % solution in toluene) (0.111 ml) was added to the solution at 0° C., and the mixture was stirred at 20° C. for 5 hrs. The reaction mixture was poured into saturated sodium hydrogen carbonate aqueous solution, and extracted with chloroform. The organic layer was washed with brine, dried over magnesium sulfate, filtered and evaporated. The crude material was purified by preparative thin-layer chromatography over silica gel with chloroform/methanol (30:1) as an eluent to give N-{4-[2-(4-{[(1,3-dioxo-1,3-dihydro-2H-isoindol-2-yl)oxy]methyl}phenyl)ethyl]-5-[4-(methylsulfonyl)phenyl]-1,3-thiazol-2-yl}acetamide as a yellow foam.

$^1$H-NMR (CDCl$_3$), δ (ppm): 2.30(3H, S), 2.95–3.00(4H, m), 3.09(3H, s), 5.15(2H, s), 7.04(2H, d, J=8.1 Hz), 7.21–7.92(10H, m), 9.31(!H, brs).

MS: 598.1(M+Na)$^+$, 574.0(M−H)$^−$

Step 6

To a solution of N-{4-[2-(4-{[(1,3-dioxo-1,3-dihydro-2H-isoindol-2-yl)oxy]methyl}phenyl)ethyl]-5-[4-(methylsulfonyl)phenyl]-1,3-thiazol-2-yl}acetamide (116.8 mg) in N,N-dimethylformamide (1.1 ml) was added methylhydrazine (11.9 μl) under N$_2$ atmosphere, and the mixture was stirred at 20° C. for 4 hrs. The reaction mixture was concentrated in vacuo. Ethyl acetate was added to the residue, and the precipitate was filtered off. The filtrate was concentrated in vacuo to give a crude yellow solid (105.1 mg). The crude material was purified by preparative thin-layer chromatography over silica gel with chloroform/methanol (30:1) as an eluent to give a pale yellow powder. The obtained powder was washed with acetonitrile, and the precipitate was collected by filtration to give N-(4-(2-{4-[(aminooxy)methyl]phenyl}ethyl)-5-[4-(methylsulfonyl)phenyl]-1,3-thiazol-2-yl)acetamide (8.4 mg) as a white solid.

$^1$H-NMR (DMSO-d$_6$), δ (ppm): 2.17(3H, s), 2.91–3.02 (4H, m), 3.24(3H, s), 4.51(2H, s), 5.98(2H, s), 7.09(2H, d, J=8.1 Hz), 7.19(2H, d, J=8.1 Hz), 7.51(2H, d, J=8.4 Hz), 7.91(2H, d, J=8.1 Hz), 12.33(1H, brs).

MS: 468.0(M+H)$^+$

PRODUCTION EXAMPLE 63

Synthesis of N-{4-{2-[4-({[amino(imino)methyl]amino}methyl)phenyl]ethyl}-5-[4-(methylsulfonyl)phenyl]-1,3-thiazol-2-yl}acetamide hydrochloride Step 1

N-{4-{2-[4-(Bromomethyl)phenyl]ethyl}-5-[4-(methylsulfonyl)phenyl]-1,3-thiazol-2-yl}acetamide was prepared from N-(4-[2-{4-(hydroxymethyl)phenyl]ethyl}-5-[4-(methylsulfonyl)phenyl]-1,3-thiazol-2-yl)acetamide in a similar manner according to Step 9 of Production Example 61.

$^1$H-NMR (DMSO-d$_6$), δ (ppm): 2.17(3H, s), 2.90–3.10 (4H, m), 3.23(3H, s), 4.67(2H, s), 7.10(2H, d, J=8.1 Hz), 7.31(2H, d, J=8.1 Hz), 7.48(2H, d, J=8.4 Hz), 7.90(2H, d, J=8.4 Hz), 12.33(21H, s).

MS: 491.0(M−H)$^−$

Step 2

To a solution of N-{4-{2-[4-(bromomethyl)phenyl]ethyl}-5-[4-(methylsulfonyl)phenyl]-1,3-thiazol-2-yl}acetamide (70 mg) in N,N-dimethylformamide (1 ml) was added diformimide sodium salt (13.5 mg), and the mixture was stirred for 10 min at 20° C. To the reaction mixture was added water, the mixture was extracted with ethyl acetate, washed with water twice, dried over magnesium sulfate, and evaporated to give a crude diformimide compound. The diformimide compound was suspended in conc. hydrocloric acid (200 μl), ethanol (2 ml) and methanol (0.5 ml). The reaction mixture was stirred at 20° C. for 3 hrs., then at 50° C. for 3 hrs. The volatails were evaporated. To the residue was added saturated sodium hydrogen carbonate aqueous solution, the mixture was extracted with chloroform, dried over maganesium sulfate and evaporated to give crude N-{4-(2-{4-[aminomethyl]phenyl}ethyl)-5-[4-(methylsulfonyl)phenyl]-1,3-thiazol-2-yl}acetamide, that was used as crude in the next reaction.

MS: 428.8(M+H)$^+$

Step 3

Di-tert-butyl ((E)-{[4-(2-{2-(acetylamino)-5-[4-(methylsulfonyl)phenyl]-1,3-thiazol-4-yl}ethyl)benzyl]amino}methylidene)biscarbamate was prepared in similar manner according to Step 3 of Production Example 31.

$^1$H-NMR (CDCl$_3$), δ (ppm): 1.48(9H, s), 1.51(9H, s), 2.30(3H, s), 2.98(4H, s), 3.08(3H, s), 4.57(2H, d, J=5.1 Hz), 7.04(2H, d, J=8.1 Hz), 7.17(2H, d, J=8.1 Hz), 7.38(2H, d, J=8.4 Hz), 7.91(2H, d, J=8.4 Hz), 8.54(1H, t, J=5.1 Hz), 8.79(1H, s), 11.53(1H, s).

MS: 672.2(M+H)$^+$

Step 4

The title compound was prepared in a similar manner according to Step 4 of Production Example 31.

$^1$H-NMR (DMSO-d$_6$), δ (ppm): 2.18(3H, s), 2.90–3.05 (4H, m), 3.25(3H, s), 4.31(2H, d, J=6.2 Hz), 6.65–7.73(4H, brs), 7.14(2H, d, J=8.1 Hz), 7.18(2H, d, J=8.1 Hz), 7.52(2H, d, J=8.4 Hz), 7.93(2H, d, J=8.4 Hz), 12.35(1H, s).

MS: 506.0(M−H)$^−$

PRODUCTION EXAMPLE 64

Synthesis of methyl 4-({2-(acetylamino)-4-[2-(4-{[amino(imino)methyl]amino}phenyl)ethyl]-1,3-thiazol-5-yl}methyl)benzoate hydrochloride Step 1

Ethyl 4-(4-iodophenyl)-2-oxobutanoate was prepared from Ethyl 3-(4-iodophenyl)propanoate in a similar manner according to Step 2 of Production Example 47.

$^1$H-NMR (CDCl$_3$), δ (ppm): 1.35(3H, t, J=7.0 Hz), 2.90 (2H, t, J=7.5 Hz), 3.15(2H, t, J=7.5 Hz), 4.31(2H, q, J=7.0 Hz), 6.96(2H, d, J=8.0 Hz), 7.61(8.5 Hz).

MS: 331.0(M−H)$^−$

Step 2

Ethyl 3-bromo-4-(4-iodophenyl)-2-oxobutanoate was prepared in a similar manner according to Step 1 of Production Example 46.

$^1$H-NMR (CDCl$_3$), δ (ppm): 1.38(3H, t, J=7.0 Hz), 3.19 (1H, dd, J=7.5, 14.6 Hz), 3.47(1H, dd, J=7.5, 14.6 Hz), 4.36(2H, q, J=7.0 Hz), 5.21(1H, dd, J=7.5, 7.5 Hz), 7.00(2H, d, J=8.5 Hz), 7.65(2H, d, J=8.5 Hz).

MS: 369.2

Step 3

Ethyl 3-bromo-4-(4-iodophenyl)-2-oxobutanoate (1.32 g) was dissolved in ethanol (26 ml), and then, thiourea (244 mg) was added to the solution. The reaction mixture was refluxed for 1 h under nitrogen atmosphere. The cooled reaction mixture was evaporated in vacuo. The crude material was triturated with diethyl ether to give ethyl 2-amino-5-(4-iodobenzyl)-1,3-thiazole-4-carboxylate hydrobromide as a pale yellow solid.

$^1$H-NMR (DMSO-d$_6$), δ (ppm): 1.27(3H, t, J=7.0 Hz), 4.28(2H, q, J=7.0 Hz), 4.31(2H, s), 7.10(2H, d, J=8.5 Hz), 7.69(2H, d, J=8.5 Hz).

MS: 389.0(M+H)$^+$, 411.0(M+Na)$^+$

Step 4

Ethyl 2-amino-5-(4-iodobenzyl)-1,3-thiazole-4-carboxylate hydrobromide (1.386 g) was dissolved in dichloromethane (14 ml) under nitrogen atmosphere. Then, pyridine (0.765 ml) and acethyl chloride (0.336 ml) were added dropwise to the solution at 0° C. The reaction mixture was stirred at 20° C. for 1 h. The organic solution was washed with 1N-hydrochloric acid, water and brine, dried over magnesium sulfate, and concentrated in vacuo. The residue was washed with diisopropyl ether to give ethyl 2-(acetylamino)-5-(4-iodobenzyl)-1,3-thiazole-4-carboxylate as a white solid.

$^1$H-NMR (DMSO-d$_6$), δ (ppm): 1.27(3H, t, J=7.0 Hz), 2.09(3H, s), 4.26(2H, q, J=7.0 Hz), 4.43(2H, s), 7.10(2H, d, J=8.0 Hz), 7.67(2H, d, J=8.0 Hz), 12.44(1H, s).

MS: 431.0(M+H)$^+$, 453.0(M+Na)$^+$

Step 5

N-[4-Formyl-5-(4-iodobenzyl)-1,3-thiazol-2-yl]acetamide was prepared in a similar manner according to Step 4 of Production Example 46.

$^1$H-NMR (DMSO-d$_6$), δ (ppm): 2.11(3H, s), 4.48(2H, s), 7.11(2H, d, J=8.5 Hz), 7.68(2H, d, J=8.5 Hz), 10.00(1H, s).

MS: 409.0(M+Na)$^+$

Step 6

N-(5-(4-Iodobenzyl)-4-[2-(4-nitrophenyl)vinyl]-1,3-thiazol-2-yl)acetamide was prepared in a similar manner according to Step 5 of Production Example 45.

$^1$H-NMR (CDCl$_3$), δ (ppm): 2.07(3H×⅔, s), 2.15(3H×⅓, s), 3.96(2H×⅔, s), 4.12(2H×⅓, s), 6.63(1H×⅔, d, J=12.6 Hz), 6.70(1H×⅔, d, J=12.6 Hz), 6.94(2H×⅔, d, J=8.0 Hz), 6.99(2H×⅓, d, J=8.0 Hz), 7.12(1H×⅓, d, J=15.6 Hz), 7.25(1H×⅓, d, J=15.6 Hz), 7.39(2H×⅔, d, J=9.0 Hz), 7.56(2H×⅓, d, J=8.5 Hz), 7.62(2H×⅔, d, J=8.0 Hz), 7.65 (2H×⅓, d, J=8.5 Hz), 8.00(2H×⅔, d, J=8.5 Hz), 8.22(2H×⅓, d, J=8.5 Hz), 9.85(1H×⅓, s), 10.18(1H×⅔, s).

MS: 528.0(M+H)$^+$

Step 7

To a solution of a mixture of N-(5-(4-iodobenzyl)-4-[(Z)-2-(4-nitrophenyl)vinyl]-1,3-thiazol-2-yl)acetamide and N-{5-(4-iodobenzyl)-4-[(E)-2-(4-nitrophenyl)vinyl]-1,3-thiazol-2-yl}acetamide (Z:E=2:1) (558.2 mg) in methanol (2.8 ml) and N,N-dimethylformamide (5.5 ml) were added palladium(II) acetate (49.6 mg), 1,3-bis(diphenylphosphino) propane (109 mg) and triethylamine (308 μl). Carbon monooxide gas was bubbled through the solution for 30 min at 25° C. Then the reaction mixture was stirred for 6 hrs. at 70° C. under carbon monooxide atmosphere. The reaction mixture was cooled to 25° C., diluted with ethyl acetete, washed with brine, dried over magnesium sulfate and evaporated to give a crude yellow foam (645 mg). The crude foam was purified by flash column chromatography over silica gel with toluene/ethyl acetate (2:1–3:2) as an eluent, and triturated with ethyl ether to give a mixture of N-{5-(4-(methoxycarbonyl)benzyl)-4-[(Z)-2-(4-nitrophenyl)vinyl]-1,3-thiazol-2-yl}acetamide and N-{5-(4-(methoxycarbonyl)benzyl)-4-[(E)-2-(4-nitrophenyl)vinyl]-1,3-thiazol-2-yl}acetamide (Z:E=2:3) as a yellow solid.

$^1$H-NMR (CDCl$_3$), δ (ppm): 2.09(3H×⅖, s), 2.20(3H×⅗, s), 3.91(3H, s), 4.10(2H×⅖, s), 4.25(2H×⅗, s), 7.27(2H×⅖, s), 7.14(1H×⅗, d, J=15.6 Hz), 7.25(2H×⅖, d, J=9.0 Hz), 7.29(1H×⅗, d, J=15.6 Hz), 7.31(2H×⅗, d, J=8.5 Hz), 7.38(2H×⅖, d, J=9.0 Hz), 7.57(2H×⅗, d, J=8.5 Hz), 7.97 (2H×⅖, d, J=8.5 Hz), 7.99(2H×⅖, d, J=9.0 Hz), 8.00(2H× ⅗, d, J=8.5 Hz), 8.20(2H×⅗, d, J=9.0 Hz), 9.55(1H×⅗, brs), 10.11(1H×⅖, brs).

MS: 460.1(M+Na)$^+$

Step 8

Methyl 4-({2-(acetylamino)-4-[2-(4-aminophenyl)ethyl]-1,3-thiazol-5-yl}methyl)benzoate was prepared in a similar manner according to Step 6 of Production Example 45.

$^1$H-NMR (CDCl$_3$), δ (ppm): 2.20(3H, s), 2.80(4H, s), 3.40–3.67(2H, m), 3.83(2H, s), 3.90(3H, s), 6.57(2H, d, J=8.5 Hz), 6.84(2H, d, J=8.5 Hz), 7.09(2H, d, J=8.0 Hz), 7.91(2H, d, J=8.5 Hz), 8.96(1H, brs).

MS: 410.2(M+H)$^+$, 432.2(M+Na)$^+$

Step 9

Methyl 4-[(2-(acetylamino)-4-{2-[4-({(Z)-[(tert-butoxycarbonyl)amino][(tert-butoxycarbonyl)imino]methyl}amino)phenyl]ethyl}-1,3-thiazol-5-yl)methyl]benzoate was prepared in a similar manner according to Step 3 of Production Example 31.

$^1$H-NMR (CDCl$_3$), δ (ppm): 1.49(9H, s), 1.54(9H, s), 2.20(2H, s), 2.83(4H, s), 3.88(2H, s), 3.89(3H, s), 7.03(2H, d, J=8.5 Hz), 7.17(2H, d, J=8.0 Hz), 7.44(2H, d, J=8.0 Hz), 7.93(2H, d, J=8.5 Hz), 9.09(1H, brs), 10.24(1H, s), 11.64 (1H, s).

MS: 652.3(M+H)$^+$, 652.3(M+Na)$^+$

Step 10

The title compound was prepared in a similar manner according to Step 4 of Production Example 31.

$^1$H-NMR (DMSO-d$_6$), δ (ppm): 2.09(3H, s), 2.86(4H, s), 3.83(3H, s), 3.96–4.10(2H, m), 7.13(2H, d, J=8.5 Hz), 7.24(2H, d, J=9.0 Hz), 7.28(2H, d, J=8.5 Hz), 7.35(4H, s), 7.89(2H, d, J=8.0 Hz), 9.71(1H, 6), 12.01(1H, s).

MS: 452.2(M+H)$^-$ free

PRODUCTION EXAMPLE 65

Synthesis of 4-({2-(acetylamino)-4-[2-(4-{[amino (imino)methyl]amino}phenyl)ethyl]-1,3-thiazol-5-yl}methyl)-N,N-dimethylbenzamide hydrochloride Step 1

Methyl 4-{[2-(acetylamino)-4-(2-{4-[(tert-butoxycarbonyl)amino]phenyl}ethyl)-1,3-thiazol-5-yl]methyl}benzoate was prepared from the compound obtained in Step 8 of Production Example 64 in a similar manner according to Step 1 of Production Example 52.

$^1$H-NMR (CDCl$_3$), δ (ppm): 1.52(9H, s), 2.23(3H, s), 2.81(4H, s), 3.86(2H, s), 3.90(3H, s), 6.93(2H, d, J=8.0 Hz), 7.13(2H, d, J=8.5 Hz), 7.19(2H, d, J=8.0 Hz), 7.91(2H, d, J=8.5 Hz), 8.48–9.69(1H, brs).

MS: 510.2(M+H)$^+$, 532.3(M+Na)$^+$

Step 2

Methyl 4-{[2-(acetylamino)-4-(2-{4-[(tert-butoxycarbonyl)amino]phenyl}ethyl)-1,3-thiazol-5-yl]methyl}benzoate (287.7 mg), 1N-sodium hydroxide (1.41 ml) and ethanol (2.9 ml) were combined, and the mixture was refluxed for 3 hrs. After cooling to 25° C., the organic solvent was removed in vacuo. The aqueous solution was acidified with 1N-hydrochloric acid (pH=4), and the precipitate was filtered in vacuo to give 312.5 mg of a pale yellow solid. The solid was dissolved in pyridine (4.3 ml) under nitrogen atmosphere, and then, acethyl chloride (0.12 ml) was added dropwise to the solution at 0° C. The reaction mixture was stirred at 25° C. for 3 hrs., and pyridine was removed in vacuo. The residue was suspended in water, and acidified with 1N-hydrochloric acid. The precipitate was collected in vacuo. The solid was washed with water and diethyl ether to give 4-{[2-(acetylamino)-4-(2-{4-[(tert-butoxycarbonyl)amino]phenyl}ethyl)-1,3-thiazol-5-yl]methyl}benzoic acid as a pale yallow solid.

$^1$H-NMR (DMSO-d$_6$), δ (ppm): 1.47(9H, s), 2.08(3H, s), 2.70–2.90(4H, m), 3.92(2H, s), 6.99(2H, d, J=8.4 Hz), 7.10(2H, d, J=8.0 Hz), 7.33(2H, d, J=8.0 Hz), 7.81(2H, d, J=8.4 Hz), 9.24(1H, s), 12.00(1H, s), 12.84(1H, brs).

MS: 494.4(M−H)$^-$

Step 3

To a solution of 4-{[2-(acetylamino)-4-(2-{4-[(tert-butoxycarbonyl)amino]phenyl}ethyl)-1,13-thiazol-5-yl]methyl}benzoic acid (50 mg) in 0.5 ml of dichloromethane were added methylamine hydrochloride (10.7 mg), 1-hydroxybenzotriazole (20.4 mg) and 1-ethyl-3-(3-dimethylaminopropyl)carbodiimide (55.3 μl), then, the mixture was stirred for 3 hrs. at 25° C. The reaction mixture was diluted with 10 ml of chloroform and washed with water and brine. The organic layer was dried over magnesium sulfate and evaporated under vaccum. The residue was triturated with ethyl acetate and diisopropylether, and collected by filtration to give tert-butyl {4-[2-(2-(acetylamino)-5-{4-[(dimethylamino)carbonyl]benzyl}-1,3-thiazol-4-yl)ethyl]phenyl}carbamate as a pale yellow solid.

$^1$H-NMR (CDCl$_3$), δ (ppm): 1.51(9H, s), 2.23(3H, s), 2.83(4H, s), 2.95(3H, s), 3.09(3H, s), 3.82(2H, s), 6.47–6.81(1H, brs), 6.94(2H, d, J=8.1 Hz), 7.05(2H, d, J=8.1 Hz), 7.18(2H, d, J=8.1 Hz), 7.28(2H, d, J=8.1 Hz), 8.50–9.09(1H, brs).

MS: 523.3(M+H)$^+$, 545.2(M+Na)$^+$

Step 4 tert-Butyl {4-[2-(2-(acetylamino)-5-{4-[(dimethylamino)carbonyl]benzyl}-1,3-thiazol-4-yl)ethyl]phenyl}carbamate (39.1 mg) and trifluoroacetic acid (1 ml) were combined at 0° C. The reaction mixture was stirred at 25° C. for 2 hrs., and concentrated in vacuo. The residue was added to chloroform (20 ml) and 1N-sodium hydroxide (10 ml). The oraganic layer was separated, dried with magnesium sulfate, and evaporated to give yellow oil (33.3 mg). The crude yellow oil, N,N'-bis(tert-butoxycarbonyl)-1H-pyrazole-1-carboxamidine (45.8 mg) and tetrahydrofuran (0.5 ml) were combined under nitrogen atmosphere, and the mixture was stirred at 25° C. for 34 hrs. To the reaction mixture was added N,N'-bis(tert-butoxycarbonyl)-1H-pyrazole-1-carboxamidine (11 mg), and the mixture was stirred at 50° C. for 3 hrs. Then, the mixture was concentrated in vacuo. The residue was purified by preparative thin-layer chromatography over silica gel with chloroform/methanol (20:1) as an eluent to give di-tert-butyl [(E)-({4-[2-(2-(acetylamino)-5-{4-[(dimethylamino)carbonyl]benzyl}-1,3-thiazol-4-yl)ethyl]phenyl}amino)methylidene]biscarbamate as colorless oil (12.9 mg).

$^1$H-NMR (CDCl$_3$), δ (ppm): 1.50(9H, s), 1.54(9H, s), 2.21(3H, s), 2.85(4H, s), 2.96(3H, brs), 3.08(3H, brs), 3.86(2H, s), 7.06(2H, d, J=8.5 Hz), 7.14(2H, d, J=8.1 Hz), 7.33(2H, d, J=8.5 Hz), 7.46(2H, d, J=8.5 Hz), 8.81–9.21(1H, brs), 10.25(1H, s), 11.63(1H, s).

MS: 665.3(M+H)$^+$, 687.2(M+Na)$^+$

Step 5

The title compound was prepared in a similar manner according to Step 4 of Production Example 31.

$^1$H-NMR (DMSO-d$_6$), δ (ppm): 2.09(3H, s), 2.86(4H, s), 2.88(3H, s), 2.96(3H, s), 3.97(2H, s), 7.12(2H, d, J=8.4 Hz), 7.16(2H, d, J=8.1 Hz), 7.23(2H, d, J=8.4 Hz), 7.32(2H, d, J=8.1 Hz), 7.34(4H, s), 9.70(1H, s), 12.01(1H, s).

MS: 465.2(M+H)$^+$ free

PRODUCTION EXAMPLE 66

Synthesis of 4-({2-(acetylamino)-4-[2-(4-{[amino(imino)methyl]amino}phenyl)ethyl]-1,3-thiazol-5-yl}methyl)-N-methylbenzamide hydrochloride Step 1 tert-Butyl {4-[2-(2-(acetylamino)-5-{4-[(methylamino)carbonyl]benzyl}-1,3-thiazol-4-yl)ethyl]phenyl}carbamate was prepared from the compound obtained in Step 2 of Production Example 65 in a similar manner according to Step 3 of Production Example 65.

$^1$H-NMR (CDCl$_3$), δ (ppm): 1.52(9H, s), 2.23(3H, s), 2.78–2.89(4H, m), 3.00(3H, d, J=4.8 Hz), 3.83(2H, s), 6.20(2H, d, J=4.8 Hz), 6.36–6.78(1H, brs), 6.94(2H, d, J=8.4 Hz), 7.05(2H, d, J=8.4 Hz), 7.18(2H, d, J=8.4 Hz), 7.63(2H, d, J=8.4 Hz), 8.60–9.09(1H, brs).

MS: 509.2(M+H)$^+$, 531.2(M+Na)$^+$

Step 2

Di-tert-butyl [(E)-({4-[2-(2-(acetylamino)-5-{4-[(methylamino)carbonyl]benzyl}-1,3-thiazol-4-yl)ethyl]phenyl}amino)methylidene]biscarbamate was prepared in a similar manner according to Step 4 of Production Example 65.

$^1$H-NMR (CDCl$_3$), δ (ppm): 1.49(9H, s), 1.54(9H, s), 2.22(3H, s), 2.83(4H, s), 2.99(3H, d, J=4.8 Hz), 3.86(2H, s), 6.16(1H, d, J=4.0 Hz), 7.01(2H, d, J=8.4 Hz), 7.13(2H, d, J=8.4 Hz), 7.42(2H, d, J=8.4 Hz), 7.66(2H, d, J=8.4 Hz), 8.77–9.10(1H, brs), 10.24(1H, s), 11.62(1H, s).

MS: 651.3(M+H)$^+$, 673.3(M+Na)$^+$

Step 3

The title compound was prepared in a similar manner according to Step 4 of Production Example 31.

$^1$H-NMR (DMSO-d$_6$), δ (ppm): 2.08(3H, s), 2.76(3H, d, J=4.8 Hz), 2.86(4H, s), 3.98(2H, s), 7.13(2H, d, J=8.4 Hz), 7.19(2H, d, J=8.1 Hz), 7.23(2H, d, J=8.4 Hz), 7.30(4H, s), 7.74(2H, d, J=8.1 Hz), 8.38(2H, d, J=4.4 Hz), 9.62(1H, s), 11.99(1H, s).

MS: 451.3(M+H)$^-$ free

PRODUCTION EXAMPLE 67

Synthesis of N-{4-[2-(4-{[amino(imino)methyl]amino}phenyl)ethyl]-5-[(dimethylamino)methyl]-1,3-thiazol-2-yl}acetamide dihydrochloride Step 1

To a solution of N-{4-[(Z)-2-(4-nitrophenyl)vinyl]-1,3-thiazol-2-yl}acetamide (500 mg) in acetic acid (3 ml) were added dimethylamine hydrochloride (169 mg) and paraformaldehyde (62.2 mg), and the mixture was stirred at 100° C. (bath temp.) for 2 hrs. The solvent was removed in vacuo, and the mixture was adjusted to pH=9 with saturated sodium hydrogen carbonate aqueous solution, extracted with ethyl acetate. The organic layer was washed with brine, dried over magnesium sulfate and evaporated. The crude compound was purified by flash column chromatography over silica gel with dichloromethane/methanol (100:1)→(20:1) as an eluent to give N-{5-[(dimethylamino)methyl]-4-[(Z)-2-(4-nitrophenyl)vinyl]-1,3-thiazol-2-yl}acetamide as a yellow amorphous substance.

$^1$H-NMR (CDCl$_3$), δ (ppm): 2.08(3H, s), 2.26(6H, s), 3.47(2H, s), 6.63(1H, d, J=12.6 Hz), 6.70(1H, d, J=12.6 Hz), 7.43(2H, d, J=9.0 Hz), 8.03(2H, d, J=9.0 Hz), 10.20(1H, brs).

MS: 347(M+H)$^+$, 369(M+Na)$^+$

Step 2

N-{4-[2-(4-Aminophenyl)ethyl]-5-[(dimethylamino)methyl]-1,3-thiazol-2-yl}acetamide was prepared in a similar manner according to Step 6 of Production Example 45.

$^1$H-NMR (CDCl$_3$), δ (ppm): 2.19(6H, s), 2.23(3H, s), 2.80(4H, s), 3.30(2H, s), 3.56(2H, s), 6.60(2H, d, J=8.4 Hz), 6.91(2H, d, J=8.4 Hz), 8.54–8.84(1H, brs).

MS: 317.2(M−H)$^-$

Step 3

Di-tert-butyl ((Z)-{[4-(2-{2-(acetylamino)-5-[(dimethylamino)methyl]-1,3-thiazol-4-yl}ethyl)phenyl]amino}methylidene)biscarbamate was prepared in a similar manner according to Step 7 of Production Example 45.

$^1$H-NMR (CDCl$_3$), δ (ppm): 1.50(9H, s), 1.53(9H, s), 2.21(6H, s), 2.22(3H, s), 2.87(4H, s), 3.36(2H, s), 7.09(2H, d, J=8.5 Hz), 7.46(2H, d, J=8.5 Hz), 8.89–9.97(1H, brs), 10.24(1H, s), 11.63(1H, s).

MS: 561.3(M+H)$^+$, 583.3(M+Na)$^+$

Step 4

The title compound was prepared in a similar manner according to Step 4 of Production Example 31.

$^1$H-NMR (DMSO-d$_6$), δ (ppm): 2.16(3H, s), 2.66(3H, s), 2.68(3H, s), 2.96(4H, s), 4.37(2H, d, J=4.8 Hz), 7.15(2H, d, J=8.4 Hz), 7.32(2H, d, J=8.4 Hz), 7.51(4H, s), 10.08(1H, s), 10.64(1H, t, J=4.8 Hz), 12.33(1H, s).

MS: 361.1(M+H)$^+$

PRODUCTION EXAMPLE 68

Synthesis of N-{5-[(4-acetyl-1-piperazinyl)methyl]-4-[2-(4-{[amino(imino)methyl]amino}phenyl)ethyl]-1,3-thiazol-2-yl}acetamide dihydrochloride Step 1

N-{5-[(4-Acetyl-1-piperazinyl)methyl]-4-[(Z)-2-(4-nitrophenyl)vinyl]-1,3-thiazol-2-yl}acetamide was prepared from N-{4-[(Z)-2-(4-nitrophenyl)vinyl]-1,3-thiazol-2-yl}acetamide in a similar manner according to Step 1 of Production Example 67.

$^1$H-NMR (CDCl$_3$), δ (ppm): 2.08(6H, s), 2.34–2.59(4H, m), 3.41–3.53(2H, m), 3.56(2H, s), 3.58–3.69(2H, m), 6.62(1H, d, J=12.6 Hz), 6.68(1H, d, J=12.6 Hz), 7.45(2H, d, J=8.5 Hz), 8.05(2H, d, J=9.0 Hz), 10.18(1H, s).

MS: 452.0(M+Na)$^+$

Step 2

N-(5-[(4-Acetyl-1-piperazinyl)methyl]-4-[(Z)-2-(4-nitrophenyl)vinyl]-1,3-thiazol-2-yl)acetamide (1080 mg), methanol (2 ml), tetrahydrofuran (2 ml), acetic acid (0.3 ml) and then 10% palladium on carbon (150 mg) were combined under nitrogen atmosphere. The mixture was stirred under 3 atm hydrogen for 3 hrs. at 25° C. The reaction mixture was filtered through a celite pad, and the filtrate was concentrated in vacuo to give a crude material (192.3 mg). To the residue was added saturated sodium hydrogen carbonate aqueous solution, and the mixture was extracted with chloroform. The organic layer was washed with brine, dried over MgSO$_4$, and concentrated in vacuo to give a pink amorphous substance (124.7 mg). The pink amorphous substance (124.7 mg), N,N'-bis(tert-butoxycarbonyl)-1H-pyrazole-1-carboxamidine (93.6 mg) and tetrahydrofuran (2 ml) were combined under nitrogen atmosphere. The reaction mixture was stirred at 25° C. for 14 hrs., and concentrated in vacuo. The residue was purified by preparative thin-layer chromatography over silica gel with chloroform/methanol (20:1) as an eluent to give di-tert-butyl ((Z)-{[4-(2-{2-(acetylamino)-5-[(4-acetyl-1-piperazinyl)methyl]-1,3-thiazol-4-yl}ethyl)phenyl]amino}methylidene)biscarbamate as colorless oil (121.1 mg).

$^1$H-NMR (CDCl$_3$), δ (ppm): 1.50(9H, s), 1.53(9H, s), 2.06(3H, s), 2.24(3H, s), 2.20–2.32(2H, m), 2.33–2.44(2H, m), 2.74–2.96(4H, m), 3.30–3.45(4H, m), 3.52–3.65(2H, m), 7.04(2H, d, J=8.5 Hz), 7.45(2H, d, J=8.5 Hz), 8.85–10.17(1H, brs), 10.25(1H, s), 11.63(1H, s).

MS: 644.3(M+H)$^+$, 666.1(M+H)$^+$

Step 3

The title compound was prepared in a similar manner according to Step 4 of Production Example 31.

$^1$H-NMR (DMSO-d$_6$), δ (ppm): 2.03(3H, s), 2.16(3H, s), 2.75–3.15(8H, m), 3.16–3.63(4H, m), 4.40(2H, s), 7.15(2H, d, J=8.0 Hz), 7.32(2H, d, J=8.0 Hz), 7.49(4H, s), 10.07(1H, s), 11.29(1H, brs), 12.33(1H, s)

MS: 444.2(M+H)$^+$ free

PRODUCTION EXAMPLE 69

Synthesis of N-(4-[2-(4-{[amino(imino)methyl]amino}phenyl)ethyl]-5-{[4-(methylsulfonyl)-1-piperazinyl]methyl}-1,3-thiazol-2-yl)acetamide dihydrochloride Step 1

N-{5-{[4-(Methylsulfonyl)-1-piperazinyl]methyl}-4-[(Z)-2-(4-nitrophenyl)vinyl]-1,3-thiazol-2-yl}acetamide was prepared from N-{4-[(Z)-2-(4-nitrophenyl)vinyl]-1,3-thiazol-2-yl}acetamide in a similar manner according to Step 1 of Production Example 67.

$^1$H-NMR (CDCl$_3$), δ (ppm): 2.08(3H, s), 2.54–2.66(4H, m), 2.80(3H, s), 3.19–3.34(4H, m), 3.58(2H, s), 6.61(1H, d, J=12.1 Hz), 6.69(1H, d, J=12.1 Hz), 7.45(2H, d, J=8.5 Hz), 8.04(2H, d, J=8.5 Hz), 10.09(1H, s).

MS: 467.2(M+H)$^+$, 488.1(M+Na)$^+$

Step 2

Di-tert-butyl [(Z)-({4-[2-(2-(acetylamino)-5-{[4-(methylsulfonyl)-1-piperazinyl]methyl}-1,3-thiazol-4-yl)ethyl]phenyl}amino)methylidene]biscarbamate was prepared in a similar manner according to Step 2 of Production Example 68.

$^1$H-NMR (CDCl$_3$), δ (ppm): 1.50(9H, s), 1.54(9H, s), 2.23(3H, s), 2.41–2.56(4H, m), 2.76(3H, s), 2.80–2.89(4H, m), 3.12–3.27(4H, m), 3.42(2H, s), 7.05(2H, d, J=8.5 Hz), 7.45(2H, d, J=8.5 Hz), 8.57–9.61(1H, brs), 10.25(1H, s), 11.63(1H, s).

MS: 680.3(M+H)$^-$, 702.2(M+Na)$^-$

Step 3

The title compound was prepared in a similar manner according to Step 4 of Production Example 31.

$^1$H-NMR (DMSO-d$_6$), δ (ppm): 2.16(3H, s), 2.97(4H, s), 3.00(3H, s), 3.05–3.28(4H, m), 3.28–3.48(2H, m), 3.59–3.81(2H, m), 4.35–4.60(2H, brs), 7.16(2H, d, J=8.1

Hz), 7.32(2H, d, J=8.1 Hz), 7.39(4H, s), 9.84(1H, s), 10.64–10.89(1H, brs), 12.34(1H, s).

MS: 480.1(M+H)⁻ free

PRODUCTION EXAMPLE 70

Synthesis of N-[4-[2-(4-{[amino(imino)methyl]amino}phenyl)ethyl]-5-(4-thiomorpholinylmethyl)-1,3-thiazol-2-yl]acetamide dihydrochloride Step 1

N-[4-[(Z)-2-(4-Nitrophenyl)vinyl]-5-(4-thiomorpholinylmethyl)-1,3-thiazol-2-yl]acetamide was prepared from N-{4-[(Z)-2-(4-nitrophenyl)vinyl]-1,3-thiazol-2-yl}acetamide in a similar manner according to Step 1 of Production Example 67.

¹H-NMR (CDCl₃), δ (ppm): 2.08(3H, s), 2.57–2.86(8H, m), 3.53(2H, s), 6.62(1H, d, J=12.6 Hz), 6.68(1H, d, J=12.6 Hz), 7.43(2H, d, J=9.0 Hz), 8.0332(2H, d, J=9.0 Hz), 10.16(1H, s).

MS: 405.1(M+H)⁺, 427.1(M+Na)⁺

Step 2

Di-tert-butyl {(Z)-[(4-{2-[2-(acetylamino)-5-(4-thiomorpholinylmethyl)-1,3-thiazol-4-yl]ethyl}phenyl)amino]methylidene}biscarbamate was prepared in a similar manner according to Step 2 of Production Example 68.

¹H-NMR (CDCl₃), δ (ppm): 1.50(9H, s), 1.53(9H, s), 2.22(3H, s), 2.63(8H, s), 2.80–2.90(4H, m), 3.39(2H, s), 7.06(2H, d, J=8.5 Hz), 7.45(2H, d, J=8.5 Hz), 8.82–9.39(1H, brs), 10.24(1H, s), 11.63(1H, s).

MS: 619.3(M+H)⁺, 641.2(M+Na)⁺

Step 3

The title compound was prepared in a similar manner according to Step 4 of Production Example 31.

¹H-NMR (DMSO-d₆), δ (ppm): 2.16(3H, s), 2.69–2.87 (2H, m), 2.97(4H, s), 3.02–3.19(4H, m), 3.48–3.61(2H, m), 4.42(2H, s), 7.15(2H, d, J=8.4 Hz), 7.31(2H, d, J=8.4 Hz), 7.40(4H, s), 9.86(1H., s), 10.51–10.69(1H, brs), 12.34(1H, s).

MS: 419.2(M+H)⁻ free

PRODUCTION EXAMPLE 71

Synthesis of 2-(acetylamino)-4-[2-(4-{[amino(imino)methyl]amino}phenyl)ethyl]-N-[2-(dimethylamino)-2-oxoethyl]-1,3-thiazole-5-carboxamide hydrochloride Step 1 tert-Butyl (4-{2-[2-(acetylamino)-5-({[2-(dimethylamino)-2-oxoethyl]amino}carbonyl)-1,3-thiazol-4-yl]ethyl}phenyl)carbamate was prepared from 2-(acetylamino)-4-(2-{4-[(tert-butoxycarbonyl)amino]phenyl}ethyl)-1,3-thiazole-5-carboxylic acid in a similar manner according to Step 1 of Production Example 32.

¹H-NMR (200 MHz, DMSO-d₆), δ (ppm): 1.46(9H, s), 2.15(3H, s), 2.72, 2.85(3H, s), 2.89, 2.98(3H, s), 3.16(4H, m), 4.01(2H, m), 7.07(2H, d, J=8.2 Hz), 7.32(2H, d, J=8.2 Hz), 7.87–7.95(1H, m), 9.21(1H, s), 12.36(1H, s).

MS: 490(M+H)⁺

Step 2

2-(Acetylamino)-4-[2-(4-aminophenyl)ethyl]-N-[2-(dimethylamino)-2-oxoethyl]-1,3-thiazole-5-carboxamide hydrochloride was prepared in a similar manner according to Step 2 of Production Example 31.

white powder

¹H-NMR (200 MHz, DMSO-d₆), δ (ppm): 2.16(3H, s), 2.85(3H, s), 2.86–2.98(5H, m), 3.22(2H, dd, J=8.9, 5.3 Hz), 4.01(2H, d, J=5.3 Hz), 7.27(2H, d, J=8.5 Hz), 7.33(2H, d, J=8.5 Hz), 7.94(1H, t, J=5.3 Hz), 10.15(2H, br), 12.38(1H, s).

MS: 390(M+H)⁺ free

Step 3

Di-tert-butyl {(Z)-[(4-{2-[2-(acetylamino)-5-({[2-(dimethylamino)-2-oxoethyl]amino}carbonyl)-1,3-thiazol-4-yl]ethyl}phenyl)amino]methylidene}biscarbamate was prepared in a similar manner according to Step 3 of Production Example 31.

white powder

¹H-NMR (200 MHz, DMSO-d₆), δ (ppm): 1.39(9H, s), 1.51(9H, s), 2.15(3H, s), 2.85(3H, s), 2.85–2.94(2H, m), 2.97(3H, s), 3.17–3.26(2H, m), 4.00–4.04(2H, m), 7.19(1H, d, J=8.0 Hz), 7.42(2H, d, J=8.0 Hz), 7.88(1H, t, J=5.4 Hz), 9.93(1H, s), 11.43(1H, s), 12.38 (1H, s).

MS: 632(M+H)⁺

Step 4

The title compound was prepared in a similar manner according to Step 4 of Production Example 31.

white powder

¹H-NMR (200 MHz, DMSO-d₆), δ (ppm): 2.16(3H, s), 2.84(3H, s), 2.89–2.695(2H, m), 2.98(3H, s), 3.19–3.26(2H, m), 3.99(2H, m), 7.13(2H, d, J=8.0 Hz), 7.28(2H, d, J=8.0 Hz), 7.43(4H, br), 7.97(1H, br), 9.86(1H, s), 12.38(1H, s).

MS: 432(M+H)⁺ free

PRODUCTION EXAMPLE 72

Synthesis of 2-(acetylamino)-4-[2-(4-{[amino(imino)methyl]amino}phenyl)ethyl]-N-[3-(dimethylamino)-3-oxopropyl]-1,3-thiazole-5-carboxamide hydrochloride Step 1 tert-Butyl (4-{2-[2-(acetylamino)-5-({[3-(dimethylamino)-3-oxopropyl]amino}carbonyl)-1,3-thiazol-4-yl]ethyl}phenyl)carbamate was prepared from 2-(acetylamino)-4-(2-{4-[(tert-butoxycarbonyl)amino]phenyl}ethyl)-1,3-thiazole-5-carboxylic acid in a similar manner according to Step 1 of Production Example 32.

¹H-NMR (200 MHz, DMSO-d₆), δ (ppm): 1.46(9H, s), 2.14(3H, s), 2.55(2H, m), 2.73–2.94(8H, m), 3.14(2H, dd, J=9.1, 6.1 Hz), 3.37(2H, m), 7.05(2H, d, J=8.5 Hz), 7.32(2H, d, J=8.5 Hz), 7.89(1H, m), 9.21(1H, s), 12.33(1H, s).

MS: 504(M+H)⁺

Step 2

2-(Acetylamino)-4-[2-(4-aminophenyl)ethyl]-N-[3-(dimethylamino)-3-oxopropyl]-1,3-thiazole-5-carboxamide hydrochloride was prepared in a similar manner according to Step 2 of Production Example 31.

white powder

¹H-NMR (200 MHz, DMSO-d₆), δ (ppm): 2.15(3H, s), 2.57(2H, m), 2.81(3H, s), 2.84–2.98(5H, m), 3.20(2H, dd, J=8.9, 5.4 Hz), 3.36(2H, dd, J=12.8, 7.1 Hz), 7.26(2H, d, J=8.6 Hz), 7.32(2H, d, J=8.6 Hz), 7.95(1H, t, J=5.4 Hz), 10.04(2H, br), 12.35(1H, br).

MS: 403(M+H)⁺ free

Step 3

Di-tert-butyl {(Z)-[(4-{2-[2-(acetylamino)-5-({[3-(dimethylamino)-3-oxopropyl]amino}carbonyl)-1,3-thiazol-4-yl]ethyl}phenyl)amino]methylidene}biscarbamate was prepared in a similar manner according to Step 3 of Production Example 31.

white powder $^1$H-NMR (200 MHz, DMSO-d$_6$), δ (ppm): 1.39(9H, s), 1.50(9H, s), 2.14(3H, s), 2.80(3H, s), 2.81–2.93(2H, m), 2.94(3H, s), 3.13–3.29(6H, m), 3.34–3.43(2H, m), 7.17(2H, d), 7.42(2H, d), 7.89(1H, m), 9.93(1H, s), 11.43(1H, s), 12.34(1H, m).

MS: 646(M+H)$^+$

Step 4

The title compound was prepared in a similar manner according to Step 4 of Production Example 31.

white powder $^1$H-NMR (200 MHz, DMSO-d$_6$), δ (ppm): 2.16(3H, s), 2.56(2H, m), 2.81(3H, s), 2.87–2.95(5H, m), 3.19(2H, m), 3.34(2H, m), 7.11–7.38(4H, m), 7.43(4H, s), 8.02(1H, m), 8.55(1H, br), 9.88(1H, br), 12.36(1H, s).

MS: 445(M+H)$^+$ free

PRODUCTION EXAMPLE 73

Synthesis of 2-(acetylamino)-N-[2-(acetylamino)ethyl]-4-[2-(4-{[amino(imino)methyl]amino}phenyl)ethyl]-1,3-thiazole-5-carboxamide hydrochloride Step 1 tert-Butyl (4-{2-[2-(acetylamino)-5-({[2-(acetylamino)ethyl]amino}carbonyl)-1,3-thiazol-4-yl]ethyl}phenyl)carbamate was prepared from 2-(acetylamino)-4-(2-{4-[(tert-butoxycarbonyl)amino]phenyl}ethyl)-1,3-thiazole-5-carboxylic acid in a similar manner according to Step 1 of Production Example 32.

$^1$H-NMR (200 MHz, DMSO-d$_6$), δ (ppm): 1.46(9H, s), 1.79(3H, s), 2.14(3H, s), 2.84(2H, m), 3.16–3.22(6H, m), 7.06(2H, d, J=8.5 Hz), 7.33(2H, d, J=8.5 Hz), 7.99(2H, m), 9.21(1H, s), 12.33(1H, s).

MS: 490(M+H)$^+$

Step 2

2-(Acetylamino)-N-[2-(acetylamino)ethyl]-4-[2-(4-aminophenyl)ethyl]-1,3-thiazole-5-carboxamide hydrochloride was prepared in a similar manner according to Step 2 of Production Example 31.

white powder $^1$H-NMR (200 MHz, DMSO-d$_6$), δ (ppm): 1.79(3H, s), 2.15(3H, s), 2.90–2.98(2H, dd, J=10.1, 6.6 Hz), 3.14–3.26 (6H, m), 7.27(2H, d, J=8.9 Hz), 7.32(2H, d, J=8.9 Hz), 7.97–8.06(2H, m), 10.18(2H, br), 12.35(1H, s).

MS: 390(M+H)$^+$ free

Step 3

Di-tert-butyl {(Z)-[(4-{2-[2-(acetylamino)-5-({[2-(acetylamino)ethyl]amino}carbonyl)-1,3-thiazol-4-yl]ethyl}phenyl)amino]methylidene}biscarbamate was prepared in a similar manner according to Step 3 of Production Example 31.

white powder $^1$H-NMR (200 MHz, DMSO-d$_6$), δ (ppm): 1.39(9H, s), 1.51(9H, s), 1.79(3H, s), 2.15(3H, s), 2.89(2H, m), 3.18(6H, m), 7.18(2H, d, J=8.0 Hz), 7.42(2H, d, J=8.0 Hz), 7.95(2H, m), 9.93(1H, s), 11.43(1H, s), 12.35(1H, s).

MS: 632(M+H)$^+$

Step 4

The title compound was prepared in a similar manner according to Step 4 of Production Example 31.

white powder $^1$H-NMR (200 MHz, DMSO-d$_6$), δ (ppm): 1.79(9H, s), 2.16(9H, s), 2.91(2H, m), 3.10–3.25(6H, m), 7.14(2H, d, J=8.2 Hz), 7.27(2H, d, J=8.2 Hz), 7.42(4H, br), 7.97(1H, br), 8.08(1H, br), 9.83(1H, s), 12.36(1H, s).

MS: 432(M+H)$^+$ free

PRODUCTION EXAMPLE 74

Synthesis of 2-(acetylamino)-4-[2-(4-{[amino(imino)methyl]amino}phenyl)ethyl]-N-{2-[(methylsulfonyl)amino]ethyl}-1,3-thiazole-5-carboxamide hydrochloride Step 1 tert-Butyl [4-(2-{2-(acetylamino)-5-[({2-[(methylsulfonyl)amino]ethyl}amino)carbonyl]-1,3-thiazol-4-yl}ethyl)phenyl]carbamate was prepared from 2-(acetylamino)-4-(2-{4-[(tert-butoxycarbonyl)amino]phenyl}ethyl)-1,3-thiazole-5-carboxylic acid in a similar manner according to Step 1 of Production Example 32.

$^1$H-NMR (200 MHz, DMSO-d$_6$), δ (ppm): 1.46(9H, s), 2.15(3H, s), 2.79–2.89(5H, m), 3.05–3.32(6H, m), 7.04–7.14(3H, m), 7.33(2H, d, J=8.3 Hz), 8.01(1H, br), 9.20(1H, s), 12.35(1H, s).

MS: 526(M+H)$^+$

Step 2

2-(Acetylamino)-4-[2-(4-aminophenyl)ethyl]-N-{2-[(methylsulfonyl)amino]ethyl}-1,3-thiazole-5-carboxamide hydrochloride was prepared in a similar manner according to Step 2 of Production Example 31.

white powder $^1$H-NMR (200 MHz, DMSO-d$_6$), δ (ppm): 2.15(3H, s), 2.89(3H, s), 2.89–3.27(8H, m), 7.12(1H, t, J=5.7 Hz), 7.24 (2H, d, J=8.5 Hz), 7.32(2H, d, J=8.5 Hz), 8.05(1H, t, J=5.4 Hz), 9.95(2H, br), 12.36(1H, s).

MS: 425(M+H)$^+$ free

Step 3

Di-tert-butyl ((Z)-{[4-(2-{2-(acetylamino)-5-[({2-[(methylsulfonyl)amino]ethyl}amino)carbonyl]-1,3-thiazol-4-yl}ethyl)phenyl]amino}methylidene)biscarbamate was prepared in a similar manner according to Step 3 of Production Example 31.

white powder $^1$H-NMR (200 MHz, DMSO-d$_6$), δ (ppm): 1.39(9H, s), 1.51(9H, s), 2.15(3H, s), 2.80–2.97(5H, m), 3.00–3.14(2H, m), 3.15–3.30(4H, 15 m), 7.11(1H, m), 7.17(2H, d, J=8.5 Hz), 7.42(2H, d, J=8.5 Hz), 8.01(1H, m), 9.93(1H, s), 11.43(1H, s), 12.37(1H, s).

MS: 668(M+H)$^+$

Step 4

The title compound was prepared in a similar manner according to Step 4 of Production Example 31.

white powder $^1$H-NMR (200 MHz, DMSO-d$_6$), δ (ppm): 2.16(3H, s), 2.90–2.96(5H, m), 3.08(2H, m), 3.19–3.29(4H, q), 7.14(2H, d, J=8.3 Hz), 7.28(2H, d, J=8.3 Hz), 7.43(4H, br), 8.07(1H, m), 9.87(1H, s), 12.38(1H, s).

MS: 467(M+H)$^+$ free

PRODUCTION EXAMPLE 75

Synthesis of 2-(acetylamino)-4-[2-(4-{[amino(imino)methyl]amino}phenyl)ethyl]-N-[3-(dimethylamino)-3-oxopropyl]-N-methyl-1,3-thiazole-5-carboxamide hydrochloride Step 1

Di-tert-butyl [(Z)-({4-[2-(2-(acetylamino)-5-{[[3-(dimethylamino)-3-oxopropyl](methyl)amino]carbonyl}-1,3-thiazol-4-yl)ethyl]phenyl}amino)methylidene]biscarbamate was prepared from the compound obtained in Step 2 of Production Example 34 in a similar manner according to Step 1 of Production Example 32.

$^1$H-NMR (200 MHz, DMSO-$d_6$), δ (ppm): 1.39(9H, s), 1.50(9H, s), 2.14(3H, s), 2.56(2H, t, J=7.3 Hz), 2.78(3H, s), 2.84–2.88(6H, m), 2.93(3H, s), 3.47(3H, m), 7.12(2H, d, J=8.4 Hz), 7.40(2H, d, J=8.4 Hz), 9.92(1H, s), 11.43(1H, s), 12.34(1H, s).

MS: 659(M+Na)$^+$

Step 2

The title compound was prepared in a similar manner according to Step 4 of Production Example 31.

$^1$H-NMR (200 MHz, DMSO-$d_6$), δ (ppm): 2.15(3H, s), 2.50–2.60(6H, m), 2.79(3H, s), 2.87(3H, s), 2.94(3H, s), 3.39–3.64(2H, m), 7.09–7.26(4H, m), 7.46(4H, br), 9.96 (1H, s), 12.35(1H, s).

MS: 460(M+H)$^+$ free

PRODUCTION EXAMPLE 76

Synthesis of 2-(acetylamino)-4-[2-(4-{[amino(imino)methyl]amino}phenyl)ethyl]-N-{3-[benzyl(methyl)amino]-3-oxopropyl}-1,3-thiazole-5-carboxamide hydrochloride Step 1

Di-tert-butyl ((Z)-{[4-(2-{2-(acetylamino)-5-[({3-[benzyl(methyl)amino]-3-oxopropyl}amino)carbonyl]-1,3-thiazol-4-yl}ethyl)phenyl]amino}methylidene)biscarbamate was prepared from the compound obtained in Step 2 of Production Example 34 in a similar manner according to Step 1 of Production Example 32.

$^1$H-NMR (200 MHz, DMSO-$d_6$), δ (ppm): 1.83(9H, s), 1.50(9H, s), 1.98–2.15(3H, m), 2.60–2.63(2H, m), 2.80–2.90(5H, m), 3.17–3.21(2H, m), 3.42–3.47(2H, m), 4.50–4.57(2H, m), 7.12–7.43(9H, 30 m), 7.95(1H, m), 9.93 (1H, s), 11.44(1H, s), 12.4(1H, s).

MS: 722(M+H)$^+$

Step 2

The title compound was prepared in a similar manner according to Step 4 of Production Example 31.

$^1$H-NMR (200 MHz, DMSO-$d_6$), δ (ppm): 2.16, 2.30(3H, s), 2.64(2H, m), 2.64(2H, m), 2.80–2.90(5H, m), 3.14–3.25 (2H, m), 3.43–3.47(2H, m), 4.51–4.57(2H, m), 7.08–7.42 (9H, m), 8.02–8.04(1H, m), 9.83–9.87(1H, m), 12.36(1H, m).

MS: 522(M+H)$^+$ free

PRODUCTION EXAMPLE 77

Synthesis of 2-(acetylamino)-4-[2-(4-{[amino(imino)methyl]amino}phenyl)ethyl]-N-[4-(dimethylamino)-4-oxobutyl]-1,3-thiazole-5-carboxamide hydrochloride Step 1

Di-tert-butyl {(Z)-[(4-{2-[2-(acetylamino)-5-({[4-(dimethylamino)-4-oxobutyl]amino}carbonyl)-1,3-thiazol-4-yl]ethyl}phenyl)amino]methylidene}biscarbamate was prepared from the compound obtained in Step 2 of Production Example 34 in a similar manner according to Step 1 of Production Example 32.

$^1$H-NMR (200 MHz, DMSO-$d_6$), δ (ppm): 1.39(9H, s), 1.50(9H, s), 1.68(2H, tt, J=6.8 Hz), 2.14(3H, s), 2.30(2H, t, J=6.8 Hz), 2.80(3H, s), 2.82–2.95(2H, m), 2.92(3H, s), 3.10–3.28(4H, m), 7.18(2H, d, J=8.5 Hz), 7.39(2H, d, J=8.5 Hz), 9.92(1H, s), 11.43(1H, br), 12.3(1H, br).

MS: 682(M+Na)$^+$

Step 2

The title compound was prepared in a similar manner according to Step 4 of Production Example 31.

$^1$H-NMR (200 MHz, DMSO-$d_6$), δ (ppm): 1.69(2H, m), 2.16(2H, s), 2.31(2H, t, J=7.2 Hz), 2.81(3H, s), 2.87–2.95 (2H, m), 2.93(3H, s), 3.16–3.24(4H, m), 3.57(3H, s), 7.11–7.44(4H, m), 8.06–8.23(1H, m), 9.83–9.92(1H, m), 12.35(1H, s).

MS: 460(M+H)$^+$ free

PRODUCTION EXAMPLE 78

Synthesis of (2R)-1-({2-(acetylamino)-4-[2-(4-{[amino(imino)methyl]amino}phenyl)ethyl]-1,3-thiazol-5-yl}carbonyl)-N,N-dimethyl-2-pyrrolidinecarboxamide hydrochloride Step 1

Di-tert-butyl {(Z)-[(4-{2-[2-(acetylamino)-5-({(2R)-2-[(dimethylamino)carbonyl]-1-pyrrolidinyl}carbonyl)-1,3-thiazol-4-yl]ethyl}phenyl)amino]methylidene}biscarbamate was prepared from the compound obtained in Step 2 of Production Example 34 in a similar manner according to Step 1 of Production Example 32.

$^1$H-NMR (200 MHz, DMSO-$d_6$), δ (ppm): 1.39(9H, s), 1.50(9H, s), 1.60–1.93(3H, m), 2.06–2.30(1H, m), 2.14(3H, s), 2.66–3.14(10H, m), 3.20–3.50(2H, m), 4.89(1H, m), 7.16(2H, d, J=8.0 Hz), 7.41(2H, d, J=8.0 Hz), 9.92(1H, s), 11.41(1H, s), 12.34(1H, s).

MS: 694(M+Na)$^+$

Step 2

The title compound was prepared in a similar manner according to Step 4 of Production Example 31.

$^1$H-NMR (200 MHz, DMSO-$d_6$), δ (ppm): 1.60–2.00(3H, m), 2.15, 2.48(3H, s ×2), 2.65–3.50(12H, m), 3.60–3.75(2H, m), 7.09–7.17(2H, d ×2), 7.23–7.31(2H, d ×2), 7.47(3H, br), 9.94(1H, br), 12.35, 12.59(1H, s ×2).

MS: 472(M+H)$^+$ free

PRODUCTION EXAMPLE 79

Synthesis of (2S)-1-({2-(acetylamino)-4-[2-(4-{[amino(imino)methyl]amino}phenyl)ethyl]-1,3-thiazol-5-yl}carbonyl)-N,N-dimethyl-2-pyrrolidinecarboxamide hydrochloride Step 1

Di-tert-butyl {(Z)-[(4-{2-[2-(acetylamino)-5-({(2S)-2-[(dimethylamino)carbonyl]-1-pyrrolidinyl}carbonyl)-1,3-thiazol-4-yl]ethyl}phenyl)amino]methylidene}biscarbamate was prepared from the compound obtained in Step 2 of Production Example 34 in a similar manner according to Step 1 of Production Example 32.

$^1$H-NMR (200 MHz, DMSO-d$_6$), δ (ppm): 1.39(3H, s), 1.50(9H, s), 1.60–1.94(H, m), 2.14(3H, s), 2.10–2.36(1H, m), 2.67–3.11(10H, m), 3.30–3.52(2H, m), 4.88(1H, m), 7.16(2H, d, J=8.0 Hz), 7.41(2H, d, J=8.0 Hz), 9.92(1H, s), 11.41(1H, s), 12.34(1H, 5 s).

MS: 694(M+Na)$^+$

Step 2

The title compound was prepared in a similar manner according to Step 4 of Production Example 31.

$^1$H-NMR (200 MHz, DMSO-d$_6$), δ (ppm): 1.60–2.00(3H, m), 2.15, 2.48(3H, s ×2), 2.65–3.50(12H, m), 3.60–3.75(2H, m), 7.09–7.17(2H, d ×2), 7.23–7.31(2H, d ×2), 7.47(3H, br), 9.94(1H, br), 12.35, 12.59(1H, s ×2).

MS: 472(M+H)$^+$ free

PRODUCTION EXAMPLE 80

Synthesis of 2-(acetylamino)-4-[2-(4-{[amino(imino)methyl]amino}phenyl)ethyl]-N-[2-(methylsulfonyl)ethyl]-1,3-thiazole-5-carboxamide hydrochloride Step 1

Di-tert-butyl {(Z)-[(4-{2-[2-(acetylamino)-5-({[2-(methylsulfonyl)ethyl]amino}carbonyl)-1,3-thiazol-4-yl]ethyl}phenyl)amino]methylidene}biscarbamate was prepared from the compound obtained in Step 2 of Production Example 34 in a similar manner according to Step 1 of Production Example 32.

$^1$H-NMR (200 MHz; DMSO-d$_6$), δ (ppm): 1.39(9H, s), 1.57(9H, s), 2.15(3H, s), 2.87(2H, dd, J=8.8, 6.5 Hz), 3.02(3H, s), 3.19–3.28(2H, dd, J=9.0, 5.5 Hz), 3.30–3.36 (2H, m), 3.59(2H, dd, J=12.0, 6.0 Hz), 7.17(2H, d, J=8.4 Hz), 7.42(2H, d, J=8.4 Hz), 8.17(1H, s), 9.93(1H, s), 11.44 (1H, s), 12.40(1H, s).

MS: 675(M+Na)$^+$

Step 2

The title compound was prepared in a similar manner according to Step 4 of Production Example 31.

$^1$H-NMR (200 MHz, DMSO-d$_6$), δ (ppm): 2.16(3H, s), 2.88–2.96(2H, m), 3.03(3H, s), 3.20–3.30(4H, m), 3.33–3.60(2H, m), 7.12–7.18(2H, m), 7.26–7.46(2H, d), 7.46(4H, br), 8.27(1H, t), 9.94(1H, s), 12.41(1H, s).

MS: 453(M+H)$^+$ free

PRODUCTION EXAMPLE 81

Synthesis of 2-(acetylamino)-4-[2-(4-{[amino(imino)methyl]amino}phenyl)ethyl]-N-(4-pyridinylmethyl)-1,3-thiazole-5-carboxamide dihydrochloride Step 1

Di-tert-butyl [(Z)-({4-[2-(2-(acetylamino)-5-{[(4-pyridinylmethyl)amino]carbonyl}-1,3-thiazol-4-yl)ethyl]phenyl}amino)methylidene]biscarbamate was prepared from the compound obtained in Step 2 of Production Example 34 in a similar manner according to Step 1 of Production Example 32.

$^1$H-NMR (200 MHz, DMSO-d$_6$), δ (ppm): 1.40–1.50 (18H, br), 2.15(3H, s), 2.89(2H, m), 3.22(2H, m), 4.39(2H, d, J=5.7 Hz), 7.09–7.18(2H, m), 7.32–7.44(3H, m), 7.66(1H, m), 8.43–8.62(3H, m), 9.94(1H, s), 11.44(1H, s), 12.40(1H, s).

MS: 660(M+Na)$^+$

Step 2

The title compound was prepared in a similar manner according to Step 4 of Production Example 31.

$^1$H-NMR (200 MHz, DMSO-d$_6$), δ (ppm): 2.18(3H, s), 2.92(2H, m), 3.13–3.28(2H, m), 4.63(2H, m), 7.12(2H, d, J=8.4 Hz), 7.24(2H, d, J=8.4 Hz), 7.47(4H, br), 7.93(2H, d, J=6.3 Hz), 8.88(3H, m), 10.00(1H, s), 12.43(1H, s).

MS: 438(M+H)$^+$ free

PRODUCTION EXAMPLE 82

Synthesis of 2-(acetylamino)-4-[2-(4-{[amino(imino)methyl]amino}phenyl)ethyl]-N-(3-pyridinylmethyl)-1,3-thiazole-5-carboxamide dihydrochloride Step 1

Di-tert-butyl [(Z)-({4-[2-(2-(acetylamino)-5-{[(3-pyridinylmethyl)amino]carbonyl}-1,3-thiazol-4-yl)ethyl]phenyl}amino)methylidene]biscarbamate was prepared from the compound obtained in Step 2 of Production Example 34 in a similar manner according to Step 1 of Production Example 32.

$^1$H-NMR (200 MHz, DMSO-d$_6$), δ (ppm): 1.39(9H, s), 1.50(9H, s), 2.16(3H, s), 2.89(2H, dd, J=8.6, 6.7 Hz), 3.22(2H, dd, J=8.6, 5.7 Hz), 4.38(2H, d, J=5.7 Hz), 7.13(2H, d, J=8.4 Hz), 7.25(2H, s ×2, J=5.7 Hz), 7.41(2H, d, J=8.4 Hz), 8.50(2H, s ×2, J=5.0 Hz), 8.62(1H, dd, J=5.0, 5.7 Hz), 9.93(1H, s), 11.43 (1H, s), 12.41(1H, s).

MS: 660(M+Na)$^+$

Step 2

The title compound was prepared in a similar manner according to Step 4 of Production Example 31.

$^1$H-NMR (200 MHz, DMSO-d$_6$), δ (ppm): 2.17(3H, s), 2.92(2H, m), 3.23(2H, m), 4.56(2H, m), 7.10–7.31(4H, m), 7.45(4H, br), 8.01(1H, dd, J=8.1, 5.9 Hz), 8.82(1H, d, J=8.0 Hz), 8.84(2H, s), 8.96(1H, s), 12.45(1H, s).

MS: 438(M+H)$^+$ free

PRODUCTION EXAMPLE 83

Synthesis of 2-(acetylamino)-4-[2-(4-{[amino(imino)methyl]amino}phenyl)ethyl]-N-{2-[(2-phenylacetyl)amino]ethyl}-1,3-thiazole-5-carboxamide hydrochloride Step 1

Di-tert-butyl ((Z)-{[4-(2-{2-(acetylamino)-5-[({2-[(2-phenylacetyl)amino]ethyl}amino)carbonyl]-1,3-thiazol-4-yl}ethyl)phenyl]amino}methylidene)biscarbamate was prepared from the compound obtained in Step 2 of Production Example 34 in a similar manner according to Step 1 of Production Example 32.

$^1$H-NMR (200 MHz, DMSO-$d_6$), δ (ppm): 1.39(9H, s), 1.51(9H, s), 2.15(3H, s), 2.88(2H, m), 3.25–3.31(6H, m), 3.38(2H, s), 7.15–7.44(7H, m), 7.32(2H, d, J=8.3 Hz), 7.98(1H, br), 8.11(1H, br), 9.93(1H, s), 11.43(1H, s), 12.35 (1H, s).

MS: 730(M+Na)$^+$

Step 2

The title compound was prepared in a similar manner according to Step 4 of Production Example 31.

$^1$H-NMR (200 MHz, DMSO-$d_6$), δ (ppm): 2.16(3H, s), 2.90(2H, br), 3.20(6H, m), 7.11–7.31(9H, m), 7.38(3H, s), 8.06–8.16(2H, m), 9.75(1H, s), 12.33(1H, s).

MS: 508(M+H)$^+$ free

PRODUCTION EXAMPLE 84

Synthesis of 2-(acetylamino)-4-[2-(4-{[amino(imino)methyl]amino}phenyl)ethyl]-N-[5-(dimethylamino)-5-oxopentyl]-1,3-thiazole-5-carboxamide hydrochloride Step 1

Di-tert-butyl {(Z)-[(4-{2-[2-(acetylamino)-5-({[5-(dimethylamino)-5-oxopentyl]amino}carbonyl)-1,3-thiazol-4-yl]ethyl}phenyl)amino]methylidene}biscarbamate was prepared from the compound obtained in Step 2 of Production Example 34 in a similar manner according to Step 1 of Production Example 32.

$^1$H-NMR (200 MHz, DMSO-$d_6$), δ (ppm): 1.39(9H, s), 1.39–1.50(4H, m), 1.57(9H, s), 2.14(3H, s), 2.29(2H, br), 2.79(3H, s), 2.84–2.94(2H, m), 2.94(3H, s), 3.15–3.23(4H, m), 7.16(2H, d, J=8.3 Hz), 7.42(2H, d, J=8.3 Hz), 7.97(1H, br), 9.93(1H, s), 11.44(1H, s), 12.35(1H, s).

MS: 696(M+Na)$^+$

Step 2

The title compound was prepared in a similar manner according to Step 4 of Production Example 31.

$^1$H-NMR (200 MHz, DMSO-$d_6$), δ (ppm): 1.39–1.56(4H, m), 2.16(2H, m), 2.29(3H, s), 2.83–2.98(5H, m), 3.06–3.28 (4H, m), 7.13(2H, d, J=8.5 Hz), 7.25(2H, d, J=8.5 Hz), 7.40(3H, br), 8.06(1H, br), 9.79(1H, s).

MS: 474(M+H)$^+$ free

PRODUCTION EXAMPLE 85

Synthesis of 2-(acetylamino)-4-[2-(4-{[amino(imino)methyl]amino}phenyl)ethyl]-N-[3-(benzylamino)-3-oxopropyl]-1,3-thiazole-5-carboxamide hydrochloride Step 1

Di-tert-butyl {(Z)-[(4-{2-[2-(acetylamino)-5-({[3-(benzylamino)-3-oxopropyl]amino}carbonyl)-1,3-thiazol-4-yl]ethyl}phenyl)amino]methylidene}biscarbamate was prepared from the compound obtained in Step 2 of Production Example 34 in a similar manner according to Step 1 of Production Example 32.

$^1$H-NMR (200 MHz, DMSO-$d_6$), δ (ppm): 1.39(9H, s), 1.50(9H, s), 2.15(3H, s), 2.45(2H, t, J=7.2 Hz), 2.73(2H, m), 3.20(2H, m), 3.39(2H, m), 4.26(2H, d, J=5.8 Hz), 7.15–7.28 (7H, m), 7.41(2H, d, J=8.4 Hz), 8.02(1H, t, J=5.5 Hz), 8.40(1H, t, J=5.5 Hz), 9.93(1H, s), 11.4(1H, br), 12.3(1H, br).

MS: 730(M+Na)$^+$

Step 2

The title compound was prepared in a similar manner according to Step 4 of Production Example 31.

$^1$H-NMR (200 MHz, DMSO-$d_6$), δ (ppm): 2.16(3H, s), 2.41(2H, t, J=7.0 Hz), 2.90(2H, m), 3.20(2H, m), 3.39(2H, m), 3.63(2H, m), 4.27(2H, d, J=5.8 Hz), 7.11–7.37(9H, m), 7.37(4H, s), 8.09(1H, t, J=5.5 Hz), 8.43(1H, t, J=6.0 Hz), 9.74(1H, s), 12.35(1H, s).

MS: 508(M+H)$^+$ free

PRODUCTION EXAMPLE 86

Synthesis of 2-(acetylamino)-4-[2-(4-{[amino(imino)methyl]amino}phenyl)ethyl]-N-[6-(dimethylamino)-6-oxohexyl]-1,3-thiazole-5-carboxamide hydrochloride Step 1

Di-tert-butyl {(Z)-[(4-{2-[2-(acetylamino)-5-({[6-(dimethylamino)-6-oxohexyl]amino}carbonyl)-1,3-thiazol-4-yl]ethyl}phenyl)amino]methylidene}biscarbamate was prepared from the compound obtained in Step 2 of Production Example 34 in a similar manner according to Step 1 of Production Example 32.

$^1$H-NMR (200 MHz, DMSO-$d_6$), δ (ppm): 1.13–1.50 (24H, m), 2.14(3H, s), 2.24(2H, t, J=8.0 Hz), 2.78(3H, s), 2.88(2H, m), 2.92(3H, s), 3.07–3.25(4H, m), 7.16(2H, d, J=8.5 Hz), 7.42(2H, d, J=8.5 Hz), 7.95(1H, t, J=5.52 Hz), 9.94(1H, s), 11.4(1H, s), 12.3(1H, s).

MS: 710(M+Na)$^+$

Step 2

The title compound was prepared in a similar manner according to Step 4 of Production Example 31.

$^1$H-NMR (200 MHz, DMSO-$d_6$), δ (ppm): 1.27–1.34(2H, m), 1.47(4H, m), 2.16(3H, s), 2.26(2H, t, J=7.2 Hz), 2.79 (3H, s), 2.94(3H, s), 2.90–2.94(2H, m), 3.17(4H, m), 7.13 (2H, d, J=8.3 Hz), 7.26(2H, d, J=8.3 Hz), 7.47(4H, br), 8.05(1H, t, J=5.4 Hz), 9.93(1H, s).

MS: 488(M+H)$^+$ free

PRODUCTION EXAMPLE 87

Synthesis of 2-(acetylamino)-4-[2-(4-{[amino(imino)methyl]amino}phenyl)ethyl]-N-[3-(4-morpholinyl)propyl]-1,3-thiazole-5-carboxamide dihydrochloride Step 1

Di-tert-butyl {(Z)-[(4-{2-[2-(acetylamino)-5-({[3-(4-morpholinyl)propyl]amino}carbonyl)-1,3-thiazol-4-yl]ethyl}phenyl)amino]methylidene}biscarbamate was prepared from the compound obtained in Step 2 of Production Example 34 in a similar manner according to Step 1 of Production Example 32.

$^1$H-NMR (200 MHz, DMSO-$d_6$), δ (ppm): 1.58(9H, br), 1.62(2H, m), 2.14(3H, s), 2.31(6H, m), 2.88(2H, m), 2.19(4H, m), 3.58(4H, m), 7.14(2H, d, J=8.4 Hz), 7.41(2H, d, J=8.4 Hz), 7.95(1H, t, J=5.2 Hz), 9.94(1H, s), 11.45(1H, s), 12.30(1H, s).

MS: 696(M+Na)$^+$

Step 2

The title compound was prepared in a similar manner according to Step 4 of Production Example 31.

$^1$H-NMR (200 MHz, DMSO-$d_6$), δ (ppm): 1.90–2.00(2H, br), 2.17(3H, s), 2.83–3.15(6H, m), 3.15–3.30(4H, m), 3.30–3.44(2H, m), 3.77–4.00(4H, m), 7.14(2H, d, J=8.5 Hz), 7.26(2H, d, J=8.5 Hz), 7.44(4H, br), 8.20(1H, t, J=5.5 Hz), 9.92(1H, s), 11.01(1H, s), 12.38(1H, s).

MS: 474(M+H)$^+$ free

PRODUCTION EXAMPLE 88

Synthesis of 2-(acetylamino)-4-[2-(4-{[amino(imino)methyl]amino}phenyl)ethyl]-N-[3-(2-oxo-1-pyrrolidinyl)propyl]-1,3-thiazole-5-carboxamide hydrochloride Step 1

Di-tert-butyl {(Z)-[(4-{2-[2-(acetylamino)-5-({[3-(2-oxo-1-pyrrolidinyl)propyl]amino}carbonyl)-1,3-thiazol-4-yl]ethyl}phenyl)amino]methylidene}biscarbamate was prepared from the compound obtained in Step 2 of Production Example 34 in a similar manner according to Step 1 of Production Example 32.

$^1$H-NMR (200 MHz, DMSO-$d_6$), δ (ppm): 1.41(9H, br), 1.49(9H, br), 1.64(2H, t, J=6.9 Hz), 1.90(2H, m), 2.14(3H, s), 2.17(2H, m), 2.91(2H, m), 3.16(6H, m), 3.32(2H, m), 7.16(2H, d, J=8.4 Hz), 7.41(2H, d, J=8.4 Hz), 7.93(1H, t, J=5.6 Hz), 9.93(1H, br), 11.73(1H, br).

MS: 694(M+Na)$^+$

Step 2

The title compound was prepared in a similar manner according to Step 4 of Production Example 31.

$^1$H-NMR (200 MHz, DMSO-$d_6$), δ (ppm): 1.65(2H, m), 1.91(2H, m), 2.16(3H, s), 2.20(2H, q, J=7.5 Hz), 2.90(2H, m), 3.02–3.27(6H, m), 3.33(2H, t, J=7.5 Hz), 7.16(2H, d, J=8.5 Hz), 7.26(2H, d, J=8.5 Hz), 8.03(1H, br), 9.92(1H, s), 12.35(1H, s).

MS: 472(M+H)$^+$ free

PRODUCTION EXAMPLE 89

Synthesis of 2-(acetylamino)-4-[2-(4-{[amino(imino)methyl]amino}phenyl)ethyl]-N-hexyl-1,3-thiazole-5-carboxamide hydrochloride Step 1

Di-tert-butyl ((Z)-{[4-(2-{2-(acetylamino)-5-[(hexylamino)carbonyl]-1,3-thiazol-4-yl}ethyl)phenyl]amino}methylidene)biscarbamate was prepared from the compound obtained in Step 2.of Production Example 34 in a similar manner according to Step 1 of Production Example 32.

$^1$H-NMR (200 MHz, DMSO-$d_6$), δ (ppm): 0.85(3H, t, J=6.4 Hz), 1.25(9H, s), 1.35–1.60(17H, br), 2.14(3H, s), 2.88(2H, m), 3.15(4H, m), 7.14(2H, d, J=8.5 Hz), 7.41(2H, d, J=8.5 Hz), 7.92(1H, t, J=5.7 Hz), 10.00(1H, br), 11.60(1H, br).

MS: 653(M+Na)$^+$

Step 2

The title compound was prepared in a similar manner according to Step 4 of Production Example 31.

$^1$H-NMR (200 MHz, DMSO-$d_6$ (+$D_2O$)), δ (ppm): 0.86(3H, t, J=6.53 Hz), 1.18–1.57(8H, m), 2.16(3H, s), 2.91(2H, dd, J=9.5, 6.0 Hz), 3.16(4H, m), 7.13(2H, d, J=8.5 Hz), 7.25(2H, d, J=8.5 Hz), 8.05(1H, br), 9.91(1H, s), 12.33(1H, s).

MS: 431(M+H)$^+$ free

PRODUCTION EXAMPLE 90

Synthesis of 2-(acetylamino)-4-[2-(4-{[amino(imino)methyl]amino}phenyl)ethyl]-N-[4-oxo-4-(1-piperidinyl)butyl]-1,3-thiazole-5-carboxamide hydrochloride Step 1

Di-tert-butyl {(Z)-[(4-{2-[2-(acetylamino)-5-({[4-oxo-4-(1-piperidinyl)butyl]amino}carbonyl)-1,3-thiazol-4-yl]ethyl}phenyl)amino]methylidene}biscarbamate was prepared from the compound obtained in Step 2 of Production Example 34 in a similar manner according to Step 1 of Production Example 32.

$^1$H-NMR (200 MHz, DMSO-$d_6$), δ (ppm): 1.29–1.59(20H, m), 1.69(2H, m), 2.14(3H, s), 2.30(2H, t, J=7.5 Hz), 2.89(4H, m), 3.32–3.45(4H, m), 7.16(2H, d, J=8.0 Hz), 7.41(2H, d, J=8.0 Hz), 7.99(1H, t, J=5.2 Hz), 9.94(1H, s), 11.43(1H, br).

MS: 722(M+Na)$^+$

Step 2

The title compound was prepared in a similar manner according to Step 4 of Production Example 31.

$^1$H-NMR (200 MHz, DMSO-$d_6$), δ (ppm): 1.30–1.79(8H, m), 2.16(3H, s), 2.31(2H, t, J=7.5 Hz), 2.92(2H, m), 3.18(4H, m), 3.38(4H, m), 7.13(2H, d, J=8.0 Hz), 7.25(2H, d, J=8.0 Hz), 7.43(4H, br), 8.09(1H, t, J=6.0 Hz), 9.87(1H, s), 12.34(1H, s).

MS: 500(M+H)$^+$ free

PRODUCTION EXAMPLE 91

Synthesis of 2-(acetylamino)-4-[2-(4-{[amino(imino)methyl]amino}phenyl)ethyl]-N-[4-(4-morpholinyl)-4-oxobutyl]-1,3-thiazole-5-carboxamide hydrochloride Step 1

Di-tert-butyl {(Z)-[(4-{2-[2-(acetylamino)-5-({[4-(4-morpholinyl)-4-oxobutyl]amino}carbonyl)-1,3-thiazol-4-yl]ethyl}phenyl)amino]methylidene}biscarbamate was prepared, from the compound obtained in Step 2 of Production Example 34 in a similar manner according to Step 1 of Production Example 32.

$^1$H-NMR (200 MHz, DMSO-d$_6$), δ (ppm): 1.40(9H, s), 1.50(9H, s), 1.71(2H, m), 2.14(3H, s), 2.32(2H, t, J=7.3 Hz), 2.89(2H, dd, J=10.1, 6.9 Hz), 3.19(4H, m), 3.42(4H, m), 3.51(4H, m), 7.16(2H, d, J=8.3 Hz), 7.42(2H, d, J=8.3 Hz), 7.99(2H, t, J=5.3 Hz), 9.94(1H, s), 11.44(1H, s), 12.33(1H, s).

MS: 724(M+Na)$^+$

Step 2

The title compound was prepared in a similar manner according to Step 4 of Production Example 31.

$^1$H-NMR (200 MHz, DMSO-d$_6$), δ (ppm): 1.70(2H, m), 2.16(3H, s), 2.33(2H, t, J=7.0 Hz), 2.91(2H, m), 3.19(4H, m), 3.42(4H, m), 3.53(4H, m), 7.13(2H, d, J=8.5 Hz), 7.25(2H, d, J=8.5 Hz), 7.44(4H, br), 8.07(1H, t, J=5.0 Hz), 9.89(1H, s), 12.34(1H, s).

MS: 502(M+H)$^+$ free

PRODUCTION EXAMPLE 92

Synthesis of 2-(acetylamino)-4-[2-(4-{[amino(imino)methyl]amino}phenyl)ethyl]-N-[4-(methylsulfonyl)phenyl]-1,3-thiazole-5-carboxamide hydrochloride Step 1

Di-tert-butyl {(Z)-[(4-{2-[2-(acetylamino)-5-({[4-(methylthio)phenyl]amino}carbonyl)-1,3-thiazol-4-yl]ethyl}phenyl)amino]methylidene}biscarbamate was prepared from the compound obtained in Step 2 of Production Example 34 in a similar manner according to Step 1 of Production Example 32.

$^1$H-NMR (200 MHz, DMSO-d$_6$), δ (ppm): 1.39(9H, s), 1.51(9H, s), 2.18(3H, s), 2.45(3H, s), 2.82–3.00(2H, m), 3.17–3.30(2H, m), 7.13(2H, d, J=8.5 Hz), 7.23(2H, d, J=8.5 Hz), 7.41(2H, d, J=8.5 Hz), 7.61(2H, d, J=8.5 Hz), 9.92(2H, s), 11.43(1H, s), 12.45(1H, s).

MS: 691(M+Na)$^+$

Step 2

Di-tert-butyl {(Z)-[(4-{2-[2-(acetylamino)-5-({[4-(methylsulfonyl)phenyl]amino}carbonyl)-1,3-thiazol-4-yl]ethyl}phenyl)amino]methylidene}biscarbamate was prepared in a similar manner according to Step 2 of Production Example 32.

$^1$H-NMR (200 MHz, DMSO-d$_6$), δ (ppm): 1.39(9H, s), 1.51(9H, s), 2.18(3H, s), 2.81–3.03(2H, m), 3.18(3H, s), 3.19–3.30(2H, m), 7.16(2H, d, J=8.5 Hz), 7.41(2H, d, J=8.5 Hz), 7.86(2H, d, J=9.0 Hz), 7.93(2H, d, J=9.0 Hz), 9.92(1H, s), 10.34(1H, s), 11.42(1H, s), 12.52(1H, s).

MS: 723(M+Na)$^+$

Step 3

The title compound was prepared in a similar manner according to Step 4-of Production Example 31.

$^1$H-NMR (200 MHz, DMSO-d$_6$), δ (ppm): 2.20(3H, s), 2.84–3.07(2H, m), 3.17–3.32(2H, m), 3.18(3H, s), 7.12(2H, d, J=8.5 Hz), 7.37(4H, br), 7.86(2H, d, J=9.0 Hz), 7.92(2H, d, J=9.0 Hz), 9.76(1H, s), 10.42(1H, s).

MS: 501(M+H)$^+$ free

PRODUCTION EXAMPLE 93

Synthesis of 2-(acetylamino)-4-[2-(4-{[amino(imino)methyl]amino}phenyl)ethyl]-N-[(1S)-2-(dimethylamino)-1-methyl-2-oxoethyl]-1,3-thiazole-5-carboxamide hydrochloride Step 1

Di-tert-butyl {(Z)-[(4-{2-[2-(acetylamino)-5-({[(1S)-2-(dimethylamino)-1-methyl-2-oxoethyl]amino}carbonyl)-1,3-thiazol-4-yl]ethyl}phenyl)amino]methylidene}biscarbamate was prepared from the compound obtained in Step 2 of Production Example 34 in a similar manner according to Step 1 of Production Example 32.

$^1$H-NMR (200 MHz, CDCl$_3$), δ (ppm): 1.40(3H, d, J=7.0 Hz), 1.49(9H, s), 1.53(9H, s), 2.22(3H, s), 2.95(2H, m), 3.00(3H, s), 3.10(3H, s), 3.26(2H, m), 5.01(1H, dt, J=7.0 Hz), 6.87(1H, d, J=7.5 Hz), 7.14(2H, d, J=8.5 Hz), 7.40(2H, d, J=8.5 Hz), 9.57(1H, br), 10.20(1H, s), 11.62(1H, s).

MS: 646(M+H)$^+$

Step 2

The title compound was prepared in a similar manner according to Step 4 of Production Example 31.

$^1$H-NMR (200 MHz, DMSO-d$_6$), δ (ppm): 1.23(3H, d), 2.16(3H, s), 2.84(3H, s), 2.87–2.95(2H, m), 3.03(3H, s), 3.15–3.24(2H, m), 3.56(1H, s), 4.78(3H, t, J=7.0 Hz), 7.13(2H, d, J=8.4 Hz), 7.25(2H, d, J=8.4 Hz), 8.09(1H, d, J=7.0 Hz), 9.67(1H, s), 12.35(1H, s).

MS: 446(M+H)$^+$ free

PRODUCTION EXAMPLE 94

Synthesis of 2-(acetylamino)-4-[2-(4-{[amino(imino)methyl]amino}phenyl)ethyl]-N-[(1S)-1-benzyl-2-(dimethylamino)-2-oxoethyl]-1,3-thiazole-5-carboxamide hydrochloride Step 1

Di-tert-butyl {(Z)-[(4-{2-[2-(acetylamino)-5-({[(1S)-1-benzyl-2-(dimethylamino)-2-oxoethyl]amino}carbonyl)-1,3-thiazol-4-yl]ethyl}phenyl)amino]methylidene}biscarbamate was prepared from the compound obtained in Step 2 of Production Example 34 in a similar manner according to Step 1 of Production Example 32.

$^1$H-NMR (200 MHz, CDCl$_3$), δ (ppm): 1.48(9H, s), 1.52(9H, s), 2.22(3H, s), 2.68(3H, s), 2.84–2.97(5H, m)-, 3.06(2H, d, J=7.5 Hz), 3.17(1H, dd, J=8.0, 6.0 Hz), 5.26(1H, q, J=7.5 Hz), 6.80(1H, d, J=8.0 Hz), 7.08(2H, d, J=8.0 Hz), 7.14–7.33(5H, m), 7.39(2H, d, J=8.0 Hz), 9.96(1H, br), 10.19(1H, s), 11.61(1H, s). MS. 722(M+H)$^+$ Step 2

The title compound was prepared in a similar manner according to Step 4 of Production Example 31.

$^1$H-NMR (200 MHz, DMSO-d$_6$), δ (ppm): 2.15(3H, s), 2.82–3.15(13H, m), 4.91(1H, q, J=6.7 Hz), 7.09(4H, s), 7.16–7.31(5H, m), 7.36(4H, br), 8.31(1H, d, J=7.7 Hz), 9.71(1H, s), 12.33(1H, s).

MS: 522(M+H)$^+$ free

PRODUCTION EXAMPLE 95

Synthesis of 2-(acetylamino)-4-[2-(4-{[amino(imino)methyl]amino}phenyl)ethyl]-N-[(1S)-2-(dimethylamino)-1-(hydroxymethyl)-2-oxoethyl]-1,3-thiazole-5-carboxamide hydrochloride Step 1

Di-tert-butyl {(Z)-[(4-{2-[2-(acetylamino)-5-({[(1S)-2-(dimethylamino)-1-(hydroxymethyl)-2-oxoethyl]amino}carbonyl)-1,3-thiazol-4-yl]ethyl}phenyl)amino]methylidene}biscarbamate was prepared from the compound obtained in Step 2 of Production Example 34 in a similar manner according to Step 1 of Production Example 32.

$^1$H-NMR (200 MHz, CDCl$_3$), δ (ppm): 1.48(9H, s), 1.52(9H, s), 2.23(3H, s), 2.94(2H, dd, J=7.0 Hz), 3.01(3H, s), 3.14(3H, s), 3.26(2H, dd, J=7.0 Hz), 3.78–3.86(3H, br), 5.04(1H, m), 6.85(1H, d, J=7.5 Hz), 7.08(2H, d, J=8.5 Hz), 7.37(2H, d, J=8.5 Hz), 9.70(1H, br), 10.20(1H, s), 11.61(1H, s).

MS: 662(M+H)$^+$

Step 2

The title compound was prepared in a similar manner according to Step 4 of Production Example 31.

$^1$H-NMR (200 MHz, DMSO-d$_6$), δ (ppm): 2.16, 2.19(3H, s ×2), 2.85–3.50(10H, m), 3.60–3.69(2H, m), 4.81(1H, m), 7.14(2H, m), 2.27(2H, m), 7.39(4H, br), 7.91(1H, br), 8.48(1H, br), 9.77, 9.94(1H, s ×2), 12.37, 12.61(1H, s ×2).

MS: 462(M+H)$^+$ free

PRODUCTION EXAMPLE 96

Synthesis of 2-(acetylamino)-4-[2-(4-{[amino(imino)methyl]amino}phenyl)ethyl]-N-{(1S,2S)-1-[(dimethylamino)carbonyl]-2-hydroxypropyl}-1,3-thiazole-5-carboxamide hydrochloride Step 1

Di-tert-butyl ((Z)-{[4-(2-{2-(acetylamino)-5-[({(1S,2S)-1-[(dimethylamino)carbonyl]-2-hydroxypropyl}amino}carbonyl]-1,3-thiazol-4-yl}ethyl)phenyl]amino}methylidene)biscarbamate was prepared from the compound obtained in Step 2 of Production Example 34 in a similar manner according to Step 1 of Production Example 32.

$^1$H-NMR (200 MHz, CDCl$_3$), δ (ppm): 1.18(3H, d, J=6.5 Hz), 1.48(9H, s), 1.52(9H, s), 2.22(3H, s), 2.95(2H, m), 2.99(3H, s), 3.16(3H, s), 3.20–3.32(2H, m), 4.06–4.12(2H, m), 5.02(1H, dd, J=9.0, 1.5 Hz), 6.55(1H, d, J=9.0 Hz), 7.09(2H, d, J=8.0 Hz), 7.38(2H, d, J=8.0 Hz), 9.70(1H, br), 10.20(1H, s), 11.62(1H, s).

MS: 676(M+H)$^+$

Step 2

The title compound was prepared in a similar manner according to Step 4 of Production Example 31.

$^1$H-NMR (200 MHz, DMSO-d$_6$), δ (ppm): 1.35(3H, d, J=6.5 Hz), 2.19(3H, s), 2.85–2.97(6H, m), 3.11(3H, s), 3.26(2H, m), 4.67(1H, br), 5.40(1H, m), 7.15(2H, d, J=8.3 Hz), 7.28(2H, d, J=8.3 Hz), 7.43(4H, br), 8.43(3H, br), 9.93(1H, s), 12.59(1H, s).

MS: 475(M+H)$^+$ free

PRODUCTION EXAMPLE 97

Synthesis of (2S)-2-[({2-(acetylamino)-4-[2-(4-{[amino(imino)methyl]amino}phenyl)ethyl]-1,3-thiazol-5-yl}carbonyl)amino]-N$^1$,N$^1$-dimethylpentanediamide hydrochloride Step 1

Di-tert-butyl ((Z)-{[4-(2-{2-(acetylamino)-5-[({(1S)-4-amino-1-[(dimethylamino)carbonyl]-4-oxobutyl}amino)carbonyl]-1,3-thiazol-4-yl}ethyl)phenyl]amino}methylidene)biscarbamate was prepared from the compound obtained in Step 2 of Production Example 34 in a similar manner according to Step 1 of Production Example 32.

$^1$H-NMR (200 MHz, CDCl$_3$), δ (ppm): 1.49(9H, s), 1.53(9H, s), 1.86–2.19(2H, m), 2.22–2.37(5H, m), 2.89(2H, m), 2.99(3H, s), 3.05–3.16(5H, m), 3.20–3.41(1H, m), 5.06(1H, m), 6.27(1H, br), 6.35(1H, br), 6.81(1H, d, J=7.5 Hz), 7.09(2H, d, J=8.5 Hz), 7.41(2H, d, J=8.5 Hz), 10.21(1H, s), 10.55(1H, br), 11.62(1H, s).

MS: 703(M+H)$^+$

Step 2

The title compound was prepared in a similar manner according to Step 4 of Production Example 31.

$^1$H-NMR (200 MHz, DMSO-d$_6$), δ (ppm): 1.70–2.00(2H, m), 2.16(5H, m), 2.84(3H, s), 2.91(2H, m), 3.08(3H, s), 3.19(2H, m), 4.75(1H, m), 6.79(1H, m), 7.12(2H, d, J=8.3 Hz), 7.25(2H, d, J=8.3 Hz), 7.39(4H, br), 8.13(1H, d), 9.77(1H, s), 12.35(1H, s).

MS: 503(M+H)$^+$ free

PRODUCTION EXAMPLE 98

Synthesis of N-{4-[2-(4-{[imino(methylamino)methyl]amino}phenyl)ethyl]-5-[4-(methylsulfonyl)benzyl]-1,3-thiazol-2-yl}acetamide The title compound was prepared from the compound obtained in Step 2 of Production Example 50 in a similar manner according to Production Example 58.

$^1$H-NMR (DMSO-d$_6$), δ (ppm): 2.09(3H, s), 2.79(3H, s), 2.86(4H, s), 3.18(3H, s), 4.08(2H, s), 4.43(2H, m), 7.08(2H, d, J=8.5 Hz), 7.22(2H, d, J=8.5 Hz), 7.39(2H, d, J=8.5 Hz), 7.85(2H, d, J=8.5 Hz), 12.05(1H, brs).

MS: 486(M+H)$^+$

PRODUCTION EXAMPLE 99

Synthesis of (2S)-1-({2-(acetylamino)-4-[2-(4-{[amino(imino)methyl]amino}phenyl)ethyl]-1,3-thiazol-5-yl}methyl)-N,N-dimethyl-2-pyrrolidinecarboxamide dihydrochloride Step 1 tert-Butyl {4-[2-(2-(acetylamino)-5-{[methoxy(methyl)amino]carbonyl}-1,3-thiazol-4-yl)ethyl]phenyl}carbamate was prepared from 2-(acetylamino)-4-(2-{4-[(tert-butoxycarbonyl)amino]phenyl}ethyl)-1,3-thiazole-5-carboxylic acid in a similar manner according to Step 1 of Production Example 32.

$^1$H-NMR (CDCl$_3$), δ (ppm): 1.46(9H, s), 2.15(3H, s), 2.74–2.93(2H, m), 3.12–3.29(2H, m), 3.22(3H, s), 3.59(3H, s), 7.05(2H, d, J=8.5 Hz), 7.33(2H, d, J=8.5 Hz), 9.21(1H, s), 12.34(1H, s).

MS: 471.1(M+Na)$^+$

Step 2

To a solution of the compound obtained in Step 1 (3.93 g) in THF (80 mL) was added lithium aluminium hydirde (499 mg) slowly (over 15 min) at 5–10° C. (under ice-cooling). The mixture was stirred at 5° C. for 1 h. 30 mL of aquaous solution of sodium pottasium tartrate (1M) was added slowly under ice-cooling, and then the mixture was stirred for another 0.5 h at r.t. The mixture was extracted with ethyl acetate, and the organic layer was dried over MgSO$_4$, and conccentrated in vacuo to give pale yellow oil. This oil was triturated with IPE and EtOAc to give tert-butyl (4-{2-[2-(acetylamino)-5-formyl-1,3-thiazol-4-yl]ethyl}phenyl)carbamate as pale yellow powder (2.67 g).

$^1$H-NMR (200 MHz, DMSO-d$_6$), δ (ppm): 1.46(9H, s), 2.19(3H, s), 2.90(2H, t, J=7.3 Hz), 3.22(2H, t, J=7.3 Hz), 7.01(2H, d, J=8.5 Hz), 7.32(2H, d, J=8.5 Hz), 9.22(1H, s), 9.77(1H, s), 12.68(1H, s).

MS: 390(M+H)$^+$

Step 3

To a solution of the compound obtained in Step 2 (200 mg) in dichloromethane (6 mL) were added (2S)-2-(N,N-dimethylaminocarbonyl)pyrrolidine hydrochloride and diisopropylethylamine (0.27 ml) at 5° C. The mixture was stirred at 5° C. for 10 min. Then sodium triacetoxyborohydride (327 mg) was added, and the mixture was stirred for 3 hrs. aq. NH$_4$Cl was added, and the mixuture was extracted with dichloromethane. The organic layer was dried over MgSO$_4$. The layer was concentrated under reduced pressure. The resulting crude mixture was purified by silica gel column chlomatography with mixed solvent (dichloromethane/methanol=15/1) as an eluent to give tert-butyl (4-{2-[2-(acetylamino)-5-({(2S)-2-[(N,N-dimethylamino) carbonyl]-1-pyrrolidinyl}methyl)-1,3-thiazol-4-yl] ethyl}phenyl)carbamate as a pale yellow amorphous substance.

$^1$H-NMR (200 MHz, CDCl$_3$), δ (ppm): 1.67–1.99(4H, m), 2.24(3H, s), 2.04(4H, s), 2.14(3H, s), 2.95–3.14(5H, m), 3.42–3.58(2H, m), 3.68–3.83(1H, m), 6.97(2H, d, J=8.3 Hz), 7.94(2H, d, J=8.3 Hz).

MS: 516(M+H)$^+$

Step 4

(2S)-1-({2-[(Acetylamino)-4-[2-(4-aminophenyl)ethyl]-1, 3-thiazol-5-yl}methyl)-N,N-dimethyl-2-pyrrolidinecarboxamide was prepared in a similar manner according to Step 2 of Production Example 31.

$^1$H-NMR (200 MHz, CDCl$_3$), δ (ppm): 1.70–2.10(4H, m), 2.22(3H, s), 2.39(1H, q, J=8.4 Hz), 2.77(4H, m), 2.91(3H, s), 3.03(3H, s), 3.30–3.81(6H, m), 6.58(2H, d, J=8.3 Hz), 6.89(2H, d, J=8.3 Hz), 8.82(1H, br).

MS: 416(M+H)$^+$

Step 5

Di-tert-butyl {(Z)-[(4-{2-[2-(acetylamino)-5-({(2S)-2-[(N,N-dimethylamino)carbonyl]-1-pyrrolidinyl}methyl)-1, 3-thiazol-4-yl]ethyl}phenyl)amino] methylidene}biscarbamate was prepared in a similar manner according to Step 3 of Production Example 31.

$^1$H-NMR (200 MHz, CDCl$_3$), δ (ppm): 1.50(9H, s), 1.52(9H, s), 1.76–1.92(4H, m), 2.04–2.14(1H, m), 2.43(1H, dd, J=8.1, 8.0 Hz), 2.45(3H, s), 2.85(2H, s), 3.07(3H, s), 3.51(1H, dd, J=5.7, 8.0 Hz), 3.60(1H, d, J=14.3 Hz), 3.84 (1H, d, J=14.3 Hz), 6.37(1H, t, J=2.0 Hz), 7.08(2H, d, J=8.4 Hz), 7.44(2H, d, J=8.4 Hz), 7.63(1H, d, J=2.0 Hz), 10.23 (1H, s), 11.62(1H, br).

MS: 658(M+H)$^+$

Step 6

The title compound was prepared in a similar manner according to Step 4 of Production Example 31.

$^1$H-NMR (200 MHz, DMSO-d$_6$), δ (ppm): 1.60–1.98(2H, br), 1.98–2.16(1H, br), 2.16(3H, s), 2.85(3H, s), 2.95(7H, br), 3.00–3.30(1H, br), 7.15(2H, d, J=8.3 Hz), 7.30(2H, d, J=8.3 Hz), 7.55(4H, br), 7.85(1H, d, J=2.2 Hz), 9.65(1H, br), 10.21(1H, s), 12.35(1H, s).

MS: 458(M+H)$^+$ free

PRODUCTION EXAMPLE 100

Synthesis of 3-[({2-(acetylamino)-4-[2-(4-{[amino (imino)methyl]amino}phenyl)ethyl]-1,3-thiazol-5-yl}methyl)(methyl)amino]-N,N-dimethylpropanamide dihydrochloride Step 1 tert-Butyl (4-{2-[2-(acetylamino)-5-({[3-(N,N-dimethylamino)-3-oxopropyl]amino}methyl)-1,3-thiazol-4-yl] ethyl}phenyl)carbamate was prepared from the compound obtained in Step 2 of Production Example 99 in a similar manner according to Step 3 of Production Example 99.

$^1$H-NMR (200 MHz, CDCl$_3$), δ (ppm): 1.50(9H, s), 2.24(3H, s), 2.47(2H, t, J=6.2 Hz), 2.74(2H, t, J=6.2 Hz), 2.82–2.88(4H, m), 2.93(3H, s), 2.97(3H, s), 3.59(2H, s), 6.94(2H, d, J=8.3 Hz), 7.21(2H, d, J=8.3 Hz), 8.02(1H, s).

MS: 490(M+H)$^+$

Step 2

To a solution of the compound obtained in Step 1 (100 mg) in dichloromethane (1.5 mL) was added formaline (35%, 87.6 µl). To this suspension was added 0.05 ml of MeOH. Then, sodium triacetoxyborohydride (433 mg) was added, and the mixture was stirred for 12 hrs. To the mixture were added water and 1N NaOH to adjust pH of aquaous phase (ca. pH 8–9). The mixture was extracted with dichloromethane. The organic layer was dried with MgSO$_4$ and concentrated under redused pressure. Resulting oil was purified by silica gel column chromatograph (mixed solvent of CH$_2$Cl$_2$/MeOH 15/1 as an eluent) to give tert-butyl {4-[2-(2-(acetylamino)-5-{[[3-(N,N-dimethylamino)-3-oxopropyl](methyl)amino]methyl}-1,3-thiazol-4-yl)ethyl] phenyl}carbamate as pale yellow oil (90.4 mg).

$^1$H-NMR (200 MHz, CDCl$_3$), δ (ppm): 1.51(9H, s), 2.18(3H, s), 2.24(3H, s), 2.45(2H, m), 2.62(2H, m), 2.80 (4H, s), 2.93(3H, s), 2.99(3H, s), 3.35(2H, s), 6.96(2H, d, J=8.3 Hz), 7.20(2H, d, J=8.3 Hz).

MS: 504(M+H)$^+$

Step 3

3-[({2-(Acetylamino)-4-[2-(4-aminophenyl)ethyl]-1,3-thiazol-5-yl}methyl)(methyl)amino]-N,N-dimethylpropanamide was prepared in a similar manner according to Step 2 of Production Example 31.

$^1$H-NMR (200 MHz, CDCl$_3$), δ (ppm): 2.19(3H, s), 2.22(2H, s), 2.43–2.51(2H, m), 2.62–2.71(4H, m), 2.78(3H, s), 2.93(3H, s), 2.99(3H, s), 3.33(2H, s), 3.65(1H, m), 3.75(1H, m), 6.58(2H, d, J=8.3 Hz), 6.87(2H, d, J=8.3 Hz).

MS: 404(M+H)$^+$

Step 4

Di-tert-butyl [(Z)-({4-[2-(2-(acetylamino)-5-{[[3-(N,N-dimethylamino)-3-oxopropyl](methyl)amino]methyl}-1,3-thiazol-4-yl)ethyl]phenyl}amino)methylidene]biscarbamate was prepared in a similar manner according to Step 3 of Production Example 31.

¹H-NMR (200 MHz, CDCl₃), δ (ppm): 1.50(9H, s), 1.53(9H, s), 2.20(3H, s), 2.22(3H, s), 2.49(2H, dd, J=6.5, 5.5 Hz), 2.71(2H, dd, J=6.5, 5.5 Hz), 2.84(4H, s), 2.93(3H, s), 2.99(3H, s), 3.43(2H, s), 7.08(2H, d, J=8.4 Hz), 7.46(2H, d, J=8.4 Hz), 7.62(1H, s), 10.24(1H, s), 11.62(1H, s).

MS: 646(M+H)⁺

Step 5

The title compound was prepared in a similar manner according to Step 4 of Production Example 31.

¹H-NMR (200 MHz, DMSO-d₆), δ (ppm): 2.15(3H, s), 2.68(3H, d, J=4.0 Hz), 2.83–2.88(6H, m), 2.96(6H, s), 3.05–3.15(2H, m), 4.44(2H, m), 7.15(2H, d, J=8.3 Hz), 7.32(2H, d, J=8.3 Hz), 7.62(4H, br), 9.90(1H, s), 12.32(1H, s).

MS: 446(M+H)⁺ free

PRODUCTION EXAMPLE 101

Synthesis of 4-(2-{2-(acetylamino)-4-[2-(4-{[amino(imino)methyl]amino}phenyl)ethyl]-1,3-thiazol-5-yl}ethyl)-N,N-dimethylbenzamide hydrochloride Step 1

Methyl 4-{2-[2-(acetylamino)-4-(2-{4-[(tert-butoxycarbonyl)amino]phenyl}ethyl)-1,3-thiazol-5-yl]vinyl}benzoate was prepared from the compound obtained in Step 2 of Production Example 99 in a similar manner according to Step 1 of Production Example 53.

¹H-NMR (CDCl₃), δ (ppm): 1.50(9H×⅘, s), 1.51(9H×⅕, s), 2.20(3H×⅕, s), 2.29(3H×⅘, s), 2.72–3.06(4H, m), 3.90(3H×⅕, s), 3.92(3H×⅘, s), 6.42–6.60(2H×⅕, m), 6.69(1H×⅘, d, J=16.6 Hz), 6.81–7.03(4H +1H×⅘, m), 7.31(2H×⅕, d, J=8.0 Hz), 7.39(2H×⅘, d, J=8.0 Hz), 7.96(2H×⅕, d, J=8.0 Hz), 7.99(2H×⅘, d, J=8.0 Hz).

MS: 522.2(M+H)⁺, 544.2(M+Na)⁺

Step 2

Methyl 4-{2-[2-(acetylamino)-4-(2-{4-[(tert-butoxycarbonyl)amino]phenyl}ethyl)-1,3-thiazol-5-yl]ethyl}benzoate was prepared in a similar manner according to Step 6 of Production Example 45.

MS: 524.25(M+H)⁺

Step 3

4-{2-[2-(Acetylamino)-4-(2-{4-[(tert-butoxycarbonyl)amino]phenyl}ethyl)-1,3-thiazol-5-yl]ethyl}benzoic acid was prepared in a similar manner according to Step 2 of Production Example 65.

¹H-NMR (DMSO-d₆), δ (ppm): 1.45(9H, s), 2.09(3H, s), 2.57–2.72(6H, m), 2.75–2.86(2H, m), 6.94(2H, d, J=8.4 Hz), 7.21(2H, d, J=8.4 Hz), 7.32(2H, d, J=8.4 Hz), 7.82(2H, d, J=8.4 Hz), 9.21(1H, s), 11.94(1H, s), 12.41–13.20(1H, brs).

MS: 510.2(M+H)⁺, 532.2(M+Na)⁺

Step 4 tert-Butyl (4-{2-[2-(acetylamino)-5-(2-{4-[(methylamino)carbonyl]phenyl}ethyl)-1,3-thiazol-4-yl]ethyl}phenyl)carbamate was prepared in a similar manner according to Step 3 of Production Example 65.

¹H-NMR (CDCl₃), δ (ppm): 1.51(9H, s), 2.24(3H, s), 2.56–2.73(4H, m), 2.73–2.86(4H, m), 2.99(3H, d, J=4.8 Hz), 6.05(1H, d, J=4.4 Hz), 6.25–6.75(1H, brs), 6.77(2H, d, J=6.6 Hz), 7.12(2H, d, J=8.1 Hz), 7.15–7.23(2H, m), 7.63(2H, d, J=8.1 Hz), 8.43–9.18(1H, brs).

MS: 523.29(M+H)⁺

Step 5

Di-tert-butyl {(Z)-[(4-{2-[2-(acetylamino)-5-(2-{4-[(methylamino)carbonyl]phenyl}ethyl)-1,3-thiazol-4-yl]ethyl}phenyl)amino]methylidene}biscarbamate was prepared in a similar manner according to Step 4 of Production Example 65.

¹H-NMR (CDCl₃), δ (ppm): 1.48(9H, s), 1.54(9H, s), 2.22(3H, s), 2.51–2.61(2H, m), 2.61–2.71(2H, m), 2.79–2.90(4H, m), 2.97(3H, d, J=4.8 Hz), 6.20(1H, d, J=4.8 Hz), 6.98(2H, d, J=8.4 Hz), 7.13(2H, d, J=8.1 Hz), 7.40(2H, d, J=8.4 Hz), 7.64(2H, d, J=8.4 Hz), 8.83–9.42(1H, brs), 10.21(1H, s), 11.62(1H, s).

MS: 687.2(M+Na)⁺

Step 6

The title compound was prepared in a similar manner according to Step 4 of Production Example 31.

¹H-NMR (DMSO-d₆), δ (ppm): 2.09(3H, s), 2.58–2.79(6H, m), 2.80–3.02(8H, m), 7.13(2H, d, J=8.4 Hz), 7.19(2H, d, J=8.1 Hz), 7.20(2H, d, J=8.4 Hz), 7.29(2H, d, J=8.1 Hz), 7.32(4H, s), 9.66(1H, s), 11.93(1H, s).

MS: 479.2(M+H)⁺ free

PRODUCTION EXAMPLE 102

Synthesis of 4-(2-{2-(acetylamino)-4-[2-(4-{[amino(imino)methyl]amino}phenyl)ethyl]-1,3-thiazol-5-yl}ethyl)-N-methylbenzamide hydrochloride Step 1 tert-Butyl (4-{2-[2-(Acetylamino)-5-(2-{4-[(dimethylamino)carbonyl]phenyl}ethyl)-1,3-thiazol-4-yl]ethyl}phenyl)carbamate was prepared from the compound obtained in Step 3 of Production Example 101 in a similar manner according to Step 3 of Production Example 65.

¹H-NMR (CDCl₃), δ (ppm): 1.51(9H, s), 2.23(3H, s), 2.66(4H, s), 2.79(4H, s), 2.93(3H, s), 3.08(3H, s), 6.90(2H, d, J=8.0 Hz), 7.11(2H, d, J=8.0 Hz), 7.18(2H, d, J=8.0 Hz), 8.56–10.01(1H, brs).

MS: 537(M+H)⁺, 559.2(M+Na)⁺

Step 2

Di-tert-butyl {(Z)-[(4-{2-[2-(acetylamino)-5-(2-{4-[(dimethylamino)carbonyl]phenyl}ethyl)-1,3-thiazol-4-yl]ethyl}phenyl)amino]methylidene}biscarbamate was prepared in a similar manner according to Step 4 of Production Example 65.

¹H-NMR (CDCl₃), δ (ppm): 1.49(9H, s), 1.53(9H, s), 2.21(3H, s), 2.57–2.78(4H, m), 2.82(4H, s), 2.94(3H, s), 3.08(3H, s), 7.03(2H, d, J=8.5 Hz), 7.13(2H, d, J=8.0 Hz), 7.33(2H, d, J=8.0 Hz), 7.45(2H, d, J=8.5 Hz), 8.28–9.61(1H, brs), 10.24(1H, s), 11.63(1H, s).

MS: 679.2(M+H)⁺, 701.2(M+Na)⁺

Step 3

The title compound was prapared in a similar manner according to Step 4 of Production Example 31.

¹H-NMR (DMSO-d₆), δ (ppm): 2.10(3H, s), 2.60–2.72(4H, m), 2.72–2.80(2H, m), 2.76(3H, d, J=4.4 Hz), 2.89(2H, t, J=7.3 Hz), 7.12(2H, d, J=8.4 Hz), 7.19(2H, d, J=8.4 Hz), 7.22(2H, d, J=8.1 Hz), 7.33(4H, s), 7.73(2H, d, J=8.1 Hz), 8.36(1H, d, J=4.4 Hz), 9.66(1H, s), 11.93(1H, s).

MS: 465.2(M+H)⁺ free

PRODUCTION EXAMPLE 103

Synthesis of methyl N-[4-({2-(acetylamino)-4-[2-(4-{[amino(imino)methyl]amino}phenyl)ethyl]-1,3-thiazol-5-yl}methyl)phenyl]carbamate hydrochloride

Step 1

To a suspension of 4-{[2-(acetylamino)-4-(2-{4-[(tert-butoxycarbonyl)amino]phenyl}ethyl)-1,3-thiazol-5-yl]methyl}benzoic acid (50 mg) in toluene (0.5 ml) and dioxane (0.5 ml) were added triethylamine (28.1 μl) and diphenylphosphoryl azide (39.1 μl), and the mixture was stirred at 25° C. for 2 hrs., then stirred at 100° C. for 1 h. To the reaction mixture was added methanol (1 ml), and the mixture was refluxed for 2 hrs., and concentrated in vacuo. The residue was purified by preparative thin-layer chromatography over silica gel with chloroform/methanol (20:1) as an eluent to give methyl N-(4-{[2-(acetylamino)-4-(2-{4-[(tert-butoxycarbonyl)amino]phenyl}ethyl)-1,3-thiazol-5-yl]methyl}phenyl)carbamate (17.2 mg).

$^1$H-NMR (CDCl$_3$), δ (ppm): 1.52(9H, s), 2.22(3H, s), 2.80(4H, s), 3.76(3H, s), 3.79(2H, s), 6.62–6.78(1H, brs), 6.83–7.05(1H, brs), 6.90(2H, d, J=8.0 Hz), 6.98(2H, d, J=8.5 Hz), 7.17(2H, d, J=8.0 Hz), 7.20–7.33(2H, m).

MS: 547.2(M+Na)$^+$

Step 2

Di-tert-butyl [(Z)-({4-[2-(2-(acetylamino)-5-{4-[(methoxycarbonyl)amino]benzyl}-1,3-thiazol-4-yl)ethyl]phenyl}amino)methylidene]biscarbamate was prepared in a similar manner according to Step 4 of Production Example 65.

$^1$H-NMR (CDCl$_3$), δ (ppm): 1.49(9H, s), 1.54(9H, s), 2.19(3H, s), 2.82(4H, s), 3.76(3H, s), 3.80(2H, s), 6.72–6.90(1H, brs), 6.98(2H, d, J=8.5 Hz), 7.00(2H, d, J=8.5 Hz), 7.26(2H, d, J=8.5 Hz), 7.39(2H, d, J=8.5 Hz), 9.10–9.59(1H, brs), 10.19(1H, s), 11.64(1H, s).

MS: 667.2(M+H)$^+$, 689.2(M+Na)$^+$

Step 3

The title compound was prepared in a similar manner according to Step 4 of Production Example 31.

$^1$H-NMR (DMSO-d$_6$), δ (ppm): 2.08(3H, s), 2.85(4H, s), 3.64(3H, s), 3.85(2H, s), 7.04(2H, d, J=8.5 Hz), 7.14(2H, d, J=8.4 Hz), 7.24(2H, d, J=8.4 Hz), 7.28–7.47(6H, m), 9.58(1H, s), 9.70(1H, s), 11.96(1H, s).

MS: 467.2(M+H)$^+$

PRODUCTION EXAMPLE 104

Synthesis of ethyl 1-({2-(acetylamino)-4-[2-(4-{[amino(imino)methyl]amino}phenyl)ethyl]-1,3-thiazol-5-yl}methyl)-4-piperidinecarboxylate dihydrochloride

Step 1

Ethyl 1-({2-(acetylamino)-4-[(Z)-2-(4-nitrophenyl)vinyl]-1,3-thiazol-5-yl}methyl)-4-piperidinecarboxylate was prepared from N-{4-[(Z)-2-(4-nitrophenyl)vinyl]-1,3-thiazol-2-yl}acetamide in a similar manner according to Step 1 of Production Example 67.

MS: 459.17(M+H)$^+$

Step 2

Ethyl 1-[(2-(acetylamino)-4-{2-[4-({(Z)-[(tert-butoxycarbonyl)amino][(tert-butoxycarbonyl)imino]methyl}amino)phenyl]ethyl}-1,3-thiazol-5-yl)methyl]-4-piperidinecarboxylate was prepared in a similar manner according to Step 2 of Production Example 68.

$^1$H-NMR (CDCl$_3$), δ (ppm): 1.24(3H, t, J=7.2 Hz), 1.50(9H, s), 1.53(9H, s), 1.65–2.09(6H, m), 2.13–2.34(4H, s), 2.71–2.95(6H, m), 3.39(2H, s), 4.12(2H, q, J=7.2 Hz), 7.07(2H, d, J=8.5 Hz), 7.46(2H, d, J=8.5 Hz), 10.24(1H, s), 11.63(1H, brs).

MS: 673.3(M+H)$^+$, 695.3(M+Na)$^+$

Step 3

The title compound was prepared in a similar manner according to Step 4 of Production Example 31.

$^1$H-NMR (DMSO-d$_6$), δ (ppm): 1.18(3H, t, J=7.1 Hz), 1.73–1.90(2H, m), 1.93–2.13(2H, m), 2.16(3H, s), 2.87–3.01(6H, m), 3.30–3.41(2H, m), 4.08(2H, q, J=7.1 Hz), 4.31–4.43(2H, m), 7.15(2H, d, J=8.4 Hz), 7.31(2H, d, J=8.4 Hz), 7.42(4H, s), 9.90(1H, s), 10.23–10.46(1H, brs), 12.3(1H, s).

MS: 473.2(M+H)$^+$, 495.2(M+Na)$^+$ free

PRODUCTION EXAMPLE 105

Synthesis of ethyl 1-({2-(acetylamino)-4-[2-(4-{[amino(imino)methyl]amino}phenyl)ethyl]-1,3-thiazol-5-yl}methyl)-4-piperidinecarboxylate hydrochloride The title compound was prepared in a similar manner according to Example 104.

PRODUCTION EXAMPLE 106

Synthesis of 4-(2-{2-(acetylamino)-5-[4-(methylsulfonyl)benzyl]-1,3-thiazol-4-yl}ethyl)-N-[amino(imino)methyl]benzamide Guanidine hydrochloride (152 mg) was dissolved in DMF (3 ml), and then 28% sodium methoxide methanol solution (0.3 ml) was added to the solution at r.t. The suspension was stirred at r.t. for 15 minutes, and methyl 4-(2-{2-(acetylamino)-5-[4-(methylsulfonyl)benzyl]-1,3-thiazol-4-yl}ethyl)benzoate (150 mg) was added to the mixture at r.t. The reaction mixture was stirred at r.t. for 14.hours, and concentrated in vacuo. The residue was dissolved in water, and neutralized with 1N-HCl. The precipitate was collected through filtration, and purified by preparative silica gel chromatography with CHCl$_3$/MeOH (10:1) as an eluent. The solid was washed with ethyl ether to give 4-(2-{2-(acetylamino)-5-[4-(methylsulfonyl)benzyl]-1,3-thiazol-4-yl}ethyl)-N-[amino(imino)methyl]benzamide (36.6 mg) as an off-white solid.

mp. 108–109.5° C.

$^1$H-NMR (DMSO-d$_6$), δ (ppm): 2.09(3H, s), 2.89(4H, s), 3.16(3H, s), 4.06(2H, s), 7.15(2H, d, J=8.0 Hz), 7.27(2H, d, J=8.0 Hz), 7.78(2H, d, J=8.0 Hz), 7.95(2H, d, J=8.0 Hz), 12.04(1H, s).

MS: 500(M+H)$^+$

PRODUCTION EXAMPLE 107

Synthesis of tert-butyl (2-{[4-(2-{2-(acetylamino)-5-[4-(methylsulfonyl)benzyl]-1,3-thiazol-4-yl}ethyl)phenyl]amino}-2-oxoethyl)carbamate The title compound was prepared from 2-(acetylamino)-4-[2-(4-aminophenyl)ethyl]-5-[4-(methylsulfonyl)benzyl]-1,3-thiazol in a similar manner according to Step 1 of Production Example 10.

mp. 186–187.5° C.
$^1$H-NMR (DMSO-$d_6$), δ (ppm): 1.39(9H, s), 2.08(3H, s), 2.84(4H, s), 3.17(3H, s), 3.71(2H, d, J=6.0 Hz), 4.00(2H, s), 7.01(1H, t, J=6.0 Hz), 7.06(2H, d, J=8.5 Hz), 7.28(2H, d, J=8.5 Hz), 7.46(2H, d, J=8.5 Hz), 7.79(2H, d, J=8.5 Hz), 9.86(1H, s), 12.04(1H, s).
MS: 587(M+H)$^+$

PRODUCTION EXAMPLE 108

Synthesis of N-[4-(2-{2-(acetylamino)-5-[4-(methylsulfonyl)benzyl]-1,3-thiazol-4-yl}ethyl)phenyl]-2-aminoacetamide hydrochloride The title compound was prepared from the compound of Production Example 107 in a similar manner according to Step 2 of Production Example 10.

mp. 142.5–144° C.
$^1$H-NMR (DMSO-$d_6$), δ (ppm): 2.09(3H, s), 2.85(4H, s), 3.18(3H, s), 3.78(2H, m), 4.00(2H, s), 7.10(2H, d, J=8.5 Hz), 7.26(2H, d, J=8.5 Hz), 7.50(2H, d, J=8.5 Hz), 7.79(2H, d, J=8.5 Hz), 8.22(3H, brs), 10.63(1H, s), 12.06(1H, s).
MS: 487(M+H)$^+$ free

PRODUCTION EXAMPLE 109

Synthesis of N-(4-{2-[4-(2-aminoethyl)phenyl]ethyl}-1,3-thiazol-2-yl)acetamide hydrochloride Step 1
N-(4-{2-[4-(Cyanomethyl)phenyl]ethyl}-1,3-thiazol-2-yl)acetamide (1 g), 1N-NaOH (7 ml) and EtOH (14 ml) were combined, and the reaction mixture was refluxed for 8 hours. After cooled to r.t., the organic solvent was removed in vacuo. The aqueous solution was neutralized with 1N-HCl, and extracted with AcOEt. The organic layer was washed with water and brine, dried over anhydrous MgSO$_4$, and concentrated in vacuo. The residual yellow wax (1.03 g) was dissolved in THF (10 ml), and then lithium aluminium hydride (266 mg) was added to the solution at 0° C. The reaction mixture was refluxed for 3 hours, and quenched with MeOH. Then Na$_2$SO$_4$/10H$_2$O was added to the mixture, the mixture was stirred at r.t. for 1 hour and filtered through a celite pad. The filtrate was concentrated in vacuo. The residual yellow amorphous (835.5 mg) was dissolved in THF (10 ml) and DMF (10 ml) under N$_2$ atmosphere. Then di(tert-butyl) dicarbonate (841 mg) in THF (5 ml) was added to the solution at r.t. The reaction mixture was stirred at r.t. for 12 hours, and concentrated in vacuo to give tert-butyl (2-{4-[2-(2-amino-1,3-thiazol-4-yl)ethyl]phenyl}ethyl)carbamate (171.6 mg) as yellow oil.
$^1$H-NMR (DMSO-$d_6$), δ (ppm): 1.38(9H, s), 2.60–2.70 (4H, m), 2.79–2.88(4H, m), 6.82(1H, s), 7.07(2H, d, J=8.0 Hz), 7.11(2H, d, J=8.0 Hz).
MS: 348(M+H)$^+$ Step 2
tert-Butyl [2-(4-{2-[2-(acetylamino)-1,3-thiazol-4-yl]ethyl}phenyl)ethyl]carbamate was prepared from the compound of Step 1 in a similar manner according to Step 3 of Production Example 45.
$^1$H-NMR (DMSO-$d_6$), δ (ppm): 1.36(9H, s), 2.11(3H, s), 2.58–2.70(1H, m), 2.80–2.97(6H, m), 3.02–3.18(1H, m), 6.72(1H, s), 7.08(2H, d, J=8.0 Hz), 7.23(2H, d, J=8.0 Hz), 12.08(1H, s).
MS: 390(M+H)$^+$ Step 3
The title compound was prepared from the compound of Step 2 in a similar manner according to Step 2 of Production Example 10.
mp. 165–167° C.
$^1$H-NMR (DMSO-$d_6$), δ (ppm): 2.12(3H, s), 2.79–3.09 (8H, m), 6.75(1H, s), 7.16(4H, s), 8.14(2H, brs), 12.13(1H, brs).
MS: 290(M+H)$^+$ free

PRODUCTION EXAMPLE 110

Synthesis of N-(4-{2-[4-(2-{[amino(imino)methyl]amino}ethyl)phenyl]ethyl}-1,3-thiazol-2-yl)acetamide hydrochloride Step 1
N-(4-{2-[4-(2-Aminoethyl)phenyl]ethyl}-1,3-thiazol-2-yl)acetamide hydrochloride (7 mg), N,N'-bis(tert-butoxycarbonyl)-1H-pyrazole-1-carboxamidine (6.57 mg), N,N-diisopropylethylamine (0.00748 ml), THF (0.5 ml) and DMF (0.1 ml) were combined under N$_2$ atmosphere. The reaction mixture was stirred at r.t. for 43 hours, and concentrated in vacuo. The residue was purified by preparative silica gel chromatography with n-hexane/AcOEt (1:1) as an eluent to give di-tert-butyl ((Z)-{[2-(4-{2-[2-(acetylamino)-1,3-thiazol-4-yl]ethyl}phenyl)ethyl]amino}methylidene)biscarbamate (5.9 mg) as colorless oil.
$^1$H-NMR [CD$_3$Cl/CD$_3$OD (1:1)], δ (ppm): 1.50(18H, s), 2.24(3H, s), 2.86(2H, t, J=7.0 Hz), 2.95(4H, s), 3.62(2H, t, J=7.0 Hz), 4.24(2H, s), 6.50(1H, s), 7.11(2H, d, J=8.5 Hz), 7.16(2H, d, J=8.5 Hz).
MS: 532(M+H)+

Step 2
The title compound was prepared from the compound of Step 1 in a similar manner according to Step 4 of Production Example 31.
$^1$H-NMR [CD$_3$Cl/CD$_3$OD (1:1)], δ (ppm): 2.41(3H, s), 2.87(2H, t, J=7.0 Hz), 3.05(4H, s), 3.44(2H, t, J=7.0 Hz), 6.86(1H, s), 7.18(4H, s).
MS: 332(M+H)$^+$ free

PRODUCTION EXAMPLE 111

Synthesis of N-(4-{4-[(2-{[amino(imino)methyl]amino}ethyl)sulfonyl]phenyl}-1,3-thiazol-2-yl)acetamide hydrochloride Step 1
1-[4-(Methylthio)phenyl]ethanone (5.5 g) was dissolved in AcOH (55 ml), and then 90% pyridinium tribromide (11.8 g) and 30% hydrobromic acid in AcOH (5.5 ml) were added to the solution at 0° C. The reaction mixture was stirred at r.t. for 30 minutes, and poured into water. The mixture was extracted with AcOEt. The organic layer was washed with saturated NaHCO₃ and brine, dried over anhydrous MgSO₄, and concentrated in vacuo. The residual solid (8.03 g), thiourea (3.78 g) and EtOH (55 ml) were combined. The reaction mixture was refluxed for 1.5 hours under N₂ atmosphere. After cooled to r.t., the precipitate was filtered in vacuo. The solid was washed with EtOH and water to give 4-[4-(methylthio)phenyl]-1,3-thiazol-2-amine (7.48 g) as a pale yellow solid.

mp. 245–246° C.

¹H-NMR (DMSO-d₆), δ (ppm): 2.51(3H, s), 7.18(1H, s), 7.35(2H, d, J=8.5 Hz), 7.67(2H, d, J=8.5 Hz).

MS: 223(M+H)⁺

Step 2

N-{4-[4-(Methylthio)phenyl]-1,3-thiazol-2-yl}acetamide was prepared from the compound of Step 1 in a similar manner according to Step 3 of Production Example 45.

mp. 235–236° C.

¹H-NMR (DMSO-d₆), δ (ppm): 2.16(3H, s), 2.50(3H, s), 7.31(2H, d, J=8.5 Hz), 7.56(1H, s), 7.83(2H, d, J=8.5 Hz), 12.24(1H, brs).

MS: 265(M+H)⁺

Step 3

N-{4-[4-(Methylthio)phenyl]-1,3-thiazol-2-yl}acetamide (2 g) was suspended in CH₂Cl₂ (20 ml), and then 3-chloroperoxybenzoic acid (1.44 g) was added portionwise to the suspension at 0° C. The reaction mixture was stirred at r.t. for 15 minutes. The precipitate was filtered in vacuo, and the solid was washed with 1N—Na₂CO₃, water and EtOH to give N-{4-[4-(methylsulfinyl)phenyl]-1,3-thiazol-2-yl}acetamide (2.80 g) as a colorless solid.

mp. 274–274.5° C.

¹H-NMR (DMSO-d₆), δ (ppm): 2.10(3H, s), 2.77(3H, s), 7.62(1H, s), 7.71(2H, d, J=8.5 Hz), 8.07(2H, d, J=8.5 Hz).

MS: 279(M–H)⁺

Step 4

N-{4-[4-(Methylsulfinyl)phenyl]-1,3-thiazol-2-yl}acetamide (1.5 g), sodium acetate (1.54 g), and acetic anhydride (30 ml) were combined under N₂ atmosphere. The reaction mixture was refluxed for 2 hours. After cooled to r.t., the mixture was diluted in AcOEt. The organic solution was washed with water and brine, dried over anhydrous MgSO₄, and concentrated in vacuo. The residual solid was washed with ethyl ether/n-hexane to give ({4-[2-(acetylamino)-1,3-thiazol-4-yl]phenyl}thio)methyl acetate (811.2 mg) as an off-white solid.

mp. 144–145° C.

¹H-NMR (DMSO-d₆), δ (ppm): 2.07(3H, s), 2.17(3H, s), 5.53(2H, s), 7.50(2H, d, J=8.5 Hz), 7.63(1H, s), 7.88(2H, d, J=8.5 Hz), 12.27(1H, brs).

MS: 323(M+H)⁺

Step 5

({4-[2-(Acetylamino)-1,3-thiazol-4-yl]phenyl}thio)methyl acetate (40 mg) was dissolved in CH₂Cl₂ (0.6 ml) and MeOH (0.3 ml) under N₂ atmosphere. Then magnesium monoperoxyphthalate (120 mg) was added to the solution at 0° C. The reaction mixture was stirred at r.t. for 2 hours. Water and CHCl₃ were added to the mixture, and the mixture was extracted. The organic layer was washed with saturated NaHCO₃ and brine, dried over anhydrous MgSO₄, and concentrated in vacuo. The residual solid was washed with ethyl ether to give ({4-[2-(acetylamino)-1,3-thiazol-4-yl]phenyl }sulfonyl)methyl acetate (29.7 mg) as a colorless solid.

mp. 237–238° C.

¹H-NMR (DMSO-d₆), δ (ppm): 2.07(3H, s), 2.18(3H, s), 5.43(2H, s), 7.94(1H, s), 7.97(2H, d, J=8.5 Hz), 8.17(2H, d, J=8.5 Hz), 12.37(1H, brs).

MS: 355(M+H)⁺

Step 6

({4-[2-(Acetylamino)-1,3-thiazol-4-yl]phenyl}sulfonyl) methyl acetate (700 mg), THF (8 ml), MeOH (4 ml) and 1N—NaOH (1.98 ml) were combined. The reaction mixture was stirred at r.t. for 1.5 hours, and concentrated in vacuo. The residual solid was washed with ethyl ether to give sodium 4-[2-(acetylamino)-1,3-thiazol-4-yl]phenylsulfinate (731 mg) as a colorless solid.

¹H-NMR (DMSO-d₆), δ (ppm): 2.16(3H, s), 7.52(2H, d, J=8.0 Hz), 7.54(1H, s), 7.84(2H, d, J=8.0 Hz).

MS: 281(M–H)⁺ free

Step 7

Sodium 4-[2-(acetylamino)-1,3-thiazol-4-yl]phenylsulfinate (600 mg) was dissolved in DMF (2 ml) under N₂ atmosphere. Then 2-bromoethanol (0.168 ml) was added to the solution at 0° C. The reaction mixture was stirred at 100° C. for 7 hours. After cooled to r.t., water and AcOEt were added to the mixture. The precipitate was filtered in vacuo to give N-(4-{4-[(2-hydroxyethyl)sulfonyl]phenyl}-1,3-thiazol-2-yl)acetamide (80.2 mg) as an off-white solid.

mp. 258–260° C.

¹H-NMR (DMSO-d₆), δ (ppm): 2.18(3H, S), 3.47(2H, t, J=6.0 Hz), 3.70(2H, q, J=6.0 Hz), 4.89(1H, t, J=6.0 Hz), 7.89(1H, s), 7.94(2H, d, J=8.5 Hz), 8.13(2H, d, J=8.5 Hz), 12.36(1H, brs).

MS: 325(M–H)⁺

Step 8

N-(4-{4-[(2-Hydroxyethyl)sulfonyl]phenyl}-1,3-thiazol-2-yl)acetamide (200 mg), Et₃N (0.102 ml) and CH₂Cl₂ (4 ml) were combined under N₂ atmosphere, and then MsCl (0.05 ml) was added to the suspension at 0° C. The reaction mixture was stirred at r.t. for 2 hours. MeOH/CHCl₃ and water were added to the mixture, and the mixture was extracted. The organic layer was washed with brine, dried over anhydrous MgSO₄, and concentrated in vacuo. The residual solid (221.6 mg) was suspended in CH₃CN (10 ml), and then 28% ammonia solution (0.5 ml) was added to the suspension at 0° C. The reaction mixture was stirred at r.t. for 15 hours, and concentrated in vacuo. The residue was purified by flash column chromatography over silica gel with [MeOH/CHCl₃ (1:30), then NH₄OH/MeOH/CHCl₃ (1:10:60)] as an eluent, and triturated with EtOH/ethyl ether to give N-(4-{4-[(2-aminoethyl)sulfonyl]phenyl}-1,3-thiazol-2-yl)acetamide (60.4 mg) as an off-white solid.

mp. 287–288° C.

¹H-NMR (DMSO-d₆), δ (ppm): 2.18(3H, s), 2.79(2H, t, J=6.5 Hz), 3.36(2H, q, J=6.5 Hz), 7.90(1H, s), 7.94(2H, d, J=8.5 Hz), 8.15(2H, d, J=8.5 Hz).

MS: 326(M+H)⁺

Step 9

Di-tert-butyl ((Z)-{[2-({4-[2-(acetylamino)-1,3-thiazol-4-yl]phenyl}sulfonyl)ethyl]amino}methylidene)biscarbamate was prepared from the compound of Step 8 in a similar manner according to Step 3 of Production Example 31.

mp. 280–281° C.

¹H-NMR (DMSO-d₆), δ (ppm): 1.38(9H, s), 1.39(9H, s), 2.18(3H, s), 3.65(4H, s), 7.88(1H, s), 7.93(2H, d, J=8.5 Hz), 8.13(2H, d, J=8.5 Hz), 8.32(1H, brs), 11.32(1H, brs), 12.35 (1H, brs).

MS: 568(M+H)⁺

Step 10

The title compound was prepared from the compound of Step 9 in a similar manner according to Step 4 of Production Example 31.

mp. 188–189.5° C.

$^1$H-NMR (DMSO-d$_6$), δ (ppm): 2.18(3H, s), 3.51(2H, m), 3.59(2H, t, J=6.0 Hz), 7.28(3H, brs), 7.62(1H, t, J=5.5 Hz), 7.93(1H, s), 7.98(2H, d, J=8.5 Hz), 8.17(2H, d, J=8.5 Hz), 12.37(1H, brs).

MS: 368(M+H)$^{+ \text{free}}$

PRODUCTION EXAMPLE 112

Synthesis of N-{4-[2-(4-{[amino(imino)methyl]amino}phenyl)ethyl]-5-[3-(methylsulfonyl)benzyl]-1,3-thiazol-2-yl}acetamide hydrochloride Step 1

N-Methoxy-N-methyl-3-(methylsulfonyl)benzamide was prepared from 3-(methylsulfonyl)benzoic acid in a similar manner according to Step 1 of Production Example 31.

$^1$H-NMR (CDCl$_3$), δ (ppm): 3.08(3H, s), 3.40(3H, s), 3.55(3H, s), 7.64(1H, t, J=8.0 Hz), 7.99(1H, dt, J=8.0, 1.5 Hz), 8.03(1H, dt, J=8.0, 1.5 Hz), 8.28(1H, t, J=1.5 Hz).

MS: 244(M+H)$^+$

Step 2

To a stirred solution of N-methoxy-N-methyl-3-(methylsulfonyl)benzamide (5 g) in dry THF (100 ml) was added dropwise DIBALH (22.6 ml) at −78° C. under N$_2$ atmosphere. The action mixture was stirred for 4 hours at r.t. and then quenched with MeOH at 0° C. AcOEt and 1N—HCl were added to the mixture, and extracted. The organic layer was washed with brine, dried over anhydrous MgSO$_4$, and concentrated in vacuo. The residual oil (3.38 g), methyl (triphenylphosphoranylidene)acetate (6.87 g) and THF (68 ml) were combined at r.t. under N$_2$ atmosphere, and the reaction mixture was refluxed for 3 hours. The solvent was removed in vacuo, and the residue was suspended in AcOEt. The solid was filtered off, and the filtrate was concentrated in vacuo. The residue was purified by flash column chromatography over silica gel with n-hexane/AcOEt (2:1) as an eluent to give methyl (2E)-3-[3-(methylsulfonyl)phenyl]acrylate (613.8 mg) as yellow oil.

$^1$H-NMR (DMSO-d$_6$), δ (ppm): 3.28(3H, s), 3.75(3H, s), 6.85(1H, d, J=16.0 Hz), 7.74(1H, s), 7.93(1H, t, J=8.0 Hz), 7.96(1H, d, J=8.0 Hz), 8.09(1H, d, J=8.0 Hz), 8.32(1H, d, J=16.0 Hz).

Step 3

Methyl (2E)-3-[3-(methylsulfonyl)phenyl]acrylate (600 mg), MeOH (6.ml) and then 10% palladium carbon (99.9 mg) were combined under N$_2$ atmosphere. The reaction mixture was stirred at r.t. for 7 hours under H$_2$ atmosphere (1 atm), and filtered through a celite pad. The filtrate was concentrated in vacuo. The residue was purified by flash column chromatography over silica gel with n-hexane/AcOEt (1:1→1:2) as an eluent to give methyl 3-[3-(methylsulfonyl)phenyl]propanoate (283.3 mg) as colorless oil.

$^1$H-NMR (DMSO-d$_6$), δ (ppm): 2.70(2H, t, J=7.5 Hz), 2.97(2H, t, J=7.5 Hz), 3.20(3H, s), 3.58(3H, s), 7.52–7.63 (2H, m), 7.73–7.80(2H, m).

Step 4

Ethyl 4-[3-(methylsulfonyl)phenyl]-2-oxobutanoate was prepared from the compound of Step 3 in a similar manner according to Step 2 of Production Example 47.

$^1$H-NMR (CDCl$_3$), δ (ppm): 1.35(3H, t, J=7.0 Hz), 3.05 (2H, t, J=7.0 Hz), 3.06(3H, s), 3.24(2H, t, J=7.0 Hz), 4.32(2H, q, J=7.0 Hz), 7.45–7.82(4H, m).

Step 5

Ethyl 3-bromo-4-[3-(methylsulfonyl)phenyl]-2-oxobutanoate was prepared from the compound of Step 4 in a similar manner according to Step 1-of Production Example 46.

$^1$H-NMR (CDCl$_3$), δ (ppm): 1.37(3H, t, J=7.0 Hz), 3.07 (3H, s), 3.34(1H, dd, J=14.5, 8.0 Hz), 3.60(1H, dd, J=14.5, 6.5 Hz), 4.35(2H, q, J=7.0 Hz), 5.26(1H, dd, J=8.0, 6.5 Hz), 7.49–7.88(4H, m).

Step 6

Ethyl 2-amino-5-[3-(methylsulfonyl)benzyl]-1,3-thiazole-4-carboxylate was prepared from the compound of Step 5 in a similar manner according to Step 2 of Production Example 46.

$^1$H-NMR (DMSO-d$_6$), δ (ppm): 1.24(3H, t, J=7.0 Hz), 3.20(3H, s), 4.20(2H, q, J=7.0 Hz), 4.46(2H, s), 7.10(2H, s), 7.57–7.61(2H, m), 7.76–7.83(2H, m).

MS: 341(M+H)$^+$

Step 7

Ethyl 2-(acetylamino)-5-[3-(methylsulfonyl)benzyl]-1,3-thiazole-4-carboxylate was prepared from the compound of Step 6 in a similar manner according to Step 3 of Production Example 45.

$^1$H-NMR (DMSO-d$_6$), δ (ppm): 1.27(3H, t, J=7.0 Hz), 2.10(3H, s), 3.20(3H, s), 4.27(2H, q, J=7.0 Hz), 4.61(2H, s), 7.56–7.66(2H, m), 7.77–7.89(2H, m), 12.47(1H, s).

MS: 383(M+H)$^+$

Step 8

Ethyl $^2$-(acetylamino)-5-[3-(methylsulfonyl)benzyl]-1,3-thiazole-4-carboxylate (54.7 mg) was suspended in THF (1 ml) under N$_2$ atmosphere, and then lithium aluminium hydride (7.79 mg) was added portionwise to the suspension at 0° C. The reaction mixture was refluxed for 2.5 hours, and quenched with MeOH and 1N—HCl at 0° C. Anhydrous MgSO$_4$ was added to the mixture, and stirred at r.t. for 1 hour. The suspension was filtered in vacuo. The filtrate was concentrated in vacuo.

The residual oil (114.8 mg), CHCl$_3$ (1 ml), CH$_3$CN (1 ml) and Dess-Martin periodinane (88 mg) were combined at 0° C. under N$_2$ atmosphere. The reaction mixture was stirred at r.t. for 1 hour, and diluted in CHCl$_3$. The organic solution was washed with saturated NaHCO$_3$, water and brine, dried over anhydrous MgSO$_4$, and concentrated in vacuo to give N-{4-formyl-5-[3-(methylsulfonyl)benzyl]-1,3-thiazol-2-yl}acetamide (61.2 mg) as a yellow amorphous.

$^1$H-NMR (DMSO-d$_6$), δ (ppm): 2.13(3H, s), 3.17(3H, s), 4.67(2H, s), 7.56–7.90(4H, m), 10.04(1H, s), 12.39(1H, s).

Step 9

N-{5-[3-(Methylsulfonyl)benzyl]-4-[(Z)-2-(4-nitrophenyl)vinyl]-1,3-thiazol-2-yl}acetamide was prepared from the compound of Step 8 in a similar manner according to Step 5 of Production Example 45.

$^1$H-NMR (DMSO-d$_6$), δ (ppm): 2.08(3H×⅔, s), 2.13(3H× ⅓, s), 3.18(3H, s), 4.23(2H×⅔, s), 4.50(2H×⅓, s), 6.69–8.31(10H, m).

Step 10

N-{4-[2-(4-Aminophenyl)ethyl]-5-[3-(methylsulfonyl)benzyl]-1,3-thiazol-2-yl}acetamide was prepared from the compound of Step 9 in a similar manner according to Step 6 of Production Example 45.

MS: 430(M+H)$^+$

Step 11
Di-tert-butyl ((Z)-{[4-(2-{2-(acetylamino)-5-[3-(methylsulfonyl)benzyl]-1,3-thiazol-4-yl}ethyl)phenyl]amino}methylidene)biscarbamate was prepared from the compound of Step 10 in a similar manner according to Step 3 of Production Example 31.

$^1$H-NMR [CD$_3$Cl/CD$_3$OD (1:1)], δ (ppm): 1.29(9H, s), 1.55(9H, s), 2.23(3H, s), 2.89(4H, m), 3.07(3H, s), 3.90(2H, s), 7.11–7.87(8H, m).
MS: 672(M+H)$^+$ Step 12
The title compound was prepared from the compound of Step 11 in a similar manner according to Step 4 of Production Example 31.

$^1$H-NMR (CD$_3$OD), δ (ppm): 2.08(3H, s), 2.98(4H, m), 3.10(3H, s), 3.98(2H, s), 7.10–7.88(8H, m).
MS: 472(M+H)$^{+ free}$

PRODUCTION EXAMPLE 113

Synthesis of N-{4-[2-(4-{[amino(imino)methyl]amino}phenyl)ethyl]-5-[(1,1-dioxido-4-thiomorpholinyl)methyl]-1,3-thiazol-2-yl}acetamide dihydrochloride Step 1
N-{5-[(1,1-Dioxido-4-thiomorpholinyl)methyl]-4-[(Z)-2-(4-nitrophenyl)vinyl]-1,3-thiazol-2-yl}acetamide was prepared from N-{4-[(Z)-2-(4-nitrophenyl)vinyl]-1,3-thiazol-2-yl}acetamide in a similar manner according to Step 1 of Production Example 67.
MS: 437.12(M+H)$^+$ Step 2
Di-tert-butyl ((Z)-{[4-(2-{2-(acetylamino)-5-[(1,1-dioxido-4-thiomorpholinyl)methyl]-1,3-thiazol-4-yl}ethyl)phenyl]amino}methylidene)biscarbamate was prepared from the compound of Step 1 in a similar manner according to Step 2 of Production Example 68.

$^1$H-NMR (CDCl$_3$), δ (ppm): 1.49(9H, s), 1.53(9H, s), 2.23(3H, s), 2.70–2.95(8H, m), 2.95–3.12(4H, s), 3.45(2H, s), 6.99(2H, d, J=8.3 Hz), 7.42(2H, d, J=8.3 Hz), 8.94–9.24 (1H, brs), 10.24(1H, s), 11.63(1H, s).
MS: 651.1(M+H)$^+$, 673.3(M+Na)$^+$ Step 3
The title compound was prepared from the compound of Step 2 in a similar manner according to Step 4 of Production Example 31.

$^1$H-NMR (DMSO-d$_6$), δ (ppm): 2.15(3H, s), 2.97(4H, s), 3.77–4.63(8H, s), 4.45(2H, s), 7.15(2H, d, J=8.3 Hz), 7.32 (2H, d, J=8.3 Hz), 7.46(4H, s), 9.96(1H, s), 12.29(1H, s).
MS: 451.3(M+H)$^+$, 473.2(M+Na)$^+$

PRODUCTION EXAMPLE 114

Synthesis of N-[4-[2-(4-{[amino(imino)methyl]amino}phenyl)ethyl]-5-(4-morpholinylmethyl)-1,3-thiazol-2-yl]acetamide dihydrochloride Step 1
N-{5-(4-Morpholinylmethyl)-4-[(Z)-2-(4-nitrophenyl)vinyl]-1,3-thiazol-2-yl}acetamide was prepared from N-{4-[(Z)-2-(4-nitrophenyl)vinyl]-1,3-thiazol-2-yl}acetamide in a similar manner according to Step 1 of Production Example 67.
MS: 389.16(M+H)$^+$ Step 2
Di-tert-butyl {(Z)-[(4-{2-[2-(acetylamino)-5-(4-morpholinylmethyl)-1,3-thiazol-4-yl]ethyl}phenyl)amino]methylidene}biscarbamate was prepared from the compound of Step 1 in a similar manner according to Step 2 of Production Example 68.

$^1$H-NMR (CDCl$_3$), δ (ppm): 1.50(9H, s), 1.53(9H, s), 2.22(3H, s), 2.30–2.46(4H, m), 2.85(4H, s), 3.39(2H, s), 3.58–3.75(4H, m), 7.07(2H, d, J=8.4 Hz), 7.45(2H, d, J=8.4 Hz), 8.80–9.31(1H, brs), 10.24(1H, s), 11.63(1H, s).
MS: 603.3(M+H)$^+$ Step 3
The title compound was prepared from the compound of Step 2 in a similar manner according to Step 4 of Production Example 31.

$^1$H-NMR(DMSO-d$_6$), δ (ppm): 2.16(3H, s), 2.97(4H, s), 3.00–3.12(2H, m), 3.16–3.27(2H, m), 3.65–3.76(2H, m), 3.86–3.97(2H, m), 4.43(2H, s), 7.15(2H, d, J=8.4 Hz), 7.31(2H, d, J=8.4 Hz), 7.40(4H, s), 9.86(1H, s), 10.54–10.84 (1H, brs), 12.34(1H, s).
MS: 403.1(M+H)$^+$, 426.1(M+Na)$^+$

PRODUCTION EXAMPLE 115

Synthesis of N-{4-[2-(4-{[amino(imino)methyl]amino}phenyl)ethyl]-5-[(3-oxo-1-piperazinyl)methyl]-1,3-thiazol-2-yl}acetamide dihydrochloride Step 1
N-{4-[(Z)-2-(4-Nitrophenyl)vinyl]-5-[(3-oxo-1-piperazinyl)methyl]-1,3-thiazol-2-yl}acetamide was prepared from N-{4-[(Z)-2-(4-nitrophenyl)vinyl]-1,3-thiazol-2-yl}acetamide in a similar manner according to Step 1 of Production Example 67.
Z:E=3:1

$^1$H-NMR (DMSO-d$_6$), δ (ppm): 2.10(3H×¾, s), 2.15(3H×¼, s), 2.54–2.59(2H×¾, m), 2.61–2.67(2H×¼, m), 2.93 (2H×¾, s), 3.02(2H×¼, m), 3.08–3.19(2H, m), 3.64(2H×¾, s), 3.95(2H×¼, s), 6.72(1H×¾, d, J=12.4 Hz), 6.78(1H×¾, d, J=12.4 Hz), 7.34(1H×¼, d, J=15.7 Hz), 7.59(1×¼, d, J=15.7 Hz), 7.62(2H×¾, d, J=8.8 Hz), 7.76(1H×¾, s), 7.78(1H×¼, s), 7.90(2H×¼, d, J=8.8 Hz), 8.14(2H×¾, d, J=8.8 Hz), 8.21(2H×¼, d, J=8.8 Hz), 11.75–12.06(1H×¾, brs), 12.08–12.33(1H×¼, brs).
MS: 402.21(M+H)$^+$ Step 2
Di-tert-butyl ((Z)-{[4-(2-{2-(acetylamino)-5-[(3-oxo-1-piperazinyl)methyl]-1,3-thiazol-4-yl}ethyl)phenyl]amino}methylidene)biscarbamate was prepared from the compound of Step 1 in a similar manner according to Step 2 of Production Example 68.

$^1$H-NMR (CDCl$_3$), δ (ppm): 1.49(9H, s), 1.53(9H, s), 2.24(3H, s), 2.47–2.55(2H, m), 2.80–2.93(4H, m), 3.13(2H, s), 3.24–3.32(2H, m), 3.43(2H, s), 6.02(1H, s), 7.04(2H, d, J=8.4 Hz), 7.44(2H, d, J=8.3 Hz), 9.02–9.26(1H, brs), 10.24(1H, s), 11.62(1H, s).
MS: 616.2(M+H)$^+$, 638.2(M+Na)$^+$ Step 3
The title compound was prepared from the compound of Step 2 in a similar manner according to Step 4 of Production Example 31.

$^1$H-NMR (DMSO-d$_6$), δ (ppm): 2.15(3H, s), 2.39–2.62 (2H, m), 2.95(4H, s), 3.08–3.86(4H, m), 4.20–4.77(2H, brs), 7.15(2H, d, J=8.3 Hz), 7.30(2H, d, J=8.0 Hz), 7.35(4H, s), 8.04–8.62(1H, brs), 9.70(1H, s), 10.67–11.38(1H, brs), 11.97–12.72(1H, brs).

MS: 416.2(M+H)$^{+\,free}$

PRODUCTION EXAMPLE 116

Synthesis of 4-({2-(acetylamino)-4-[2-(4-{[amino(imino)methyl]amino}phenyl)ethyl]-1,3-thiazol-5-yl}methyl)-N,N-dimethyl-1-piperazinecarboxamide dihydrochloride Step 1

9H-Fluoren-9-ylmethyl 4-({2-(acetylamino)-4-[(Z)-2-(4-nitrophenyl)vinyl]-1,3-thiazol-5-yl}methyl)-1-piperazinecarboxylate was prepared from N-{4-[(Z)-2-(4-nitrophenyl)vinyl]-1,3-thiazol-2-yl}acetamide in a similar manner according to Step 1 of Production Example 67.

$^1$H-NMR (CDCl$_3$), δ (ppm): 2.10(3H, s), 2.26–2.61(4H, m), 3.39–3.64(6H, m), 4.19–4.30(1H, m), 4.37–4.49(2H, m), 6.66(2H, s), 7.07–7.67(8H, m), 7.76(2H, d, J=6.9 Hz), 8.05(2H, d, J=8.9 Hz), 10.03(1H, s).

MS: 610.2(M+H)$^+$, 632.2(M+Na)$^+$

Step 2

9H-Fluoren-9-ylmethyl 4-({2-(acetylamino)-4-[2-(4-aminophenyl)ethyl]-1,3-thiazol-5-yl }methyl)-1-piperazinecarboxylate was prepared from the compound of Step 1 in a similar manner according to Step 6 of Production Example 45.

$^1$H-NMR (CDCl$_3$), δ (ppm): 2.16–2.33(7H, m), 2.80(4H, s), 3.34(2H, s), 3.36–3.84(6H, m), 4.17–4.30(1H, m), 4.36–4.47(2H, m), 6.57(2H, d, J=8.4 Hz), 6.86(2H, d, J=8.3 Hz), 7.26–7.46(4H, m), 7.56(2H, d, J=7.0 Hz), 7.76(2H, d, J=6.9 Hz), 8.60–9.52(1H, brs).

MS: 582.2(M+H)$^+$, 604.3(M+Na)$^+$

Step 3

9H-Fluoren-9-ylmethyl 4-[(2-(acetylamino)-4-{2-[4-({(Z)-[(tert-butoxycarbonyl)amino][(tert-butoxycarbonyl)imino]methyl}amino)phenyl]ethyl}-1,3-thiazol-5-yl)methyl]-1-piperazinecarboxylate was prepared from the compound of Step 2 in a similar manner according to Step 3 of Production Example 31.

$^1$H-NMR (CDCl$_3$), δ (ppm): 1.50(9H, s), 1.52(9H, s), 2.23(3H, s), 2.28–2.43(4H, m), 2.86(4H, s), 3.36–3.55(6H, m), 4.18–4.29(1H, m), 4.35–4.48(2H, m), 7.05(2H, d, J=8.5 Hz), 7.13–7.66(8H, m), 7.75(2H, d, J=7.0 Hz), 8.85–9.76(1H, brs), 10.25(1H, Ss), 11.63(1H, s).

MS: 824.2(M+H)$^+$, 847.3(M+Na)$^+$

Step 4

To a solution of 9H-fluoren-9-ylmethyl 4-[2-(acetylamino)-4-{2-[4-({(Z)-[(tert-butoxycarbonyl)amino][(tert-butoxycarbonyl)imino]methyl}amino)phenyl]ethyl}-1,3-thiazol-5-yl)methyl]-1-piperazinecarboxylate (400 mg) in DMF (0.8 ml) was added piperidine (0.16 ml), and the mixture was stirred for 2 h at 20° C. To the reaction mixture was added piperidine (0.16 ml), stirred at 20° C. for 1 h and 40° C. for 1 h, then cooled to 20° C., added AcOEt (50 ml), and the mixture was washed with water (10 ml×3) and brine (10 ml), dried over MgSO$_4$, filtered and concentrated in vacuo to give crude pale yellow oil (463 mg). The crude oil was purified by flash column chromatography over NH silica gel with dichloromethane/methanol (100:0)→(100:1) as an eluent to give di-tert-butyl {(Z)-[(4-{2-[2-(acetylamino)-5-(1-piperazinylmethyl)-1,3-thiazol-4-yl]ethyl}phenyl)amino]methylidene}biscarbamate as a colorless amorphous.

$^1$H-NMR (CDCl$_3$), δ (ppm): 1.50(9H, s), 1.53(9H, s), 2.21(3H, s), 2.27–2.47(4H, m), 2.71–3.00(8H, m), 3.40(2H, s), 7.07(2H, d, J=8.4 Hz), 7.45(2H, d, J=8.4 Hz), 10.24(1H, s), 11.47–11.74(1H, brs).

MS: 602.3(M+H)$^+$, 624.2(M+Na)$^+$

Step 5

To a solution of di-tert-butyl {(Z)-[(4-{2-[2-(acetylamino)-5-(1-piperazinylmethyl)-1,3-thiazol-4-yl]ethyl}phenyl)amino]methylidene}biscarbamate (30 mg) in dichloromethane (0.3 ml) were added N,N-diisopropylethylamine (9.55 μl) and dimethylcarbamyl chloride (4.59 μl), and the mixture was stirred for 14 h at 20° C. To the reaction mixture was added saturated sodium hydrogen carbonate aqueous solution (2 ml), then the mixture was extracted with diclhloromethane (5 ml×3) and the extract was dried over diatomaceous earth. The organic layer was concentrated in vacuo to give crude oil. The residue was purified by preparative silica gel thin-layer chromatography with chloroform/methanol (20:1) as an eluent to give di-tert-butyl {(Z)-[(4-{2-[2-(acetylamino)-5-({4-[(dimethylamino)carbonyl]-1-piperazinyl }methyl)-1,3-thiazol-4-yl]ethyl}phenyl)amino]methylidene}biscarbamate as colorless oil.

$^1$H-NMR (CDCl$_3$), δ (ppm): 1.50(9H, s), 1.54(9H, s), 2.23(3H, s), 2.35–2.42(4H, m), 2.80(6H, s), 2.81–2.89(4H, m), 3.17–3.27(4H, m), 3.41(2H, s), 7.07(2H, d, J=8.4 Hz), 7.46(2H, d, J=8.4 Hz), 8.73–8.90(1H, brs), 10.25(1H, s), 11.63(1H, s).

MS: 673.3(M+H)$^+$, 695.2(M+Na)$^+$

Step 6

The title compound was prepared from the compound of Step 5 in a similar manner according to Step 4 of Production Example 31.

$^1$H-NMR(DMSO-d$_6$), δ (ppm): 2.16(3H, s), 2.76(6H, s), 2.91–3.06(6H, m), 3.07–3.19(2H, m), 3.20–3.30(2H, m), 3.57–3.65(2H, m), 4.36–4.51(2H, m), 7.15(2H, d, J=8.4 Hz), 7.31(2H, d, J=8.4 Hz), 7.41(4H, s), 9.87(1H, s), 10.51–10.69 (1H, brs), 12.33(1H, s).

MS: 473.2(M+H)$^+$

PRODUCTION EXAMPLE 117

Synthesis of N-(4-[2-(4-{[amino(imino)methyl]amino}phenyl)ethyl]-5-{[4-(4-morpholinylcarbonyl)-1-piperazinyl]methyl}-1,3-thiazol-2-yl)acetamide dihydrochloride Step 1

Di-tert-butyl [(Z)-({4-[2-(2-(acetylamino)-5-{[4-(4-morpholinylcarbonyl)-1-piperazinyl]methyl}-1,3-thiazol-4-yl)ethyl]phenyl}amino)methylidene]biscarbamate was prepared from the compound of Step 4 of Production Example 116 in a similar manner according to Step 5 of Production Example 116.

$^1$H-NMR (CDCl$_3$), δ (ppm): 1.50(9H, s), 1.54(9H, s), 2.23(3H, s), 2.32–2.46(4H, m), 2.78–2.91(4H, m), 3.20–3.30(8H, m), 3.42(2H, s), 3.63–3.71(4H, m), 7.07(2H, d, J=8.4 Hz), 7.46(2H, d, J=8.4 Hz), 8.72–8.89(1H, brs), 10.25(1H, s), 11.64(1H, s).

MS: 715.3(M+H)$^+$, 737.2(M+Na)$^+$

Step 2

The title compound was prepared from the compound of Step 1 in a similar manner according to Step 4 of Production Example 31.

$^1$H-NMR (DMSO-d$_6$), δ (ppm): 2.16(3H, s), 2.90–3.07 (6H, m), 3.11–3.32(8H, m), 3.48–3.76(6H, m), 4.42(2H, s), 7.15(2H, d, J=8.4 Hz), 7.31(2H, d, J=8.4 Hz), 7.40(4H, s), 9.85(1H, s), 10.51–10.72(1H, brs), 12.34(1H, s).

MS: 515.3(M+H)$^{+ \, free}$

PRODUCTION EXAMPLE 118

Synthesis of N-(4-[2-(4-{[amino(imino)methyl] amino}phenyl)ethyl]-5-{[4-(1-pyrrolidinylcarbonyl)-1-piperazinyl]methyl}-1,3-thiazol-2-yl)acetamide dihydrochloride Step 1

Di-tert-butyl [(Z)-({4-[2-(2-(acetylamino)-5-{[4-(1-pyrrolidinylcarbonyl)-1-piperazinyl]methyl}-1,3-thiazol-4-yl)ethyl]phenyl}amino)methylidene]biscarbamate was prepared from the compound of Step 4 of Production Example 116 in a similar manner according to Step 5 of Production Example 116.

$^1$H-NMR (CDCl$_3$), δ (ppm): 1.50(9H, s), 1.54(9H, s), 1.72–1.89(4H, m), 2.23(3H, s), 2.28–2.48(4H, m), 2.84(4H, s), 3.19–3.39(8H, m), 3.41(2H, s), 7.07(2H, d, J=8.4 Hz), 7.46(2H, d, J=8.4 Hz), 8.71–8.99(1H, brs), 10.24(1H, s), 11.64(1H, s).

MS: 699.2(M+H)$^+$, 721.3(M+Na)$^+$

Step 2

The title compound was prepared from the compound of Step 1 in a similar manner according to Step 4 of Production Example 31.

$^1$H-NMR (DMSO-d$_6$), δ (ppm): 1.70–1.83(4H, m), 2.16 (3H, s), 2.89–3.05(6H, m), 3.06–3.19(2H, m), 3.20–3.32 (6H, m), 3.64–3.84(2H, m), 4.36–4.50(2H, m), 7.15(2H, d, J=8.2 Hz), 7.31(2H, d, J=8.3 Hz), 7.42(4H, s), 9.88(1H, s), 10.50–10.75(1H, brs), 12.34(1H, s).

MS: 499.3(M+H)$^{+ \, free}$

PRODUCTION EXAMPLE 119

Synthesis of N-[4-[2-(4-{[amino(imino)methyl] amino}phenyl)ethyl]-5-({4-[(4-methyl-1-piperazinyl)carbonyl]-1-piperazinyl}methyl)-1,3-thiazol-2-yl]acetamide trihydrochloride Step 1

Di-tert-butyl {(Z)-[(4-{2-[2-(acetylamino)-5-({4-[(4-methyl-1-piperazinyl)carbonyl]-1-piperazinyl}methyl)-1,3-thiazol-4-yl]ethyl}phenyl)amino] methylidene}biscarbamate was prepared from the compound of Step 4 of Production Example 116 in a similar manner according to Step 5 of Production Example 116.

$^1$H-NMR (CDCl$_3$), δ (ppm): 1.50(9H, s), 1.54(9H, s), 2.23(3H, s), 2.29(3H, s), 2.32–2.48(8H, m), 2.84(4H, s), 3.16–3.35(8H, m), 3.42(2H, s), 7.07(2H, d, J=8.4 Hz), 7.46(2H, d, J=8.4 Hz), 8.69–9.04(1H, brs), 10.24(1H, s), 11.64(1H, s).

MS: 728.2(M+H)$^+$, 750.3(M+Na)$^+$

Step 2

The title compound was prepared from the compound of Step 1 in a similar manner according to Step 4 of Production Example 31.

$^1$H-NMR (DMSO-d$_6$), δ (ppm): 2.16(3H, s), 2.76(3H, d, J=4.6 Hz), 2.89–3.09(8H, m), 3.17–3.39(8H, m), 3.62–3.77 (4H, m), 4.34–4.51(2H, brs), 7.15(2H, d, J=8.3 Hz), 7.31 (2H, d, J=8.2 Hz), 7.41(4H, s), 9.87(1H, s), 10.68–10.97(1H, brs), 12.34(1H, s).

MS: 528.3(M+H)$^{+ \, free}$

PRODUCTION EXAMPLE 120

Synthesis of 3-{2-(acetylamino)-4-[2-(4-{[amino(imino)methyl]amino}phenyl)ethyl]-1,3-thiazol-5-yl}-N,N-dimethylpropanamide hydrochloride Step 1

Ethyl 3-[2-(acetylamino)-4-(2-{4-[(tert-butoxycarbonyl)amino]phenyl}ethyl)-1,3-thiazol-5-yl]acrylate was prepared from 2-(acetylamino)-4-(2-{4-[(tert-butoxycarbonyl)amino]phenyl}ethyl)-1,3-thiazole-5-carbaldehyde in a similar manner according to Step 7 of Production Example 61.

$^1$H-NMR (CDCl$_3$), δ (ppm): 1.16–1.40(3H, m), 1.52(9H, s), 2.23–2.38(3H, m), 2.70–3.06(4H, m), 4.15–4.33(2H, m), 5.53–6.15(1H, m), 6.64–7.85(6H, m).

MS: 482.2(M+Na)$^+$

Step 2

A mixture of ethyl (2E)-3-[2-(acetylamino)-4-(2-{4-[(tert-butoxycarbonyl)amino]phenyl}ethyl)-1,3-thiazol-5-yl]acrylate and ethyl (2Z)-3-[2-(acetylamino)-4-(2-{4-[(tert-butoxycarbonyl)amino]phenyl}ethyl)-1,3-thiazol-5-yl] acrylate (200 mg), THF (7 ml) and 10% Pd/C (392 mg) were combined under nitrogen atmosphere. The mixture was stirred under 3 atm hydrogen atmosphere at 20° C. for 3 h. The reaction mixture was filtered through a celite pad, and the filtrate was concentrated in vacuo to give ethyl 3-[2-(acetylamino)-4-(2-{4-[(tert-butoxycarbonyl)amino] phenyl}ethyl)-1,3-thiazol-5-yl]propanoate as a colorless amorphous.

$^1$H-NMR (CDCl$_3$), δ (ppm): 1.24(3H, t, J=7.0 Hz), 1.51 (9H, s), 2.24(3H, s), 2.41(2H, t, J=7.5 Hz), 2.73–2.93(6H, m), 4.12(2H, q, J=7.0 Hz), 6.95(2H, d, J=7.2 Hz), 7.23(2H, d, J=7.7 Hz).

MS: 484.1(M+Na)$^+$

Step 3

Ethyl 3-(2-(acetylamino)-4-{2-[4-({(Z)-[(tert-butoxycarbonyl)amino][(tert-butoxycarbonyl)imino]methyl}amino) phenyl]ethyl}-1,3-thiazol-5-yl)propanoate was prepared from the compound of Step 2 in a similar manner according to Step 4 of Production Example 65.

$^1$H-NMR (CDCl$_3$), δ (ppm): 1.24(3H, t, J=7.1 Hz), 1.50 (9H, s), 1.53(9H, s), 2.21(3H, s), 2.41(2H, t, J=7.6 Hz), 2.70–3.00(6H, m), 4.12(2H, q, J=7.2 Hz), 7.07(2H, d, J=8.4 Hz), 7.46(2H, d, J=8.4 Hz), 8.80–9.20(1H, brs), 10.24(1H, s), 11.63(1H, s).

MS: 604.3(M+H)$^+$, 626.2(M+Na)$^+$

Step 4

3-(2-(Acetylamino)-4-{2-[4-({(Z)-[(tert-butoxycarbonyl)amino][(tert-butoxycarbonyl)imino]methyl}amino)phenyl] ethyl}-1,3-thiazol-5-yl)propanoic acid was prepared from the compound of Step 3 in a similar manner according to Step 1 of Production Example 42.

$^1$H-NMR (CDCl$_3$), δ (ppm): 1.47(9H, s), 1.53(9H, s), 2.19(3H, s), 2.25–2.45(2H, m), 2.60–3.00(6H, m), 6.96(2H, d, J=8.3 Hz), 7.34(2H, d, J=8.3 Hz), 10.17(1H, s), 11.30–11.90(1H, brs).

MS: 598.2(M+Na)$^+$

Step 5

Di-tert-butyl ((Z)-{[4-(2-{2-(acetylamino)-5-[3-(dimethylamino)-3-oxopropyl]-1,3-thiazol-4-yl}ethyl)phenyl]amino}methylidene)biscarbamate was prepared from the compound of Step 4 in a similar manner according to Step 1 of Production Example 32.

$^1$H-NMR (CDCl$_3$), δ (ppm): 1.49(9H, s), 1.53(9H, s), 2.21(3H, s), 2.28–2.43(2H, m), 2.79–2.99(12H, m), 7.05 (2H, d, J=8.5 Hz), 7.44(2H, d, J=8.5 Hz), 8.85–9.37(1H, brs), 10.23(1H, s), 11.62(1H, s).

MS: 603.3(M+H)$^+$, 625.3(M+Na)$^+$

Step 6

The title compound was prepared from the compound of Step 5 in a similar manner according to Step 4 of Production Example 31.

$^1$H-NMR (DMSO-d$_6$), δ (ppm): 2.10(3H, s), 2.40(2H, t, J=7.3 Hz), 2.75(2H, t, J=7.3 Hz), 2.77–2.84(5H, m), 2.84–2.95(5H, m), 7.14(2H, d, J=8.4 Hz), 7.24(2H, d, J=8.4 Hz), 7.36(4H, s), 9.72(1H, s), 11.93(1H, s).

MS: 403.3(M+H)$^{+\,free}$

PRODUCTION EXAMPLE 121

Synthesis of 3-{2-(acetylamino)-4-[2-(4-{[amino(imino)methyl]amino}phenyl)ethyl]-1,3-thiazol-5-yl}-N-methylpropanamide hydrochloride Step 1

Di-tert-butyl ((Z)-{[4-(2-{2-(acetylamino)-5-[3-(methylamino)-3-oxopropyl]-1,3-thiazol-4-yl}ethyl)phenyl]amino}methylidene)biscarbamate was prepared from the compound of Step 4 of Production Example 120 in a similar manner according to Step 1 of Production Example 32.

$^1$H-NMR (CDCl$_3$), δ (ppm): 1.45(9H, s), 1.54(9H, s), 1.79–1.88(2H, m), 2.23(3H, s), 2.65(3H, d, J=4.8 Hz), 2.69–2.77(2H, m), 2.79–2.86(2H, m), 2.86–2.95(2H, m), 6.04(2H, d, J=4.4 Hz), 6.93(2H, d, J=8.4 Hz), 7.28(2H, d, J=8.4 Hz), 8.79–9.17(1H, brs), 10.28(1H, s), 11.60(1H, s).

MS: 589.3(M+H)$^+$, 611.3(M+Na)$^+$

Step 2

The title compound was prepared from the compound of Step 1 in a similar manner according to Step 4 of Production Example 31.

$^1$H-NMR (DMSO-d$_6$), δ (ppm): 2.10(3H, s), 2.22(2H, t, J=7.3 Hz), 2.53(3H, d, J=4.8 Hz), 2.72–2.82(4H, m), 2.82–2.90(2H, m), 7.15(2H, d, J=8.4 Hz), 7.26(2H, d, J=8.4 Hz), 7.38(4H, s), 7.79(1H, d, J=4.5 Hz), 9.76(1H, s), 11.95 (1H, s).

MS: 389.2(M+H)$^+$, 411.2(M+Na)$^{+\,free}$

PRODUCTION EXAMPLE 122

Synthesis of 3-{2-(acetylamino)-4-[2-(4-{[amino(imino)methyl]amino}phenyl)ethyl]-1,3-thiazol-5-yl}propanamide hydrochloride Step 1

Di-tert-butyl {(Z)-[(4-{2-[2-(acetylamino)-5-(3-amino-3-oxopropyl)-1,3-thiazol-4-yl]ethyl}phenyl)amino]methylidene}biscarbamate was prepared from the compound of Step 4 of Production Example 120 in a similar manner according to Step 1 of Production Example 32.

$^1$H-NMR (CDCl$_3$), δ (ppm): 1.47(9H, s), 1.53(9H, s), 1.57–1.67(2H, m), 2.24(3H, s), 2.65–2.76(2H, m), 2.76–2.87(2H, m), 2.87–2.99(2H, m), 5.37(1H, s), 6.14(1H, s), 6.90(2H, d, J=8.4 Hz), 7.28(2H, d, J=8.4 Hz), 8.88–9.28 (1H, brs), 10.12(1H, s), 11.58(1H, s).

MS: 575.0(M+H)$^+$, 597.3(M+Na)$^+$

Step 2

The title compound was prepared from the compound of Step 1 in a similar manner according to Step 4 of Production Example 31.

$^1$H-NMR (DMSO-d$_6$), δ (ppm): 2.10(3H, s), 2.23(2H, t, J=7.3 Hz), 2.71–2.83(4H, m), 2.83–2.91(2H, m), 6.81(1H, s), 7.14(2H, d, J=8.4 Hz), 7.26(2H, d, J=8.4 Hz), 7.31(1H, s), 7.35(4H, s), 9.70(1H, s), 11.94(1H, s).

MS: 375.2(M+H)$^+$, 397.0(M+Na)$^{+\,free}$

PRODUCTION EXAMPLE 123

Synthesis of 1-({2-(acetylamino)-4-[2-(4-{[amino(imino)methyl]amino}phenyl)ethyl]-1,3-thiazol-5-yl}methyl)-N,N-dimethyl-4-piperidinecarboxamide dihydrochloride Step 1

1-[(2-(Acetylamino)-4-{2-[4-({(Z)-[(tert-butoxycarbonyl)amino][(tert-butoxycarbonyl)imino]methyl}amino)phenyl]ethyl}-1,3-thiazol-5-yl)methyl]-4-piperidinecarboxylic acid was prepared from ethyl 1-[(2-(acetylamino)-4-{2-[4-({(Z)-[(tert-butoxycarbonyl)amino][(tert-butoxycarbonyl)imino]methyl}amino)phenyl]ethyl}-1,3-thiazol-5-yl)methyl]-4-piperidinecarboxylate in a similar manner according to Step 1 of Production Example 42.

$^1$H-NMR (CDCl$_3$), δ (ppm): 1.49(9H, s), 1.51(9H, s), 1.76–2.49(10H, m), 2.69–3.00(6H, m), 3.71(2H, s), 7.04 (2H, d, J=8.5 Hz), 7.42(2H, d, J=8.5 Hz), 10.23(1H, s), 11.13–12.07(1H, brs).

MS: 645.3(M+H)$^+$, 667.2(M+Na)$^+$

Step 2

Di-tert-butyl {(Z)-[(4-{2-[2-(acetylamino)-5-({4-[(dimethylamino)carbonyl]-1-piperidinyl}methyl)-1,3-thiazol-4-yl]ethyl}phenyl)amino]methylidene}biscarbamate was prepared from the compound of Step 1 in a similar manner according to Step 1 of Production Example 32.

$^1$H-NMR (CDCl$_3$), δ (ppm): 1.50(9H, s), 1.54(9H, s), 1.75–1.89(2H, m), 1.92–2.03(2H, m), 2.22(3H, s), 2.37–2.49(1H, m), 2.80–2.95(9H, m), 3.02(3H, s), 3.43(2H, s), 7.08(2H, d, J=8.4 Hz), 7.46(2H, d, J=8.4 Hz), 8.61–9.19 (1H, brs), 10.24(1H, s), 11.63(1H, s).

MS: 672.2(M+H)$^+$, 694.3(M+Na)$^+$

Step 3

The title compound was prepared from the compound of Step 2 in a similar manner according to Step 4 of Production Example 31.

$^1$H-NMR (DMSO-d$_6$), δ (ppm): 1.71–2.01(4H, m), 2.16 (3H, s), 2.76–2.87(4H, m), 2.87–3.1(9H, m), 3.3–3.4(2H, m), 4.32–4.45(2H, m), 7.15(2H, d, J=4.2 Hz), 7.31(2H, d, J=4.2 Hz), 7.41(4H, s), 9.83–9.93(1H, m), 9.99–10.19(1H, m), 12.32–12.37(1H, m).

MS: 472.3(M+H)$^+$, 494.0(M+Na)$^{+\,free}$

PRODUCTION EXAMPLE 124

Synthesis of 1-({2-(acetylamino)-4-[2-(4-{[amino(imino)methyl]amino}phenyl)ethyl]-1,3-thiazol-5-yl}methyl)-N-methyl-4-piperidinecarboxamide dihydrochloride Step 1

Di-tert-butyl {(Z)-[(4-{2-[2-(acetylamino)-5-({4-[(methylamino)carbonyl]-1-piperidinyl}methyl)-1,3-thiazol-4-yl]ethyl}phenyl)amino]methylidene}biscarbamate was prepared from the compound of Step 1 of Production Example 123 in a similar manner according to Step 1 of Production Example 32.

$^1$H-NMR (CDCl$_3$), δ (ppm): 1.5(9H, s), 1.54(9H, s), 1.65–1.74(2H, m), 1.75–1.84(2H, m), 1.87–1.98(2H, m), 2–2.11(1H, m), 2.22(3H, s), 2.8(3H, d, J=4.8 Hz), 2.82–2.91 (6H, m), 3.39(2H, s), 5.5(1H, d, J=4.4 Hz), 7.07(2H, d, J=8.4 Hz), 7.45(2H, d, J=8.4 Hz), 8.72–8.99(1H, brs), 10.23(1H, s), 11.62(1H, s).

MS: 658.3(M+H)$^+$, 680.3(M+Na)$^+$

Step 2

The title compound was prepared from the compound of Step 1 in a similar manner according to Step 4 of Production Example 31.

$^1$H-NMR (DMSO-d$_6$), δ (ppm): 1.71–2.04(4H, m), 2.16 (3H, s), 2.25–2.37(1H, m), 2.54–2.61(3H, m), 2.82–2.94 (2H, m), 2.96(4H, s), 3.27–3.37(2H, m), 4.31–4.44(2H, m), 7.15(2H, d, J=8.4 Hz), 7.30(2H, d, J=8.4 Hz), 7.41(4H, s), 7.89–8.00(1H, m), 9.83–10.16(2H, m).

MS: 458.2(M+H)$^+$, 480.0(M+Na)$^+$ free

PRODUCTION EXAMPLE 125

Synthesis of 1-({2-(acetylamino)-4-[2-(4-{[amino(imino)methyl]amino}phenyl)ethyl]-1,3-thiazol-5-yl}methyl)-4-piperidinecarboxamide dihydrochloride Step 1

Di-tert-butyl [(Z)-({4-[2-(2-(acetylamino)-5-{[4-(aminocarbonyl)-1-piperidinyl]methyl}-1,3-thiazol-4-yl)ethyl]phenyl}amino)methylidene]biscarbamate was prepared from the compound of Step 1 of Production Example 123 in a similar manner according to Step 1 of Production Example 32.

$^1$H-NMR (CDCl$_3$), δ (ppm): 1.50(9H, s), 1.53(9H, s), 1.66–1.75 (2H, m), 1.78–1.87(2H, m), 1.88–1.99(2H, m), 2.07–2.17(1H, m), 2.23(3H, s), 2.77–2.92(6H, m), 3.39(2H, s), 5.5(2H, s), 7.06(2H, d, J=8.4 Hz), 7.45(2H, d, J=8.4 Hz), 8.94–9.25(1H, brs), 10.23(1H, s), 11.61(1H, s).

MS: 644.2(M+H)$^+$, 666.3(M+Na)$^+$

Step 2

The title compound was prepared from the compound of Step 1 in a similar manner according to Step 4 of Production Example 31.

$^1$H-NMR (DMSO-d$_6$), δ (ppm): 1.68–2.08(4H, m), 2.16 (3H, s), 2.25–2.36(1H, m), 2.82–3.09(6H, m), 3.27–3.44 (2H, m), 4.30–4.45 (2H, m), 6.87–7.06(1H, m), 7.15(2H, d, J=8.4 Hz), 7.30(2H, d, J=8.3 Hz), 7.36–7.52(5H, m), 9.87–10.25(2H, m), 12.30–12.37(1H, m).

MS: 444.2(M+H)$^+$, 466.2(M+Na)$^{+\ free}$

PRODUCTION EXAMPLE 126

Synthesis of (3R)-1-({2-(acetylamino)-4-[2-(4-{[amino(imino)methyl]amino}phenyl)ethyl]-1,3-thiazol-5-yl}methyl)-N,N-dimethyl-3-piperidinecarboxamide dihydrochloride Step 1

Ethyl (3R)-1-({2-(acetylamino)-4-[(Z)-2-(4-nitrophenyl)vinyl]-1,3-thiazol-5-yl}methyl)-3-piperidinecarboxylate was prepared from N-{4-[(Z)-2-(4-nitrophenyl)vinyl]-1,3-thiazol-2-yl}acetamide in a similar manner according to Step 1 of Production Example 67.

MS: 459.20(M+H)$^+$

Step 2

Ethyl (3R)-1-[(2-(acetylamino)-4-{2-[4-({(Z)-[(tert-butoxycarbonyl)amino][(tert-butoxycarbonyl)imino]methyl}amino)phenyl]ethyl}-1,3-thiazol-5-yl)methyl]-3-piperidinecarboxylate was prepared from the compound of Step 1 in a similar manner according to Step 2 of Production Example 68.

$^1$H-NMR (CDCl$_3$), δ (ppm): 1.22(3H, t, J=7.2 Hz), 1.31–1.78(21H, m), 1.79–2.06(2H, m), 2.07–2.18(1H, m), 2.22(3H, s), 2.43–2.62(1H, m), 2.62–2.75(1H, m), 2.84(4H, s), 2.88–3.01(1H, m), 3.42(2H, s), 4.11(2H, q, J=7.1 Hz), 7.08(2H, d, J=8.4 Hz), 7.46(2H, d, J=8.4 Hz), 8.76–9.16(1H, brs), 10.24(1H, s), 11.64(1H, s).

MS: 673.3(M+H)$^+$, 695.2(M+Na)$^+$

Step 3

(3R)-1-[(2-(Acetylamino)-4-{2-[4-({(Z)-[(tert-butoxycarbonyl)amino][(tert-butoxycarbonyl)imino]methyl}amino)phenyl]ethyl}-1,3-thiazol-5-yl)methyl]-3-piperidinecarboxylic acid was prepared from the compound of Step 2 in a similar manner according to Step 1 of Production Example 42.

MS: 645.37(M+H)$^+$

Step 4

Di-tert-butyl {(Z)-[(4-{2-[2-(acetylamino)-5-({(3R)-3-[(dimethylamino)carbonyl]-1-piperidinyl}methyl)-1,3-thiazol-4-yl]ethyl}phenyl)amino]methylidene}biscarbamate was prepared from the compound of Step 3 in a similar manner according to Step 1 of Production Example 32.

$^1$H-NMR (CDCl$_3$), δ (ppm): 1.39–1.57(20H, m), 1.66–1.73(1H, m), 1.74–1.83(1H, m), 1.87–1.98(1H, m), 2.08–2.19(1H, m), 2.22(3H, s), 2.72–2.94(10H, m), 3.02 (3H, s), 3.41(2H, s), 7.08(2H, d, J=8.4 Hz), 7.46(2H, d, J=8.4 Hz), 8.70–9.02(1H, brs), 10.24(1H, s), 11.63(1H, s).

MS: 672.41(M+H)$^+$

Step 5

The title compound was prepared from the compound of Step 4 in a similar manner according to Step 4 of Production Example 31.

$^1$H-NMR (DMSO-d$_6$), δ (ppm): 1.29–1.94(4H, m), 2.16 (3H, s), 2.77–3.33(15H, m), 4.27–4.46(2H, m), 7.16(2H, d, J=8.3 Hz), 7.27–7.35(2H, m), 7.36–7.48(4H, m), 9.8–9.98 (1H, m), 10.22–10.51 (1H, brs), 12.29–12.36(1H, m).

MS: 472.3(M+H)$^+$, 494.2(M+Na)$^{+\ free}$

PRODUCTION EXAMPLE 127

Synthesis of (3R)-1-({2-(acetylamino)-4-[2-(4-{[amino(imino)methyl]amino}phenyl)ethyl]-1,3-thiazol-5-yl}methyl)-N-methyl-3-piperidinecarboxamide dihydrochloride

Step 1

Di-tert-butyl {(Z)-[(4-{2-[2-(acetylamino)-5-({(3R)-3-[(methylamino)carbonyl]-1-piperidinyl}methyl)-1,3-thiazol-4-yl]ethyl}phenyl)amino]methylidene}biscarbamate was prepared from the compound of Step 3 of Production Example 126 in a similar manner according to Step 1 of Production Example 32.

$^1$H-NMR (CDCl$_3$), δ (ppm): 1.50(9H, s), 1.52–1.72(12H, m), 1.84–1.98(1H, m), 2.01–2.14(1H, m), 2.14–2.23(1H, m), 2.24(3H, s), 2.43–2.51(1H, m), 2.64–2.76(1H, m), 2.76–2.94(8H, m), 3.32(1H, d, J=14 Hz), 3.41(1H, d, J=14 Hz), 7.06(2H, d, J=8.4 Hz), 7.45(2H, d, J=8.4 Hz), 7.53(1H, brs), 8.84(1H, brs), 10.24(1H, s), 11.63(1H, s).

MS: 658.39(M+H)$^+$

Step 2

The title compound was prepared from the compound of Step 1 in a similar manner according to Step 4 of Production Example 31.

$^1$H-NMR (DMSO-d$_6$), δ (ppm): 1.31–1.94(4H, m), 2.16 (3H, s), 2.54–3.36(12H, m), 4.27–4.48(2H, m), 7.12–7.19 (2H, m), 7.25–7.35(2H, m), 7.35(4H, brs), 8.05–8.37(1H, m), 9.79–9.92(1H, m), 10.16–10.42(1H, brs), 12.29–12.37 (1H, m).

MS: 458.2(M+H)$^+$, 480.1(M+Na)$^{+\ free}$

PRODUCTION EXAMPLE 128

Synthesis of (3S)-1-({2-(acetylamino)-4-[2-(4-{[amino(imino)methyl]amino}phenyl)ethyl]-1,3-thiazol-5-yl}methyl)-N,N-dimethyl-3-piperidinecarboxamide dihydrochloride

Step 1

Ethyl (3S)-1-({2-(acetylamino)-4-[(Z)-2-(4-nitrophenyl)vinyl]-1,3-thiazol-5-yl}methyl)-3-piperidinecarboxylate was prepared from N-{4-[(Z)-2-(4-nitrophenyl)vinyl]-1,3-thiazol-2-yl}acetamide in a similar manner according to Step 1 of Production Example 67.

MS: 459.21(M+H)$^+$

Step 2

Ethyl (3S)-1-[(2-(acetylamino)-4-{2-[4-({(Z)-[(tert-butoxycarbonyl)amino][(tert-butoxycarbonyl)imino]methyl}amino)phenyl]ethyl}-1,3-thiazol-5-yl)methyl]-3-piperidinecarboxylate was prepared from the compound of Step 1 in a similar manner according to Step 2 of Production Example 68.

$^1$H-NMR (CDCl$_3$), δ (ppm): 1.22(3H, t, J=7.2 Hz), 1.3–1.79(21H, m), 1.8–2.06(2H, m), 2.08–2.18(1H, m), 2.22 (3H, s), 2.43–2.62(1H, m), 2.62–2.75(1H, m), 2.84(4H, s), 2.88–3.01(1H, m), 3.42(2H, s), 4.11(2H, q, J=7.1 Hz), 7.08(2H, d, J=8.4 Hz), 7.46(2H, d, J=8.4 Hz), 8.71–9.23(1H, brs), 10.24(1H, s), 11.64(1H, s).

MS: 673.3(M+H)$^+$, 695.2(M+Na)$^+$

Step 3

(3S)-1-[(2-(Acetylamino)-4-{2-[4-({(Z)-[(tert-butoxycarbonyl)amino][(tert-butoxycarbonyl)imino]methyl}amino)phenyl]ethyl}-1,3-thiazol-5-yl)methyl]-3-piperidinecarboxylic acid was prepared from the compound of Step 2 in a similar manner according to Step 1 of Production Example 42.

MS: 645.36(M+H)$^+$

Step 4

Di-tert-butyl {(Z)-[(4-{2-[2-(acetylamino)-5-({(3S)-3-[(dimethylamino)carbonyl]-1-piperidinyl}methyl)-1,3-thiazol-4-yl]ethyl}phenyl)amino]methylidene}biscarbamate was prepared from the compound of Step 3 in a similar manner according to Step 1 of Production Example 32.

$^1$H-NMR (CDCl$_3$), δ (ppm): 1.4–1.64(20H, m), 1.65–1.73 (1H, m), 1.73–1.82(1H, m), 1.86–1.97(1H, m), 2.08–2.18 (1H, m), 2.22(3H, s), 2.7–2.93(10H, m), 3.02(3H, s), 3.41 (2H, s), 7.08(2H, d, J=8.4 Hz), 7.46(2H, d, J=8.3 Hz), 8.61–8.99(1H, brs), 10.24(1H, s), 11.63(1H, s).

MS: 672.39(M+H)$^+$

Step 5

The title compound was prepared from the compound of Step 4 in a similar manner according to Step 4 of Production Example 31.

$^1$H-NMR (DMSO-d$_6$), δ (ppm): 1.29–1.93(4H, m), 2.16 (3H, s), 2.77–3.35(15H, m), 4.27–4.45(2H, m), 7.16(2H, d, J=8.4 Hz), 7.28–7.35(2H, m), 7.35–7.47(4H, m), 9.8–9.96 (1H, m), 10.21–10.46(1H, brs), 12.29–12.36(1H, m).

MS: 472.3(M+H)$^+$, 494.2(M+Na)$^{+\ free}$

PRODUCTION EXAMPLE 129

Synthesis of (3S)-1-({2-(acetylamino)-4-[2-(4-{[amino(imino)methyl]amino}phenyl)ethyl]-1,3-thiazol-5-yl}methyl)-N-methyl-3-piperidinecarboxamide dihydrochloride

Step 1

Di-tert-butyl {(Z)-[(4-{2-[2-(acetylamino)-5-({(3S)-3-[(methylamino)carbonyl]-1-piperidinyl}methyl)-1,3-thiazol-4-yl]ethyl}phenyl)amino]methylidene}biscarbamate was prepared from the compound of Step 3 of Production Example 128 in a similar manner according to Step 1 of Production Example 32.

$^1$H-NMR (CDCl$_3$), δ (ppm): 1.46–1.72(21H, m), 1.84–1.97(1H, m), 1.99–2.14(1H, m), 2.15–2.22(1H, m), 2.24(3H, s), 2.43–2.51(1H, m), 2.65–2.76(1H, m), 2.76–2.91(8H, m), 3.32(1H, d, J=14 Hz), 3.41(1H, d, J=14 Hz), 7.06(2H, d, J=8.4 Hz), 7.45(2H, d, J=8.4 Hz), 7.54(1H, brs), 8.84–9.02(1H, brs), 10.24(1H, s), 11.63(1H, s).

MS: 658.40(M+H)$^+$

Step 2

The title compound was prepared from the compound of Step 1 in a similar manner according to Step 4 of Production Example 31.

$^1$H-NMR (DMSO-d$_6$), δ (ppm): 1.31–1.94(4H, m), 2.16 (3H, s), 2.53–3.36(12H, m), 4.24–4.46(2H, m), 7.12–7.19 (2H, m), 7.25–7.35(2H, m), 7.36(4H, brs), 8.06–8.37(1H, m), 9.83–9.99(1H, m), 10.28–10.54(1H, brs), 12.33(1H, s).

MS: 458.2(M+H)$^+$, 480.2(M+Na)$^{+\ free}$

PRODUCTION EXAMPLE 130

Synthesis of N-{4-[2-(2-amino-1H-benzimidazol-6-yl)ethyl]-5-[4-(methylsulfonyl)benzyl]-1,3-thiazol-2-yl}acetamide Step 1

N-{4-[2-(3,4-Dinitrophenyl)vinyl]-5-[4-(methylthio)benzyl]-1,3-thiazol-2-yl}acetamide was prepared from 2-(acetylamino)-5-[4-(methylthio)benzyl]-1,3-thiazole-4-carbaldehyde in a similar manner according to Step 5 of Production Example 45.

Z:E=3:1

$^1$H-NMR(CDCl$_3$), δ (ppm): 2.08(3H×¾, s), 2.12(3H×¼, s), 2.44(3H, s), 4.13(2H×¾, s), 4.32(2H×¼, s), 6.71(1H×¾, d, J=12.5 Hz), 6.97(1H×¾, d, J=12.3 Hz), 7.06–8.61(7H+2H×¼, m), 11.85(1H×¾, s), 12.18(1H×¼, s).

MS: 471.1(M+H)$^+$, 493.9(M+Na)$^+$

Step 2

N-{4-[2-(3,4-Diaminophenyl)ethyl]-5-[4-(methylsulfonyl)benzyl]-1,3-thiazol-2-yl}acetamide was prepared from the compound of Step 1 in a similar manner according to Step 2 of Production Example 32 and Step 6 of Production Example 45.

$^1$H-NMR (CDCl$_3$), δ (ppm): 2.23(3H, s), 2.70–2.85(4H, m), 3.03(3H, s), 3.88(2H, s), 6.34(1H, d, J=1.8 Hz), 6.39 (1H, dd, J=1.8, 7.8 Hz), 6.56(1H, d, J=7.7 Hz), 7.14(2H, d, J=8.3 Hz), 7.79(2H, d, J=8.4 Hz), 8.30–9.45(1H, brs).

MS: 445.0(M+H)$^+$, 467.0(M+Na)$^+$

Step 3

To a suspension of N-{4-[2-(3,4-diaminophenyl)ethyl]-5-[4-(methylsulfonyl)benzyl]-1,3-thiazol-2-yl}acetamide (70.8 mg) in MeOH (0.7 ml) was added cyanogen bromide (25.3 mg), then the mixture was stirred for 14 h at 20° C. To the reaction mixture was added 1N—NaOH (0.239 ml) and the mixture was concentrated in vacuo. To the residue was added CHCl$_3$: MeOH=10:1 (10 ml), and an insoluble material was removed by filtration. The filtrate was purified by flash column chromatography over NH silica gel with CHCl$_3$/MeOH (100:1→10:1) as an eluent to give colorless oil. The oil was solidified with CH$_2$Cl$_2$: Et$_2$O=2:1 to give N-{4-[2-(2-amino-1H-benzimidazol-6-yl)ethyl]-5-[4-(methylsulfonyl)benzyl]-1,3-thiazol-2-yl}acetamide as a white solid.

$^1$H-NMR (CDCl$_3$), δ (ppm): 2.09(3H, s), 2.85(4H, s), 3.16(3H, s), 3.97(2H, s), 6.01(2H, s), 6.55–6.77(1H, m), 6.78–6.90(1H, m), 6.96(1H, d, J=7.8 Hz), 7.10–7.30(2H, brs), 7.72(2H, d, J=8.1 Hz), 10.55(1H, d, J=10.5 Hz), 11.50–12.20(1H, brs).

MS: 470.2(M+H)$^+$, 492.1(M+Na)$^+$

PRODUCTION EXAMPLE 131

Synthesis of N-{4-[2-(2-amino-1H-benzimidazol-6-yl)ethyl]-1,3-thiazol-2-yl}acetamide Step 1

N-{4-[2-(3,4-Dinitrophenyl)vinyl]-1,3-thiazol-2-yl}acetamide was prepared from 2-(acetylamino)-1,3-thiazole-4-carbaldehyde in a similar manner according to Step 5 of Production Example 1.

Z:E=8:1

$^1$H-NMR (DMSO-d$_6$), δ (ppm): 2.13(3H×⁸⁄₉, s), 2.17(3H×⅑, s), 6.64(1H×⁸⁄₉, d, J=12.6 Hz), 6.80(1H×⁸⁄₉, d, J=12.6 Hz), 7.29(1H×⅑, d, J=15.7 Hz), 7.33(1H×⁸⁄₉, s), 7.39(1H×⅑, s), 7.63(1H×⅑, d, J=15.7 Hz), 8.00–8.50(3H, m), 11.97 (1H×⁸⁄₉, s), 12.30(1H×⅑, s)

MS: 335.0(M+H)$^+$, 357.1(M+Na)$^+$

Step 2

N-{4-[2-(3,4-Diaminophenyl)ethyl]-1,3-thiazol-2-yl}acetamide was prepared from the compound of Step 1 in a similar manner according to Step 6 of Production Example 1.

$^1$H-NMR (CDCl$_3$), δ (ppm): 2.22(3H, s), 2.58–3.17(8H, m), 6.46–6.56(3H, m), 6.62(1H, d, J=8.3 Hz), 8.84–10.42 (1H, brs).

MS: 277.1(M+H)$^+$, 299.2(M+Na)$^+$

Step 3

The title compound was prepared from the compound of Step 2 in a similar manner according to Step 3 of Production Example 130.

$^1$H-NMR (CDCl$_3$), δ (ppm): 2.11(3H, s), 2.79–2.97(4H, m), 6(2H, s), 6.59–6.8(2H, m), 6.91(1H, s), 6.97(1H, d, J=7.9 Hz), 10.34–10.73(1H, brs), 11.94–12.22(1H, brs).

MS: 302.2(M+H)$^+$, 324.1(M+Na)$^+$

PRODUCTION EXAMPLE 132

Synthesis of N-({2-(acetylamino)-4-[2-(4-{[amino(imino)methyl]amino}phenyl)ethyl]-1,3-thiazol-5-yl}methyl)-N-methylacetamide hydrochloride Step 1

N-{5-[(Methylamino)methyl]-4-[(Z)-2-(4-nitrophenyl)vinyl]-1,3-thiazol-2-yl}acetamide was prepared from N-{4-[(Z)-2-(4-nitrophenyl)vinyl]-1,3-thiazol-2-yl}acetamide in a similar manner according to Step 1 of Production Example 67.

$^1$H-NMR (CDCl$_3$), δ (ppm): 2.05(3H, s), 2.46(3H, s), 3.75(2H, s), 6.67(2H, s), 7.41(2H, d, J=8.9 Hz), 8.01(2H, d, J=8.8 Hz), 9.7–11.69(1H, brs).

MS: 333.1(M+H) t, 355.1(M+Na)$^+$

Step 2

To a suspension of N-{5-[(methylamino)methyl]-4-[(Z)-2-(4-nitrophenyl)vinyl]-1,3-thiazol-2-yl}acetamide (46.8 mg) in dichloromethane (0.5 ml) were added N,N-diisopropylehtylamine (27 μl) and acetyl chloride (10 μl), and the mixture was stirred for 2 h at 20° C. To the reaction mixture were added dichloromethane (5 ml), N,N-diisopropylehtylamine (27 μl) and acetyl chloride (10 μl), and the mixture was stirred for 5 min. at 20° C., then washed with saturated sodium hydrogen carbonate aqueous solution (5 ml) and brine (5 ml), dried over MgSO$_4$, filtered and evaporated to give a yellow solid (67.8 mg). The crude compound was purified by preparative silica gel thin-layer chromatography with chloroform/methanol (20:1) as an eluent to give N-({2-(acetylamino)-4-[(Z)-2-(4-nitrophenyl)vinyl]-1,3-thiazol-5-yl}methyl)-N-methylacetamide as a yellow solid.

$^1$H-NMR (CDCl$_3$), δ (ppm): 2.12(3H×⅔, s), 2.13(3H×⅓, s), 2.14(3H×⅔, s), 2.24(3H×⅓, s), 3.02(3H×⅔, s), 3.05 (3H×⅓, s), 4.62(2H×⅔, s), 4.79(2H×⅓, s), 6.61(1H×⅓, d, J=12.6 Hz), 6.70(1H×⅔, d, J=12.6 Hz), 6.77(1H×⅓, d, J=12.6 Hz), 6.82(1H×⅔, d, J=12.6 Hz), 7.43(2H×⅔, d, J=8.8 Hz), 7.65(2H×⅓, d, J=8.8 Hz), 8.06(2H×⅔, d, J=8.8 Hz), 8.22(2H×⅓, d, J=8.8 Hz), 9.09–9.26(1H×⅓, brs), 9.26–9.51(1H×⅔, brs).

MS: 375.2(M+H)$^+$, 397.1(M+Na)$^+$

Step 3

N-({2-(Acetylamino)-4-[2-(4-aminophenyl)ethyl ]-1,3-thiazol-5-yl}methyl)-N-methylacetamide was prepared from the compound of Step 2 in a similar manner according to Step 6 of Production Example 45.

MS: 347.25(M+H)$^+$

Step 4

Di-tert-butyl [(Z)-({4-[2-(2-(acetylamino)-5-{[acetyl(methyl)amino]methyl}-1,3-thiazol-4-yl)ethyl]phenyl}amino)methylidene]biscarbamate was prepared from the compound of Step 3 in a similar manner according to Step 3 of Production Example 31.

$^1$H-NMR (CDCl$_3$), δ (ppm): 1.49(9H, s), 1.53(9H, s), 2.06(3H×¾, s), 2.12(3H×¼, s), 2.23(3H, s), 2.77(3H×¼, s), 2.81(3H×¾, s), 2.90(4H, s), 4.20(2H×¼, s), 4.46(2H×¾, s), 7.01(2H×¼, d, J=8.6 Hz), 7.07(2H×¾, d, J=8.5 Hz), 7.43 (2H×¾, d, J=8.5 Hz), 7.46(2H×¼, d, J=8.0 Hz), 8.81–9.09 (1H, brs), 10.22(1H×¾, s), 10.25(1H×¼, s), 11.62(1H, s).

MS: 589.2(M+H)$^+$, 611.2(M+Na)$^+$

Step 5

The title compound was prepared from the compound of Step 4 in a similar manner according to Step 4 of Production Example 31.

$^1$H-NMR (DMSO-d$_6$), δ (ppm): 1.98(3H×¾, s), 2.02(3H×¼, s), 2.11(3H×¾, s), 2.12(3H×¼, s), 2.60(3H×¼, s), 2.82(3H×¾, s), 2.89(4H, s), 4.39(2H×¾, s), 4.45(2H×¼, s), 7.13(2H×¼, d, J=8.1 Hz), 7.14(2H×¾, d, J=8.4 Hz), 7.22 (2H×¼, d, J=8.4 Hz), 7.25(2H×¾, d, J=8.4 Hz), 7.31(4H, s), 9.61(1H, s), 12.03(1H×¾, s), 12.13(1H×¼, s).

MS: 389.19(M+H)$^{+\ free}$

PRODUCTION EXAMPLE 133

Synthesis of N-[4-(2-{4-[(2-aminoethyl)amino]phenyl}ethyl)-1,3-thiazol-2-yl]acetamide dihydrochloride Step 1

To a suspension of N-{4-[2-(4-aminophenyl)ethyl]-1,3-thiazol-2-yl}acetamide (100 mg) in toluene were added tert-butyl (2-bromoethyl)carbamate (87.5 mg) and N,N-diisopropylethylamine (52 µl), and the mixture was stirred at 80° C. for 24 h. The reaction mixture was allowed to cool to room temperature, water (10 ml) was added, and the organic layer was separated, washed with saturated aqueous NaCl, dried over MgSO$_4$, filtered, and concentrated in vacuo to give tert-butyl {2-[(4-{2-[2-(acetylamino)-1,3-thiazol-4-yl]ethyl}phenyl)amino]ethyl}carbamate as a pale brown amorphous.

$^1$H-NMR (CDCl$_3$), δ (ppm): 1.45(9H, s), 2.23(3H, s), 2.86(4H, s), 3.15–3.28(2H, m), 3.15–3.47(2H, m), 4.64–5.02(1H, brs), 6.49(1H, s), 6.52(2H, d, J=8.0 Hz), 6.95(2H, d, J=8.0 Hz), 9.22–10.10(1H, brs).

MS: 405.2(M+H)$^+$, 427.3(M+Na)$^+$

Step 2

The title compound was prepared from the compound of Step 2 in a similar manner according to Step 2 of Production Example 10.

$^1$H-NMR (DMSO-d$_6$), δ (ppm): 2.11(3H, s), 2.81(4H, s), 2.92–3.05(2H, m), 3.29(2H, t, J=6.2 Hz), 6.67(2H, d, J=7.7 Hz), 7.01(2H, d, J=8.1 Hz), 7.87–8.24(3H, brs), 12.08(1H, s).

MS: 305.2(M+H)$^+$, 327.2(M+Na)$^+$

PRODUCTION EXAMPLE 134

Synthesis of N-{4-[3-(2-{[amino(imino)methyl]amino}ethyl)phenyl]-1,3-thiazol-2-yl}acetamide hydrochloride Step 1

To a suspension of lithium aluminium hydride in dry tetrahydrofuran (50 ml) was added (3-bromophenyl)acetic acid (10 g) in tetrahydrofuran (100 ml) under ice cooling. The mixture was refluxed for 2 hurs. After cooling, to the reaction mixture were added water and aqueous Rochelle salt.

The mixture was stirred for another 30 min. Aqueous layer was extracted with ethyl acetate. The organic layer was dried over anhydrous magnesium sulfate, and concentrated in vacuo to give 2-(3-bromophenyl)ethanol. This compound was used for the next reaction without further purification.

$^1$H-NMR (200 MHz, CDCl$_3$), δ (ppm): 1.66(1H, brs), 2.84(2H, dd, J=6.5, 14 Hz), 3.85(2H, dt, J=6.5, 2.6 Hz), 7.13–7.39(4H, m).

Step 2

To a solution of 2-(3-bromophenyl)ethanol (7 g) in N,N-dimethylformamide (100 ml) were added tert-butyldimethylsilyl chloride (5.77 g) and imidazole (2.84 g) at 25° C. The mixture was stirred at 25° C. for 12 h. The reaction mixture was poured into water (500 ml) and extracted with ethyl acetate (100 ml×2). The combined organic layer was dried over magnesium sulfate and concentrated in vacuo. The residue was purified by silica gel column chromatography with mixed solvent of n-hexane and ethyl acetate to give [2-(3-bromophenyl)ethoxy](tert-butyl)dimethylsilane as colorless oil.

$^1$H-NMR (200 MHz, CDCl$_3$), δ (ppm): 0.01(6H, s), 0.88(9H, s), 2.81(2H, dt, J=6.5, 9.5 Hz), 3.81(2H, dt, J=3.0, 6.5 Hz), 7.14–7.39 (5H, brs).

Step 3

To a solution of 1.6 g of [2-(3-bromophenyl)ethoxy](tert-butyl)dimethylsilane in tetrahydrofuran (20 ml) was added n-BuLi in hexane (1.57M, 3.88 ml) at −70° C., then the reaction mixture was stirred at same temperature for 30 min. To the solution was added dimethylacetamide (1.42 ml) drop wise at the same temperature. The mixture was stirred for another 1 hour. To the reaction mixture were added water and 8 ml of 1N HCl under ice-cooling. The mixture was stirred for 1 hour, then extracted with ethyl acetate. The organic layer was washed with brine, dried over magnesium sulfate and concentrated in vacuo. The residue was purified by silica gel column chromatography with n-hexane and ethyl acetate (20/1–10/1) as an eluent to give 1-[3-(2-{[tert-butyl(dimethyl)silyl]oxy}ethyl)phenyl]ethanone (350 mg) as colorless oil.

$^1$H-NMR (200 MHz, CDCl$_3$), δ (ppm): 0.03(6H, s), 0.85(9H, s), 2.61(3H, s), 2.87(2H, t, J=6.7 Hz), 3.82(2H, t, J=6.7 Hz), 7.20–7.24(1H, m), 7.35–7.44(2H, m), 7.77–7.82 (2H, m).

MS: 279(M+H)$^+$

Step 4

To a solution of 1-[3-(2-{[tert-butyl(dimethyl)silyl]oxy}ethyl)phenyl]ethanone (755 mg) in tetrahydrofuran (4 ml) was added bromine (168 ml) drop wise at 0° C. The mixture was stirred at 25° C. for 1 h. To the reaction mixture was added aq. saturated NaHCO$_3$, and the mixture was extracted with ethyl acetate. The organic layer was washed with brine, dried over magnesium sulfate and concentrated under reduced pressure to give crude of 2-bromo-1-[3-(2-hydroxyethyl)phenyl]ethanone as colorless oil. This compound was used for the next reaction without further purification.

Step 5

To a solution of 2-bromo-1-[3-(2-hydroxyethyl)phenyl]ethanone (crude, 658 mg) in tetrahydrofuran (15 ml) was added 1-acetyl-2-thiourea (320 mg) at 25° C. The mixture was stirred at 60° C. for 2 h. The residual colorless crystals were collected by filtration. The crystals were washed with isopropyl ether, dried under reduced pressure to give N-{4-[3-(2-hydroxyethyl)phenyl]-1,3-thiazol-2-yl}acetamide (514 mg) as a colorless crystal.

$^1$H-NMR (200 MHz, DMSO-d$_6$), δ (ppm): 2.16(3H, s), 2.76(2H, t, J=6.9 Hz), 3.63(2H, t, J=6.9 Hz), 4.89(1H, brs), 7.16(1H, d, J=7.7 Hz), 7.32(1H, dd, J=7.7, 7.6 Hz), 7.56(1H, s), 7.70(2H, d, J=7.6 Hz), 7.76(1H, s), 12.24(1H, s).

MS: 263(M+H)$^+$

Step 6

To a suspension of N-{4-[3-(2-hydroxyethyl)phenyl]-1,3-thiazol-2-yl}acetamide (300 mg) in CH$_2$Cl$_2$ (10 ml) were added methansulfonyl chloride (106 μl) and triethylamine (207 μl) at 5° C. The mixture was stirred at 25° C. for 2 h. The reaction mixture was poured into water and extracted with dichloromethane. The organic layer was washed with brine, dried over magnesium sulfate and concentrated under reduced pressure. Resulting residue was purified by silica gel column chromatography with n-hexane and ethyl acetate (1:1) as an eluent to give 2-{3-[2-(acetylamino)-1,3-thiazol-4-yl]phenyl}ethyl methanesulfonate (388 mg) as a colorless solid.

$^1$H-NMR (200 MHz, DMSO-d$_6$), δ (ppm): 2.16(3H, s), 3.04(2H, t, J=6.9 Hz), 3.12(3H, s), 4.45(2H, t, J=6.9 Hz), 7.23–7.42(2H, m), 7.60(1H, s), 7.75–7.81(2H, m), 12.26(1H, s).

MS: 341(M+H)$^+$

Step 7

To a solution of 2-{3-[2-(acetylamino)-1,3-thiazol-4-yl]phenyl}ethyl methanesulfonate (388 mg) in N,N-dimethylformamide (5-ml) were added di-tert-butyliminodicarboxylate (322 mg) and K$_2$CO$_3$ (236 mg) at 25° C. The mixture was stirred at 80° C. for 2 hours. The reaction mixture was poured into water and extracted with ethyl acetate. The organic layer was washed with brine, dried over magnesium sulfate and concentrated under reduced pressure. Resulting colorless oil containing N-{4-(3-[2-{di-(tert-butoxycarbonyl)amino}ethyl]phenyl)-1,3-thiazol-2-yl}acetamide was used for the next reaction without further purification.

Step 8

N-{4-[3-(2-Aminoethyl)phenyl]-1,3-thiazol-2-yl}acetamide was prepared from the compound of Step 7 in a similar manner according to Step 2 of Production Example 31.

$^1$H-NMR (200 MHz, DMSO-d$_6$), δ (ppm): 2.16(1H, s), 2.74(2H, dd, J=6.8, 6.2 Hz), 2.88(2H, dd, J=7, 7.8 Hz), 7.17(1H, d, J=7.7 Hz), 7.35(1H, dd, J=7.7, 8 Hz), 7.58(1H, s), 7.73(1H, d, J=8 Hz), 7.74(1H, s).

MS: 262(M+H)$^+$

Step 9

Di-tert-butyl {(Z)-[(2-{3-[2-(acetylamino)-1,3-thiazol-4-yl]phenyl}ethyl)amino]methylidene}biscarbamate was prepared from the compound of Step 8 in a similar manner according to Step 5 of Production Example 18.

$^1$H-NMR (200 MHz, CDCl$_3$), δ (ppm): 1.45(9H, s), 1.50(3H, s), 2.27(3H, s), 2.92(2H, t, J=7.5 Hz), 3.71(2H, dt, J=7.5, 7.2 Hz), 7.11–7.41(4H, d), 7.65–7.78(1H, m).

MS: 504(M+H)$^+$

Step 10

The title compound was prepared from the compound of Step 9 in a similar manner according to Step 4 of Production Example 31.

$^1$H-NMR (200 MHz, CDCl$_3$), δ (ppm): 2.16(3H, s), 2.83(2H, t, J=6.9 Hz), 3.41(2H, m), 7.23(1H, d, J=7.7 Hz), 7.38(1H, dd, J=7.7, 7.8 Hz), 7.52(1H, t, J=5.5 Hz), 7.59(1H, s), 7.75(1H, d, J=8.1 Hz), 7.79(1H, s), 12.23(1H, s).

MS: 304(M+H)$^{+\ free}$

PRODUCTION EXAMPLE 135

Synthesis of N-(4-[2-(4-{[amino(imino)methyl]amino}phenyl)ethyl]-5-{2-[4-(methylsulfonyl)phenyl]ethyl}-1,3-thiazol-2-yl)acetamide hydrochloride Step 1 tert-Butyl N-{4-[2-(2-(acetylamino)-5-{(E)-2-[4-(methylsulfonyl)phenyl]vinyl}-1,3-thiazol-4-yl)ethyl]phenyl}carbamate was prepared from 2-(acetylamino)-4-{2-[4-(tert-butoxycarbonylamino)phenyl]ethyl}-1,3-thiazole-5-carbaldehyde in a similar manner according to Step 5 of Production Example 45.

MS: 542(M+H)$^{+\ free}$

Step 2 tert-Butyl N-{4-[2-(2-(acetylamino)-5-{2-[4-(methylsulfonyl)phenyl]ethyl}-1,3-thiazol-4-yl)ethyl]phenyl}carbamate was prepared from the compound of Step 1 in a similar manner according to Step 6 of Production Example 45.

MS: 544(M+H)$^+$

Step 3

N-(4-[2-(4-Aminophenyl)ethyl]-5-{2-[4-(methylsulfonyl)phenyl]ethyl}-1,3-thiazol-2-yl)acetamide was prepared from the compound of Step 2 in a similar manner according to Step 2 of Production Example 31.

$^1$H-NMR (200 MHz, CDCl$_3$), δ (ppm): 2.23(3H, s), 2.61(4H, s), 2.78(4H, s), 2.98(3H, s), 3.55(2H, brs), 6.57(2H, d, J=8.5 Hz), 6.81(2H, d, J=8.5 Hz), 7.25(2H, d, J=8.5 Hz), 7.82(2H, d, J=8.5 Hz), 8.80(1H, s).

MS: 444(M+H)$^+$

Step 4

Di-tert-butyl [(E)-({4-[2-(2-(acetylamino)-5-{2-[4-(methylsulfonyl)phenyl]ethyl}-1,3-thiazol-4-yl)ethyl]phenyl}amino)methylidene]biscarbamate was prepared from the compound of Step 3 in a similar manner according to Step 5 of Production Example 18.

$^1$H-NMR (200 MHz, CDCl$_3$), δ (ppm): 1.49(9H, s), 1.53(9H, s), 2.22(3H, s), 2.59–2.73(4H, m), 2.84(4H, s), 2.98(3H, s), 6.99(2H, d, J=8.4 Hz), 7.28(2H, d, J=8.4 Hz), 7.44(2H, d, J=8.4 Hz), 7.83(2H, d, J=8.4 Hz), 8.99(1H, bra), 10.23(1H, s), 11.62(1H, s).

MS: 686(M+H)$^+$

Step 5

The title compound was prepared from the compound of Step 4 in a similar manner according to Step 4 of Production Example 31.

$^1$H-NMR (200 MHz, DMSO-d$_6$), δ (ppm): 2.16(3H, s), 2.67(4H, brs), 2.82–2.94(4H, m), 3.14(3H, s), 7.12(2H, d, J=8.4 Hz), 7.20(2H, d, J=8.4 Hz), 7.43(2H, d, J=8.4 Hz), 7.82(2H, d, J=8.4 Hz), 9.87(1H, s), 11.97(1H, s).

MS: 486(M+H)$^+$

The compounds according to the present invention useful as VAP-1 inhibitors are listed in the following tables.

| No. | Structure |
|---|---|
| 1 | (Compound A) |
| 2 | 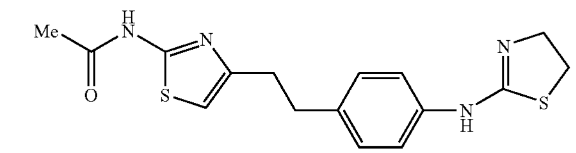 |
| 3 | 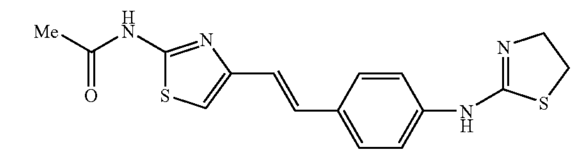 |
| 4 | (HI) |
| 5 | 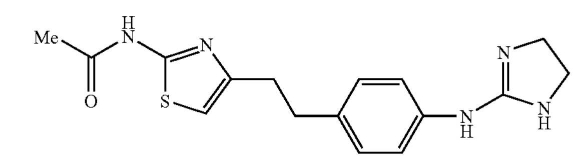 |
| 6 | 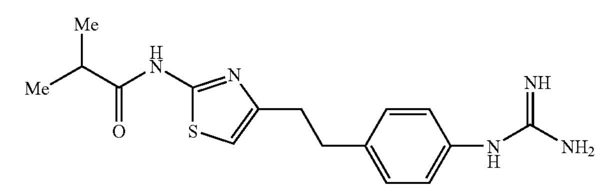 |
| 7 | 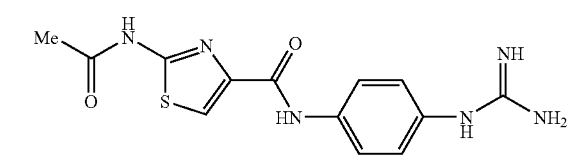 |
| 8 | 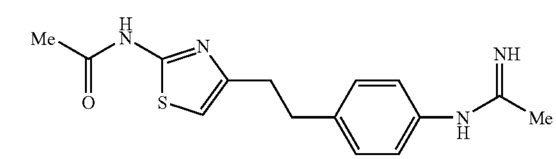 |

-continued

| No. | Structure |
|---|---|

9: Thiazole compound with acetamido group, ethylene linker, phenyl ring, and amidine group (HCl salt)

10: Thiazole compound with acetamido group, ethylene linker, phenyl ring, NH-C(O)-CH2-NH-guanidine (HCl salt)

11: Thiazole compound with acetamido group, phenyl ring, ethylene linker, NH-guanidine (HCl salt)

12: Thiazole compound with acetamido group, ethylene linker, phenyl ring, CH2NH2

13: Thiazole compound with EtO-C(O)-NH group, ethylene linker, phenyl ring, NH-guanidine (HCl salt)

14: Thiazole compound (5-Br substituted) with acetamido group, ethylene linker, phenyl ring (meta-substituted), NH-guanidine (HCl salt)

15: Thiazole compound (5-Br substituted) with acetamido group, ethylene linker, phenyl ring, NH-guanidine (HCl salt)

16: Thiazole compound with acetamido group, ethylene linker, phenyl ring, CH2-O-NH2

17: Thiazole compound with acetamido group, ethylene linker, phenyl ring, CH2-O-N=CH2

-continued

| No. | Structure |
|---|---|
| 18 | Me-C(=O)-NH-[thiazole]-CH2CH2-[C6H4]-NH-C(=NH)-NH2 · HCl |
| 19 | Me-C(=O)-NH-[thiazole]-CH2CH2-[C6H4]-NH-C(=NH)-NHMe |
| 20 | Me-C(=O)-NH-[thiazole(5-Cl)]-CH2CH2-[C6H4]-NH-C(=NH)-NH2 · HCl |
| 21 | Me-C(=O)-NH-[thiazole]-CH2CH2-[C6H4]-CH2-NH-C(=NH)-NH2 · HCl |
| 22 | Me-C(=O)-NH-[thiazole(5-CO2Et)]-CH2CH2-[C6H4]-NH-C(=NH)-NH2 · HCl |
| 23 | Me-C(=O)-NH-[thiazole]-CH2CH2-[C6H4]-NH-C(=NH)-NHEt |
| 24 | PhCH2O-C(=O)-NH-[thiazole]-CH2CH2-[C6H4]-NH-C(=NH)-NH2 |
| 25 | Ph-C(=O)-NH-[thiazole]-CH2CH2-[C6H4]-NH-C(=NH)-NH2 · HCl |

-continued

| No. | Structure |
|---|---|
| 26 | 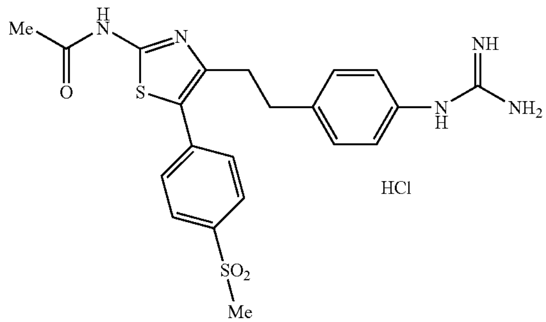 |
| 27 | 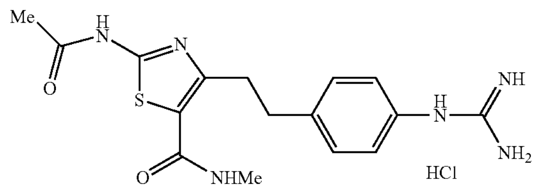 |
| 28 | 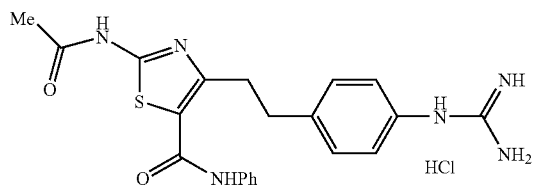 |
| 29 | 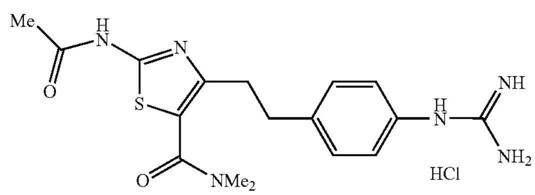 |
| 30 | 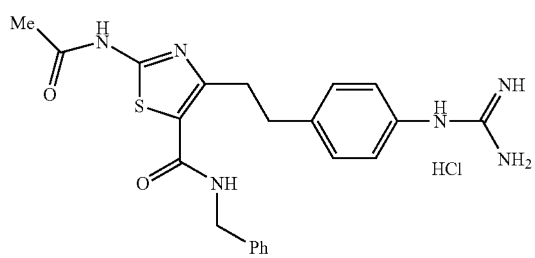 |
| 31 | 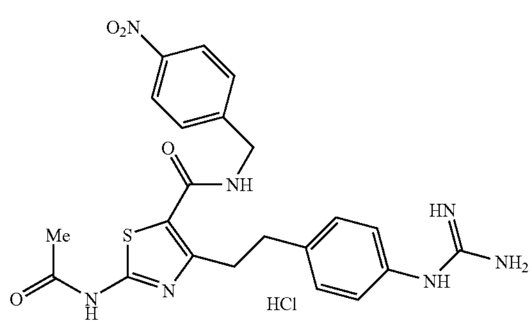 |

-continued

| No. | Structure |
|---|---|
| 32 | (structure: 2-acetamido-thiazole with 4-(methylsulfonyl)benzyl carboxamide at 5-position and 4-guanidinophenethyl at 4-position; HCl) |
| 33 | (structure: 2-acetamido-thiazole with 4-(trifluoromethyl)benzyl carboxamide at 5-position and 4-guanidinophenethyl at 4-position; HCl) |
| 34 | (structure: 2-acetamido-thiazole with pyridin-3-yl carboxamide at 5-position and 4-guanidinophenethyl at 4-position; 2HCl) |
| 35 | (structure: 2-acetamido-thiazole with 4-phenoxybenzyl carboxamide at 5-position and 4-guanidinophenethyl at 4-position; HCl) |

-continued
| No. | Structure |
|---|---|
| 36 | 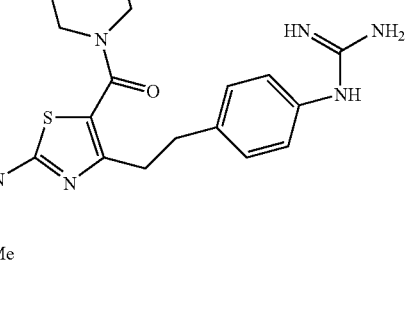 |
| 37 | 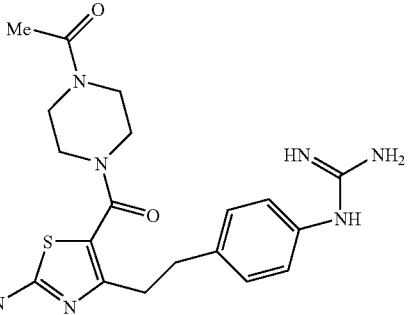 |
| 38 | 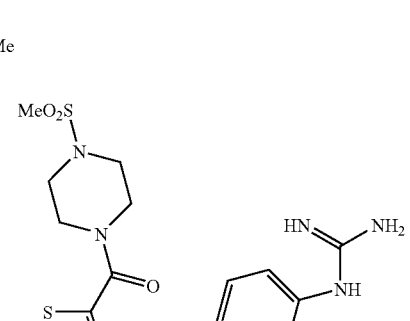 |
| 39 | 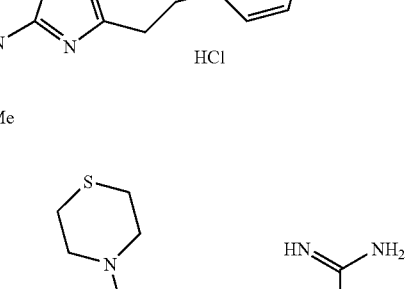 |

-continued

| No. | Structure |
|---|---|
| 40 | Thiazole with 2-acetamido, 4-[2-(4-guanidinophenyl)ethyl], 5-[(1,1-dioxothiomorpholin-4-yl)carbonyl]; HCl |
| 41 | Thiazole with 2-acetamido, 4-[2-(4-guanidinophenyl)ethyl], 5-[(4-ethoxycarbonylpiperidin-1-yl)carbonyl]; HCl |
| 42 | Thiazole with 2-acetamido, 4-[2-(4-guanidinophenyl)ethyl], 5-[(4-carbamoylpiperidin-1-yl)carbonyl]; HCl |
| 43 | Thiazole with 2-acetamido, 4-[2-(4-guanidinophenyl)ethyl], 5-[(4-(N-methylcarbamoyl)piperidin-1-yl)carbonyl]; HCl |

-continued
| No. | Structure |
|---|---|
| 44 | 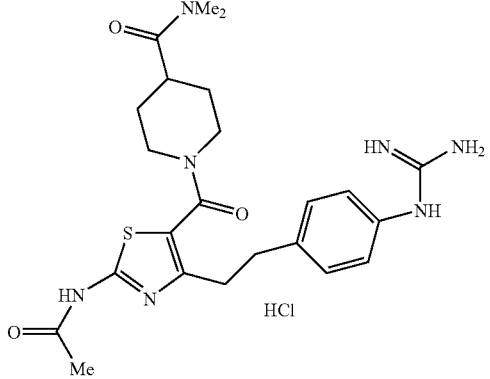 |
| 45 | 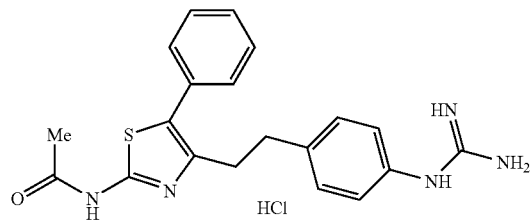 |
| 46 | 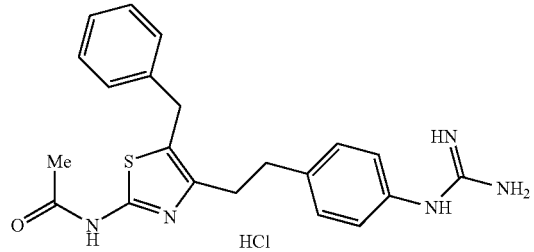 |
| 47 | 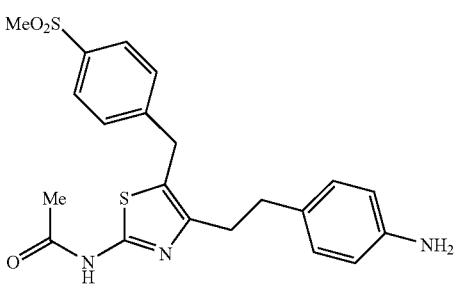 |
| 48 | 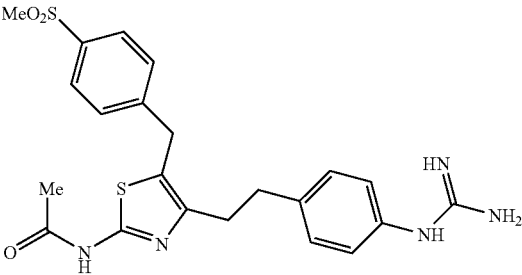 |

-continued
| No. | Structure |
|---|---|
| 49 | 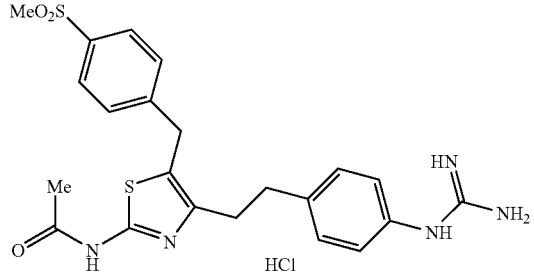 |
| 50 | 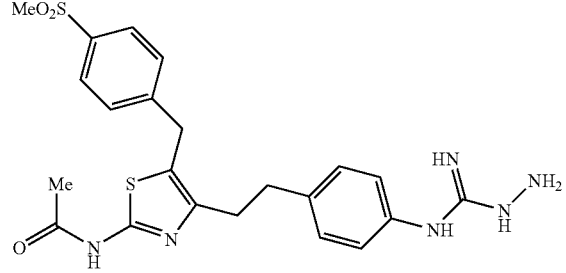 |
| 51 | 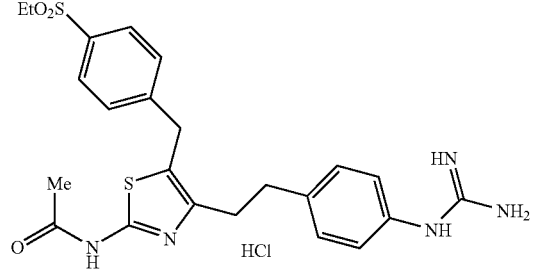 |
| 52 | 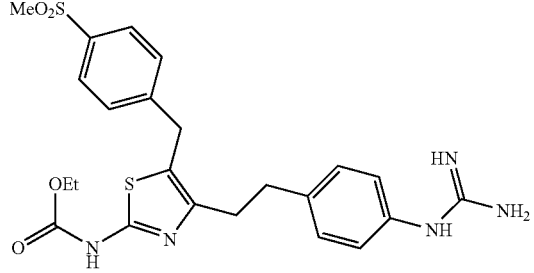 |
| 53 | 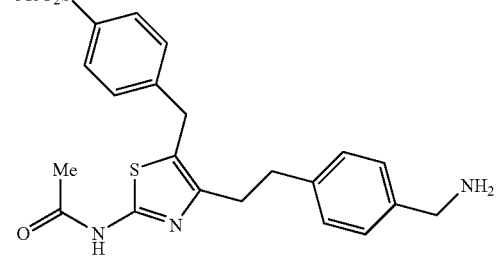 |

-continued

| No. | Structure |
|---|---|
| 54 | (structure) |
| 55 | (structure) |
| 56 | (structure) |
| 57 | (structure) |
| 58 | (structure) |
| 59 | (structure) |

-continued

| No. | Structure |
|---|---|
| 60 | (structure) |
| 61 | (structure) |
| 62 | (structure) |
| 63 | (structure) |
| 64 | (structure) |

-continued

| No. | Structure |
|---|---|
| 65 | (structure: 2-acetamido-thiazole with 5-(4-CONMe₂-benzyl) and 4-(2-(4-guanidinophenyl)ethyl) substituents; HCl) |
| 66 | (structure: 2-acetamido-thiazole with 5-(4-CONHM-benzyl) and 4-(2-(4-guanidinophenyl)ethyl) substituents; HCl) |
| 67 | (structure: 2-acetamido-thiazole with 5-(Me₂N-CH₂) and 4-(2-(4-guanidinophenyl)ethyl) substituents; 2HCl) |
| 68 | (structure: 2-acetamido-thiazole with 5-((4-acetylpiperazin-1-yl)methyl) and 4-(2-(4-guanidinophenyl)ethyl) substituents; 2HCl) |
| 69 | (structure: 2-acetamido-thiazole with 5-((4-methanesulfonylpiperazin-1-yl)methyl) and 4-(2-(4-guanidinophenyl)ethyl) substituents; 2HCl) |

-continued
| No. | Structure |
|---|---|
| 70 | 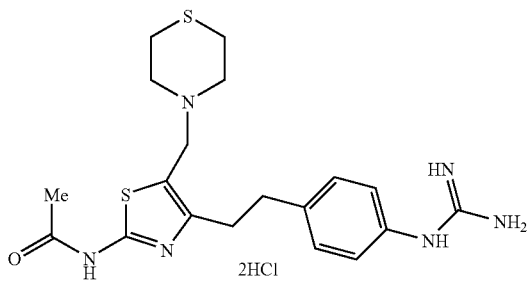 |
| 71 | 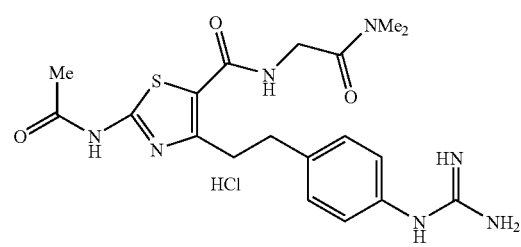 |
| 72 | 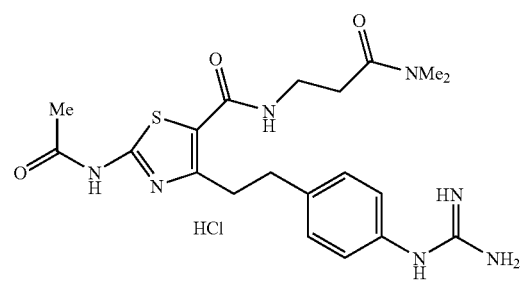 |
| 73 | 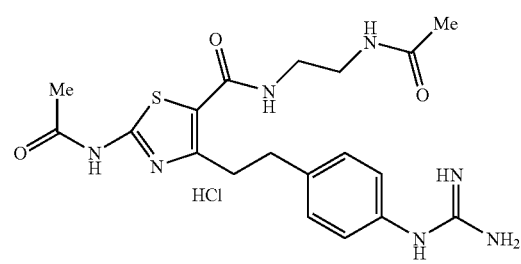 |
| 74 | 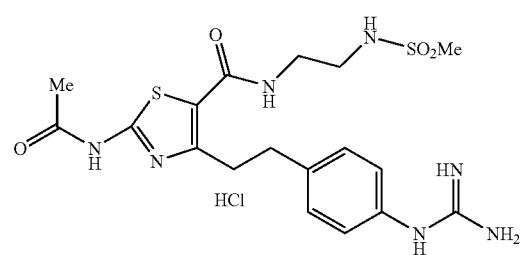 |

-continued

| No. | Structure |
|---|---|
| 75 | 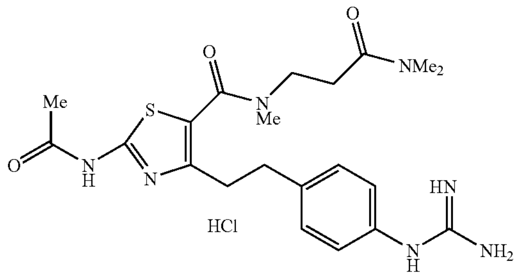 |
| 76 | 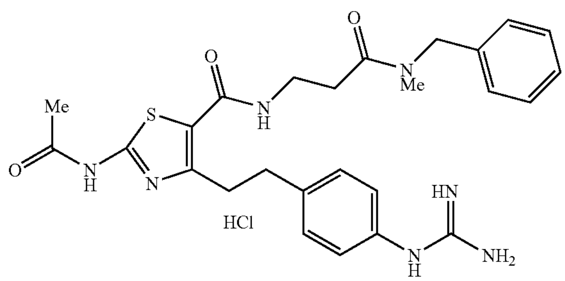 |
| 77 | 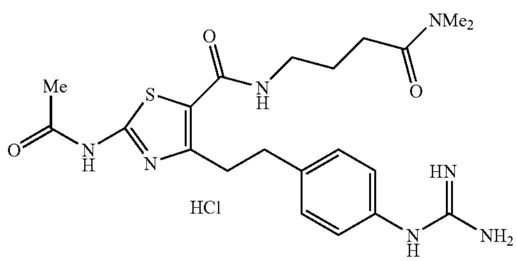 |
| 78 | 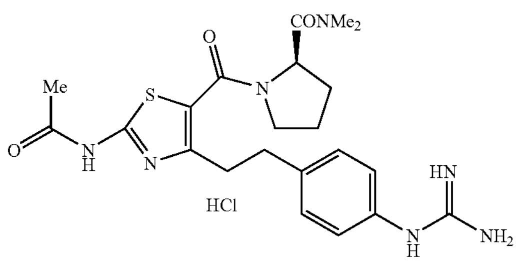 |
| 79 | 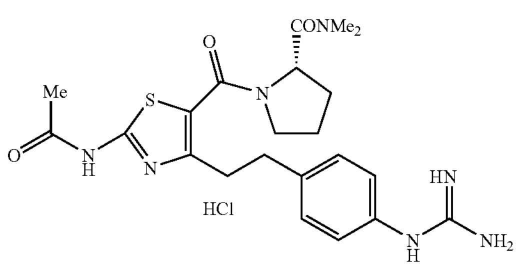 |

-continued
| No. | Structure |
|---|---|
| 80 | 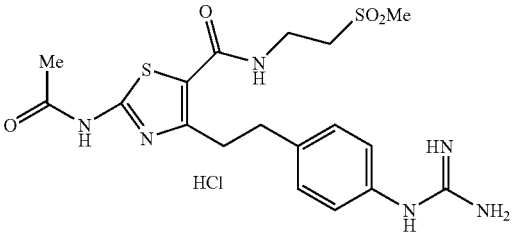 |
| 81 | 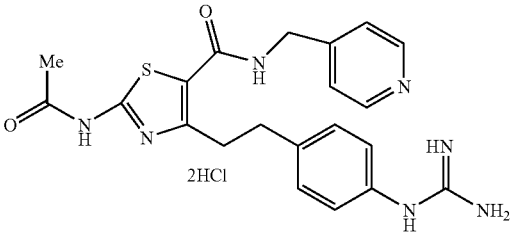 |
| 82 | 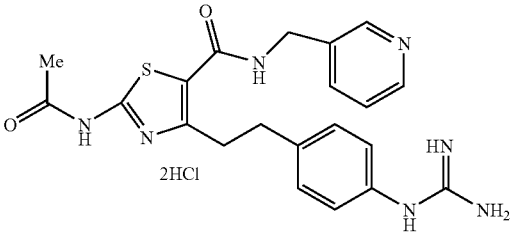 |
| 83 | 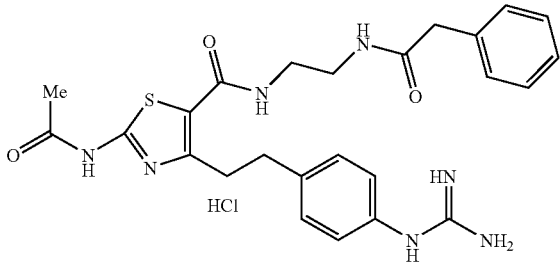 |
| 84 | 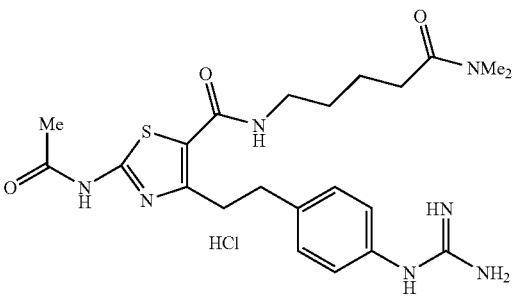 |

-continued

| No. | Structure |
|---|---|
| 85 | (structure) |
| 86 | (structure) |
| 87 | (structure) |
| 88 | (structure) |
| 89 | (structure) |

-continued
| No. | Structure |
|---|---|
| 90 | 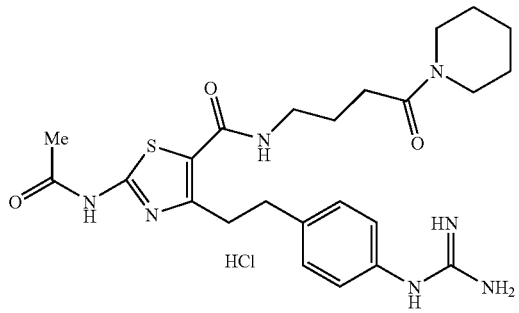 |
| 91 | 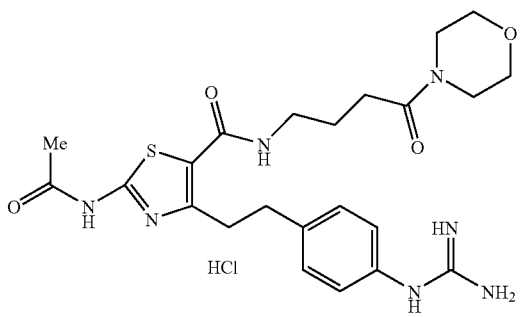 |
| 92 | 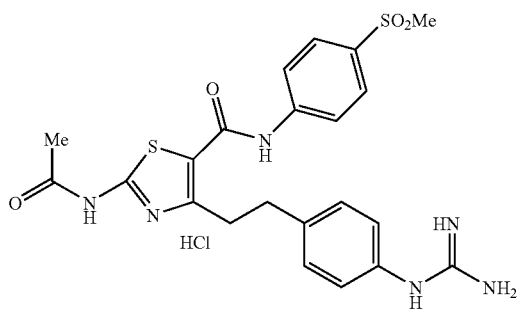 |
| 93 | 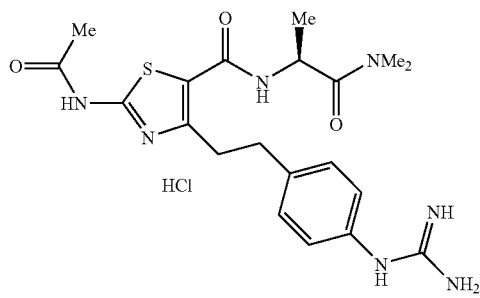 |

-continued
| No. | Structure |
|---|---|
| 94 | 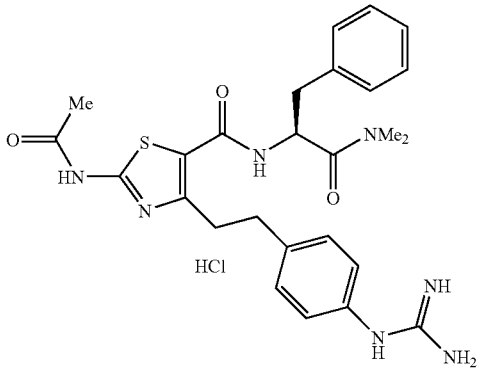 |
| 95 | 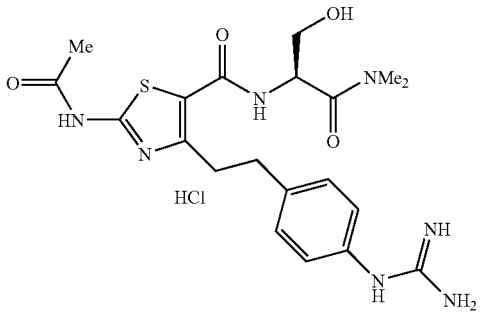 |
| 96 | 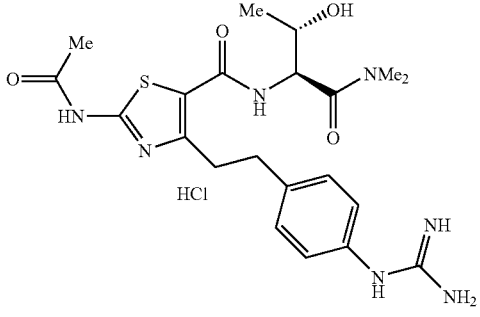 |
| 97 | 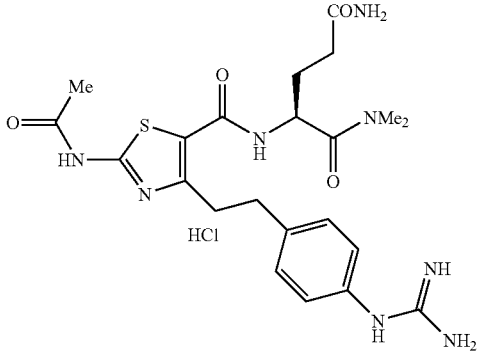 |

-continued
| No. | Structure |
|---|---|
| 98 | 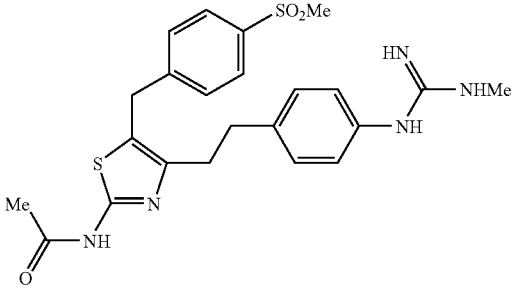 |
| 99 | 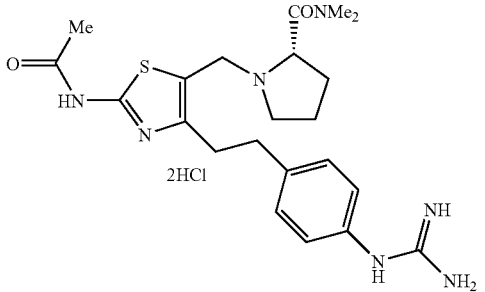 |
| 100 | 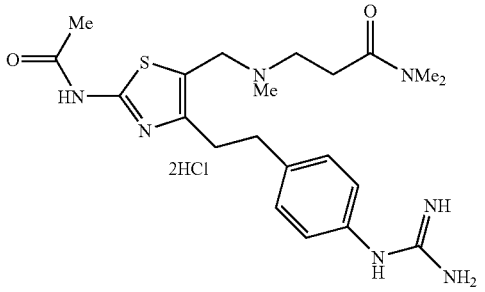 |
| 101 | 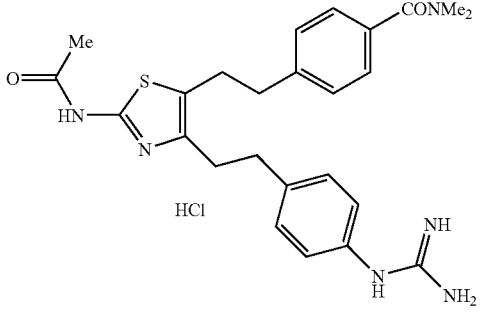 |
| 102 | 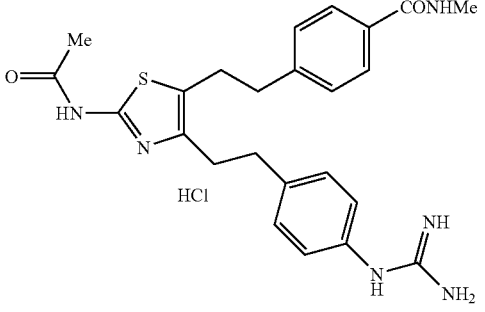 |

-continued
| No. | Structure |
|---|---|
| 103 | 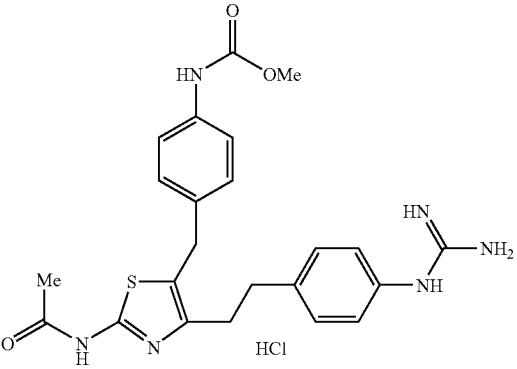 |
| 104 | 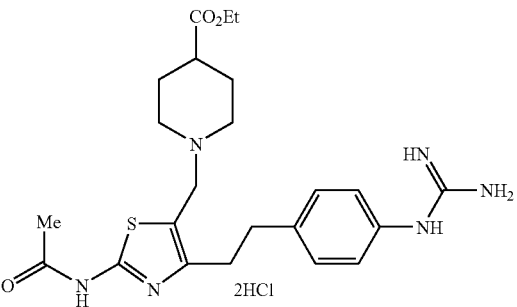 |
| 105 | 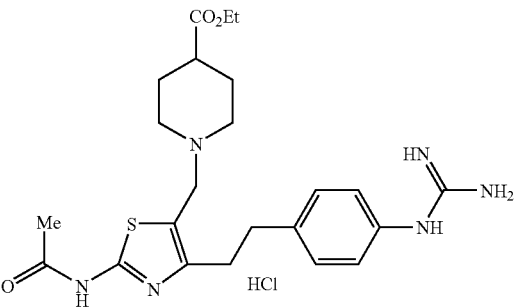 |
| 106 | 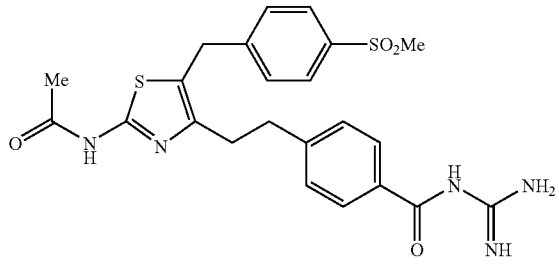 |
| 107 | 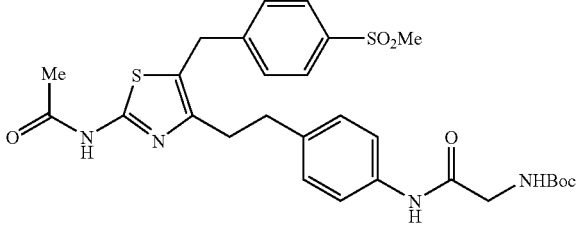 |

| No. | Structure |
|---|---|
| 108 | (structure: 2-acetamido-4-[2-(4-aminoacetamidophenyl)ethyl]-5-[4-(methylsulfonyl)benzyl]thiazole · HCl) |
| 109 | (structure: 2-acetamido-4-[2-(4-(2-aminoethyl)phenyl)ethyl]thiazole · HCl) |
| 110 | (structure: 2-acetamido-4-[2-(4-(2-guanidinoethyl)phenyl)ethyl]thiazole · HCl) |
| 111 | (structure: 2-acetamido-4-[4-(2-guanidinoethylsulfonyl)phenyl]thiazole · HCl) |
| 112 | (structure: 2-acetamido-4-[2-(4-guanidinophenyl)ethyl]-5-[3-(methylsulfonyl)benzyl]thiazole · HCl) |

-continued
| No. | Structure |
|---|---|
| 113 | 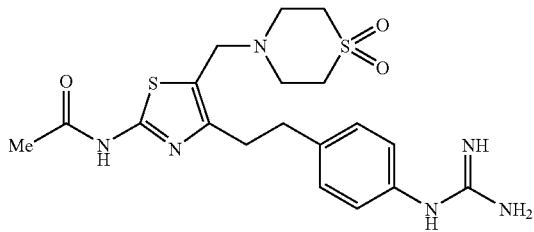<br>2HCl |
| 114 | 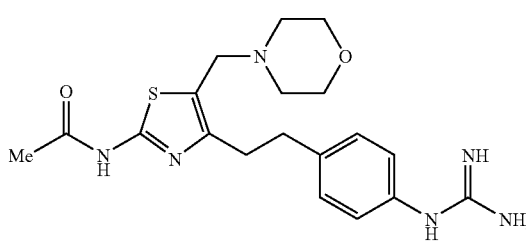<br>2HCl |
| 115 | 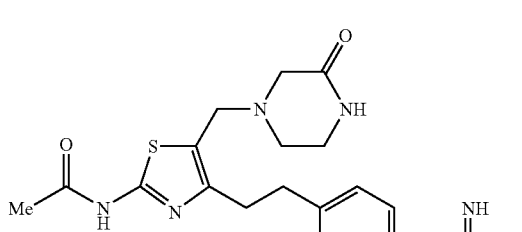<br>2HCl |
| 116 | 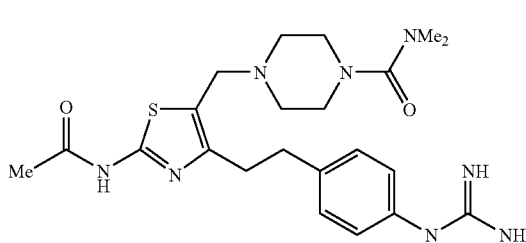<br>2HCl |
| 117 | 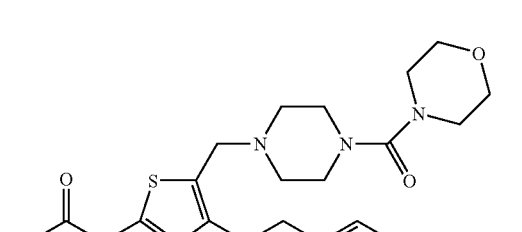<br>2HCl |

|No.|Structure|
|---|---|
|118|(structure shown) 2HCl|
|119|(structure shown) 3HCl|
|120|(structure shown) HCl|
|121|(structure shown) HCl|
|122|(structure shown) HCl|

-continued
| No. | Structure |
|---|---|
| 123 | 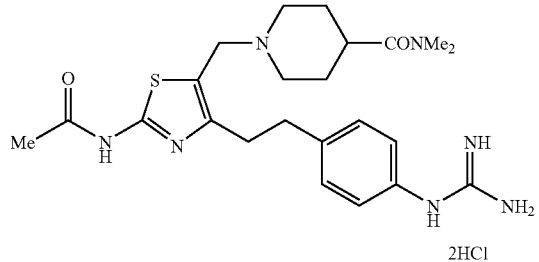 |
| 124 | 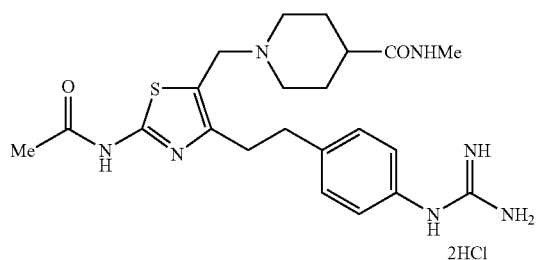 |
| 125 | 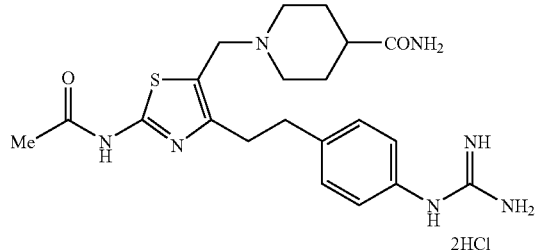 |
| 126 | 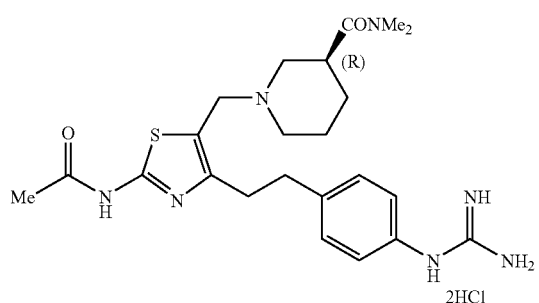 |
| 127 | 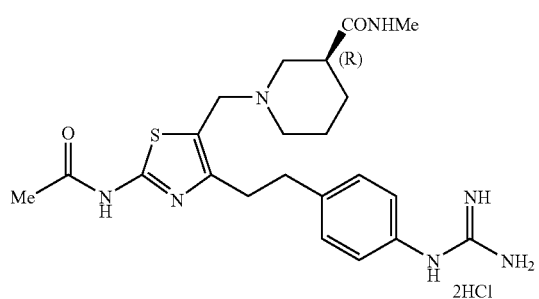 |

-continued
| No. | Structure |
|---|---|
| 128 | 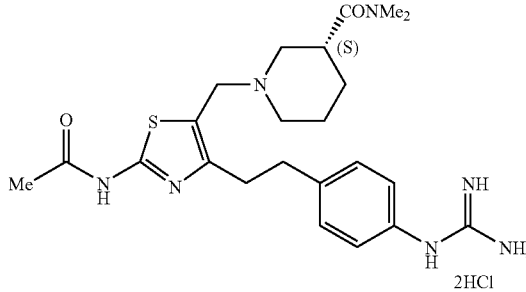 |
| 129 | 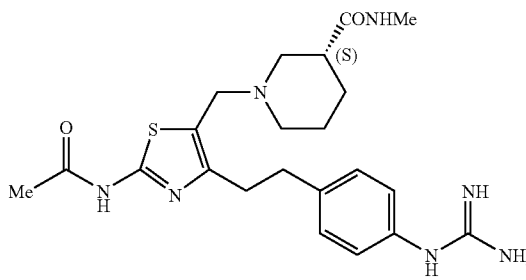 |
| 130 | 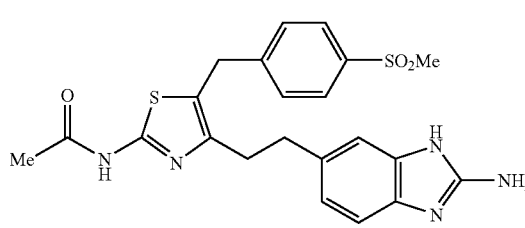 |
| 131 | 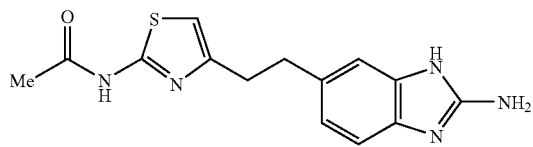 |
| 132 | 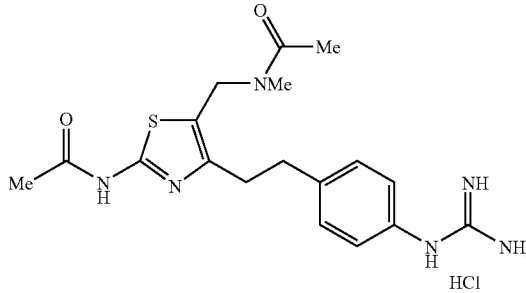 |
| 133 | 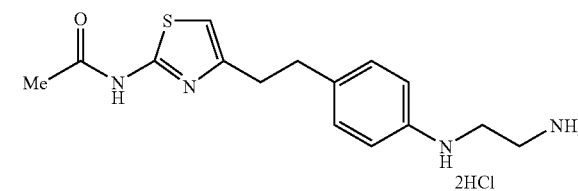 |

-continued

| No. | Structure |
|---|---|
| 134 | 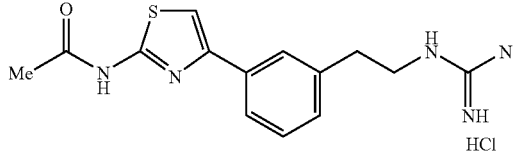 |
| 135 | 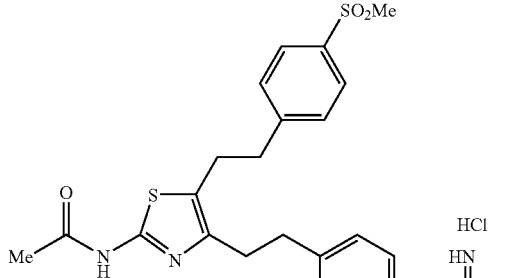 |

EXAMPLE 1

Inhibitory Effect of Compound A on VAP-1 enzyme (SSAO) Activity in Human and Rat Plasma.

VAP-1 enzyme (SSAO) activity in both human and rat plasma was determined by a radiochemical-enzyme assay using $^{14}C$-benzylamine as artificial substrate. The enzyme suspension prepared from blood plasma was pre-incubated with Compound A in 96-well microplate at room temperature for 30 min. The enzyme suspension was then incubated with $^{14}C$-benzylamine ($2 \times 10^{-5}$ mol/l final concentration) in a final volume of 50 µl at 37° C. for 1 hour. The enzyme reaction was terminated by adding 2 mol/l (50 µl) citric acid. The oxidized products were directly extracted into a 200 µl toluene scintillator, and its radioactivity was measured by a scintillation spectrometer. Monoamine oxidase (MAO) and diamine oxidase (DAO, histaminase) activities were also determined by similar method using $^{14}C$-phenylethylamine and $^{14}C$-putrescine as substrate, respectively. Cloned DAO from cDNA libraries was used in human DAO assay. Inhibition activity was expressed as $IC_{50}$ (µmol/l) value.

Compound A completely inhibited the enzyme activity of human and rat plasma SSAO, but not the enzyme activities of other amine oxidases, such as human platelet MAO and cloned DAO, shown in Table 1.

TABLE 1

Inhibitory effect ($IC_{50}$ values, µM) of Compound A on various amine oxidase activities

| Human plasma SSAO | Rat plasma SSAO | Human platelet MAO | Cloned human DAO |
|---|---|---|---|
| 0.15 | 0.012 | >100 | >100 |

EXAMPLE 2

Effect of Compound A on Ocular Permeability in Diabetic Rats.

Diabetes in rat was induced with an intraperitoneal (i.p.) injection of 65 mg/ml/kg of streptozotocin (STZ) in 2 mmol/l citrate buffer (pH 4.5) after a 20-h fast. At the same time control rat were injected with an equal volume of 2 mmol/l citrate buffer. Plasma glucose level was checked by a colorimetric method. At day 3 of STZ treatment, the rat was diagnosed with diabetes showing a plasma glucose level of 350 mg/dl.

The treatment of Compound A was given daily from 2 weeks after STZ treatment for 2 weeks. At 24 hrs after final treatment of Compound A, the vascular permeability in oculus was investigated based on the leakage of dye into the vitreous 30 min after intravenous injection of fluorescein solution (40 mg/ml/kg). Permeability was expressed as vitreous/plasma ratio of fluorescein concentration measured by a fluorophotometer. At the same time, the plasma SSAO activity was checked by the radiochemical-enzyme assay using $^{14}C$-benzylamine ($2 \times 10^{-5}$ mol/l final concentration) as substrate.

The significant increase of ocular permeability in diabetic rats was examined at 4 weeks after treatment of STZ and compared with that of normoglycemic normal rats. The treatment of Compound A (10 mg/kg, s.c. u.i.d.) given daily from 2 weeks after STZ treatment improved the ocular permeability, in comparison with the STZ control group (Table 2). Plasma SSAO enzyme activity also increased in diabetic rats at 4 weeks after STZ treatment, but the treatment with Compound A exhibited dose-dependent inhibition of the increased plasma SSAO activity (Table 3).

TABLE 2

Vitreous/Plasma Ratio of Fluorescein Concentration (×10⁻³)

| Normal | STZ control | Compound A treatment |
|---|---|---|
| 3.30 ± 0.38** | 8.93 ± 1.14 | 5.39 ± 0.73** |

Values are mean ± S.E.M.s for 10 rats.
**p < 0.01 vs corresponding value for STZ control by Dunnett's test.

TABLE 3

Plasma SSAO activity (pmol/min/ml)

| Normal | STZ control | Compound A treatment |
|---|---|---|
| 4.40 ± 0.34** | 10.0 ± 0.73 | 2.51 ± 0.26** |

Values are mean ± S.E.M.s for 10 rats.
**p < 0.01 vs corresponding value for STZ control by Dunnett's test.
U.S. 60/442,509; 60/458,369; and 60/517,377 are each incorporated herein by reference in their entirety.

INDUSTRIAL APPLICABILITY

The present invention provides a compound of the formula (I): $R^1$—NH—X—Y-Z (I) wherein each symbol is as defined above, or a parmaceutically acceptable salt thereof useful as a VAP-1 inhibitor, a pharmaceutical composition, a method for preventing or treating a VAP-1 associated disease, especially macular edema such as diabetic macular edema and non-diabetic macular edema, which method comprises administering to a patient in need thereof a VAP-1 inhibitor in an amount sufficient to treat the patient for the VAP-1 associated disease, and the like.

The invention claimed is:
1. A compound of the formula (I):

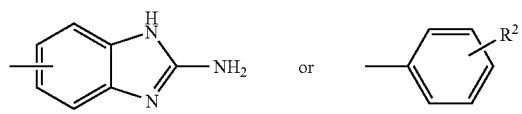

wherein the 1,3-thiazole ring is optionally substituted at the 5-position;
Y is lower alkylene, lower alkenylene or —CONH—; and
Z is a group of the formula:

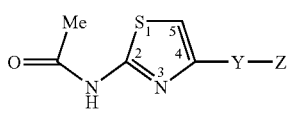

wherein $R^2$ is a group of the formula: -A-B-D-E, wherein
A is a bond, lower alkylene, —NH— or —SO$_2$—;
B is a bond, lower alkylene, —CO— or —O—;
D is a bond, lower alkylene, —NH— or —CH$_2$NH—; provided that B and D are not both simultaneously bonds, and
E is amino, which may be optionally protected, —N═CH$_2$,

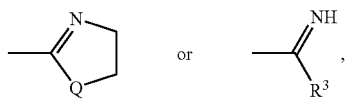

wherein
Q is —S— or —NH—; and
$R^3$ is hydrogen, lower alkyl, lower alkylthio, or —NH—$R^4$, wherein $R^4$ is hydrogen, —NH$_2$ or lower alkyl;
or a pharmaceutically acceptable salt thereof.

2. The compound of claim 1, wherein Z is a group of the formula:

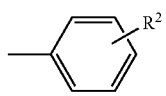

wherein $R^2$ is a group of the formula:

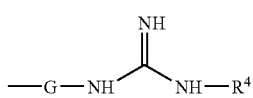

(wherein G is a bond, —NHCOCH$_2$— or lower alkylene and $R^4$ is hydrogen, —NH$_2$ or lower alkyl);
—NH$_2$;
—CH$_2$NH$_2$;
—CH$_2$ONH$_2$;
—CH$_2$ON═CH$_2$;

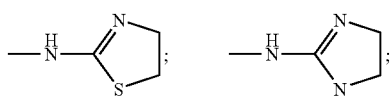

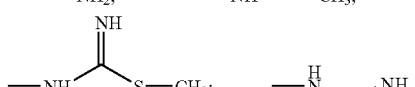

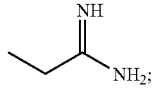

or a pharmaceutically acceptable salt thereof.

3. The compound of claim 2, wherein $R^2$ is a group of the formula:

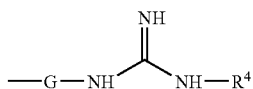

(wherein G is a bond, —NHCOCH₂— or lower alkylene and R⁴ is hydrogen or lower alkyl);
—CH₂NH₂;
—CH₂ONH₂;
—CH₂ON=CH₂;

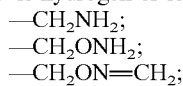

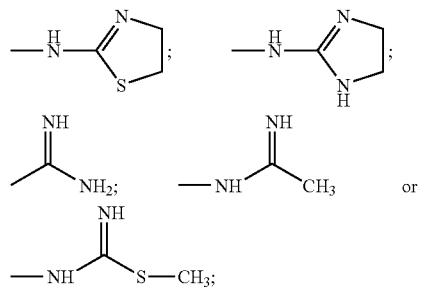

or a pharmaceutically acceptable salt thereof.

4. The compound of claim 1, wherein the compound is:
N-{4-[2-(4-{[amino(imino)methyl]amino}phenyl)ethyl]-1,3-thiazol-2-yl}acetamide,
N-{4-[2-(4-{[amino(imino)methyl]amino}phenyl)ethyl]-5-[4-(methylsulfonyl)benzyl]-1,3-thiazol-2-yl}acetamide,
N-{4-[2-(4-{[hydrazino(imino)methyl]amino}phenyl)ethyl]-5-[4-(methylsulfonyl)benzyl]-1,3-thiazol-2-yl}acetamide,
N-{4-[2-(4-{[hydrazino(imino)methyl]amino}phenyl)ethyl]-1,3-thiazol-2-yl}acetamide, or
N-(4-{2-[4-(2-{[amino(imino)methyl]amino}ethyl)phenyl]ethyl}-1,3-thiazol-2-yl)acetamide;
or a pharmaceutically acceptable salt thereof.

5. A pharmaceutical composition, which comprises:
the compound of claim 1 or a pharmaceutically acceptable salt thereof, and
a pharmaceuticaly acceptable carrier or excipient.

6. A method for producing a compound of formula (I):

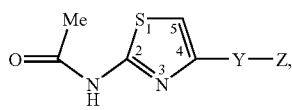

wherein the 1,3-thiazole ring is optionally substituted at the 5-position;
Y is lower alkylene, lower alkenylene or —CONH—; and
Z is a group of the formula:

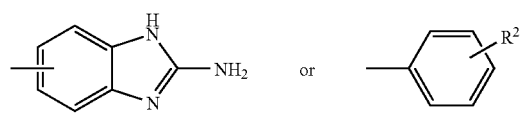

wherein R² is a group of the formula: -A-B-D-E
wherein
A is a bond, lower alkylene, —NH— or —SO₂—;
B is a bond, lower alkylene, —CO— or —O—;
D is a bond, lower alkylene, —NH— or —CH₂NH—; provided that B and D are not simultaneously bonds; and
E is amino, which is optionally protected, —N=CH₂,

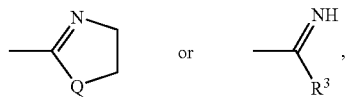

wherein Q is —S— or —NH—; and R³ is hydrogen, lower alkyl, lower alkylthio or —NH—R⁴, wherein R⁴ is hydrogen, —NH₂ or lower alkyl;
or a pharmaceutically acceptable salt thereof;
which method comprises at least one step selected from the group consisting of (ii), (iii), (iv) and (v):
(ii) reacting Compound (3):

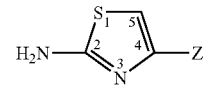

wherein Z is as defined above and the 1,3-thiazole ring is optionally substituted at the 5-position, or a salt thereof with Compound (4):

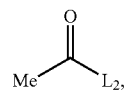

wherein L₂ is a leaving group;
(iii) reacting Compound (6):

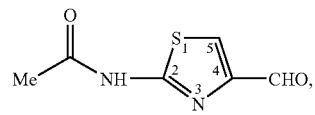

wherein the 1,3-thiazole ring is optionally substituted at the 5-position or a salt thereof with Compound (7): L₃-CH₂-Z, wherein L₃ is a leaving group and Z is as defined above, or a salt thereof;
(iv) reduction of Compound (10):

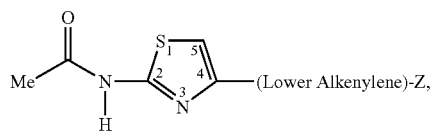

wherein Z is as defined above and the 1,3-thiazole ring is optionally substituted at the 5-position, or a salt thereof;
to Compound (11):

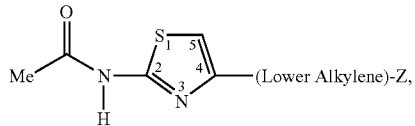

wherein Z is as defined above and the 1,3-thiazole ring is optionally substituted at the 5-position; or a salt thereof; and (v) reacting Compound (12):

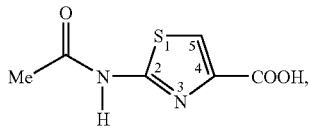

wherein the 1,3-thiazole ring is optionally substituted at the 5-position or a reactive derivative thereof, or a salt thereof with Compound (13): $L_4$-NH-Z, wherein $L^4$ is a hydrogen atom or a protecting group and Z is as defined above; or a salt thereof.

7. A method for treating macular edema comprising: administering to a subject in need thereof the compound of claim 1 in an amount sufficient to treat said subject for macular edema.

8. The method of claim 7, wherein the compound is:
N-{4-[2-(4-{[amino(imino)methyl]amino}phenyl)ethyl]-1,3-thiazol-2-yl}acetamide,
N-{4-[2-(4-{[amino(imino)methyl]amino}phenyl)ethyl]-5-[4-(methylsulfonyl)benzyl]-1,3-thiazol-2-yl}acetamide,
N-{4-[2-(4-{[hydrazino(imino)methyl]amino}phenyl)ethyl]-5-[4-(methylsulfonyl)benzyl]-1,3-thiazol-2-yl}acetamide,
N-{4-[2-(4-{[hydrazino(imino)methyl]amino}phenyl)ethyl]-1,3-thiazol-2-yl}acetamide, or
N-(4-{2-[4-(2-{[amino(imino)methyl]amino}ethyl)phenyl]ethyl}-1,3-thiazol-2-yl)acetamide,
or a pharmaceutically acceptable salt thereof.

9. The method of claim 7, wherein said macular edema is diabetic macular edema.

10. The method of claim 7, wherein said macular edema is non-diabetic macular edema.

* * * * *